(12) United States Patent
Benesova et al.

(10) Patent No.: US 11,629,201 B2
(45) Date of Patent: Apr. 18, 2023

(54) PSMA-BINDING AGENTS AND USES THEREOF

(71) Applicants: ITM Isotope Technologies Munich SE, Garching bei München (DE); Paul Scherrer Institut, Villigen PSI (CH)

(72) Inventors: Martina Benesova, Turgi (CH); Cristina Müller, Nussbaumen (CH); Christoph Umbricht, Baden (CH); Roger Schibli, Baden (CH); Konstantin Zhernosekov, Munich (DE)

(73) Assignees: ITM Isotope Technologies Munich SE, Garching bei München (DE); Paul Scherrer Institut, Villigen (CH)

( * ) Notice: Subject to any disclaimer, the term of this patent is extended or adjusted under 35 U.S.C. 154(b) by 462 days.

(21) Appl. No.: 16/616,744

(22) PCT Filed: May 24, 2018

(86) PCT No.: PCT/EP2018/063734
§ 371 (c)(1),
(2) Date: Nov. 25, 2019

(87) PCT Pub. No.: WO2018/215627
PCT Pub. Date: Nov. 29, 2018

(65) Prior Publication Data
US 2021/0009715 A1    Jan. 14, 2021

(30) Foreign Application Priority Data

May 24, 2017 (EP) .................................... 17000891
Jun. 20, 2017 (WO) ................. PCT/EP2017/000717

(51) Int. Cl.
*C07K 16/44* (2006.01)
*A61B 6/00* (2006.01)

(52) U.S. Cl.
CPC ............ *C07K 16/44* (2013.01); *A61B 6/5235* (2013.01)

(58) Field of Classification Search
CPC ................................. C07K 16/44; A61B 6/00
See application file for complete search history.

(56) References Cited

FOREIGN PATENT DOCUMENTS

WO    2018/031809    2/2018

OTHER PUBLICATIONS

Cindy Choy et al. 177Lu-Labeled Phosphoramidate-Based PSMA Inhibitors: The effect of an albumin binder on biodistribution and therapeutic efficacy in prostate tumor-bearing mice, Thernostics, 7(7), 1928-1939. (Year: 2017).*
Benešová, M. et al., Albumin-Binding PSMA Ligands: Optimization of the Tissue Distribution Profile, Mol Pharm. Mar. 5, 2018;15(3):934-946. doi: 10.1021/acs.molpharmaceut.7b00877. Epub Feb. 5, 2018.
Umbricht, C. et al., Preclinical Development of Novel PSMA—Targeting Radioligands: Modulation of Albumin-Binding Properties to Improve Prostate Cancer Therapy, Molecular Pharmaceutics, 15(6): 2297-2306, Apr. 23, 2018.
Choy, C. et al., 177Lu-Labeled Phosphoramidate-Based PSMA Inhibitors: The Effect of an Albumin Binder on Biodistribution and Therapeutic Efficacy in Prostate Tumor-Bearing Mice, Theranostics, 7(7): 1928-1939, Apr. 27, 2017.
Kelly. J. et al., Dual-Target Binding Ligands with Modulated Pharmacokinetics for Endoradiotherapy of Prestate Cancer, J Nucl Med., 58(9): 1442-1449, Apr. 27, 2017.
Nicolas, G. et al., Biodistribution, Pharmacokinetics, and Dosimetry of 177Lu-, 90Y-, and 111In-Labeled Somatostatin Receptor Antagonist OPS201 in Comparison to the Agonist 177Lu-DOTATATE: The Mass Effect, The Journal of Nuclear Medicine, 58(9): 1435-1441, Sep. 2017.
Notice of Reasons for Rejection, JP Application No. JP 2019 562312, dated Oct. 18, 2022.
English Translation of Notice of Reasons for Rejection, JP Application No. JP 2019 562312, dated Oct. 18, 2022.

* cited by examiner

*Primary Examiner* — Michael G. Hartley
*Assistant Examiner* — Jagadishwar R Samala
(74) *Attorney, Agent, or Firm* — Julie K. Staple; Dinsmore & Shohl LLP

(57) ABSTRACT

The present invention provides novel compounds that are useful as radiopharmaceuticals, imaging agents and for treatment of cancer.

61 Claims, 33 Drawing Sheets

B

C

C

A

PSMA-ALB-02

B

PSMA-ALB-05

C

PSMA-ALB-07

PSMA-BINDING AGENTS AND USES THEREOF

The present invention relates to novel compounds and radiolabeled complexes comprising a chelating agent, a PSMA-binding entity and an albumin-binding entity connected via suitable linkers and spacers, which are envisaged for use as diagnostic and/or therapeutic radiopharmaceuticals. Specifically, the compounds and complexes according to the invention lend themselves as (theragnostic) tracers, imaging agents and therapeutic agents for detecting PSMA-expressing target cells and tissues and treating and diagnosing cancer.

Prostate cancer (PCa) is the leading cancer in the US and European population. At least 1-2 million men in the western hemisphere suffer from prostate cancer and it is estimated that the disease will strike one in six men between the ages of 55 and 85. According to the American Cancer Society, approximately 161,000 new cases of prostate cancer are diagnosed each year in USA. The 5-year survival rate of patients with stage IV metastatic prostate cancers is only about 29%.

Once a metastatic PCa becomes hormone-refractory there are only a few therapy options left, often with rather poor clinical success. According to the current medical guidelines, antimitotic chemotherapy with docetaxel is typically recommended. However, treatment is often associated with severe side effects, and only marginally improved survival rates. Early diagnosis and close monitoring of potential relapses are therefore crucial. Prostate cancer diagnosis is based on examination of histopathological or cytological specimens from the gland. Existing imaging techniques for therapeutic monitoring of progressing or recurring prostate cancer, include computed tomography (CT), magnetic resonance (MR) imaging and ultrasound, but are often insufficient for effective monitoring and management of the disease. Consequently, there is a high clinical demand for more effective tools for both early diagnosis and treatment of PCa.

It is well known that tumor cells may express unique proteins exhibiting a modified structure due to mutation, or may over-express normal (i.e. non-mutated) proteins that are normally produced in extremely small quantities in non-malignant cells. Tumor antigens may be broadly classified into two categories based on their expression pattern: Tumor-Specific Antigens (TSA), which are present only on tumor cells and not on non-malignant cells and Tumor-Associated Antigens (TAA), which are present on some tumor cells and also non-malignant cells. TSAs typically emerge as a result of the mutation of protooncogenes and tumor suppressors which lead to abnormal protein production, whereas TAA expression is generally caused by mutation of other genes unrelated to the tumor formation.

The expression of such proteins on the surface of tumor cells offers the opportunity to diagnose and characterize disease by detecting such tumor markers. Proteinaceous binding agents or small molecule drugs carrying visualizable labels and specifically recognizing such tumor markers are typically employed for diagnosing and imaging cancers under non-invasive conditions.

A promising new series of low molecular-weight imaging agents targets the prostate-specific membrane antigen (PSMA). PSMA, also known as folate hydrolase I (FOLH1), is a trans-membrane, 750 amino acid type II glycoprotein. The PSMA gene is located on the short arm of chromosome 11 and functions both as a folate hydrolase and neuropeptidase. It has neuropeptidase function that is equivalent to glutamate carboxypeptidase II (GCPII), which is referred to as the "brain PSMA", and may modulate glutamatergic transmission by cleaving N-acetyl-aspartyl-glutamate (NAAG) to N-acetylaspartate (NAA) and glutamate (Nan, F.; et al.) Med Chem 2000, 43, 772-774).

DF
PSMA is (i) mainly restricted to the prostate (although is also detected in lower amounts in the neovasculature of numerous other solid tumors, including bladder, pancreas, lung, and kidney cancers, but not in normal vasculature), (ii) abundantly expressed as protein at all stages of prostate cancer (in amounts of up to $10^6$ PSMA molecules per cancer cell) (iii) presented at the cell surface but not shed into the circulation, and (iv) associated with enzymatic or signaling activity. Moreover, PSMA expression is further up-regulated in poorly differentiated, androgen-insensitive or metastatic cancers and the expression usually correlated with disease progression.

The unique expression of PSMA makes it an important marker of prostate cancer (and a few other cancers as well). Furthermore, PSMA represents a large extracellular target for imaging agents. PSMA is internalized after ligand binding and, thus, it is not only an excellent target for targeted radionuclide therapy (using particle-emitting radionuclides) but also for other therapeutic strategies including the tumor cell-specific delivery of immunotoxins, retargeting of immune cells, pro-drug activation, PSMA vaccines, and plasmid DNA and adenoviral immunizations. Because of low expression levels in healthy tissue, PSMA has additionally the potential for high-dose therapy, with minimized side effects.

In the past, several PSMA-targeting agents carrying therapeutic or diagnostic moieties were developed. The FDA-approved radio-immunoconjugate of the anti-PSMA monoclonal antibody (mAb) 7E11, known as PROSTASCINT®, has been used to diagnose prostate cancer metastasis and recurrence. The success of this radiopharmaceutical agent is limited due to the fact that this antibody binds to the intracellular domain of PSMA, hence, can target only dead cells. Moreover, the use of monoclonal antibodies and antibody fragments as imaging agents is often limited due to their slow renal clearance, heterogenous distribution, poor tumor penetration and immunogenic potential. In order to overcome these problems, various small-molecule PSMA targeting agents capable of binding to the extracellular domain of PSMA were developed for PET/CT and SPECT/CT imaging, including radiolabeled N—[N—[(S)-1,3-dicarboxypropyl]carbamoyl]-S-[11C]methyl-1-cysteine (DCFBC) and several urea-based peptidomimetic PSMA-inhibitors (cf. Bouchelouche et al. Discov Med. 2010 January; 9(44): 55-61), including MIP-1095 (Hillier et al. Cancer Res. 2009 Sep. 1; 69(17):6932-40), a PSMA ligand currently in clinical evaluation, and DOTA-conjugated PSMA-inhibitor PSMA-617 developed by BeneovA et al (JNM 2015, 56: 914-920 and EP 2862 857 A1), which distributes throughout the body and rapidly clears from the blood (Nucl Med. 2015; 56(11):1697-705). However, although rapid and systemic access advantageously facilitates tumor targeting and—penetration, currently available PSMA-targeting agents bear the risk of mediating unspecific "off-target" interactions in normal tissues expressing the target, and of accumulation of the radiopharmaceuticals in excretory organs (such as the kidneys). Thereby, non-tumorous tissues may be exposed to radiation doses ultimately leading to irreversible tissue damage. It was demonstrated that different radiolabeled small-molecule PSMA-targeting agents (including PSMA-617) accumulate in patients' lacrimal and salivary glands and may cause damage to the glandular tissue, especially if used in combination with alpha-emitting radionuclides (Zechmann et al. Eur J Nucl Med Mol Imaging. 2014; 41(7):1280-92 and Kratochwil et al. J Nucl Med. 2017 Apr. 13. pii: jnumed.117.191395. doi: 10.2967/jnumed.117.191395 [Epub]). One possible solution to that problem involves the use of PSMA-binding agents with a high-affinity towards PSMA (Kratochwil et al. J Nucl Med. 2015; 293-298 and Chatalic et al. Theragnostics. 2016; 6: 849-861).

Recently, Kelly et al. (Nucl Med. 2017 pii: jnumed.116.188722. doi: 10.2967/jnumed.116.188722. [Epub ahead of print]) evaluated agents exhibiting affinity for both PSMA and for human serum albumin (HSA). The ligands developed by Kelly et al. comprise a p-(iodophenyl) butyric acid entity for HSA binding and an urea-based PSMA binding entity. In the compounds developed by Kelly et al., radiotherapeutic iodine ($^{131}$I) is covalently attached to the HSA binding moiety, which is in turn directly connected to the PSMA binding entity via a hydrocarbyl chain. However, the evaluated compounds are considerably limited in terms of the applied radionuclide which is limited to iodine. Further, no improved internalization/uptake in target cells was demonstrated for the evaluated compounds.

Another approach was followed by Choy et al. Theranostics 2017; 7(7):1928-1939, who evaluated $^{177}$Lu-labeled phosphoramidate-based PSMA inhibitor with an albumin-binding entity. A DOTA chelator complexing the $^{177}$Lu radionuclide was ether-linked to the irreversible PSMA inhibitor CTT1298 (EP 2970345 A). Phosphoramidate-based PSMA binding motive, however, exhibits only poor stability, especially at elevated temperatures (elevated temperatures under extended acidic conditions lead to hydrolysis of phosphoramidate P—N bond), which are required for the coordinative radiolabeling reaction via chelators such as DOTA. Therefore a direct radiolabeling reaction cannot be applied and a multi-step pre-labeling approach has to be used. Thus, $^{177}$Lu-DOTA-azide as precursor should be prepared; subsequently the precursor has to be coupled to a dibenzocyclooctyne-derivatized PSMA motive. Finally, elaborate HPLC purification of the coupled compound must be undertaken; reformulation with evaporation (under $N_2$ atmosphere) of the HPLC-eluent and dissolving in a physiological medium need to be performed. This procedure is likely not possible for a clinical application when high activities are being produced. Pre-clinical biodistribution data demonstrate poor performance of the radiolabeled agent especially regarding tumour-to-kidney ratios which did not exceed far above 1.

Despite advances over the years, diagnosis and management of prostate cancer still remains challenging. New diagnostic or imaging agents capable of targeting PCa tumor cells in a highly selective manner and exhibiting favorable pharmacokinetic properties for rapid and non-invasive tumor visualization and therapy are needed to enable early detection and treatment of PCa.

It is thus an object of the present invention to overcome the disadvantages in the prior art and comply with the need in the art.

That object is solved by the subject-matter disclosed herein, more specifically as set out by the claim set.

General Comments

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

In the present invention, if not otherwise indicated, different features of alternatives and embodiments may be combined with each other.

For the sake of clarity and readability the following definitions are provided. Any technical feature mentioned for these definitions may be read on each and every embodiment of the invention. Additional definitions and explanations may be specifically provided in the context of these embodiments.

Definitions

The term "hydrocarbyl" refers to residues of hydrocarbon groups, i.e., hydrocarbon chain radicals, preferably independently selected from the group alkyl, alkenyl, alkynyl, aryl and aralkyl.

The term "alkyl" comprises linear ("straight-chain"), branched and cyclic chain radicals having 1-30 carbon atoms, preferably 1-20, 1-15, 1-10, 1-8, 1-6, 1-4, 1-3 or 1-2 carbon atoms. For instance, the term "$C_{1-12}$ alkyl" refers to a hydrocarbon radical whose carbon chain is straight-chain or branched or cyclic and comprises 1 to 12 carbon atoms. Specific examples for alkyl residues are methyl, ethyl, propyl, isopropyl, butyl, pentyl, hexyl, octyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl or triacosyl, including the various branched-chain and/or cyclic isomers thereof, e.g. tert.-butyl or isopentyl, and so on. Cyclic alkyl isomers are also referred to as "cycloalkyl" herein to refer to saturated alicyclic hydrocarbons comprising 3 ring carbon atoms. "Substituted" linear, branched and cyclic alkyl groups are generally also encompassed by the term. The term further includes "heteroalkyl", referring to alkyl groups wherein one or more C-atoms of the carbon chain are replaced with a heteroatom such as, but not limited to, N, O, and S. Accordingly, the term further includes "heterocyclyl" or "heterocycloalkyl", referring to non-aromatic ring compounds containing 3 or more ring members, of which one or more ring carbon atoms are replaced with a heteroatom such as, but not limited to, N, O, and S. Heterocyclyl groups encompass unsaturated, partially saturated and saturated ring systems, such as, for example, imidazolyl, imidazolinyl and imidazolidinyl groups. Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Heterocyclyl groups may be substituted or unsubstituted. Representative substituted heterocyclyl groups may be monosubstituted or substituted more than once, such as, but not limited to, pyridyl or morpholinyl groups, which are 2-, 3-, 4-, 5-, or 6-substituted, or disubstituted with various substituents such as those listed above.

The term "cyclic" includes the term "polycyclic", referring to structures having more than one ring structure. In particular, the term "cyclic" also refers to spirocyclic structures, wherein two or more rings have one atom in common, and 5 fused polycyclic structures, wherein two or more rings have at least two atoms in common.

The term "alkenyl" as employed herein comprises linear, branched and cyclic chain 10 radicals having 2-30 carbon atoms, preferably 2-20, 2-15, 2-10, 2-8, 2-6, 2-4, or 2-3 carbon atoms, including at least one carbon-to-carbon double bond. Specific examples of "alkenyl" groups are the various alkenic unsaturated equivalents of those given with respect to alkyl groups, named after the conventions known to the person skilled in the art, depending on the number and location of carbon-to-carbon double bond or bonds, e.g. butanediylidene, 1-propanyl-3-ylidene. "Alkenyl" groups preferably contain at least 1, more preferably at least 2, 3, 4, 6, 7, 8, 9, 10, 11, 12, 13, 14, 15, or 16 double bonds, wherein a double bond is preferably located at position 1, 2, 3, 4, 5, 6, 7, 8, 9, 10, 12, 13, 14, 15, 16, 17, 18, 19, 20, 21, 22, 23, 24, 25, 26, 27, 28 or 29 of the hydrocarbyl chain. Alkenyl groups may be substituted or unsubstituted.

The term "alkynyl" as employed herein comprises straight, branched and cyclic chain radicals having 2-30 carbon atoms, preferably 2-20, 2-15, 2-10, 2-8, 2-6, 2-4, or 2-3 carbon atoms, including at least one carbon-to-carbon triple bond. Specific examples of "alkynyl" groups are the various alkynic unsaturated equivalents of those given with respect to alkyl and alkenyl groups, named after the conventions known to the person skilled in the art, depending on the number and location of carbon-to-carbon triple bond or bonds. "Alkynyl" groups preferably contain at least 1, more preferably at least 2, 3, 4, 6, 7, 8, 9, 10, 11, 12, 13, 14, 15, or 16 triple bonds, wherein a double triple bond is preferably located at position 1, 2, 3, 4, 5, 6, 7, 8, 9, 10, 12, 13, 14, 15, 16, 17, 3018, 19, 20, 21, 22, 23, 24, 25, 26, 27, 28 or 29 of the hydrocarbyl chain. Alkynyl groups may be substituted or unsubstituted.

The term "aryl" refers to monocyclic or polycyclic or fused polycyclic aromatic ring systems. The term includes monocyclic or polycyclic or fused polycyclic aromatic "heteroaryl" ring systems wherein at least one carbon atom of the ring system is substituted by a heteroatom. Typically, the terms "aryl" and "heteroaryl" refers to groups having 3-30 carbon atoms, such as 3-10, in particular 2-6 carbon atoms.

The terms "arylalkyl" or "aralkyl" are used interchangeably herein to refer to groups comprising at least one alkyl group and at least one aryl group as defined herein. In an aralkyl group as defined herein, the aralkyl group is bonded to another moiety of the compounds or conjugates of the invention via the alkyl group as exemplified by a benzyl group.

The term "halogen" or "halo" as used herein includes fluoro (F), chloro (Cl), bromo (Br), iodo (I).

The term "heteroatom" includes N, O, S and P, preferably N and O.

The term "substituted" refers to a hydrocarbyl group, as defined herein (e.g., an alkyl or alkenyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a "substituted" group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN), haloalkyl, aminoalkyl, hydroxyalkyl, cycloalkyl and the like.

Conjugates

The present invention provides novel plasma protein-binding PSMA ligands with improved tumor targeting properties and favorable pharmacokinetic profiles. As used herein, the term "pharmacokinetics" preferably includes the stability, bioavailability, absorption, biodistribution, biological half-life and/or clearance of a therapeutic or diagnostic agent in a subject. The present inventors provided novel conjugates by covalently coupling a PSMA-peptidomimetic urea-based binding entity via suitable spacers and linkers to a chelator capable of complexing therapeutic/diagnostic radionuclides on the one hand, and a human serum albumin (HSA) binding entity on the other hand. The spacer and linker groups connecting the binding entities and chelator were found to be crucial for the targeting and pharmacokinetic properties of the resulting conjugates. The novel conjugates preferably exhibit superior and specific cellular uptake and internalization characteristics. The inventors demonstrated that the HSA binding entity advantageously effected (1) compartmentalization of the conjugates in the blood (where off-target effects in healthy tissues are limited, without compromising access to the tumor vasculature), (2) extended blood clearance, and (3) increased tumor uptake and retention (by increasing the number of passes through the tumor bed). Introduction of a HSA binding entity thereby advantageously improves biodistribution and, eventually, therapeutic efficacy of the inventive compounds.

In particular, the conjugates provided herein advantageously exhibit an increased tumor uptake as compared to other PSMA ligands known in the art. The conjugates' favourable tumor uptake characteristics in particular allow reducing the administered activity to achieve the desired dose for a therapeutic effect or sufficient uptake allowing imaging (diagnosis). To that end, the conjugates are commonly provided in the form of radiolabeled complexes with the chelator complexing a therapeutic and/or diagnostic radionuclide (often a metal isotope). A decrease in the required dose of the novel conjugates (and in particular their radiolabeled (metal) complexes) inter alia has the following advantages: (1) a lower quantity of radionuclides (radioactivity) is required (resulting in lower manufacturing costs, better availability—both are particularly relevant in case of alpha-emitters such as e.g. $^{225}$Ac which are difficult to produce and costly—and preferably a longer shelf-life due to a decreased self-irradiation which commonly results in degradation of radiolabeled complexes (i.e. radiolysis); (2) the patient is subjected to a lower total absorbed dose of irradiation (preferably rendering ambulant treatment possible, and placing a lower burden on the environment).

The inventive conjugates are thus promising theragnostic agents with optimal characteristics both for nuclear imaging and endoradiotherapy.

Generally, the novel PSMA ligands according to the invention (also referred to as "conjugates" or "compounds" herein) thus include a first terminal group (a chelating agent), a second terminal group (an albumin binding entity) and a third terminal group (a PSMA binding entity) that are covalently connected or linked to each other via appropriate linkers or spacers.

In a first aspect, the present invention relates to a compound of General Formula (1):

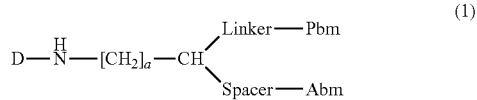
(1)

wherein
D is a chelator, preferably as defined herein,
Abm is an albumin binding entity, preferably as defined herein,
Pbm is a PSMA binding entity, preferably as defined herein,
the spacer comprises at least one C—N bond,
the linker is characterized by General Formula (6) as defined herein,
a is an integer selected from 0, 1, 2, 3, 4, 5, 6, 7, 8, 9 or 10, and
the —CH— group in General Formula (1) is a "branching point" connecting the PSMA binding entity (Pbm) and the albumin binding entity (Abm),
or pharmaceutically acceptable salts, esters, solvates or radiolabeled complexes thereof.

D, Abm, Pbm, Linker and Spacer are preferably defined as described herein.

Specifically, the present invention provides compounds according to General Formula (1)(i) or (1)(ii):

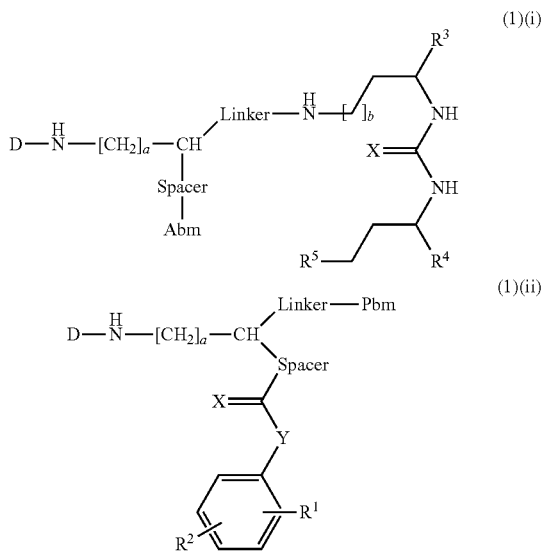

wherein
Abm is an albumin binding entity, preferably as defined herein,
Pbm is a PSMA binding entity, preferably as defined herein,
D is a chelator, preferably selected from 1,4,7,10-tetraaza-cyclododecane-1,4,7,10-tetraacetic acid (DOTA), N,N"-bis[2-hydroxy-5-(carboxyethyl)-benzyl]ethyl-enediamine-N,N"-diacetic acid (HBED-CC), 1,4,7-triazacyclononane-1,4,7-triacetic acid (NOTA), 2-(4,7-bis(carboxymethyl)-1,4,7-triazonan-1-yl)pentanedioic acid (NODAGA), 2-(4,7,10-tris(carboxymethyl)-1,4,7,10-tetraazacyclododecan-1-yl)-pentanedioic acid (DOTAGA), 1,4,7-triazacyclononane phosphinic acid (TRAP), 1,4,7-triazacyclononane-1-[methyl(2-carboxyethyl)-phosphinic acid]-4,7-bis[methyl(2-hydroxymethyl)phosphinic acid] (NOPO), 3,6,9, 15-tetraazabicyclo[9,3,1]pentadeca-1(15),11,13-triene-3,6,9-triacetic acid (PCTA), N'-{5-[Acetyl(hydroxy)amino]pentyl}-N-[5-({4-[(5-aminopentyl)(hydroxy)amino]-4-oxobutanoyl}amino)pentyl]-N-hydroxysuccinamide (DFO), and Diethylenetriaminepentaacetic acid (DTPA), or derivatives thereof, X is each independently selected from O, N, S or P, $R^1$ and $R^2$ are each independently selected from H, F, Cl, Br, I, branched, unbranched or cyclic $C_1$-$C_{12}$ hydrocarbyl, $C_2$-$C_{12}$ alkenyl, $C_2$-$C_{12}$ alkylnyl, $OR^6$, $OCOR^6$, CHO, $COR^6$, $CH_2OR^6$, $NR^6R^7$, $CONR^6R^7$, $COOR^6$, $CH_2NR^6R^7$, $SR^6$, =O, =S or =NH, or $R^1$ and $R^2$ are joined to form a cyclic structure comprising a branched, unbranched or cyclic $C_1$-$C_{10}$ hydrocarbyl group, wherein said hydrocarbyl group is optionally interrupted by up to 2 heteroatoms and optionally substituted by up to 3 groups independently selected from F, Cl, Br, I, $OR^6$, $OCOR^6$, $COOR^6$, CHO, $COR^6$, $CH_2OR^6$, $NR^6R^7$, $CH_2NR^6R^7$, and $SR^6$, =O, =S and =NH, Y is selected from a single bond or a linear, branched or cyclic, optionally substituted $C_1$-$C_{12}$ alkyl, optionally interrupted by up to two heteroatoms, $OR^6$, $OCOR^6$, CHO, $COR^6$, $CH_2OR^6$, $NR^6R^7$, $COOR^6$, $CH_2NR^6R^7$, $SR^6$, =O, =S or =NH, wherein one or more of the non-adjacent $CH_2$-groups may independently be replaced by —O—, —CO—, —CO—O—, —CO—, —$NR^6$—, —$NR^6$—CO—, —CO—$NR^6$—, —$NR^6$—COO—, —O—CO—$NR^6$—, —$NR^6$—CO—$NR^6$—, —CH=CH—, —C≡C—, —O—CO—O—, $SR^6$—, $SO_3R^6$—, $R^6$ and $R^7$ are each independently selected from H or branched, unbranched or cyclic $C_{1-12}$ hydrocarbyl, $R^3$, $R^4$ and $R^5$ are each independently selected from —COH, —$CO_2H$, —$SO_2H$, —$SO_3H$, —$SO_4H$, —$PO_2H$, —$PO_3H$, —$PO_4H_2$, —C(O)—($C_1$-$C_{10}$)alkyl, —C(O)—O($C_1$-$C_{10}$)alkyl, —C(O)—$NHR^8$, or —C(O)—$NR^8R^9$, wherein $R^8$ and $R^9$ are each independently selected from H, bond, ($C_1$-$C_{10}$)alkylene, F, Cl, Br, I, C(O), C(S), —C(S)—NH-benzyl-, —C(O)—NH-benzyl, —C(O)—($C_1$-$C_{10}$)alkylene, —$(CH_2)_p$—NH, —$(CH_2)_p$—($C_1$-$C_{10}$)alkylene, —$(CH_2)_p$—NH—C(OH—$CH_2)_q$, —$(CH_rCH_2)_t$—NH—C(O)—$(CH_2)_p$, —$(CH_2)_p$—CO—COH, —$(CH_2)_p$—CO—$CO_2H$, —$(CH_2)_p$—C(O)NH—C[$(CH_2)_q$—$COH]_3$, —C[$(CH_2)_p$—$COH]_3$, —$(CH_2)_p$—C(O)NH—C[$(CH_2)_q$—$CO_2H]_3$, —C[$(CH_2)_r$—$CO_2H]_3$ or —$(CH_2)_p$—($C_5$-$C_{14}$)heteroaryl, the spacer comprises at least one C—N bond, the linker is characterized by General Formula (6) as defined herein, and a, b, p, q, r, t is each independently an integer selected from 0, 1, 2, 3, 4, 5, 6, 7, 8, 9, or 10, or pharmaceutically acceptable salts, esters, solvates or radiolabeled complexes thereof.

It is particularly envisaged that the structure highlighted in Formula (1) below comprises at least one peptide bond:

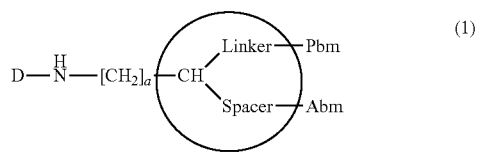

(1)

The inventive conjugates are ligands exhibiting affinity towards both PSMA and HSA. The term "ligand" as used herein refers to a compound capable of interacting with (targeting, binding to) a target (here: PSMA or HSA). The inventive conjugates may also be defined functionally as "PSMA targeting agents". Preferably, "ligands" are capable of selectively binding to their target. The term "selectively binding" means that a compound binds with a greater affinity to its intended target than it binds to another, non-target entity.

"Binding affinity" is the strength of the binding interaction between a ligand (e.g. a small organic molecule, protein or nucleic acid) to its target/binding partner. Binding affinity is typically measured and reported by the equilibrium dissociation constant ($K_D$), a ratio of the "off-rate" ($k_{off}$) and the "on-rate" ($k_{on}$), which is used to evaluate and rank order strengths of bimolecular interactions. The "on-rate" ($K_{on}$) characterizes how quickly a ligand binds to its target, the "off-rate" ($K_{off}$) characterizes how quickly a ligand dissociates from its target. $K_D$ ($K_{off}/K_{on}$) and binding affinity are inversely related. Thus, the term "selectively binding" preferably means that a ligand binds to its intended target with a $K_D$ that is lower than the $K_D$ of its binding to another, non-target entity. There are many ways to measure binding affinity and dissociation constants, such as ELISA, gel-shift assays, pull-down assays, equilibrium dialysis, analytical ultracentrifugation, surface plasmon resonance, and spectroscopic assays.

In the context of the present invention, the $K_D$ for binding of the PSMA binding entity (HSA binding entity) to a non-target entity may be at least 1.5-fold, preferably at least 2-, 3-, 5-, 10-, 15-, 20-, 25-, 30-, 35-, 40-, 45-, 50-, 60-, 70-, 80-, 90-, 100-200-, 300-, 400-, 500-, 750-, or 1000-fold the $K_D$ for binding of said conjugate or moiety to human PSMA (HSA).

In the context of the present invention, it may further be preferred that the conjugates bind to PSMA with high binding affinity with $K_D$ values in the nanomolar (nM) range and with moderate affinity to HSA in the micromolar range (μM (micromolar)).

Specifically, it may be preferred to balance the PSMA and HSA-binding affinities so as to increase tumor uptake and retention and extend blood clearance, while reducing potentially damaging off-target effects. In particular, the inventive conjugates may exhibit a higher binding affinity towards PSMA than towards HSA.

In particular, the present invention provides compounds according to General Formula (1)(i):

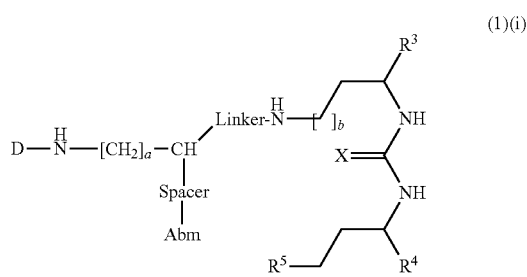

wherein

Abm is an albumin binding entity,

D is a chelator, preferably selected from 1,4,7,10-tetraazacyclododecane-1,4,7,10-tetraacetic acid (DOTA), N,N"-bis[2-hydroxy-5-(carboxyethyl)-benzyl]ethylenediamine-N,N"-diacetic acid (HBED-CC), 1,4,7-triazacyclononane-1,4,7-triacetic acid (NOTA), 2-(4,7-bis(carboxymethyl)-1,4,7-triazonan-1-yl)pentanedioic acid (NODAGA), 2-(4,7,10-tris(carboxymethyl)-1,4,7,10-tetraazacyclododecan-1-yl)-pentanedioic acid (DOTAGA), 1,4,7-triazacyclononane phosphinic acid (TRAP), 1,4,7-triazacyclononane-1-[methyl(2-carboxyethyl)-phosphinic acid]-4,7-bis[methyl(2-hydroxymethyl)phosphinic acid] (NOPO), 3,6,9, 15-tetraazabicyclo[9,3,1.]pentadeca-1(15),11,13-triene-3,6, 9-triacetic acid (PCTA), N'-{5-[Acetyl(hydroxy)amino]pentyl}-N-[5-({4-[(5-aminopentyl)(hydroxy)amino]-4-oxobutanoyl}amino)pentyl]-N-hydroxysuccinamide (DFO), and Diethylenetriaminepentaacetic acid (DTPA), or derivatives thereof, X is selected from O, N, S or P, $R^3$, $R^4$ and $R^5$ are each independently selected from —COH, —$CO_2H$, —$SO_2H$, —$SO_3H$, —$SO_4H$, —$PO_2H$, —$PO_3H$, —$PO_4H_2$, —C(O)—($C_1$-$C_{10}$)alkyl, —C(O)—O($C_1$-$C_{10}$)alkyl, —C(O)—$NHR^8$, or —C(O)—$NR^8R^9$, wherein $R^8$ and $R^9$ are each independently selected from H, bond, ($C_1$-$C_{10}$)alkylene, F, Cl, Br, I, C(O), C(S), —C(S)—NH-benzyl-, —C(O)—NH-benzyl, —C(O)—($C_1$-$C_{10}$)alkylene, —$(CH_2)_p$—NH, —$(CH_2)_p$—($C_1$-$C_{10}$)alkylene, —$(CH_2)_p$—NH—C(O)$CH_2)_q$, —$(CH_rCH_2)_t$—NH—C(O)$(CH_2)_p$, —$(CH_2)_p$—CO—COH, —$(CH_2)_p$—CO—$CO_2H$, —$(CH_2)_p$—C(O)NH—C[$(CH_2)_q$—COH]$_3$, —C[$(CH_2)_p$—COH]$_3$, —$(CH_2)_p$—C(O)NH—C[$(CH_2)_q$—$CO_2H$]$_3$, —C[$(CH_2)$,—$CO_2H$]$_3$ or —$(CH_2)_p$—($C_5$-$C_{14}$)heteroaryl, the spacer comprises at least one C—N bond, and the linker is characterized by General Formula (6) as defined herein, and a, b, p, q, r, t is each independently an integer selected from 0, 1, 2, 3, 4, 5, 6, 7, 8, 9, or 10, or a pharmaceutically acceptable salt, ester, solvate or radiolabeled complex thereof.

More specifically, the present invention provides particularly preferred conjugates characterized by General Formula (11):

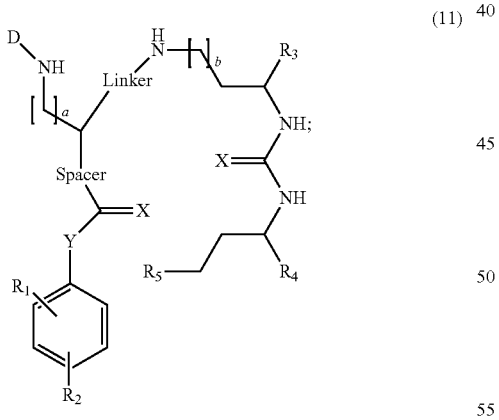

(11)

wherein

D is a chelator, preferably selected from 1,4,7,10-tetraazacyclododecane-1,4,7,10-tetraacetic acid (DOTA), N,N''-bis[2-hydroxy-5-(carboxyethyl)benzyl]ethylenediamine-N,N''-diacetic acid (HBED-CC), 1,4, 7-triazacyclononane-1,4, 7-triacetic acid (NOTA), 2-(4,7-bis(carboxymethyl)-1,4, 7-triazonan-1-yl)pentanedioic acid (NODAGA), 2-(4,7,10-tris(carboxymethyl)-1,4, 7,1 O-tetraazacyclododecan-1-yl)pentanedioic acid (DOTAGA), 1,4,7-triazacyclononane phosphinic acid (TRAP), 1,4,7-triazacyclononane-1-[methyl(2-carboxyethyl)phosphinic acid]-4,7-bis[methyl(2-hydroxymethyl)phosphinic acid](NOPO), 3,6,9,15-tetraazabicyclo[9,3,1.]pentadeca-1(15),11, 13-triene-3,6, 9-triacetic acid (PCTA), N'-{5-[Acetyl(hydroxy)amino]pentyl}-N-[5-({4-[(5-aminopentyl)(hydroxy)amino]-4-oxobutanoyl}amino)pentyl]-hydroxysuccinamide (DFO), and Diethylenetriaminepentaacetic acid (DTPA) or derivatives thereof, X is each independently selected from O, N, S or P, $R^1$ and $R^2$ are each independently selected from H, F, Cl, Br, I, branched, unbranched or cyclic, optionally substituted, $C_1$-$C_{12}$ hydrocarbyl, $C_2$-$C_{12}$ alkenyl, $C_2$-$C_{12}$ alkylnyl, $OR^6$, $OCOR^6$, CHO, $COR^6$, $CH_2OR^6$, $NR^6R^7$, $CONR^6R^7$, $COOR^6$, $CH_2NR^6R^7$, $SR^6$, =O, =S or =NH, or $R^1$ and $R^2$ are joined to form a cyclic structure comprising a branched, unbranched or cyclic $C_1$-$C_{10}$ hydrocarbyl group, wherein said hydrocarbyl group is optionally interrupted by up to 2 heteroatoms and optionally substituted by up to 3 groups independently selected from F, Cl, Br, I, $OR^6$, $OCOR^6$, $COOR^6$, CHO, $COR^6$, $CH_2OR^6$, $NR^6R^7$, $CH_2NR^6R^7$, and $SR^6$, =O, =S and =NH, Y is selected from a single bond or a linear, branched or cyclic, optionally substituted $C_1$-$C_{12}$ alkyl, optionally interrupted by up to two heteroatoms, $OR^6$, $OCOR^6$, CHO, $COR^6$, $CH_2OR^6$, $NR^6R^7$, $COOR^6$, $CH_2NR^6R^7$, $SR^6$, =O, =S or =NH, wherein one or more of the non-adjacent $CH_2$-groups may independently be replaced by —O—, —CO—, —CO—O—, —O—CO—, —$NR^6$—, —$NR^6$—CO—, —CO—$NR^6$—, —$NR^6$—COO—, —O—CO—$NR^6$—, —$NR^6$—CO—$NR^6$—, —CH=CH—, —C≡C—, —O—CO—O—, $SR^6$—, $SO_3R^6$—, $R^6$ and $R^7$ are each independently selected from H or branched, unbranched or cyclic $C_{1-12}$ hydrocarbyl, $R^3$, $R^4$ and $R^5$ are each independently selected from —COH, —$CO_2H$, —$SO_2H$, —$SO_3H$, —$SO_4H$, —$PO_2H$, —$PO_3H$, —$PO_4H_2$, —C(O)—($C_1$-$C_{10}$)alkyl, —C(O)—O($C_1$-$C_{10}$)alkyl, —C(O)—$NHR^8$, or —C(O)—$NR^8R^9$, wherein $R^8$ and $R^9$ are each independently selected from H, bond, (C1-C10)alkylene, F, Cl, Br, I, C(O), C(S), —C(S)—NH-benzyl-, —C(O)—NH—benzyl, —C(O)—($C_1$-$C_{10}$)alkylene, —$(CH_2)_p$—NH, —$(CH_2)_p$—($C_1$-$C_{10}$)alkylene, —$(CH_2)_p$—NH—C(O)—$(CH_2)_q$, —$(CH_rCH_2)_t$—NH—C(O)—$(CH_2)_p$, —$(CH_2)_p$—CO—COH, —$(CH_2)_p$—CO—$CO_2H$, —$(CH2)_p$—C(O)NH—C[$(CH_2)_q$—COH]$_3$, —C[$(CH_2)_p$—COH]$_3$, —$(CH2)_p$—C(O)NH—C[$(CH_2)_q$—$CO_2H$]$_3$, —C[$(CH_2)_p$—$CO_2H$]$_3$ or —$(CH_2)_p$—($C_5$-$C_{14}$)heteroaryl, the spacer comprises at least one C—N bond, the linker is characterized by the Structural Formula (6):

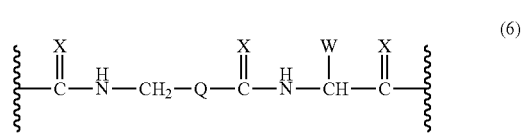

(6)

wherein

X is each independently selected from O, N, S or P,

Q is selected from substituted or unsubstituted alkyl, alkylaryl and cycloalkyl, preferably from substituted or unsubstituted $C_5$-$C_{14}$ aryl, $C_5$-$C_{14}$ alkylaryl or $C_5$-$C_{14}$ cycloalkyl, W is selected from —(CH$_2$)$_c$-aryl or —(CH$_2$)$_c$-heteroaryl, wherein c is an integer selected
from 0, 1, 2, 3, 4, 5, 6, 7, 8, 9 or 1, and
a, b, p, q, r, t is each independently an integer selected from 0, 1, 2, 3, 4, 5, 6, 7, 8, 9, or 10,
or a pharmaceutically acceptable salt, ester, solvate or radiolabeled complex thereof.

Albumin Binding Entity

The inventive conjugates comprise an (additional—as compared to known PSMA ligands) albumin binding entity (also referred to as an "albumin binding moiety") as described herein, which is preferably capable of selectively binding to human serum albumin (HSA). The term "selectively binding" is defined above.

The albumin binding entity (Abm) may be any albumin binding entity. Particularly preferred albumin binding entities are described herein below. The albumin binding entity may preferably bind non-covalently to serum albumin, preferably HSA, typically with a binding affinity of less than about 100 µM (micromolar), e.g. of about 3 µM (micromolar) to 50 µM (micromolar).

Human Serum Albumin (HSA) is the most abundant protein in human plasma and constitutes about half of serum protein. The term "Human Serum Albumin" or "HSA" as used herein preferably refers to the serum albumin protein encoded by the human ALB gene. More preferably, the term refers to the protein as characterized under UniProt Acc. No. P02768 (entry version 240, last modified May 10, 2017, or functional variants, isoforms, fragments or (post-translationally or otherwise modified) derivatives thereof.

Without wishing to be bound by specific theory, it is hypothesized that the albumin binding entity (Abm) of the inventive conjugates preferably extends circulation half-life of the conjugates, and effects compartmentalization of the inventive conjugates in the blood and improved delivery to the PSMA-expressing (tumor) target cells or tissues, resulting in increased tumor:non-target ratios for PSMA expressing normal (non-tumorous) organs (like kidneys, lacrimal glands, and salivary glands). The albumin binding entity is thus envisaged to confer improved pharmacokinetic properties to the inventive conjugate, preferably without interfering with (reducing or abolishing) the desired function of the chelating agent and the PSMA binding entity.

In terms of structure, typical albumin binding entities in accordance with the present invention may preferably comprise linear and branched lipophilic groups comprising 1-40 carbon atoms and a distal acidic group. Suitable albumin binding entities are inter alia described in US 2010/172844 A1, WO 2013/024035 A1 and WO 2008/053360 A2, which are incorporated by reference in their entirety herein.

In accordance with the above, in the conjugates of the present invention, the albumin binding entity is preferably characterized by General Formula (2):

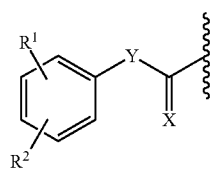

(2)

wherein
R$^1$ and R$^2$ are each independently selected from H, F, Cl, Br, I, branched, unbranched or cyclic C$_1$-C$_{12}$ hydrocarbyl, C$_2$-C$_{12}$ alkenyl, C$_2$-C$_{12}$ alkylnyl, OR$^6$, OCOR$^6$, CHO, COR$^6$, CH$_2$OR$^6$, NR$^6$R$^7$, CONR$^6$R$^7$, COOR$^6$, CH$_2$NR$^6$R$^7$, SR$^6$, =O, =S or =NH, or R$^1$ and R$^2$ are joined to form a cyclic structure comprising a branched, unbranched or cyclic C$_1$-C$_{10}$ hydrocarbyl group, wherein said hydrocarbyl group is optionally interrupted by up to 2 heteroatoms and optionally substituted by up to 3 groups independently selected from F, Cl, Br, I, OR$^6$, OCOR$^6$, COOR$^6$, CHO, COR$^6$, CH$_2$OR$^6$, NR$^6$R$^7$, CH$_2$NR$^6$R$^7$, and SR$^7$, =O, =S and =NH.

Y is selected from a single bond or a linear, branched or cyclic, optionally substituted C$_1$-C$_{12}$ alkyl, optionally interrupted by up to two heteroatoms, OR$^6$, OCOR$^6$, CHO, COR$^6$, CH$_2$OR$^6$, NR$^6$R$^7$, COOR$^6$, CH$_2$NR$^6$R$^7$, SR$^6$, =O, =S or =NH, wherein one or more of the non-adjacent CH$_2$-groups may independently be replaced by —O—, —CO—, —CO—O—, —O—CO—, —NR$^6$—, —NR$^6$—CO—, —CO—NR$^6$—, —NR$^6$—COO—, —O—CO—NR$^6$—, —NR$^6$—CO—NR$^6$—, —CH=CH—, —C≡C—, —O—CO—O—, SR$^6$—, SO$_3$R$^6$—, R$^6$ and R$^7$ are each independently selected from H or branched, unbranched or cyclic C$_{1\text{-}12}$ hydrocarbyl, and X is selected from O, N, P or S.

R$^1$ and R$^2$ may be in ortho-, meta or para-position.

When R$^1$ and R$^2$ are joined in order to, together, form a cyclic structure, said cyclic structure is preferably a linear or branched hydrocarbyl chain of 3-12, more preferably 3-10, even more preferably 3-9, 3-8, 3-7, 3-6, 3-5, 3-4 or 4 carbon atoms bonded at two positions to the phenyl ring, i.e. forming two bonds to said phenyl ring, such as to form a ring structure fused to said phenyl ring. Specifically, said cyclic structure may be selected from (substituted or unsubstituted) adamantyl. Preferably, said two bonds are preferably situated at the meta (3-) and para (4-) positions, at the ortho (2-) and meta positions or at the ortho and para positions of said phenyl ring. Said cyclic structure is optionally interrupted by up to 2, preferably 1 or none heteroatoms. Preferably, said cyclic structure may be a C$_4$ chain fragment (1,4-diradical) linked by its 1- and 4-atoms to said phenyl ring to form a six-membered ring fused to said phenyl ring, preferably at the meta and para positions of said phenyl ring, i.e., preferably forming a meta- and para-fused six-membered ring.

Preferably, R$^1$ and R$^2$ may each be independently selected from H, halogen, preferably iodine or bromine, and C$_{1\text{-}6}$ alkyl, preferably C$_{1\text{-}3}$ alkyl, even more preferably methyl. More preferably, R$^1$ is H and R$^2$ is selected from halogen, preferably iodine or bromine, and C$_{1\text{-}6}$ alkyl, preferably C$_{1\text{-}3}$ alkyl, even more preferably methyl. Even more preferably, R$^1$ is H and R$^2$ is H or is in the para position and selected from iodine, bromine and methyl.

Preferably, Y may be a linear or branched, optionally substituted, C$_1$-C$_{12}$ hydrocarbyl, more preferably a linear or branched, optionally substituted, C$_1$-C$_{10}$ hydrocarbyl, even more preferably a linear or branched, optionally substituted, C$_1$-C$_6$ hydrocarbyl, even more preferably a linear or branched, optionally substituted, C$_1$-C$_3$ hydrocarbyl.

Most preferably, Y may be —(CH$_2$)—.

Preferably, X may be O.

Accordingly, the albumin binding entity according to Formula (2) may preferably comprise or consist of any one of Formulae (2a)-(2c):

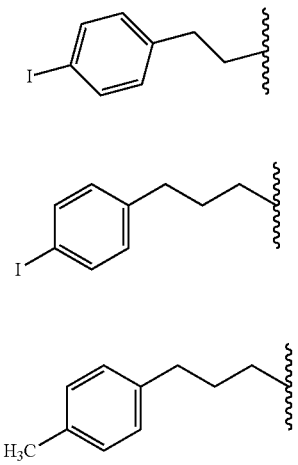

Other possible—potentially less preferred—albumin binding entities are disclosed inter alia in US 2010/0172844 A1.

In preferred embodiments, the compounds according to the present invention may be characterized by any one of General Formulas (11.1)-(11.3):

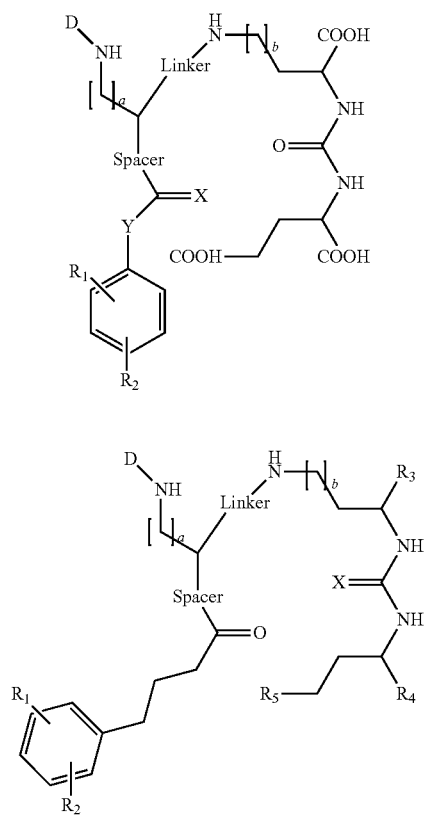

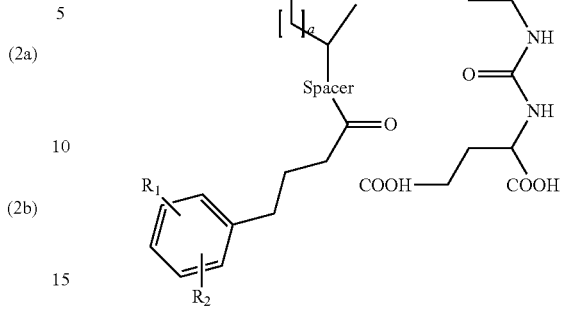

wherein D, spacer, linker, X, $R_1$-$R_5$, a and b are as defined for General Formula (11).

Spacer

In the inventive conjugates, the albumin binding entity is conjugated (i.e. covalently linked or attached to) to the —CH— "branching point" via a "spacer". The term "spacer" is used herein to specifically refer to the group connecting and spanning the distance between the albumin binding entity and the —CH— "branching point", and/or "spacing" these groups apart from the remaining groups/entities of the conjugate.

The spacer may preferably avoid sterical hindrance between the albumin binding entity and the other groups or entities of the inventive conjugate and ensure sufficient mobility and flexibility. Further, the spacer may preferably be designed so as to confer, support and/or allow sufficient HSA binding, high affinity PSMA binding, and rapid and optionally selective penetration of PSMA positive cells through internalization of the PSMA-conjugate complex.

The present inventors determined that the spacer should preferably comprise at least one C—N bond. Suitable spacers should preferably be stable in vivo. Spacer design may typically depend on the overall conjugate and may preferably be chosen to promote the functionality of the remaining conjugate (e.g. PSMA binding, HSA binding, internalization etc.). Accordingly, spacers may be for instance be rigid or flexible, influencing either lipophilicity or hydrophilicity of the overall conjugate, and so on.

Preferably, the spacer may comprise a linear or branched, optionally substituted $C_1$-$C_{20}$ hydrocarbyl comprising up to 5 heteroatoms, more preferably $C_1$-$C_{12}$ hydrocarbyl, even more preferably $C_2$-$C_6$ hydrocarbyl, even more $C_2$-$C_4$ hydrocarbyl. The hydrocarbyl may preferably comprise at least one, optionally up to 4 heteroatoms preferably selected from N.

Preferably, the spacer may be —[$CHR^{10}$]$_u$—$NR^{11}$—, wherein $R^{10}$ and $R^{11}$ may each be independently selected from H and branched, unbranched or cyclic $C_1$-$C_{12}$ hydrocarbyl and wherein u may be an integer selected from 1, 2, 3, 4, 5, 6, 7, 8, 9 or 10. More preferably, $R^{10}$ and $R^{11}$ may be H, and u may be an integer selected from 2, 3 or 4. Most preferably, $R^{10}$ and $R^{11}$ may be H and u may be 4.

Accordingly, the inventive conjugates may preferably comprise a spacer of Formula (3a):

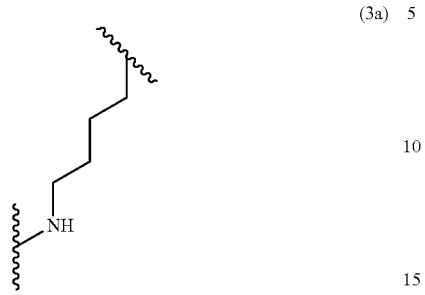
(3a)

Accordingly, preferred conjugates according to the invention (e.g. PSMA-ALB-03 and PSMA-ALB-06 evaluated in the appended examples), comprise an albumin binding entity of Formula (2a)-(2c) connected to the "branching point" via a spacer of Formula (3a).

Alternatively or additionally, the spacer may comprise at least one amino acid residue. As used herein, the term "amino acid residue" refers to a specific amino acid monomer as a moiety within the spacer.

An "amino acid" is any organic molecule comprising both an acidic (typically carboxy (—COOH)) and an amine (—NH$_2$) functional group. One or both of said groups may optionally be derivatized. The amino and the acidic group may be in any position relative to each other, but amino acids typically comprise 2-amino carboxylic acids, 3-amino carboxylic acids, 4-amino carboxylic acids, etc. The amine group may be attached to the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$ (etc.) up to the 20$^{th}$ carbon atom of the amino acid(s). In other words, the amino acid(s) may be (an) alpha-, beta-, gamma-, delta-, epsilon- (etc.) up to an omega-amino acid(s). Preferably, the acidic group is a carboxy (—COOH) group. However, other acidic groups selected from —OPO$_3$H, —PO$_3$H, —OSO$_3$H or —SO$_3$H are also conceivable.

Preferably, the amino acid residue(s) is/are derived from naturally occurring amino acid(s), or derivatives thereof. It is further preferred that the amino acid residues(s) is/are derived from alpha (α-)amino acid(s), wherein the amino acid(s) may be (a) D- or L-amino acid(s).

More preferably, said amino acid(s) is/are the D- or the L-enantiomer of an amino acid selected from the group arginine, asparagine, aspartate, cysteine, glutamate, glutamine, glycine, histidine, leucine, lysine, methionine, phenylalanine, proline, serine, threonine, tryptophan, tyrosine and/or valine.

Most preferably, said amino acid(s) is/are (D-/L-) aspartate, glutamate or lysine. The spacer may comprise 1, 2, 3, 4 or 5 amino acid residue(s), in particular D-aspartate, D-glutamate or L-Lysine residues. In conjugates comprising the D-enantiomer, the use of the D-enantiomer may provide the beneficial effect of further reducing the rate of metabolisation and thus clearance from the bloodstream. Preferably, the spacer may comprise between 2 and 3 of such amino acid residues in particular D-aspartate or D-glutamate residues. In other words, the spacer may comprise a peptide, which preferably consists of 2 to 5 amino acids, more preferably of 2 to 3 amino acids. Alternatively, the spacer may comprise between 1 and 2 amino acids selected from L-Lysine.

Accordingly, the inventive conjugates may comprise a spacer of Formula (3b):

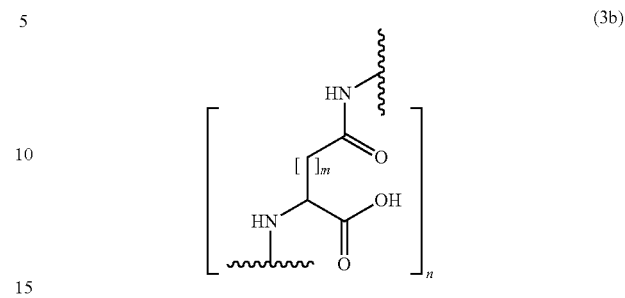
(3b)

wherein
m is an integer selected from 1 or 2,
n is an integer selected from 1, 2, 3, 4 or 5, preferably from 2 or 3.

Alternatively, the spacer may comprise an amino acid residue connected to the "branching point" via a linear or branched, optionally substituted, C$_1$-C$_{20}$ hydrocarbyl group comprising at least one N heteroatom.

Accordingly, the inventive conjugates may comprise a spacer of Formula (3c):

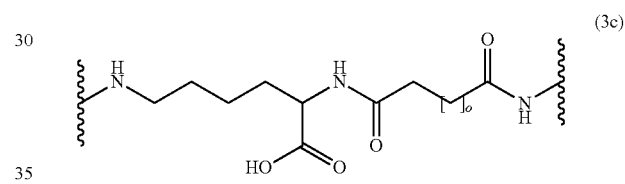
(3c)

wherein o is an integer selected from 0, 1, 2, 3, 4, 5, 6, 7, 8, 9 or 10. Preferably, o may be 5.

Accordingly, in preferred embodiments, the inventive conjugates may be characterized by any one of General Formulas (12.1)-(12.4) or (13.1)-(13.4):

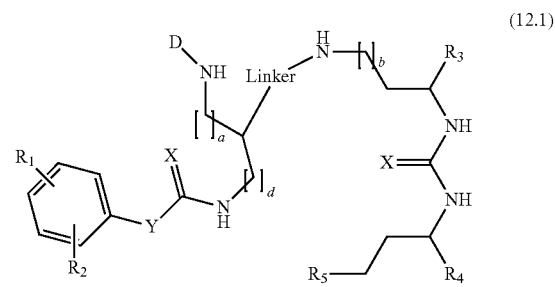
(12.1)

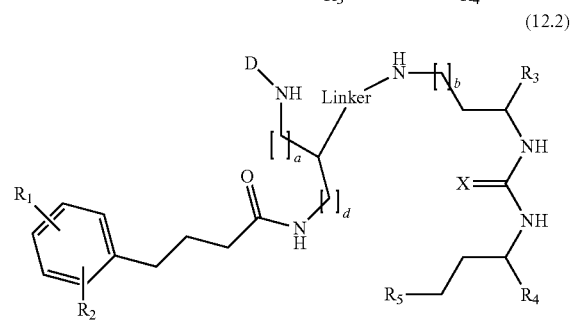
(12.2)

-continued (12.3)

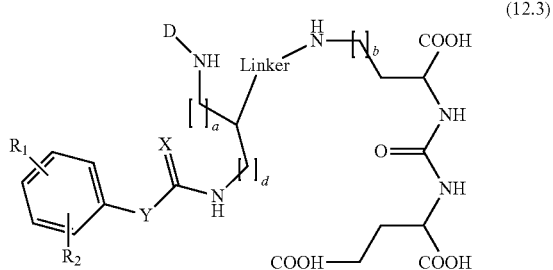

(12.4)

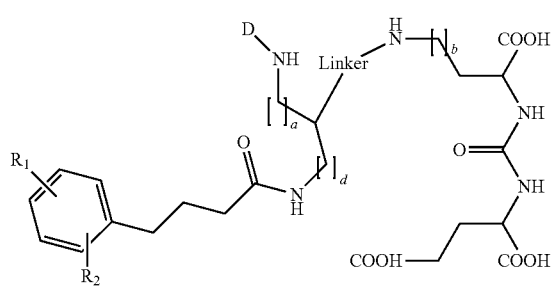

(13.1)

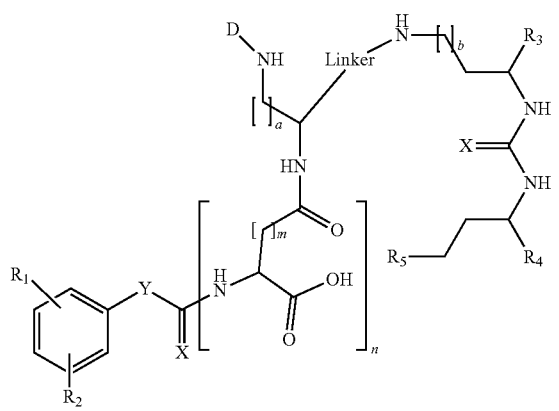

(13.2)

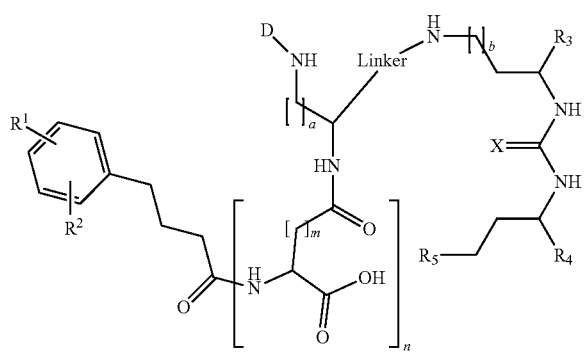

-continued (13.3)

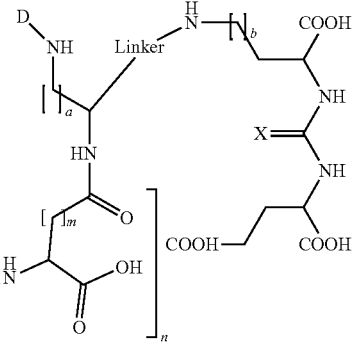

(13.4)

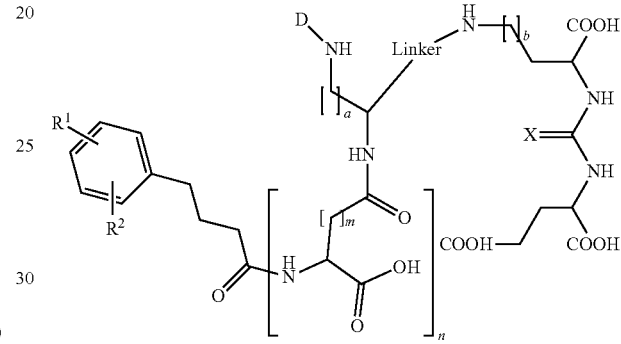

wherein in General Formulas (12.1)-(12.4) and (13.1)-(13.4), D, spacer, linker, X, $R^1$-$R^5$, a, b, m, n are as defined in the context of General Formulas (1) and (11), and d is an integer selected from 1, 2, 3, 4, 5, 6, 7, 8, 9, or 10, more preferably from 1, 2, 3, 4, 5 or 6.

Chelator

The inventive conjugates further comprise a chelator.

The terms "chelator" or "chelating moiety" are used interchangeably herein to refer to polydentate (multiple bonded) ligands capable of forming two or more separate coordinate bonds with ("coordinating") a central (metal) ion. Specifically, such molecules or molecules sharing one electron pair may also be referred to as "Lewis bases". The central (metal) ion is usually coordinated by two or more electron pairs to the chelating agent. The terms, "bidentate chelating agent", "tridentate chelating agent", and "tetradentate chelating agent" are art-recognized and refer to chelating agents having, respectively, two, three, and four electron pairs readily available for simultaneous donation to a metal ion coordinated by the chelating agent. Usually, the electron pairs of a chelating agent forms coordinate bonds with a single central (metal) ion; however, in certain examples, a chelating agent may form coordinate bonds with more than one metal ion, with a variety of binding modes being possible.

The terms "coordinating" and "coordination" refer to an interaction in which one multi-electron pair donor coordinatively bonds (is "coordinated") to, i.e. shares two or more unshared pairs of electrons with, one central (metal) ion.

The chelating agent is preferably chosen based on its ability to coordinate the desired central (metal) ion, usually a radionuclide as specified herein.

Accordingly, the chelator D may be characterized by one of the following Formulas (4a)-(4jj):
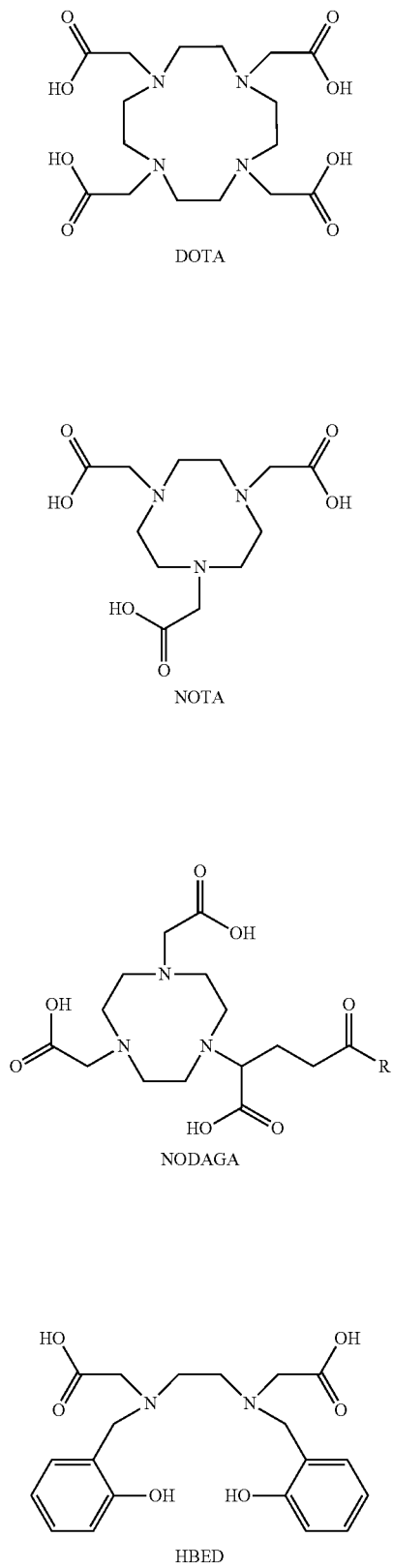

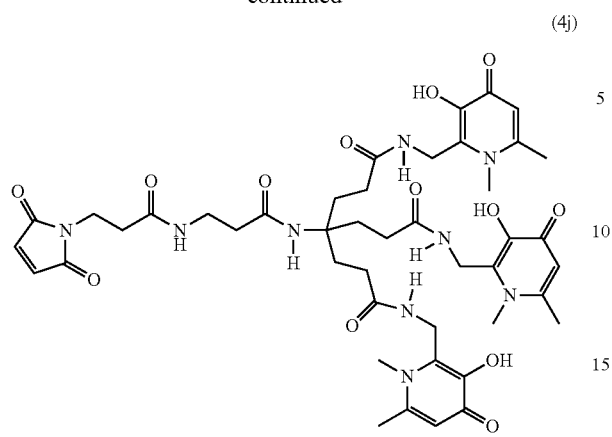
YM103
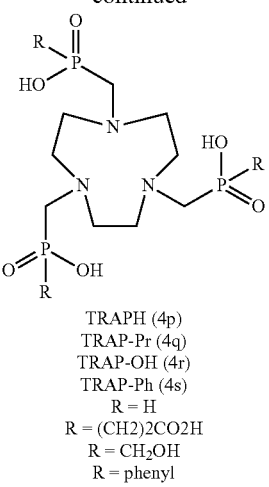
TRAPH (4p)
TRAP-Pr (4q)
TRAP-OH (4r)
TRAP-Ph (4s)
R = H
R = (CH2)2CO2H
R = CH₂OH
R = phenyl
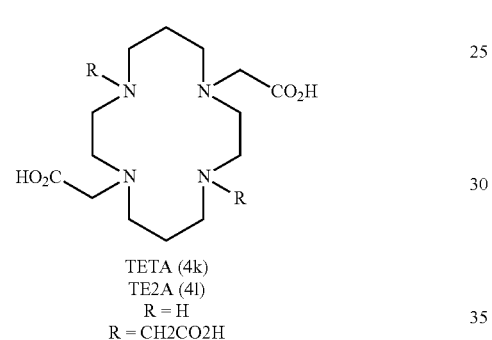
TETA (4k)
TE2A (4l)
R = H
R = CH2CO2H
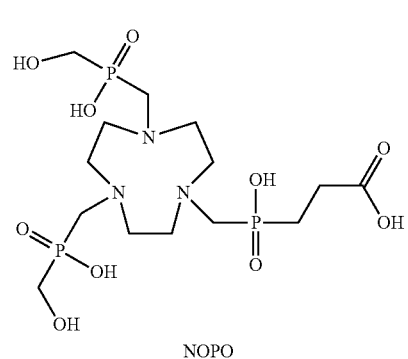
NOPO
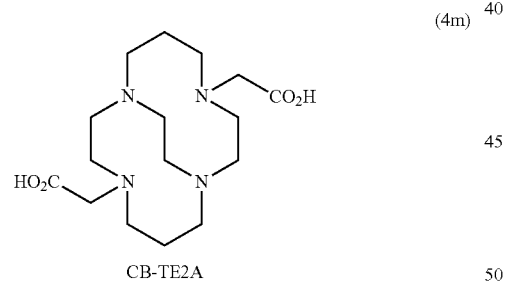
CB-TE2A
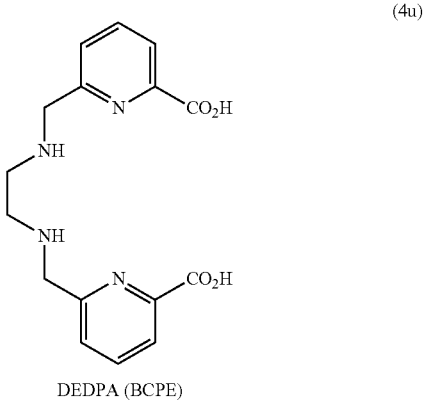
DEDPA (BCPE)
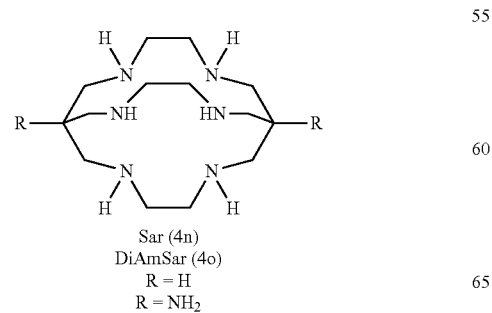
Sar (4n)
DiAmSar (4o)
R = H
R = NH₂
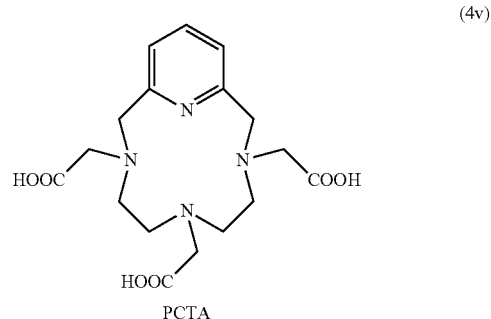
PCTA

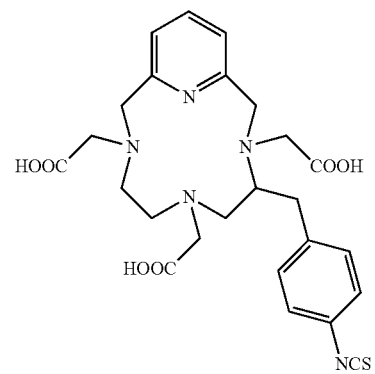
177
(4w)
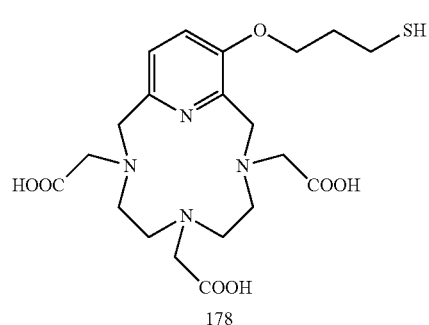
178
(4x)
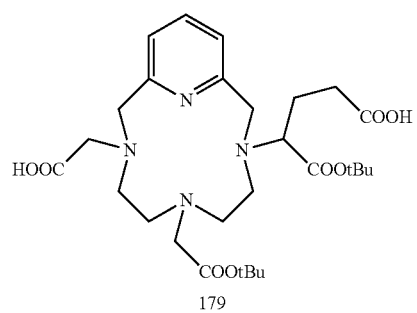
179
(4y)
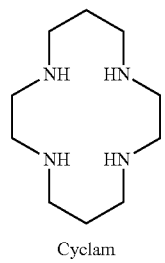
Cyclam
(az)
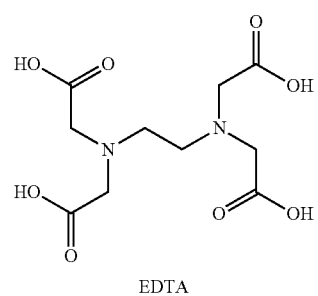
EDTA
(4aa)
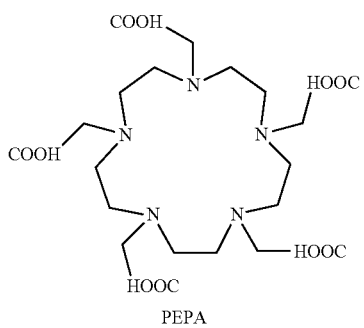
PEPA
(4bb)
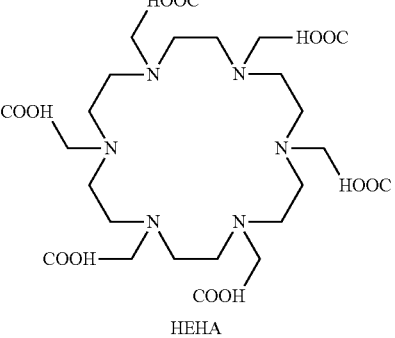
HEHA
(4cc)
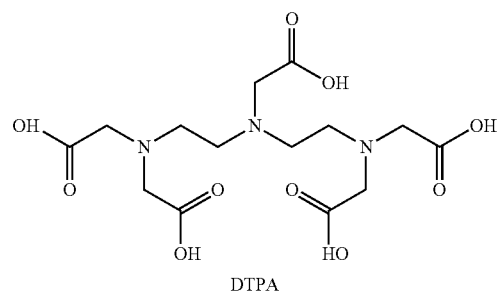
DTPA
(4dd)
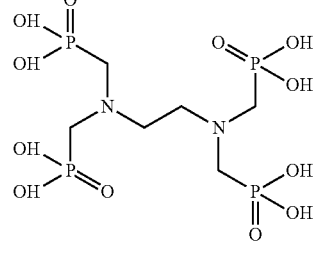
EDTMP
(4ee)
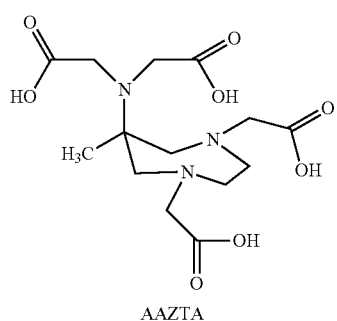
AAZTA
(4ff)

(4gg)

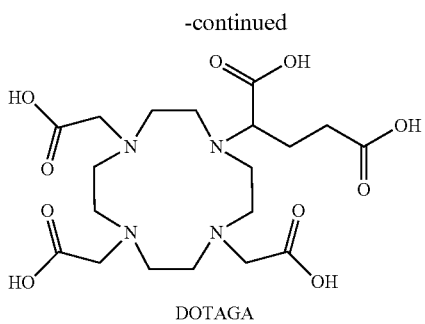

DOTAGA (4hh)

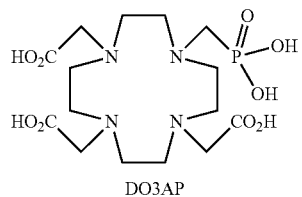

DO3AP (4ii)

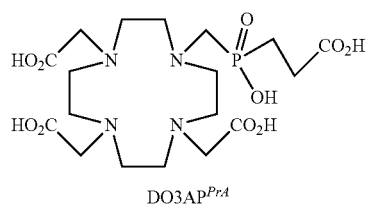

DO3AP$^{PrA}$ (4jj)

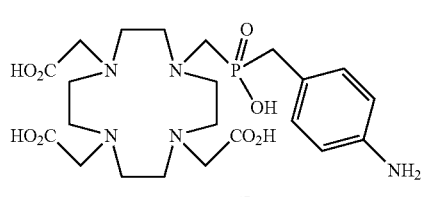

DO3AP$^{ABn}$

Preferably, the chelator may be DOTA (1,4,7,10-tetraaza-cyclododecane-1,4,7,10-tetraacetic acid, which may be characterized by Formula (4a)), NODAGA (2-(4,7-bis(carboxymethyl)-1,4,7-triazonan-1-yl)-pentanedioic acid, which may be characterized by Formula (4c)), or derivatives thereof.

In some preferred embodiments, the chelator may be DOTA. In some preferred embodiments, the chelator may be NODAGA.

Advantageously, DOTA effectively forms complexes with diagnostic (e.g. $^{68}$Ga) and therapeutic (e.g. $^{90}$Y or $^{177}$Lu) radionuclides and thus enables the use of the same conjugate for both imaging and therapeutic purposes, i.e. as a theragnostic agent. DOTA derivatives capable of complexing Scandium radionuclides ($^{43}$Sc, $^{44}$Sc, $^{47}$Sc), including DO3AP (which may be characterized by Formula (4hh)), DO3AP$^{PrA}$ (which may be characterized by Formula (4ii)), or DO3AP$^{ABn}$ (which may be characterized by Formula (4jj)) may also be preferred and are described in Kerdjoudj et al. Dalton Trans., 2016, 45, 1398-1409.

Other preferred chelators in the context of the present invention include N,N"-bis[2-hydroxy-5-(carboxyethyl) benzyl]ethylenediamine-N,N"-diacetic acid (HBED-CC), 1,4,7-triazacyclo-nonane-1,4,7-triacetic acid (NOTA), 2-(4,7,10-tris(carboxymethyl)-1,4,7,10-tetra-azacyclododecan-1-yl)-pentanedioic acid (DOTAGA), 1,4,7-triazacyclo-nonane phosphinic acid (TRAP), 1,4,7-triazacyclo-nonane-1-[methyl(2-carboxyethyl)-phosphinic acid]-4,7-bis-[methyl(2-hydroxymethyl)-phosphinic acid] (NOPO),3,6,9,15-tetra-azabicyclo[9,3,1]-pentadeca-1(15),11,13-triene-3,6,9-triacetic acid (PCTA), N'-{5-[Acetyl(hydroxy)amino]-pentyl}-N-[5-({4-[(5-aminopentyl)(hydroxy)amino]-4-oxobutanoyl}-amino)pentyl]-N-hydroxysuccinamide (DFO), and Diethylene-triaminepentaacetic acid (DTPA).

The chelator group, for example, the DOTA group may be complexed with a central (metal) ion, in particular a radionuclide as defined herein. Alternatively, the chelator group, for example DOTA, may not be complexed with a central (metal) ion, in particular a radionuclide as defined herein, and may thus be present in uncomplexed form. In cases where the chelator (e.g. DOTA) is not complexed with said metal ion, the carboxylic acid groups of the chelator can be in the form of a free acid, or in the form of a salt.

PSMA Binding Entity

The inventive conjugates comprise a PSMA binding entity (also referred to as "PSMA binding moiety") herein, which is preferably capable of selectively binding to human PSMA. The term "selectively binding" is defined above.

In particular, the present invention provides compounds according to General Formula (1)(ii):

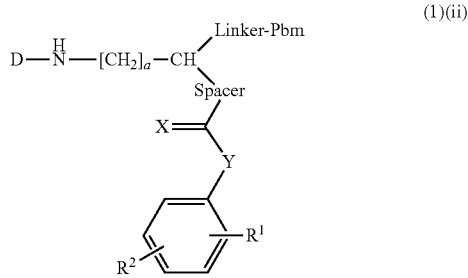

(1)(ii)

wherein

Pbm is a PSMA binding entity,

D is a chelator, preferably selected from 1,4,7,10-tetraazacyclododecane-1,4,7,10-tetraacetic acid (DOTA), N,N"-bis[2-hydroxy-5-(carboxyethyl)-benzyl]ethylenediamine-N,N"-diacetic acid (HBED-CC), 1,4,7-triazacyclononane-1,4,7-triacetic acid (NOTA), 2-(4,7-bis(carboxymethyl)-1,4,7-triazonan-1-yl)pentanedioic acid (NODAGA), 2-(4,7,10-tris(carboxymethyl)-1,4,7,10-tetraazacyclododecan-1-yl)-pentanedioic acid (DOTAGA), 1,4,7-triazacyclononane phosphinic acid (TRAP), 1,4,7-triazacyclononane-1-[methyl(2-carboxyethyl)-phosphinic acid]-4,7-bis[methyl(2-hydroxymethyl)phosphinic acid] (NOPO), 3,6,9, 15-tetraazabicyclo[9,3,1.]pentadeca-1(15),11,13-triene-3,6,9-triacetic acid (PCTA), N'-{5-[Acetyl(hydroxy)amino]pentyl}-N-[5-({4-[(5-aminopentyl)(hydroxy)amino]-4-oxobutanoyl}amino)pentyl]-N-hydroxysuccinamide (DFO), and Diethylene-triaminepentaacetic acid (DTPA), or derivatives thereof, X is O, N, S or P, $R^1$ and $R^2$ are each independently selected from H, F, Cl, Br, I, branched, unbranched or cyclic $C_1$-$C_{12}$ hydrocarbyl, $C_2$-$C_{12}$ alkenyl, $C_2$-$C_{12}$ alkylnyl, $OR^6$, $OCOR^6$, CHO, $COR^6$, $CH_2OR^6$, $NR^6R^7$, $CONR^6R^7$, $COOR^6$, $CH_2NR^6R^7$, $SR^6$, =O, =S or =NH, or $R^1$ and $R^2$ are joined to form a cyclic structure comprising a branched, unbranched or cyclic $C_1$-$C_{10}$ hydrocarbyl group, wherein said hydrocarbyl group is optionally interrupted by up to 2 heteroatoms and optionally substituted by up to 3 groups independently selected from F, Cl, Br, I, $OR^6$, $OCOR^6$, $COOR^6$, CHO, $COR^6$, $CH_2OR^6$, $NR^6R^7$, $CH_2NR^6R^7$, and $SR^7$, =O, =S and =NH, Y is selected from a single bond or a linear, branched or cyclic, optionally substituted $C_1$-$C_{12}$ alkyl, optionally interrupted by up to two heteroatoms, $OR^6$, $OCOR^6$, CHO, $COR^6$, $CH_2OR^6$, $NR^6R^7$, $COOR^6$, $CH_2NR^6R^7$, $SR^6$, =O, =S or =NH, wherein one or more of the non-adjacent $CH_2$-groups may independently be replaced by —O—, —CO—, —CO—O—, —O—CO—, —$NR^6$—, —$NR^6$—CO—, —CO—$NR^6$—, —$NR^6$—COO—, —O—CO—$NR^6$—, —$NR^6$—CO—$NR^6$—, —CH=CH—, —C≡C—, —O—CO—O—, $SR^6$—, $SO_3R^6$—, $R^6$ and $R^7$ are each independently selected from H or branched, unbranched or cyclic $C_{1-12}$ hydrocarbyl, the spacer comprises at least one C—N bond, the linker is characterized by General Formula (6) as defined herein, and a, b, p, q, r, t is each independently an integer selected from 0, 1, 2, 3, 4, 5, 6, 7, 8, 9, or 10, or a pharmaceutically acceptable salt, ester, solvate or radiolabeled complex thereof.

The PSMA binding entity may bind reversibly or irreversibly to PSMA, typically with a binding affinity less than about 100 μM (micromolar).

Human Prostate-specific membrane antigen (PSMA) (also referred to as glutamate carboxypeptidase II (GCPII), folate hydrolase 1, folypoly-gamma-glutamate carboxypeptidase (FGCP), and N-acetylated-alpha-linked acidic dipeptidase I (NAALADase I)) is a type II transmembrane zinc metallopeptidase that is most highly expressed in the nervous system, prostate, kidney, and small intestine. It is considered a tumor marker in prostate cancer. The term "Human Prostate-specific membrane antigen" or "PSMA" as used herein preferably refers to the protein encoded by the human FOLH1 gene. More preferably, the term refers to the protein as characterized under UniProt Acc. No. Q04609 (entry version 186, last modified May 10, 2017, or functional variants, isoforms, fragments or (post-translationally or otherwise modified) derivatives thereof.

The PSMA-binding entity may generally be a binding entity capable of selectively (and optionally irreversibly) binding to (human) Prostate-Specific Membrane Antigen (cf. Chang Rev Urol. 2004; 6(Suppl 10): S13-S18).

The PSMA binding entity is preferably chosen by its ability to confer selective affinity towards PSMA. Preferred PSMA binding moieties are described in WO 2013/022797 A1, WO 2015/055318 A1 and EP 2862857 A1, which are incorporated by reference in their entirety herein.

Accordingly, in the conjugates of the present invention, the PSMA binding entity may preferably be characterized by General Formula (5):

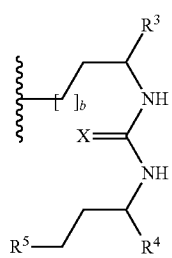

(5)

wherein

X is selected from O, N, S or P, $R^3$, $R^4$ and $R^5$ are each independently selected from —COH, —$CO_2H$, —$SO_2H$, —$SO_3H$, —$SO_4H$, —$PO_2H$, —$PO_3H$, —$PO_4H_2$, —C(O)—($C_1$-$C_{10}$)alkyl, —C(O)—O($C_1$-$C_{10}$)alkyl, —C(O)—$NHR^8$, or —C(O)—$NR^8R^9$, wherein $R^8$ and $R^9$ are each independently selected from H, bond, (C1-C10)alkylene, F, Cl, Br, I, C(O), C(S), —C(S)—NH-benzyl-, —C(O)—NH-benzyl, —C(O)—($C_1$-$C_{10}$)alkylene, —$(CH_2)_p$—NH, —$(CH_2)_p$—($C_1$-$C_{10}$)alkylene, —$(CH_2)_p$—NH—C(O)—$(CH_2)_q$, —$(CH_rCH_2)_r$—NH—C(O)—$(CH_2)_p$, —$(CH_2)_p$—CO—COH, —$(CH_2)_p$—CO—$CO_2H$, —$(CH_2)_p$—C(O)NH—C$[(CH_2)_q$—COH$]_3$, —C$[(CH_2)_p$—COH$]_3$, —$(CH_2)_p$—C(O)NH—C$[(CH_2)_q$—$CO_2H]_3$, —C$[(CH_2)_p$—$CO_2H]_3$ or —$(CH_2)_p$—($C_5$-$C_{14}$)heteroaryl, and b, p, q, r, t is each independently an integer selected from 0, 1, 2, 3, 4, 5, 6, 7, 8, 9, or 10.

In preferred PSMA binding entities, b may be an integer selected from 1, 2, 3, 4 or 5, $R^3$, $R^4$ and $R^5$ may each be $CO_2H$, X may be O.

Linker

In the inventive conjugates, the PSMA binding entity is attached/connected to the —CH— "branching point" via a suitable linker. The term "linker" is used herein to specifically refer to the group connecting or linking and thus spanning the distance between the PSMA binding entity and the —CH— "branching point", and/or "spacing" the PSMA binding entity apart from the remaining conjugate.

The linker may preferably avoid sterical hindrance between the PSMA binding entity and the other groups or entities of the inventive conjugate and ensure sufficient mobility and flexibility. Further, the linker may preferably be designed so as to confer, support and/or allow sufficient HSA binding, high affinity PSMA binding, and rapid and optionally selective penetration of PSMA positive cells through internalization of the PSMA-conjugate complex.

PSMA binding entities, and in particular preferred PSMA binding entities of General Formula (5), may preferably be linked to the inventive conjugate via a suitable linker as described, e.g. in EP 2 862 857 A1. Said linker may preferably confer optimized lipophilic properties to the inventive conjugate to increase PSMA binding and cellular uptake and internalization. The linker may preferably comprise at least one cyclic group and at least one aromatic group (in particular in group Q and W).

Accordingly, in the inventive conjugates, preferred linkers may be characterized by General Formula (6):

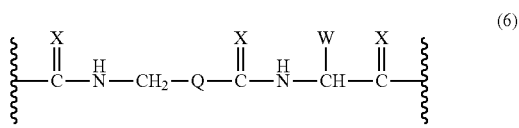

(6)

wherein

X is each independently selected from O, N, S or P,

Q is selected from substituted or unsubstituted aryl, alkylaryl or cycloalkyl, preferably from substituted or unsubstituted $C_5$-$C_{14}$ aryl, $C_5$-$C_{14}$ alkylaryl or $C_5$-$C_{14}$ cycloalkyl, W is selected from —$(CH_2)_c$-aryl or —$(CH_2)_c$-heteroaryl, wherein c is an integer selected from 0, 1, 2, 3, 4, 5, 6, 7, 8, 9 or 1.

Without wishing to be bound by specific theory, it is thought that hydrophilic or polar functional groups within or pendant from the linker (in particular Q, W) may advantageously enhance the PSMA-binding properties of the inventive conjugate.

Where Q is a substituted aryl, alkylaryl or cycloalkyl, exemplary substituents are listed in the "Definitions" section above and include, without limitation, halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN), haloalkyl, aminoalkyl, hydroxyalkyl, cycloalkyl.

Preferably, Q may be selected from substituted or unsubstituted $C_5$-$C_7$ cycloalkyl.

Preferably, W may be selected from —$(CH_2)_c$-naphtyl, —$(CH_2)_c$-phenyl, —$(CH_2)_c$-biphenyl, —$(CH_2)_c$-indolyl, —$(CH_2)_c$-benzothiazolyl, wherein c is an integer selected from 0, 1, 2, 3, 4, 5, 6, 7, 8, 9 or 10. More preferably, W may be selected from —$(CH_2)$-naphthyl, —$(CH_2)$-phenyl, —$(CH_2)$-biphenyl, —$(CH_2)$-indolyl or —$(CH_2)$-benzothiazolyl.

Preferably, each X may be O.

Accordingly, a particularly preferred linker connecting the PSMA binding entity to the inventive conjugate may be characterized by the following Structural Formula (6a):

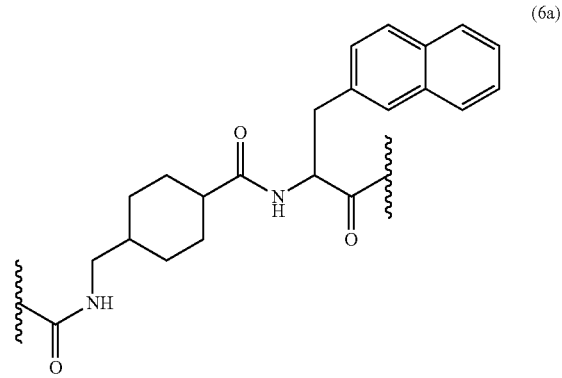 [SMILES: *C(=O)NCC1CCC(C(=O)NC(Cc2ccc3ccccc3c2)C(*)=O)CC1]

(6a)

In the conjugates according to the present invention and characterized by any of the structural formulas presented herein, the substituents or groups identified by placeholders may be (where applicable) defined as follows.

D may preferably be selected from 1,4,7,10-tetraazacyclododecane-1,4,7,10-tetraacetic acid (DOTA), N,N''-bis[2-hydroxy-5-(carboxyethyl)-benzyl]ethylenediamine-N,N''-diacetic acid (HBED-CC), 1,4,7-triazacyclononane-1,4,7-triacetic acid (NOTA), 2-(4,7-bis(carboxymethyl)-1,4,7-triazonan-1-yl)pentanedioic acid (NODAGA), 2-(4,7,10-tris(carboxymethyl)-1,4,7,10-tetraazacyclododecan-1-yl)-pentanedioic acid (DOTAGA), 1,4,7-triazacyclononane phosphinic acid (TRAP), 1,4,7-triazacyclononane-1-[methyl(2-carboxyethyl)-phosphinic acid]-4,7-bis[methyl (2-hydroxymethyl)phosphinic acid] (NOPO), 3,6,9, 15-tetraazabicyclo[9,3,1.]pentadeca-1(15),11,13-triene-3,6,9-triacetic acid (PCTA), N'-{5-[Acetyl(hydroxy)amino] pentyl}-N-[5-({4-[(5-aminopentyl)(hydroxy)amino]-4-oxobutanoyl}-amino)-pentyl]-N-hydroxysuccinamide (DFO), and Diethylenetriamine-pentaacetic acid (DTPA), and derivatives thereof. More preferably, D may be selected from DOTA, NODAGA, or derivatives thereof.

X may preferably be each independently selected from O, N, S or P. More preferably, each X may be O.

$R^1$ and $R^2$ may preferably be each independently selected from H, F, Cl, Br, I, branched, unbranched or cyclic $C_1$-$C_{12}$ hydrocarbyl, $C_2$-$C_{12}$ alkenyl, $C_2$-$C_{12}$ alkylnyl, $OR^6$, $OCOR^6$, CHO, $COR^6$, $CH_2OR^6$, $NR^6R^7$, $CONR^6R^7$, $COOR^6$, $CH_2NR^6R^7$, $SR^6$, =O, =S or =NH, or $R^1$ and $R^2$ are joined to form a cyclic structure comprising a branched, unbranched or cyclic $C_1$-$C_{10}$ hydrocarbyl group, wherein said hydrocarbyl group is optionally interrupted by up to 2 heteroatoms and optionally substituted by up to 3 groups independently selected from F, Cl, Br, I, $OR^6$, $OCOR^6$, $COOR^6$, CHO, $COR^6$, $CH_2OR^6$, $NR^6R^7$, $CH_2NR^6R^7$, and $SR^7$, =O, =S and =NH, wherein $R^6$ and $R^7$ are each independently selected from H or branched, unbranched or cyclic $C_{1-12}$ hydrocarbyl. More preferably, $R^1$ may be H and $R^2$ may be selected from halogen, preferably iodine or bromine, and $C_{1-6}$ alkyl, preferably $C_{1-3}$ alkyl, even more preferably methyl. Even more preferably, $R^1$ may be H and $R^2$ may be H or may be in the para position and selected from iodine, bromine and methyl.

Y may preferably be selected from a single bond or a linear, branched or cyclic $C_1$-$C_{12}$ alkyl, optionally interrupted by up to two heteroatoms, optionally substituted by at least one halogen, branched, unbranched or cyclic $C_1$-$C_{10}$ hydrocarbyl, $OR^6$, $OCOR^6$, CHO, $COR^6$, $CH_2OR^6$, $NR^6R^7$, $COOR^6$, $CH_2NR^6R^7$, $SR^6$, =O, =S or =NH, wherein one or more of the non-adjacent $CH_2$-groups may independently be replaced by —O—, —CO—, —CO—O—, —O—O—, —$NR^6$—, —$NR^6$—CO—, —CO—$NR^6$—, —$NR^6$—COO—, —O—CO—$NR^6$—, —$NR^6$—CO—$NR^6$—, —CH=CH—, —C≡C—, —O—CO—O—, $SR^6$—, $SO_3R^6$—, wherein $R^6$ and $R^7$ are each independently selected from H or branched, unbranched or cyclic $C_{1-12}$ hydrocarbyl. More preferably, Y may be may be a linear or branched, optionally substituted, $C_1$-$C_{12}$ hydrocarbyl, more preferably a linear or branched, optionally substituted, $C_1$-$C_{10}$ hydrocarbyl, even more preferably a linear or branched, optionally substituted, $C_1$-$C_6$ hydrocarbyl, even more preferably a linear or branched, optionally substituted, $C_1$-$C_3$ hydrocarbyl. Most preferably, Y may be —$(CH_2)_3$—.

$R^3$, $R^4$ and $R^5$ may preferably each be independently selected from —COH, —$CO_2H$, —$SO_2H$, —$SO_3H$, —$SO_4H$, —$PO_2H$, —$PO_3H$, —$PO_4H_2$, —C(O)—($C_1$-$C_{10}$) alkyl, —C(O)—O($C_1$-$C_{10}$)alkyl, —C(O)—$NHR^8$, or —C(O)—$NR^8R^9$, wherein $R^8$ and $R^9$ are each independently selected from H, bond, ($C_1$-$C_{10}$)alkylene, F, Cl, Br, I, C(O), C(S), —C(S)—NH-benzyl-, —C(O)—NH-benzyl, —C(O)—($C_1$-$C_{10}$)alkylene, —$(CH_2)_p$—NH, —$(CH_2)_p$—($C_1$-$C_{10}$)alkylene, —$(CH_2)_p$—NH—C(O)—$(CH_2)_q$, —$(CH_rCH_2)_t$—NH—C(O)—$(CH_2)_p$, —$(CH_2)_p$—CO—COH, —$(CH_2)_p$—CO—$CO_2H$, —$(CH_2)_p$—C(O)NH—C[$(CH_2)_q$—COH]$_3$, —C[$(CH_2)_p$—COH]$_3$, —$(CH_2)_p$—C(O)NH—C[$(CH_2)_q$—$CO_2H$]$_3$, —C[$(CH_2)_p$—$CO_2H$]$_3$ or —$(CH_2)_p$—($C_5$-$C_{14}$)heteroaryl. More preferably, $R^3$, $R^4$ and $R^5$ may be —$CO_2H$.

The spacer may preferably comprise at least one C—N bond. More preferably, the spacer may be characterized by Formula (3a), (3b) or (3c) as defined herein.

The linker may preferably be characterized by General Formula (6) as defined herein. More preferably, the linker may be characterized by Formula (6a) as defined herein.

Q may preferably be selected from substituted or unsubstituted aryl, alkylaryl or cycloalkyl, preferably from substituted or unsubstituted $C_5$-$C_{14}$ aryl, $C_5$-$C_{14}$ alkylaryl or $C_5$-$C_{14}$ cycloalkyl.

W may preferably be selected from —$(CH_2)_c$-aryl or —$(CH_2)_c$-heteroaryl, wherein c is preferably an integer selected from 0, 1, 2, 3, 4, 5, 6, 7, 8, 9 or 1.

A may preferably be an amino acid residue. More preferably, A may be selected from (D-)Aspartate, (D-)Glutamate or (L-Lysine).

V may preferably be selected from a single bond, N, or an optionally substituted $C_1$-$C_{12}$ hydrocarbyl comprising up to 3 heteroatoms, wherein said heteroatom is preferably selected from N.

n may preferably an integer selected from 1, 2, 3, 4 or 5, preferably from 1, 2 or 3, m may preferably be 0 or 1.

a, b, p, q, r, t may preferably each be independently an integer selected from 0, 1, 2, 3, 4, 5, 6, 7, 8, 9, or 10.

In accordance with the above, preferred conjugates according to the present invention may be characterized by General Formula (1a):

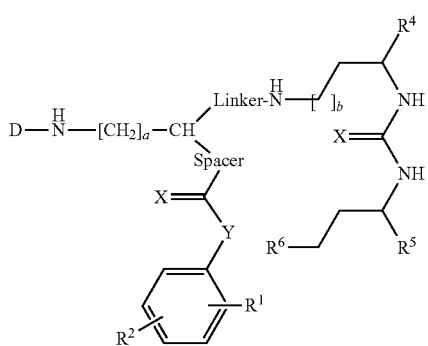

(1a)

wherein

D is a chelator, preferably selected from 1,4,7,10-tetraazacyclododecane-1,4,7,10-tetraacetic acid (DOTA), N,N"-bis [2-hydroxy-5-(carboxyethyl)-benzyl]ethylenediamine-N,N"-diacetic acid (HBED-CC), 1,4,7-triazacyclononane-1,4,7-triacetic acid (NOTA), 2-(4,7-bis(carboxymethyl)-1,4,7-triazonan-1-yl)pentanedioic acid (NODAGA), 2-(4,7,10-tris (carboxymethyl)-1,4,7,10-tetraazacyclododecan-1-yl)-pentanedioic acid (DOTAGA), 1,4,7-triazacyclononane phosphinic acid (TRAP), 1,4,7-triazacyclononane-1-[methyl(2-carboxyethyl)-phosphinic acid]-4,7-bis[methyl (2-hydroxymethyl)phosphinic acid](NOPO), 3,6,9, 15-tetraazabicyclo[9,3,1.]pentadeca-1(15),11,13-triene-3,6,9-triacetic acid (PCTA), N'-{5-[Acetyl(hydroxy)amino] pentyl}-N-[5-({4-[(5-aminopentyl) (hydroxy)amino]-4-oxobutanoyl}amino)pentyl]-N-hydroxysuccinamide (DFO), and Diethylenetriaminepentaacetic acid (DTPA), or derivatives thereof, X is each independently selected from O, N, S or P, $R^1$ and $R^2$ are each independently selected from H, F, Cl, Br, I, branched, unbranched or cyclic $C_1$-$C_{12}$ hydrocarbyl, $C_2$-$C_{12}$ alkenyl, $C_2$-$C_{12}$ alkylnyl, $OR^6$, $OCOR^6$, CHO, $COR^6$, $CH_2OR^6$, $NR^6R^7$, $CONR^6R^7$, $COOR^6$, $CH_2NR^6R^7$, $SR^6$, =O, =S or =NH, or $R^1$ and $R^2$ are joined to form a cyclic structure comprising a branched, unbranched or cyclic $C_1$-$C_{10}$ hydrocarbyl group, wherein said hydrocarbyl group is optionally interrupted by up to 2 heteroatoms and optionally substituted by up to 3 groups independently selected from F, Cl, Br, I, $OR^6$, $OCOR^6$, $COOR^6$, CHO, $COR^6$, $CH_2OR^6$, $NR^6R^7$, $CH_2NR^6R^7$, and $SR^7$, =O, =S and =NH, Y is selected from a single bond or a linear, branched or cyclic, optionally substituted $C_1$-$C_{12}$ alkyl, optionally interrupted by up to two heteroatoms, $OR^6$, $OCOR^6$, CHO, $COR^6$, $CH_2OR^6$, $NR^6R^7$, $COOR^6$, $CH_2NR^6R^7$, $SR^6$, =O, =S or =NH, wherein one or more of the non-adjacent $CH_2$-groups may independently be replaced by —O—, —CO—, —CO—O—, —O—CO—, —$NR^6$—, —$NR^6$—CO—, —CO—$NR^6$—, —$NR^6$—COO—, —O—CO—$NR^6$—, —$NR^6$—CO—$NR^6$—, —CH=CH—, —C≡C—, —O—CO—O—, $SR^6$—, $SO_3R^6$—, $R^6$ and $R^7$ are each independently selected from H or branched, unbranched or cyclic $C_{1\text{-}12}$ hydrocarbyl, $R^3$, $R^4$ and $R^5$ are each independently selected from —COH, —$CO_2H$, —$SO_2H$, —$SO_3H$, —$SO_4H$, —$PO_2H$, —$PO_3H$, —$PO_4H_2$, —C(O)—($C_1$-$C_{10}$)alkyl, —C(O)—O ($C_1$-$C_{10}$)alkyl, —C(O)—$NHR^8$, or —C(O)—$NR^8R^9$, wherein $R^8$ and $R^9$ are each independently selected from H, bond, ($C_1$-$C_{10}$)alkylene, F, Cl, Br, I, C(O), C(S), —C(S)—NH-benzyl-, —C(O)—NH-benzyl, —C(O)—($C_1$-$C_{10}$)alkylene, —$(CH_2)_p$—NH, —$(CH_2)_p$—($C_1$-$C_{10}$)alkylene, —$(CH_2)_p$—NH—C(O)—$(CH_2)_q$, —$(CH_rCH_2)_t$—NH—C (O)—$(CH_2)_p$, —$(CH_2)_p$—CO—COH, —$(CH_2)_p$—CO—$CO_2H$, —$(CH_2)_p$—C(O)NH—C[$(CH_2)_q$—$COH]_3$, —C[$(CH_2)_p$—$COH]_3$, —$(CH_2)_p$—C(O)NH—C[$(CH_2)_q$—$CO_2H]_3$, —C[$(CH_2)_p$—$CO_2H]_3$ or —$(CH_2)_p$—($C_5$-$C_{14}$)heteroaryl, the spacer comprises at least one C—N bond, the linker is characterized by General Formula (6) as defined above, and a, b, p, q, r, t is each independently an integer selected from 0, 1, 2, 3, 4, 5, 6, 7, 8, 9, or 10, or a pharmaceutically acceptable salt, ester, solvate or radiolabeled complex thereof.

More preferably, the inventive conjugates may be characterized by General Formula (12.4) or (13.4):

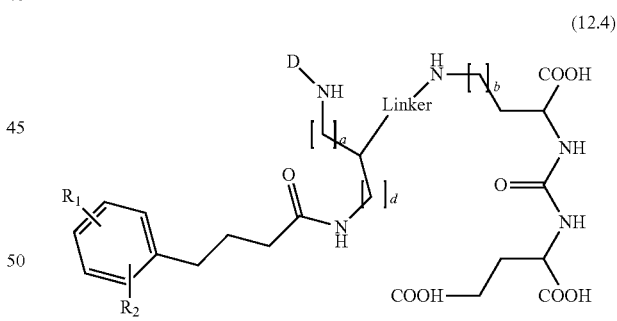

(12.4)

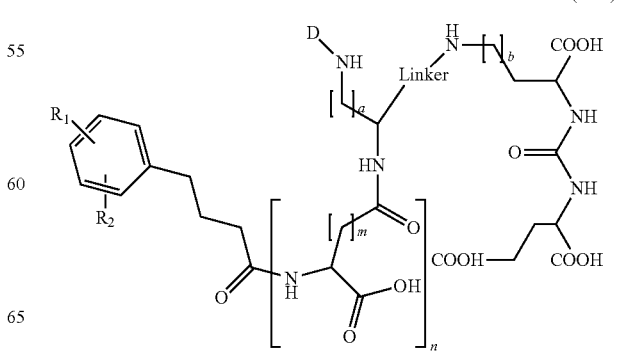

(13.4)

wherein

D is a chelator, preferably selected from 1,4,7,10-tetraazacyclododecane-1,4,7,10-tetraacetic acid (DOTA), N,N"-bis[2-hydroxy-5-(carboxyethyl)-benzyl]ethylenediamine-N,N"-diacetic acid (HBED-CC), 1,4,7-triazacyclononane-1,4,7-triacetic acid (NOTA), 2-(4,7-bis(carboxymethyl)-1,4,7-triazonan-1-yl)pentanedioic acid (NODAGA), 2-(4,7,10-tris(carboxymethyl)-1,4,7,10-tetraazacyclododecan-1-yl)-pentanedioic acid (DOTAGA), 1,4,7-triazacyclononane phosphinic acid (TRAP), 1,4,7-triazacyclononane-1-[methyl(2-carboxyethyl)-phosphinic acid]-4,7-bis[methyl(2-hydroxymethyl)phosphinic acid](NOPO), 3,6,9, 15-tetraazabicyclo[9,3,1.]pentadeca-1(15),11,13-triene-3,6,9-triacetic acid (PCTA), N'-{5-[Acetyl(hydroxy)amino]pentyl}-N-[5-({4-[(5-aminopentyl)(hydroxy)amino]-4-oxobutanoyl}amino)pentyl]-N-hydroxysuccinamide (DFO), and Diethylenetriaminepentaacetic acid (DTPA), or derivatives thereof, $R^1$ and $R^2$ are preferably each independently selected from H, halogen, preferably iodine or bromine, and $C_{1-6}$ alkyl, preferably $C_{1-3}$ alkyl, even more preferably methyl;

the linker is characterized by General Formula (6) as defined above, more preferably, the linker is characterized by General Formula (6a) as defined above, a, b, d, m, n is each independently an integer selected from 0, 1, 2, 3, 4, 5, 6, 7, 8, 9, or 10, more preferably, a and b is each independently an integer selected from 0, 1, 2, 3, 4, 5 or 6; b, d and m is each independently an integer selected from 1, 2, 3, 4, 5 or 6.

More preferably, the inventive conjugates may be characterized by General Formula (1b)

$R^1$ and $R^2$ are each independently selected from H, F, Cl, Br, I, branched, linear or cyclic $C_1$-$C_{12}$ hydrocarbyl optionally comprising up to 2 heteroatoms and optionally substituted by up to 3 groups independently selected from F, Cl, Br, I, branched, unbranched or cyclic $C_1$-$C_{12}$ hydrocarbyl, $OR^7$, $OCOR^7$, $COOR^7$, CHO, $COR^7CH_2OR^7$, $NR^7R^8$, $CH_2NR^7R^8$, and $SR^8$, =O, =S and =NH, wherein $R^7$ and $R^8$ are each independently selected from H or branched, unbranched or cyclic $C_{1-12}$ hydrocarbyl; preferably $R^1$ and $R^2$ are each independently selected from H, Br, I and linear $C_1$-$C_{12}$ alky;

$R^3$, $R^4$ and $R^5$ are each independently selected from —COH, —CO$_2$H, —SO$_2$H, —SO$_3$H, —SO$_4$H, —PO$_2$H, —PO$_3$H, —PO$_4$H$_2$, —C(O)—(C$_1$-C$_{10}$)alkyl, —C(O)—O(C$_1$-C$_{10}$)alkyl, —C(O)—NHR$^8$, or —C(O)—NR$^8$R$^9$, wherein $R^8$ and $R^9$ are each independently selected from H, bond, (C$_1$-C$_{10}$)alkylene, F, Cl, Br, I, C(O), C(S), —C(S)—NH-benzyl-, —C(O)—NH-benzyl, —C(O)—(C$_1$-C$_{10}$)alkylene, —(CH$_2$)$_p$—NH, —(CH$_2$)$_p$—(C$_1$-C$_{10}$)alkylene, —(CH$_2$)$_p$—NH—C(O)—(CH$_2$)$_q$, —(CH$_r$CH$_2$)$_t$—NH—C(O)—(CH$_2$)$_p$, —(CH$_2$)$_p$—CO—COH, —(CH$_2$)$_p$—CO—CO$_2$H, —(CH$_2$)$_p$—C(O)NH—C[(CH$_2$)$_q$—COH]$_3$, —C[(CH$_2$)$_p$—COH]$_3$, —(CH$_2$)$_p$—C(O)NH—C[(CH$_2$)$_q$—CO$_2$H]$_3$, —C[(CH$_2$)$_p$—CO$_2$H]$_3$ or —(CH$_2$)$_p$—(C$_5$-C$_{14}$)heteroaryl, a, b, d, p, q, r, s and t are each independently an integer selected from 0, 1, 2, 3, 4, 5, 6, 7, 8, 9 or 10, and the spacer comprises at least one C—N bond, or a pharmaceutically acceptable salt, ester, solvate or radiolabeled complex thereof.

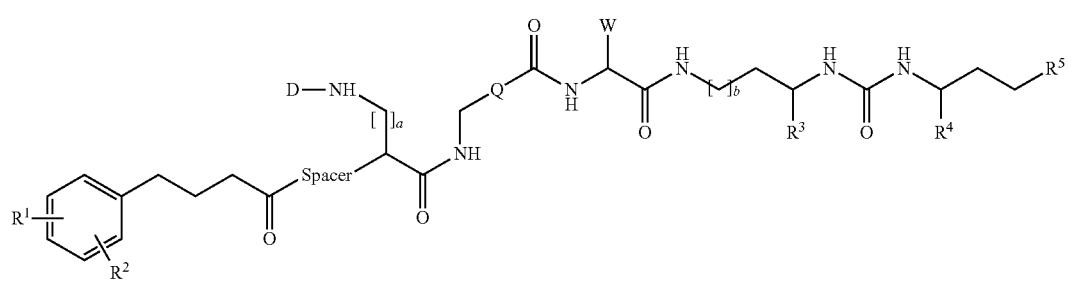

(1b)

wherein

D is a chelator, preferably selected from 1,4,7,10-tetraazacyclododecane-1,4,7,10-tetraacetic acid (DOTA), N,N"-bis[2-hydroxy-5-(carboxyethyl)benzyl]-ethylenediamine-N,N"-diacetic acid (HBED-CC), 1,4,7-triazacyclononane-1,4,7-triacetic acid (NOTA), 2-(4,7-bis(carboxymethyl)-1,4,7-triazonan-1-yl)pentanedioic acid (NODAGA), 2-(4,7,10-tris(carboxymethyl)-1,4,7,10-tetraazacyclododecan-1-yl)pentanedioic acid (DOTAGA), 1,4,7-triazacyclononane phosphinic acid (TRAP), 1,4,7-triazacyclononane-1-[methyl(2-carboxyethyl)phosphinic acid]-4,7-bis[methyl(2-hydroxymethyl)phosphinic acid] (NOPO), 3,6,9,15-tetraazabicyclo-[9,3,1.]pentadeca-1(15),11,13-triene-3,6,9-triacetic acid (PCTA), N'-{5-[Acetyl(hydroxy)amino]pentyl}-N-[5-({4-[(5-aminopentyl)(hydroxy)amino]-4-oxobutanoyl}-amino)pentyl]-N-hydroxysuccinamide (DFO), and Diethylenetriamine-pentaacetic acid (DTPA), or derivatives thereof, Q is selected from substituted or unsubstituted aryl, alkylaryl or cycloalkyl, W is selected from —(CH$_2$)$_d$-aryl or —(CH$_2$)$_d$-heteroaryl, In preferred conjugates of the invention according to General Formula (1b), any one of the following definitions, preferably at least two, more preferably at least three, more preferably at least four, or most preferably all of the following definitions may apply for "D", "Q", "W", "a", "b", "R$^1$" "R$^2$" "R$^3$", "R$^4$" and/or "R$^5$":

D may be selected from any suitable chelator (e.g. as defined herein), more preferably D may be selected from DOTA, DOTA, HBED-CC, NOTA, NODAGA, DOTAGA, TRAP, NOPO, PCTA, DFO, DTPA or derivatives thereof. Most preferably, D may be selected from DOTA, NODAGA, DO3AP, DO3AP$^{PrA}$ or DO3AP$^{ABn}$.

Q may be selected from substituted or unsubstituted $C_5$-$C_7$ cycloalkyl. W may be selected from —(CH$_2$)-naphthyl, —(CH$_2$)-phenyl, —(CH$_2$)-biphenyl, —(CH$_2$)-indolyl or —(CH$_2$)-benzothiazolyl, more preferably W may be —(CH$_2$)-naphthyl.

a, b may each independently be an integer selected from 0, 1, 2, 3, 4, 5 or 6.

$R^1$ and $R^2$ may each independently be selected from H, iodine and $C_1$-$C_3$ alkyl, and $R^3$, $R^4$ and $R^5$ may each be CO$_2$H.

Such preferred conjugates may be characterized by General Formula (1c):

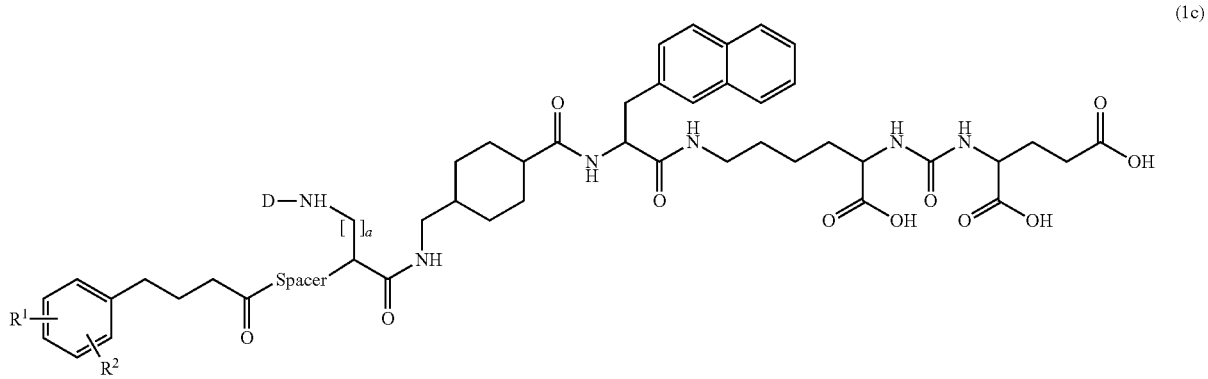

(1c)

wherein
any one, preferably at least two, more preferably at least three, or most preferably all of the below definitions may apply for "D", "a", "R$^1$", and/or "R$^2$":
D may be selected from DOTA, DOTA, HBED-CC, NOTA, NODAGA, DOTAGA, TRAP, NOPO, PCTA, DFO, DTPA or derivatives thereof. Most preferably, D may be selected from DOTA, NODAGA, DO3AP, DO3AP$^{PrA}$ or DO3AP$^{ABn}$,
a may be an integer selected from 0, 1, 2, 3, 4, 5 or 6,
R$^1$ and R$^2$ are each independently selected from H, iodine or C$_1$-C$_3$ alkyl, and
the spacer comprises at least one C—N bond, or pharmaceutically acceptable salts, esters, solvates or radiolabeled complexes thereof.

In preferred conjugates of General Formula (1c),
a may be 0, and
the spacer may be —[CHR$^{10}$]$_u$—NR$^{11}$—, wherein R$^{10}$ and R$^{11}$ may each be independently selected from H and branched, unbranched or cyclic C$_1$-C$_{12}$ hydrocarbyl and wherein u may be an integer selected from 1, 2, 3, 4, 5, 6, 7, 8, 9 or 10. In preferred conjugates of General Formula (1a), the spacer is characterized by Formula (3a). Accordingly, such preferred conjugates may be characterized by General Formula (7a):

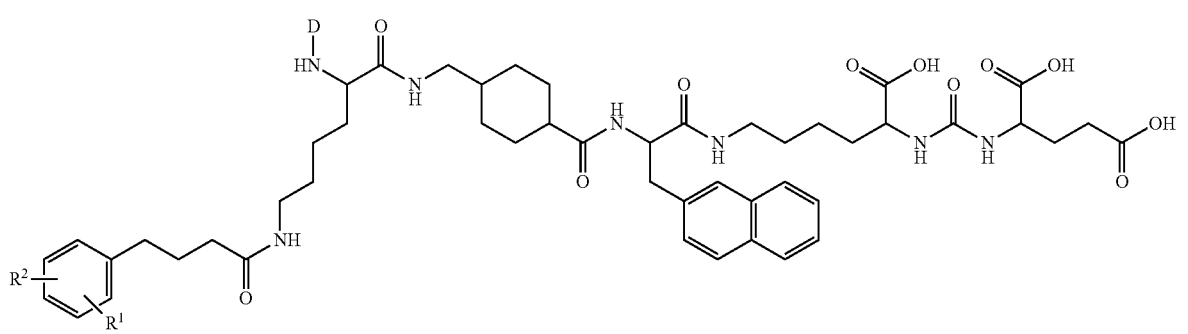

(7a)

wherein
D may be selected from DOTA, DOTA, HBED-CC, NOTA, NODAGA, DOTAGA, TRAP, NOPO, PCTA, DFO, DTPA or derivatives thereof. Most preferably, D may be selected from DOTA, NODAGA, DO3AP, DO3APPrA or DO3APABn, R$^1$ and R$^2$ may each be independently selected from H, iodine or C$_1$-C$_3$ alkyl, or pharmaceutically acceptable salts, esters, solvates or radiolabeled complexes thereof, Specifically, preferred conjugates according to the invention may be characterized by Formula (7a)(i), (7a)(ii) or (7a)(iii):

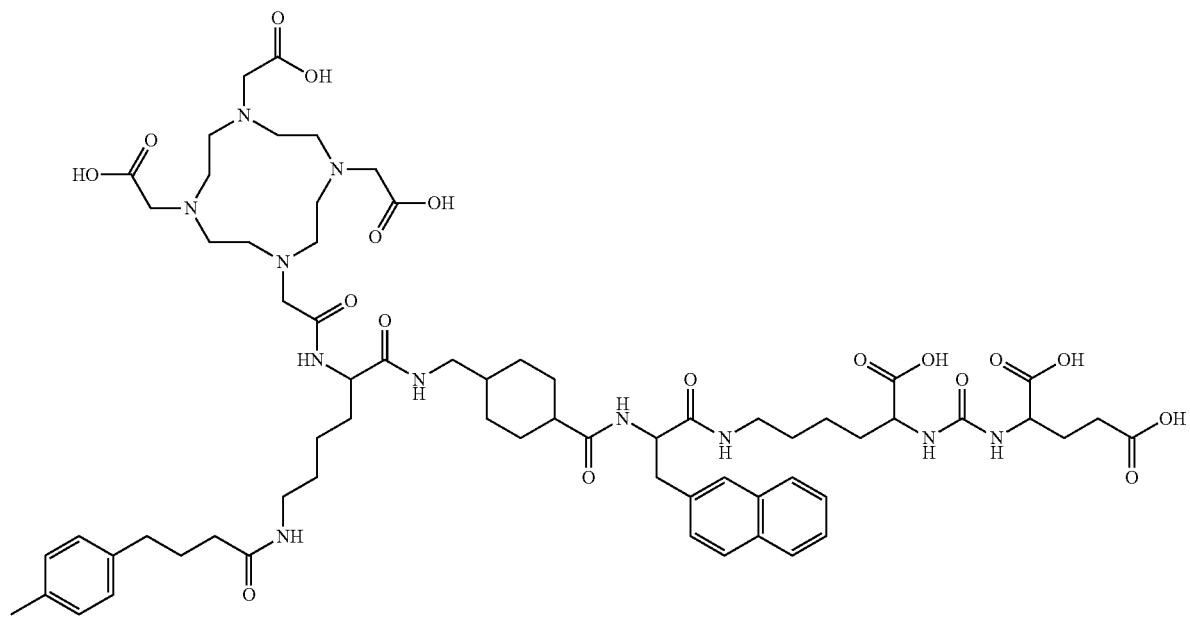
(7a)(i)
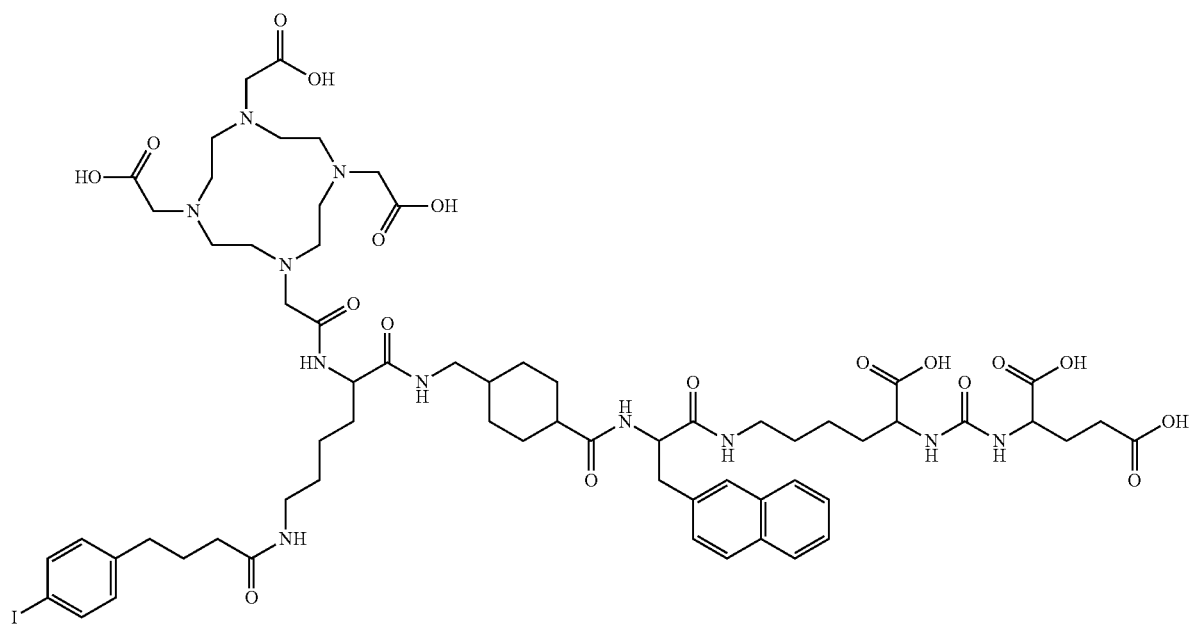
(7a)(ii)

(7a)(iii)

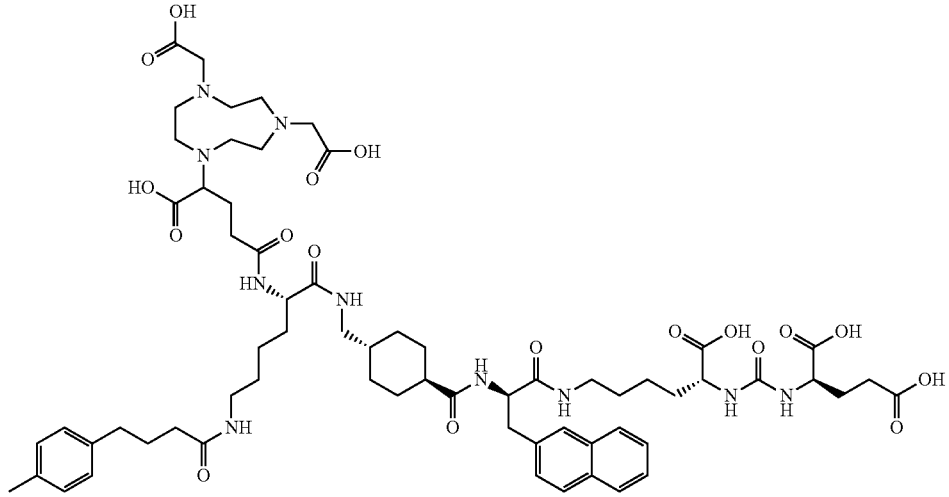

or pharmaceutically acceptable salts, esters, solvates or radiolabeled complexes thereof.

Conjugates characterized by Formula (7a)(i) are also referred to as "PSMA-06" or "PSMA-ALB-06" herein.

Conjugates characterized by Formula (7a)(ii) are also referred to as "PSMA-03" or "PSMA-ALB-03" herein.

Conjugates characterized by Formula (7a)(iii) are also referred to as "PSMA-89" or "PSMA-ALB-89" herein.

In alternatively preferred conjugates of General Formula (1c), the spacer comprises at least one amino acid residue, preferably selected from (D-/L-) aspartate, glutamate or lysine. Preferably, the spacer may comprise at least 1, 2, 3, 4 or up to five 5 amino acids residue(s), preferably independently selected from (D-/L-) aspartate, glutamate or lysine amino acid residues.

Such conjugates may preferably comprise a spacer according to General Formula (3b) or (3c). Accordingly, such preferred conjugates may be characterized by General Formula (7b):

(7b)

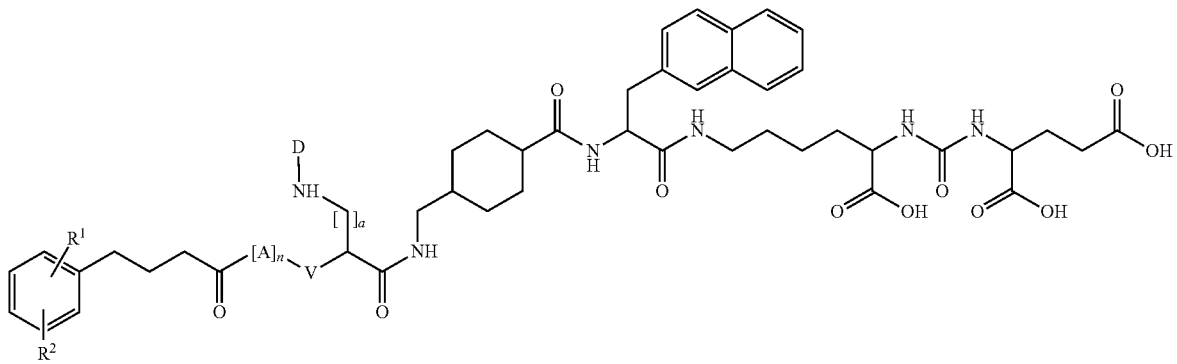

wherein

D may be selected from DOTA, DOTA, HBED-CC, NOTA, NODAGA, DOTAGA, TRAP, NOPO, PCTA, DFO, DTPA or derivatives thereof. Most preferably, D may be selected from DOTA, NODAGA, DO3AP, DO3AP$^{PrA}$ or DO3AP$^{ABn}$, $R^1$ and $R^2$ are each independently selected from H, iodine or $C_1$-$C_3$ alkyl, A is an amino acid residue preferably selected from (D-)Aspartate, (D-)Glutamate or (L-Lysine), V is selected from a single bond, N, or an optionally substituted $C_1$-$C_{12}$ hydrocarbyl comprising up to 3 heteroatoms, wherein said heteroatom is preferably selected from N, n is an integer selected from 1, 2, 3, 4 or 5, preferably from 1, 2 or 3, and a is an integer selected from 1, 2, 3, 4, 5 or 6.

or pharmaceutically acceptable salts, esters, solvates or radiolabeled complexes thereof.

Specifically, such conjugates may be characterized by Formula (7a)(i), (7a)(ii) or (7a)(iii):

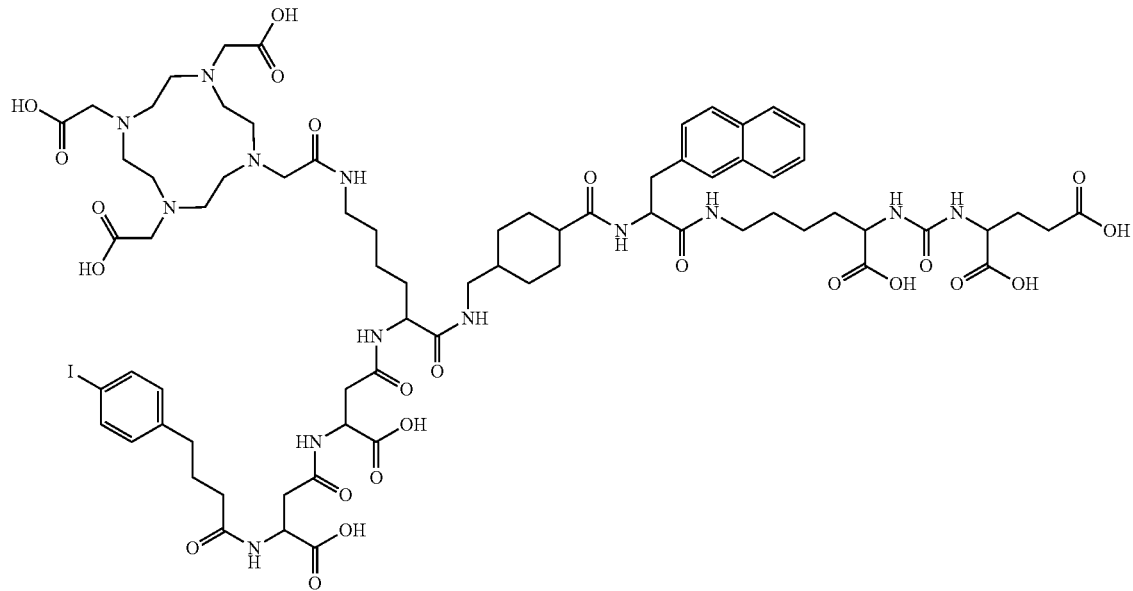

(7b)(i)

or pharmaceutically acceptable salts, esters, solvates or radiolabeled complexes thereof.

Conjugates characterized by Formula (7b)(i) are also referred to as "PSMA-05" or "PSMA-ALB-05" herein.

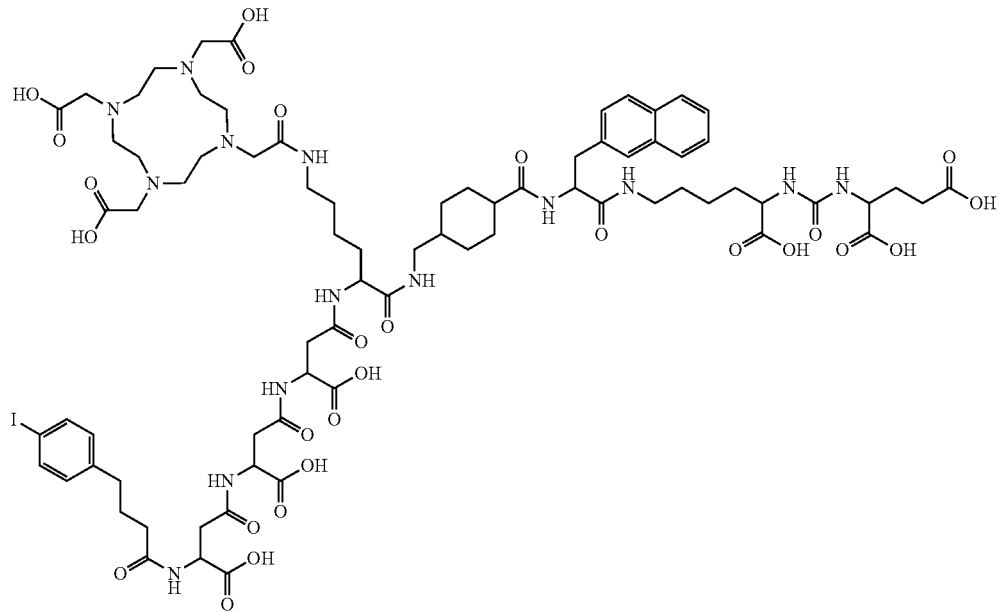

(7b)(ii)

or pharmaceutically acceptable salts, esters, solvates or radiolabeled complexes thereof.

Conjugates characterized by Formula (7b)(ii) are also referred to as "PSMA-07" or "PSMA-ALB-07" herein.

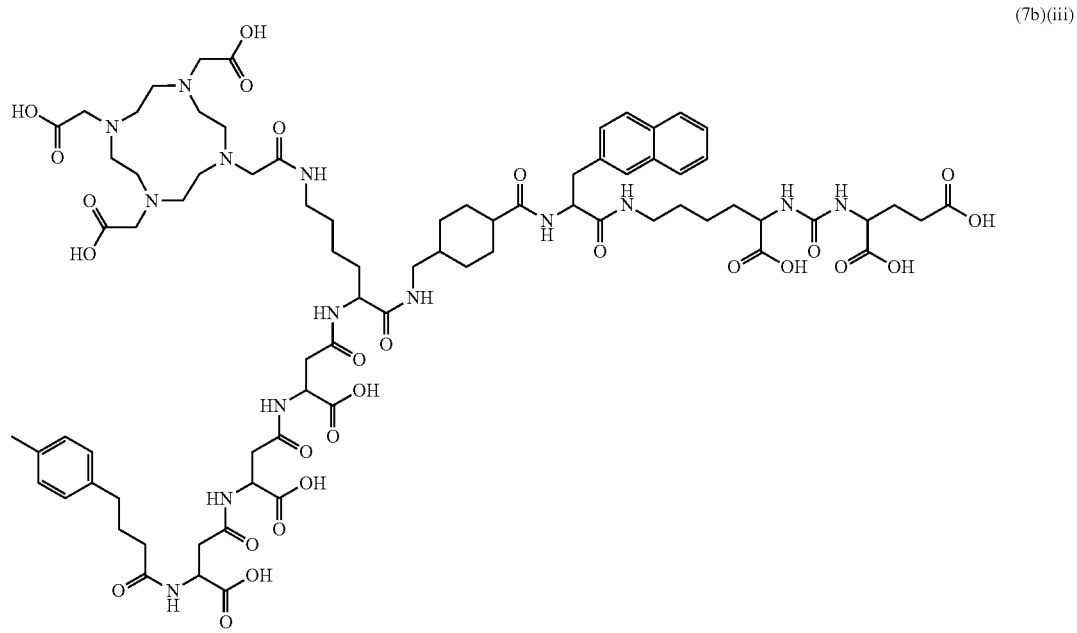 [SMILES: Cc1ccc(CCCC(=O)NC(CC(=O)NC(CC(=O)NC(CC(=O)NC(CCCCNC(=O)CN2CCN(CC(=O)O)CCN(CC(=O)O)CCN(CC(=O)O)CC2)C(=O)NCC2CCC(C(=O)NC(Cc3ccc4ccccc4c3)C(=O)NCCCCC(NC(=O)NC(CCC(=O)O)C(=O)O)C(=O)O)CC2)C(=O)O)C(=O)O)C(=O)O)cc1]

(7b)(iii)

or pharmaceutically acceptable salts, esters, solvates or radiolabeled complexes thereof.

Conjugates characterized by Formula (7b)(iii) are also referred to as "PSMA-08" or "PSMA-ALB-08" herein.

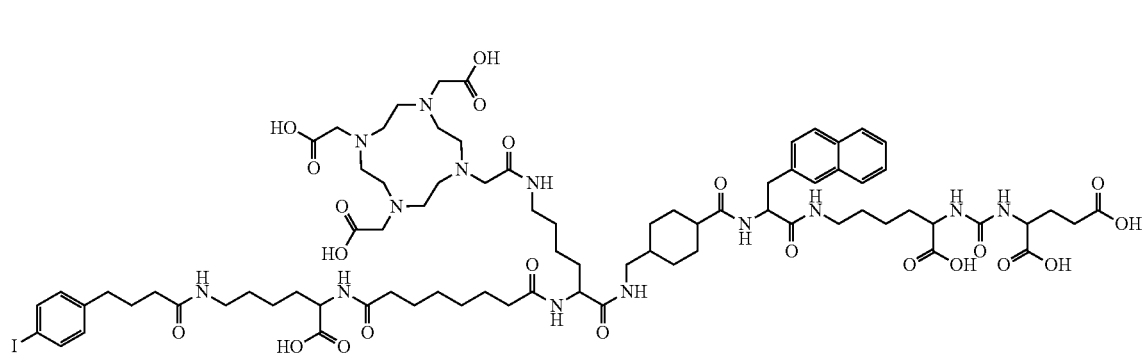

(7b)(iv)

or pharmaceutically acceptable salts, esters, solvates or radiolabeled complexes thereof.

Conjugates characterized by Formula (7b)(iv) are also referred to as "PSMA-04" or "PSMA-ALB-04" herein.

The present invention further provides conjugates characterized by Structural Formula (14), (15) and (16)

(14)
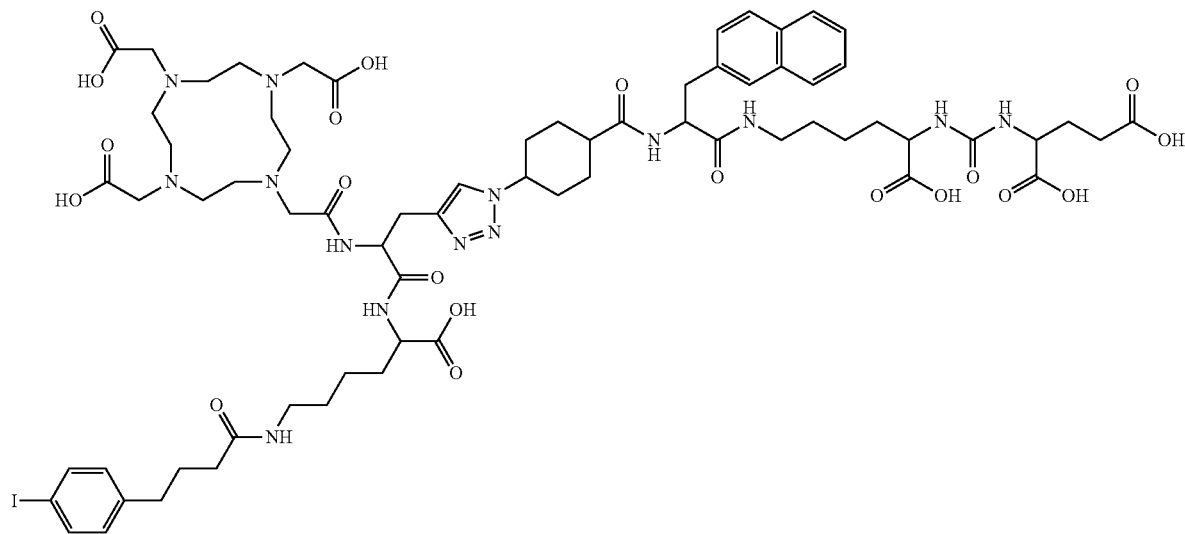
(15)
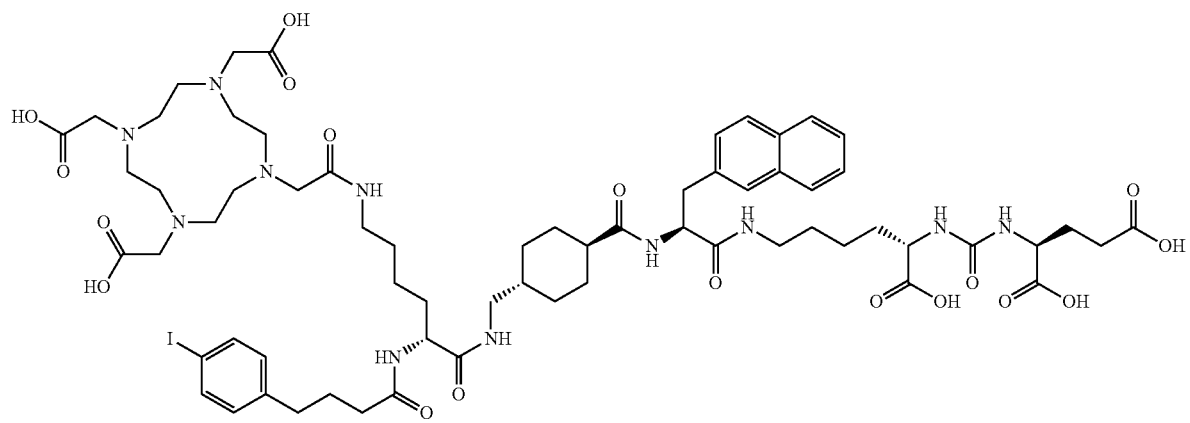
(16)
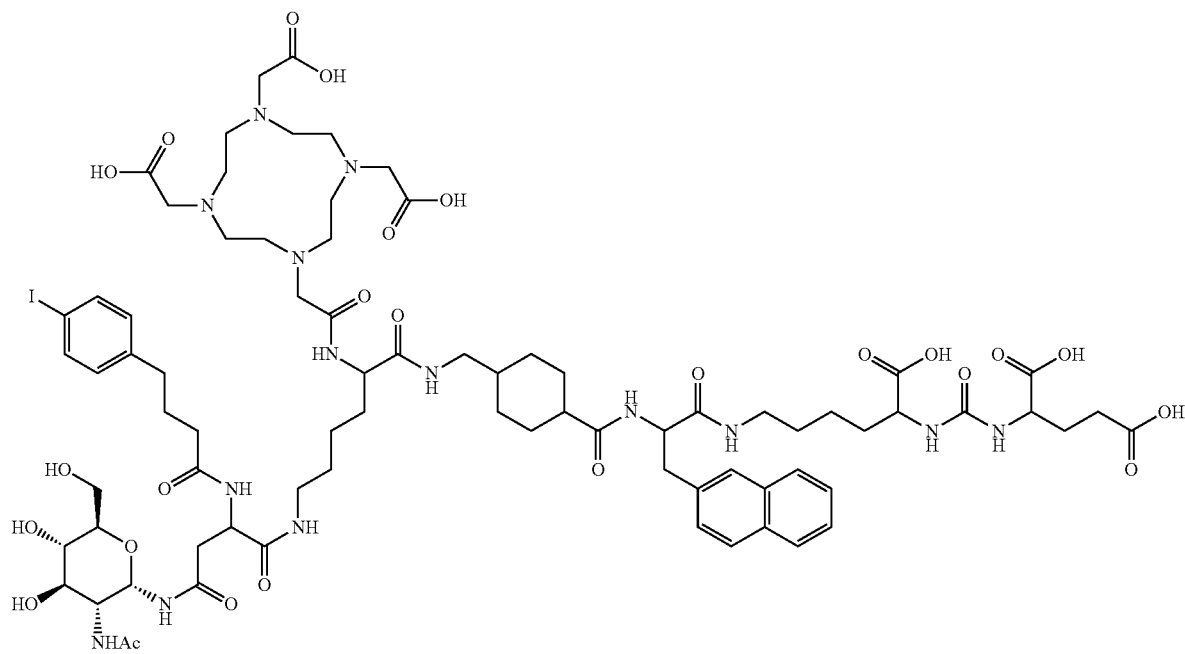

Pharmaceutically Acceptable Salts

The present invention further encompasses pharmaceutically acceptable salts of the conjugates described herein.

The preparation of pharmaceutical compositions is well known to the person skilled in the art. Pharmaceutically acceptable salts of the conjugates of the invention can be prepared by conventional procedures, such as by reacting any free base and/or acid of a conjugate according to the invention with at least a stoichiometric amount of the desired salt-forming acid or base, respectively.

Pharmaceutically acceptable salts of the inventive include salts with inorganic cations such as sodium, potassium, calcium, magnesium, zinc, and ammonium, and salts with organic bases. Suitable organic bases include N-methyl-D-glucamine, argmine, benzathine, diolamine, olamine, procame and tromethamine. Pharmaceutically acceptable salts according to the invention also include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide.

Complexed/Non-Complexed Forms

The present invention further encompasses the conjugates described herein, wherein the chelating agent D may be complexed with a metal ion (such as a radionuclide) or may not be complexed.

The term "radionuclide" (or "radioisotope") refers to isotopes of natural or artificial origin with an unstable neutron to proton ratio that disintegrates with the emission of corpuscular (i.e. protons (alpha-radiation) or electrons (beta-radiation) or electromagnetic radiation (gamma-radiation). In other words, radionuclides undergo radioactive decay. chelating agent D may be complexed with any known radionuclide. Said radionuclide which may preferably be useful for cancer imaging or therapy. Such radionuclides include, without limitation, $^{94}$Tc, $^{99m}$Tc, $^{90}$In, $^{111}$In, $^{67}$Ga, $^{68}$Ga, $^{86}$Y, $^{90}$Y, $^{177}$Lu, $^{151}$Tb, $^{186}$Re, $^{188}$Re, $^{64}$Cu, $^{67}$Cu, $^{55}$Co, $^{57}$Co, $^{43}$Sc, $^{44}$Sc, $^{47}$Sc, $^{225}$Ac, $^{213}$Bi, $^{212}$Bi, $^{212}$Pb, $^{227}$Th, $^{153}$Sm, $^{166}$Ho, $^{152}$Gd, $^{153}$Gd, $^{157}$Gd, or $^{166}$Dy. The choice of suitable radionuclides may depend inter alia on the chemical structure and chelating capability of the chelating agent D, and the intended application of the resulting (complexed) conjugate (e.g. diagnostic vs. therapeutic). For instance, the beta-emitters such as $^{90}$Y, $^{131}$I, $^{161}$Tb and $^{177}$Lu may be used for concurrent systemic radionuclide therapy. Providing DOTA as a chelator may advantageously enable the use of either $^{68}$Ga, $^{43,44,47}$Sc, $^{177}$Lu, $^{161}$Tb, $^{225}$Ac, $^{213}$Bi, $^{212}$Bi, $^{212}$Pb as radionuclides.

In some preferred embodiments, the radionuclide may be $^{177}$Lu. In some preferred embodiments, the radionuclide may be $^{44}$Sc. In some preferred embodiments, the radionuclide may be $^{64}$Cu. In some preferred embodiments, the radionuclide may be $^{68}$Ga.

It is within the skill and knowledge of the skilled person in the art to select suitable combinations conjugates and radionuclides. For instance, in some preferred embodiments, the chelator may be DOTA and the radionuclide may be $^{177}$Lu. In other preferred embodiments, the chelator may be DOTA and the radionuclide may be $^{68}$Ga. In other preferred embodiments, the chelator may be DOTA and the radionuclide may be $^{44}$Sc. In yet further preferred embodiments, the chelator may be DOTA and the radionuclide may be $^{64}$Cu.

In other preferred embodiments, the chelator may be NODAGA and the radionuclide may be $^{64}$Cu.

Esters and Prodrugs

The present invention further encompasses the inventive conjugates in their esterified form, in particular where free carboxylic acid groups are esterified. Such esterified compounds may be prodrug forms of the inventive conjugates. Suitable ester prodrugs include various alkyl esters, including saturated and unsaturated $C_8$-$C_{18}$ fatty acids.

Enantiomers

The conjugates disclosed herein may exist in particular geometric or stereoisomeric forms. In addition, compounds may also be optically active. The inventive conjugates may also include cis- and trans-isomers, R- and S-enantiomers, diastereomers, (D)-isomers, (L)-isomers, the racemic mixtures thereof, and other mixtures thereof. Additional asymmetric carbon atoms may be present in a substituent such as an alkyl group. If, for instance, a particular enantiomer of a group or conjugate is desired, it may be prepared by asymmetric synthesis, or by derivation with a chiral auxiliary, where the resulting diastereomeric mixture is separated and the auxiliary group cleaved to provide the pure desired enantiomers. Alternatively, where the group or conjugate contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

A "stereoisomer" is one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereo isomer of the compound and less than about 20% by weight of other stereo isomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereo isomer of the compound and less than about 3% by weight of the other stereoisomers of the compound.

Accordingly, all Formulas disclosed herein comprise enantiomers and/or stereoisomers thereof.

Radiolabeled Complexes

According to a further aspect, the present invention relates to the use of the inventive conjugate for the preparation of radiolabeled complexes. Such radiolabeled complexes preferably comprise a conjugate according to the present invention, and a radionuclide. The chelating agent D preferably coordinates the radionuclide, forming a radiolabeled complex. Suitable radionuclides may be selected from theragnostic metal isotopes and comprise without limitation, $^{94}$Tc, $^{99m}$Tc, $^{90}$In, $^{111}$In, $^{67}$Ga, $^{68}$Ga, $^{86}$Y, $^{90}$Y, $^{177}$Lu, $^{151}$Tb, $^{186}$Re, $^{188}$Re, $^{64}$Cu, $^{67}$Cu, $^{55}$Co, $^{57}$Co, $^{43}$Sc, $^{44}$Sc, $^{47}$Sc, $^{225}$Ac, $^{213}$Bi, $^{212}$Bi, $^{212}$Pb, $^{227}$Th, $^{153}$Sm, $^{166}$Ho, $^{152}$Gd, $^{153}$Gd, $^{157}$Gd, or $^{166}$Dy.

According to a further aspect, the present invention further provides a complex comprising a radionuclide (preferably selected from the group above) and a conjugate according to the invention.

Pharmaceutical Composition

According to a further aspect, the present invention provides a pharmaceutical composition comprising the inventive conjugate (including pharmaceutically acceptable salts, esters, solvates or radiolabeled complexes as described herein), and a pharmaceutically acceptable carrier and/or excipient.

The term "pharmaceutically acceptable" refers to a compound or agent that is compatible with the inventive conjugate and does not interfere with and/or substantially reduce its diagnostic or therapeutic activities. Pharmaceutically acceptable carriers preferably have sufficiently high purity and sufficiently low toxicity to make them suitable for administration to a subject to be treated.

Formulations, Carriers and Excipients

Pharmaceutically acceptable excipients can exhibit different functional roles and include, without limitation, diluents, fillers, bulking agents, carriers, disintegrants, binders, lubricants, glidants, coatings, solvents and co-solvents, buffering agents, preservatives, adjuvants, anti-oxidants, wetting agents, anti-foaming agents, thickening agents, sweetening agents, flavouring agents and humectants.

Suitable pharmaceutically acceptable excipients are typically chosen based on the formulation of the (pharmaceutical) composition.

For (pharmaceutical) compositions in liquid form, useful pharmaceutically acceptable excipients in general include solvents, diluents or carriers such as (pyrogen-free) water, (isotonic) saline solutions such phosphate or citrate buffered saline, fixed oils, vegetable oils, such as, for example, groundnut oil, cottonseed oil, sesame oil, olive oil, corn oil, ethanol, polyols (for example, glycerol, propylene glycol, polyethylene glycol, and the like); lecithin; surfactants; preservatives such as benzyl alcohol, parabens, chlorobutanol, phenol, ascorbic acid, thimerosal, and the like; isotonic agents such as sugars, polyalcohols such as manitol, sorbitol, or sodium chloride; aluminum monostearate or gelatin; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. pH can be adjusted with acids or bases, such as hydrochloric acid or sodium hydroxide. Buffers may be hypertonic, isotonic or hypotonic with reference to the specific reference medium, i.e. the buffer may have a higher, identical or lower salt content with reference to the specific reference medium, wherein preferably such concentrations of the aforementioned salts may be used, which do not lead to damage of cells due to osmosis or other concentration effects. Reference media are e.g. liquids occurring in in vivo methods, such as blood, lymph, cytosolic liquids, or other body liquids, or e.g. liquids, which may be used as reference media in in vitro methods, such as common buffers or liquids. Such common buffers or liquids are known to a skilled person.

Liquid (pharmaceutical) compositions administered via injection and in particular via i.v. injection should preferably be sterile and stable under the conditions of manufacture and storage. Such compositions are typically formulated as parenterally acceptable aqueous solutions that are pyrogen-free, have suitable pH, are isotonic and maintain stability of the active ingredient(s).

For liquid pharmaceutical compositions, suitable pharmaceutically acceptable excipients and carriers include water, typically pyrogen-free water; isotonic saline or buffered (aqueous) solutions, e.g phosphate, citrate etc. buffered solutions. Particularly for injection of the inventive (pharmaceutical) compositions, water or preferably a buffer, more preferably an aqueous buffer, may be used, which may contain a sodium salt, e.g. at least 50 mM of a sodium salt, a calcium salt, e.g. at least 0.01 mM of a calcium salt, and optionally a potassium salt, e.g. at least 3 mM of a potassium salt.

The sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. $CaCl_2$), $CaI_2$, $CaBr_2$, $CaCO_3$, $CaSO_4$, $Ca(OH)_2$. Furthermore, organic anions of the aforementioned cations may be contained in the buffer.

Buffers suitable for injection purposes as defined above, may contain salts selected from sodium chloride (NaCl), calcium chloride ($CaCl_2$)) and optionally potassium chloride (KCl), wherein further anions may be present additional to the chlorides. $CaCl_2$) can also be replaced by another salt like KCl. Typically, the salts in the injection buffer are present in a concentration of at least 50 mM sodium chloride (NaCl), at least 3 mM potassium chloride (KCl) and at least 0.01 mM calcium chloride ($CaCl_2$)). The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects.

For (pharmaceutical) compositions in (semi-)solid form, suitable pharmaceutically acceptable excipients and carriers include binders such as microcrystalline cellulose, gum tragacanth or gelatin; starch or lactose; sugars, such as, for example, lactose, glucose and sucrose; starches, such as, for example, corn starch or potato starch; cellulose and its derivatives, such as, for example, sodium carboxymethylcellulose, ethylcellulose, cellulose acetate; disintegrants such as alginic acid; lubricants such as magnesium stearate; glidants such as stearic acid, magnesium stearate; calcium sulphate, colloidal silicon dioxide and the like; sweetening agents such as sucrose or saccharin; and/or flavoring agents such as peppermint, methyl salicylate, or orange flavoring.

Generally, (pharmaceutical) compositions for topical administration can be formulated as creams, ointments, gels, pastes or powders. (Pharmaceutical) compositions for oral administration can be formulated as tablets, capsules, liquids, powders or in a sustained release format. However, according to preferred embodiments, the inventive (pharmaceutical) composition is administered parenterally, in particular via intravenous or intratumoral injection, and is accordingly formulated in liquid or lyophilized form for parenteral administration as discussed elsewhere herein.

Parenteral formulations are typically stored in vials, IV bags, ampoules, cartridges, or prefilled syringes and can be administered as injections, inhalants, or aerosols, with injections being preferred.

The (pharmaceutical) composition may be provided in lyophilized form. Lyophilized (pharmaceutical) compositions are preferably reconstituted in a suitable buffer, advantageously based on an aqueous carrier, prior to administration.

The (pharmaceutical) composition preferably comprises a safe and effective amount of the inventive conjugate(s) or radiolabeled complexe(s).

As used herein, "safe and effective amount" means an amount of the agent(s) that is sufficient to allow for diagnosis and/or significantly induce a positive modification of the disease to be treated. At the same time, however, a "safe and effective amount" is small enough to avoid serious side-effects, that is to say to permit a sensible relationship between advantage and risk. A "safe and effective amount" will furthermore vary in connection with the particular condition to be diagnosed or treated and also with the age and physical condition of the patient to be treated, the severity of the condition, the duration of the treatment, the nature of the accompanying therapy, of the particular pharmaceutically acceptable excipient or carrier used, and similar factors.

The inventive conjugates are also provided for use in the preparation of a medicament, preferably for treating cancer, in particular for treating and/or preventing prostate cancer, pancreatic cancer, renal cancer or bladder cancer.

Kit

According to a further aspect, the present invention relates to a kit comprising the inventive conjugate(s) (including pharmaceutically acceptable salts, esters, solvates or radiolabeled complexes thereof) and/or a pharmaceutical composition(s) of the invention.

Optionally, the kit may comprise at least one further agent as defined herein in the context of the pharmaceutical composition, including radionuclides, antimicrobial agents, solubilizing agents or the like.

The kit may be a kit of two or more parts comprising any of the components exemplified above in suitable containers. For example, each container may be in the form of vials, bottles, squeeze bottles, jars, sealed sleeves, envelopes or pouches, tubes or blister packages or any other suitable form, provided the container preferably prevents premature mixing of components. Each of the different components may be provided separately, or some of the different components may be provided together (i.e. in the same container).

A container may also be a compartment or a chamber within a vial, a tube, a jar, or an envelope, or a sleeve, or a blister package or a bottle, provided that the contents of one compartment are not able to associate physically with the contents of another compartment prior to their deliberate mixing by a pharmacist or physician.

The kit or kit-of-parts may furthermore contain technical instructions with information on the administration and dosage of any of its components.

Therapeutic and Diagnostic Methods and Uses

According to a further aspect, the present invention relates to the inventive conjugate (including pharmaceutically acceptable salts, esters, solvates and radiolabeled complexes thereof), pharmaceutical composition or kit for use in medicine and/or diagnostics. Preferably, said inventive conjugates, pharmaceutical compositions or kits are used for human medical purposes. Accordingly, the invention further encompasses these inventive conjugates, pharmaceutical composition or kit for use as a medicament.

The inventive conjugates are preferably capable of targeting prostate-specific membrane antigen (PSMA) in a selective manner. According to a specific aspect, the invention thus provides the inventive conjugates, pharmaceutical compositions or kits for use in a method of detecting the presence of cells and/or tissues expressing prostate-specific membrane antigen (PSMA).

PSMA is in particular expressed on malignant cancer cells. As used herein, the term "cancer" refers to a neoplasm characterized by the uncontrolled and usually rapid proliferation of cells that tend to invade surrounding tissue and to metastasize to distant body sites. The term encompasses benign and malignant neoplasms. Malignancy in cancers is typically characterized by anaplasia, invasiveness, and metastasis; whereas benign malignancies typically have none of those properties. The terms include neoplasms characterized by tumor growth as well as cancers of blood and lymphatic system.

Specifically, PSMA may be expressed, optionally in increased amounts, in prostate cancer cells, pancreatic cancer cells, renal cancer cells or bladder cancer cells.

According to a further specific aspect, the invention provides the inventive conjugate (including pharmaceutically acceptable salts, esters, solvates and radiolabeled complexes thereof), pharmaceutical composition or kit for use in a method of diagnosing, treating and/or preventing prostate cancer, pancreatic cancer, renal cancer or bladder cancer.

The term "diagnosis" or "diagnosing" refers to act of identifying a disease from its signs and symptoms and/or as in the present case the analysis of biological markers (such as genes or proteins) indicative of the disease.

The term "treatment" or "treating" of a disease includes preventing or protecting against the disease (that is, causing the clinical symptoms not to develop); inhibiting the disease (i.e., arresting or suppressing the development of clinical symptoms; and/or relieving the disease (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing." The term "treatment" thus includes "prophylaxis".

The term "subject", "patient" or "individual" as used herein generally includes humans and non-human animals and preferably mammals (e.g., non-human primates, including marmosets, tamarins, spider monkeys, owl monkeys, vervet monkeys, squirrel monkeys, and baboons, macaques, chimpanzees, orangutans, gorillas; cows; horses; sheep; pigs; chicken; cats; dogs; mice; rat; rabbits; guinea pigs etc.), including chimeric and transgenic animals and disease models. In the context of the present invention, the term "subject" preferably refers a non-human primate or a human, most preferably a human.

The uses and methods described herein and relating to the diagnosis, treatment or prophylaxis of cancer, in particular prostate cancer, pancreatic cancer, renal cancer or bladder cancer, may preferably comprise the steps of (a) administering the inventive conjugate (including pharmaceutically acceptable salts, esters, solvates and radiolabeled complexes thereof), pharmaceutical composition or kit to a patient, and (b) obtaining a radiographic image from said patient.

The inventive conjugates, pharmaceutical compositions or kits are typically administered parenterally. Administration may preferably be accomplished systemically, for instance by intravenous (i.v.), subcutaneous, intramuscular or intradermal injection.

Alternatively, administration may be accomplished locally, for instance by intra-tumoral injection.

The inventive conjugates, pharmaceutical compositions or kits may be administered to a subject in need thereof several times a day, daily, every other day, weekly, or monthly. Preferably, treatment, diagnosis or prophylaxis is effected with an effective dose of the inventive conjugates, pharmaceutical compositions or kits.

Effective doses of the inventive conjugates may be determined by routine experiments, e.g. by using animal models. Such models include, without implying any limitation, rabbit, sheep, mouse, rat, dog and non-human primate models. Therapeutic efficacy and toxicity of inventive conjugates or radiolabeled complexes can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. The data obtained from the cell culture assays and animal studies can be used in determining a dose range for use in humans. The dose of said conjugates lies preferably within a range of circulating concentrations that include the ED50 with little or no toxicity.

For instance, therapeutically or diagnostically effective doses of the inventive conjugates may range from about 0.001 mg to 10 mg, preferably from about 0.01 mg to 5 mg, more preferably from about 0.1 mg to 2 mg per dosage unit or from about 0.01 nmol to 1 mmol per dosage unit, in particular from 1 nmol to 1 mmol per dosage unit, preferably from 1 micromol to 1 mmol per dosage unit. It is also envisaged that therapeutically or diagnostically effective doses of the inventive conjugates may range (per kg body weight) from about 0.01 mg/kg to 10 g/kg, preferably from about 0.05 mg/kg to 5 g/kg, more preferably from about 0.1 mg/kg to 2.5 g/kg. Advantageously, due to their favorable pharmacokinetic properties, the inventive conjugates may preferably be administered at lower doses than other PSMA ligands.

As established above, the inventive conjugates particularly lend themselves for theragnostic applications involving the targeting of PSMA-expressing cells. As used herein, the term "therangostic" includes "therapeutic-only", "diagnostic-only" and "therapeutic and diagnostic" applications. In a further aspect, the present invention relates to an in vitro method of detecting the presence of cells and/or tissues expressing prostate-specific membrane antigen (PSMA) comprising (a) contacting said PSMA-expressing cells and/or tissues with the inventive conjugates (including pharmaceutically acceptable salts, esters, solvates and radiolabeled complexes thereof), pharmaceutical compositions or kits and (b) applying detection means, optionally radiographic imaging, to detect said cells and/or tissues.

In the in vivo and in vitro uses and methods of the present invention, radiographic imaging may be accomplished using any means and methods known in the art. Preferably, radiographic imaging may involve positron emission tomography (PET) or single-photon emission computed tomography (SPECT). The targeted cells or tissues detected by radiographic imaging of the inventive conjugate may preferably comprise (optionally cancerous) prostate cells or tissues, (optionally cancerous) spleen cells or tissues, or (optionally cancerous) kidney cells or tissues.

In the in vivo and in vitro uses and methods of the present invention, the presence of PSMA-expressing cells or tissues may be indicative of a prostate tumor (cell), a metastasized prostate tumor (cell), a renal tumor (cell), a pancreatic tumor (cell), a bladder tumor (cell), and combinations thereof. Hence, the inventive conjugates (including pharmaceutically acceptable salts, esters, solvates and radiolabeled complexes thereof), pharmaceutical compositions and kit may particularly be employed for diagnosis (and optionally treatment) of prostate cancer, renal cancer, pancreatic cancer, or bladder cancer.

EXAMPLES

Figure 1:
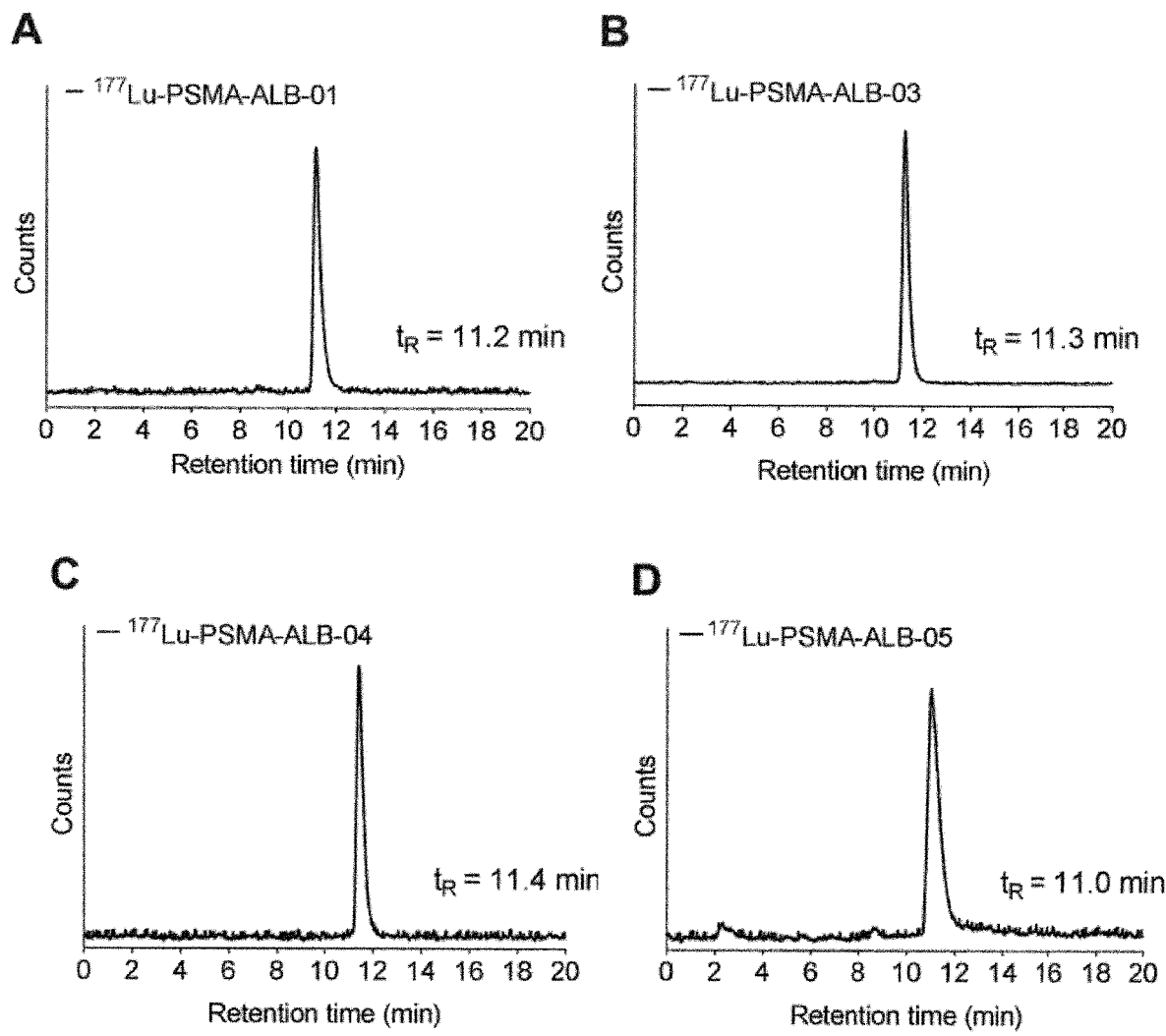
FIG. 1: Chromatograms of the HPLC-based quality control of (A) $^{177}$Lu-PSMA-ALB-01, (B) $^{177}$Lu-PSMA-ALB-03, (C) $^{177}$Lu-PSMA-ALB-04, (D) $^{177}$Lu-PSMA-ALB-05, (E) $^{177}$Lu-PSMA-ALB-06, (F) $^{177}$Lu-PSMA-ALB-07, and (G) $^{177}$Lu-PSMA-ALB-08 labeled at 50 MBq/nmol.
Figure 1:
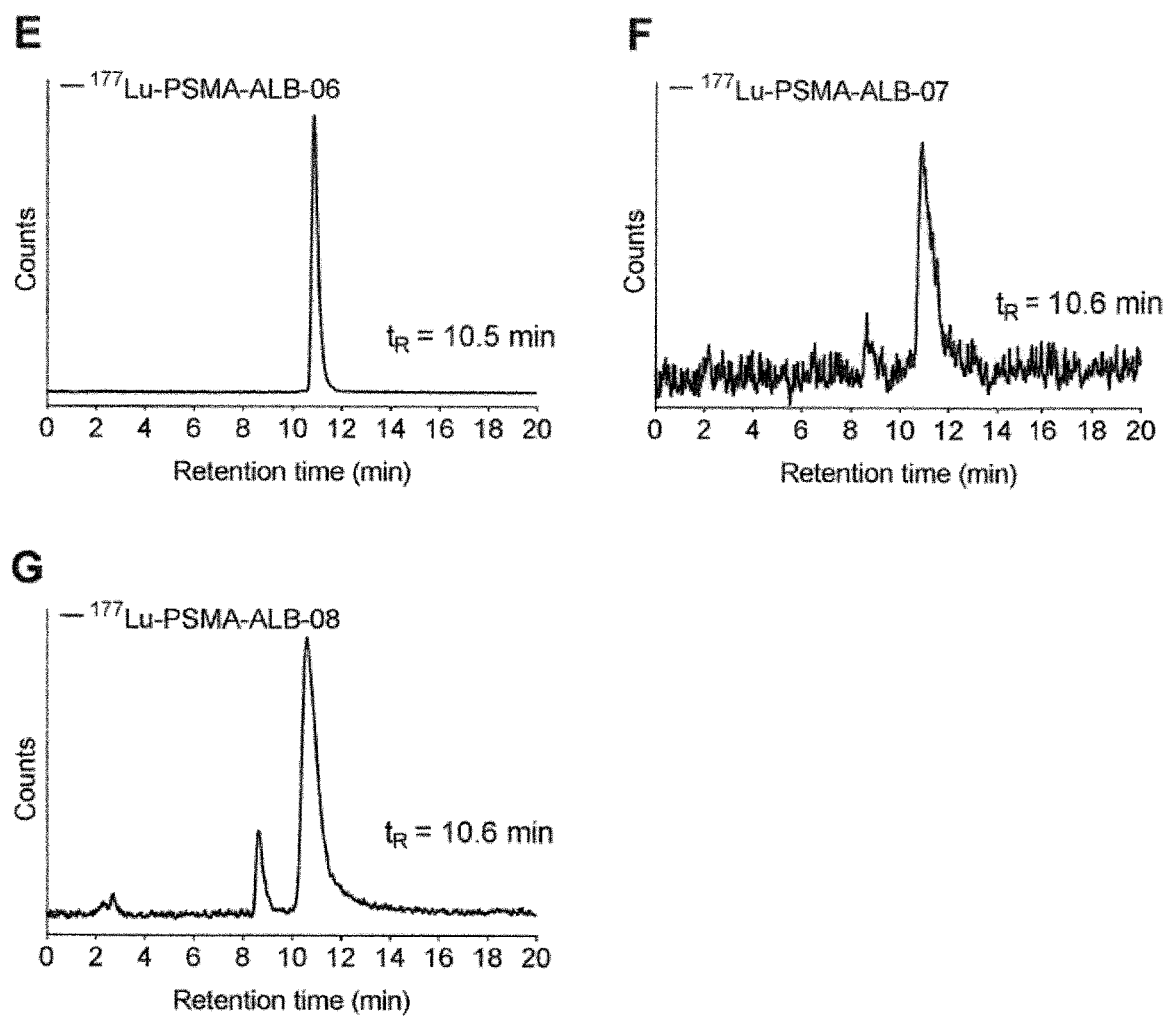

Example 1: Design and In Vitro Evaluation of DOTA-Functionalized Albumin-Binding PSMA Ligands 1.1 Material and Methods
1.1.1 Novel PSMA Ligands (Overview):

All seven suggested PSMA ligands with a portable albumin-binding moiety were synthesized via a solid-phase platform which was shown to be very useful for the development of above described albumin-affine PSMA ligands.

A multistep synthesis (19 steps for PSMA-ALB-01, 17 steps for PSMA-ALB-03, 20 steps for PSMA-ALB-04 and PSMA-ALB-05, 17 steps for PSMA-ALB-06, 23 steps for PSMA-ALB-07 and PSMA-ALB-08) provided these compounds in isolated overall yields of 26-49%. Crude products were purified by semi-preparative RP-HPLC assuring the final products with purities >98%. The characterization of above described compounds was performed by analytical RP-HPLC and MALDI-MS or ESI-MS, respectively. Analytical data are presented in Table 1.1.

TABLE 1.1

Analytical Data of PSMA-ALB-01/03/04/05/06/07/08.

| Compound Code | Chemical Formula | MW [g/mol] | m/z$^a$ | t$_r^b$ [min] |
|---|---|---|---|---|
| PSMA-ALB-01 | $C_{69}H_{95}IN_{14}O_{20}$ | 1567.50 | 1568.59 | 8.15 |
| PSMA-ALB-03 | $C_{65}H_{92}IN_{11}O_{18}$ | 1442.41 | 1443.57 | 7.57 |
| PSMA-ALB-04 | $C_{79}H_{116}IN_{13}O_{22}$ | 1726.77 | 1727.42 | 8.17 |
| PSMA-ALB-05 | $C_{73}H_{102}IN_{13}O_{24}$ | 1672.59 | 1673.41 | 8.09 |
| PSMA-ALB-06 | $C_{66}H_{95}N_{11}O_{18}$ | 1330.55 | 1331.47 | 7.24 |
| PSMA-ALB-07 | $C_{77}H_{107}IN_{14}O_{27}$ | 1787.68 | 1788.63 | 7.89 |
| PSMA-ALB-08 | $C_{78}H_{110}N_{14}O_{27}$ | 1675.81 | 1676.79 | 7.13 |

• Mass spectrometry of the unlabeled ligand detected as [M + H]; • Retention time of unlabeled ligand on analytical RP-HPLC. Analytical column (100 × 4.6 mm) utilized Chromolith RP-18e stationary phase with mobile phases consisting of 0.1% TFA in water (A) and ACN (B). For analytical runs, a linear gradient of solvent A (90-10% in 10 min) in solvent B at a flow rate of 1 mL/min was used.

The peptidomimetic pharmacophore for PSMA (L-Glu-NH—CO—NH-L-Lys binding entity; step 1-6) was synthesized analogically as described by Eder et al. Bioconjug. Chem. 2012, 23: 688-697. The linker moiety (2-naphthyl-L-Ala-NH—CO-trans-CHX—N3 or 2-naphthyl-L-Ala-NH—CO-trans-CHx-Me-NH2; step 7-10) was prepared according to standard Fmoc (9-fluorenylmethyloxycarbonyl) protocol as previously introduced by Benesovi et al. JNM 2015, 56: 914-920. These two synthetic intermediate stages providing the PSMA ligand precursor were applied analogically for all four compounds (step 1-8). However, the last building block of the linker area for PSMA-ALB-01

[trans-4-azidocyclohexanecarboxylic acid; step 9-10] was replaced for trans-4-(Fmoc-aminomethyl)cyclohexane-carboxylic acid (step 9-10) in case of PSMA-ALB-03/04/05/06/07/08.

PSMA-ALB-01

For synthesis of PSMA-ALB-01, time-efficient "head-to-tail" click coupling of the purified PSMA-precursor with the free azido group and the purified albumin-binding moiety [4-(p-iodophenyl)butyric acid-L-Lys] with propargyl-Gly (step 11-17) was employed. After the efficient coupling of these two precursors via a triazole ring (step 18), an additional purification was performed to remove an excess of $CuSO_4 \cdot 5H_2O$. Finally, PSMA-ALB-01 was obtained by the conjugation of the DOTA chelator in a form of its active ester (DOTA-NHS ester; step 19).

The Structural Formula of PSMA-ALB-01 is shown below:

(8)

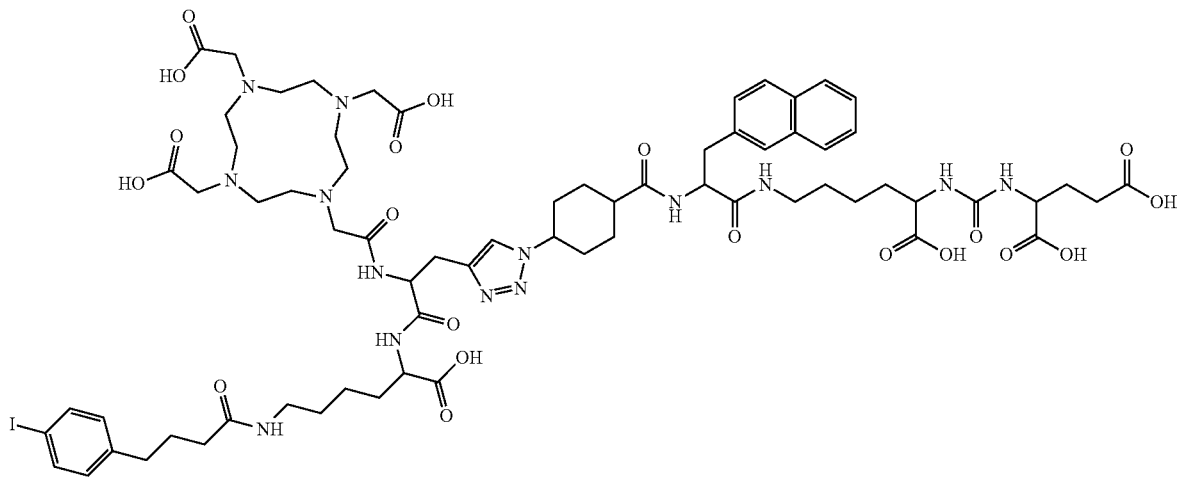

(PSMA-ALB-01)

PSMA-ALB-03

For the preparation of PSMA-ALB-03, straight one-way synthesis on the resin support was employed. After the Fmoc-L-Lys(Alloc)-OH coupling to PSMA-precursor, Fmoc deprotection, DOTA tris(tBu)-ester conjugation, Alloc deprotection and 4-(p-iodophenyl)butyric acid conjugation followed (step 11-16). Finally, PSMA-ALB-03 was obtained by agitation and subsequent cleavage from the resin with TFA:TIPS:$H_2O$ mixture (step 17).

The Structural Formula of PSMA-ALB-03 is shown below:

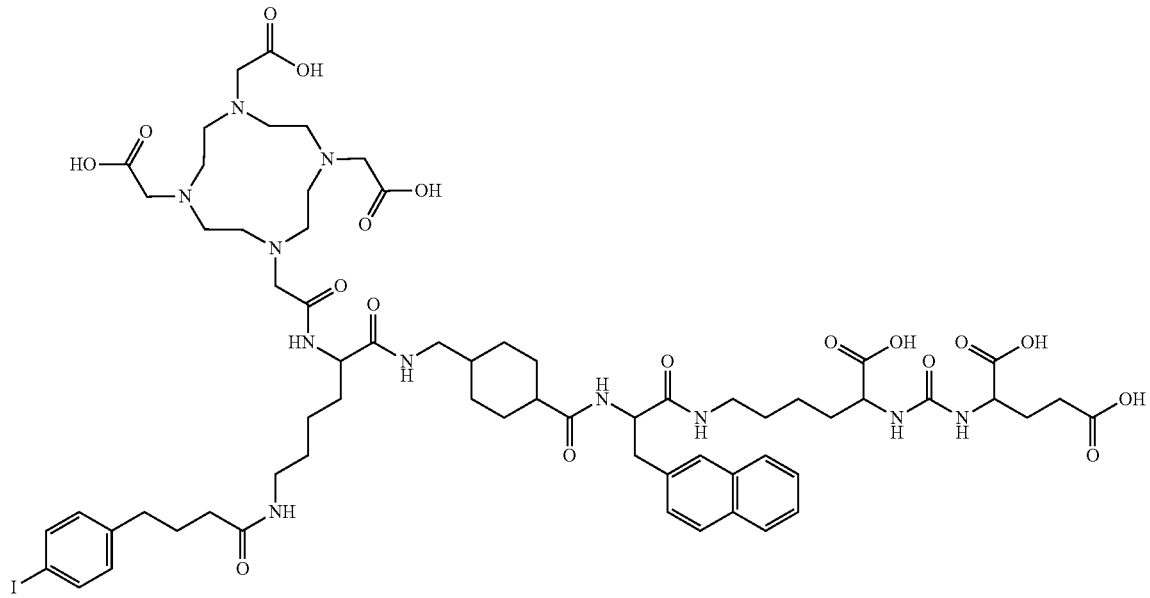

(PSMA-ALB-03)

PSMA-ALB-04

For the synthesis of PSMA-ALB-04, time-efficient "head-to-tail" coupling of the resin-coated PSMA-precursor with the DOTA-conjugated L-Lys and the purified albumin-binding moiety [4-(p-iodophenyl)butyric acid-L-Lys] through direct conjugation of two secondary amines (step 11-18) was employed. After the efficient coupling of these two precursors using suberic acid bis(N-hydroxysuccinimide) ester (step 19), PSMA-ALB-04 was obtained by agitation and subsequent cleavage from the resin with TFA:TIPS:H$_2$O mixture (step 20).

The Structural formula of PSMA-ALB-04 is shown below:

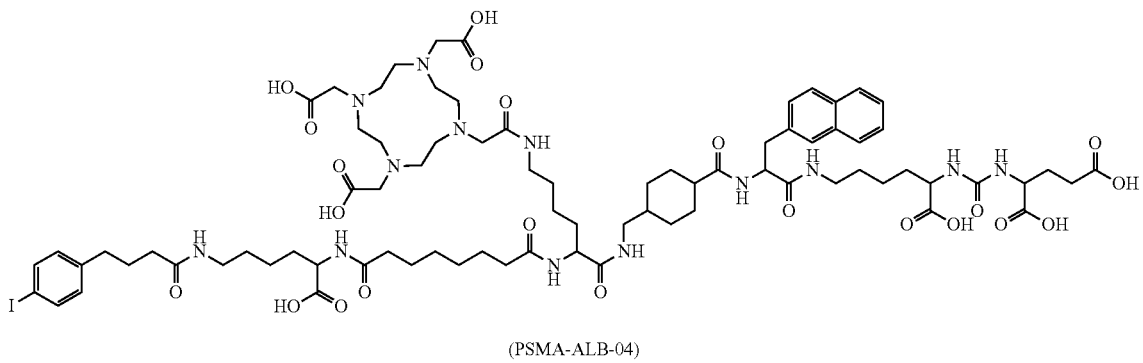 [SMILES: O=C(O)CCC(NC(=O)NC(CCCCNC(=O)C(Cc1ccc2ccccc2c1)NC(=O)C1CCC(CNC(=O)C(CCCCNC(=O)CN2CCN(CC(=O)O)CCN(CC(=O)O)CCN(CC(=O)O)CC2)NC(=O)CCCCCCC(=O)NC(CCCCNC(=O)CCCc2ccc(I)cc2)C(=O)O)CC1)C(=O)O)C(=O)O]

(PSMA-ALB-04)

PSMA-ALB-05

For the preparation of PSMA-ALB-05, straight one-way synthesis on the resin support was employed. After the Fmoc-L-Lys(Alloc)-OH coupling to PSMA-precursor, Fmoc deprotection, Fmoc-D-Asp-OtBu conjugation, Fmoc deprotection, second Fmoc-D-Asp-OtBu conjugation, Fmoc deprotection, 4-(p-iodophenyl)butyric acid conjugation, Alloc deprotection and DOTA tris(tBu)-ester conjugation followed (step 11-19). PSMA-ALB-05 was obtained by agitation and subsequent cleavage from the resin with TFA:TIPS:H$_2$O mixture (step 20).

The Structural Formula of PSMA-ALB-05 is shown below:

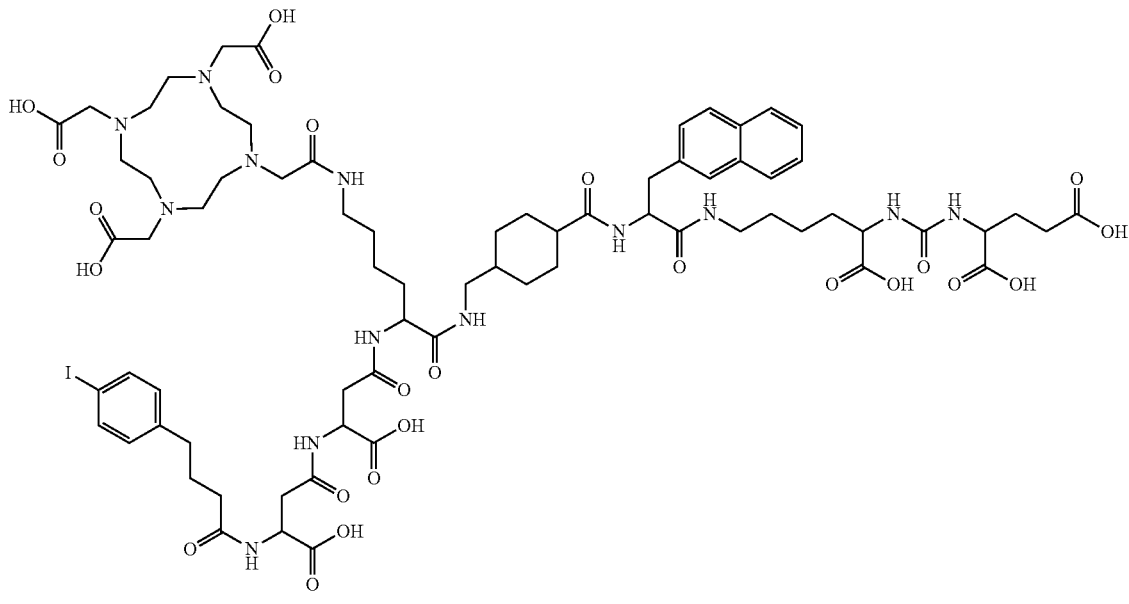

(PSMA-ALB-05)

PSMA-ALB-06

For the synthesis of PSMA-ALB-06, straight one-way synthesis on the resin support was employed. After the Fmoc-L-Lys(Alloc)-OH coupling to PSMA-precursor, Fmoc deprotection, DOTA tris(tBu)-ester conjugation, Alloc deprotection and p-(tolyl)butyric acid conjugation followed (step 11-16). Finally, PSMA-ALB-06 was obtained by agitation and subsequent cleavage from the resin with TFA:TIPS:H$_2$O mixture (step 17).

The Structural Formula of PSMA-ALB-06 is shown below:

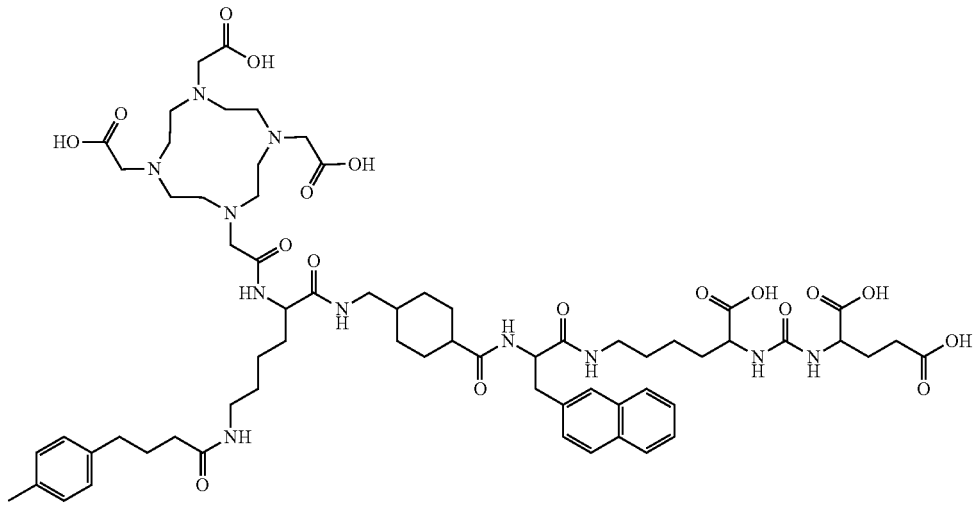

(PSMA-ALB-06)

PSMA-ALB-07

For the preparation of PSMA-ALB-07, straight one-way synthesis on the resin support was employed. After the Fmoc-L-Lys(Alloc)-OH coupling to PSMA-precursor, Fmoc deprotection, Fmoc-D-Asp-OtBu conjugation, Fmoc deprotection, second Fmoc-D-Asp-OtBu conjugation, Fmoc deprotection, third Fmoc-D-Asp-OtBu conjugation, Fmoc deprotection, 4-(p-iodophenyl)butyric acid conjugation, Alloc deprotection and DOTA tris(tBu)-ester conjugation followed (step 11-22). PSMA-ALB-07 was obtained by agitation and subsequent cleavage from the resin with TFA:TIPS:H$_2$O mixture (step 23).

The Structural Formula of PSMA-ALB-07 is shown below:

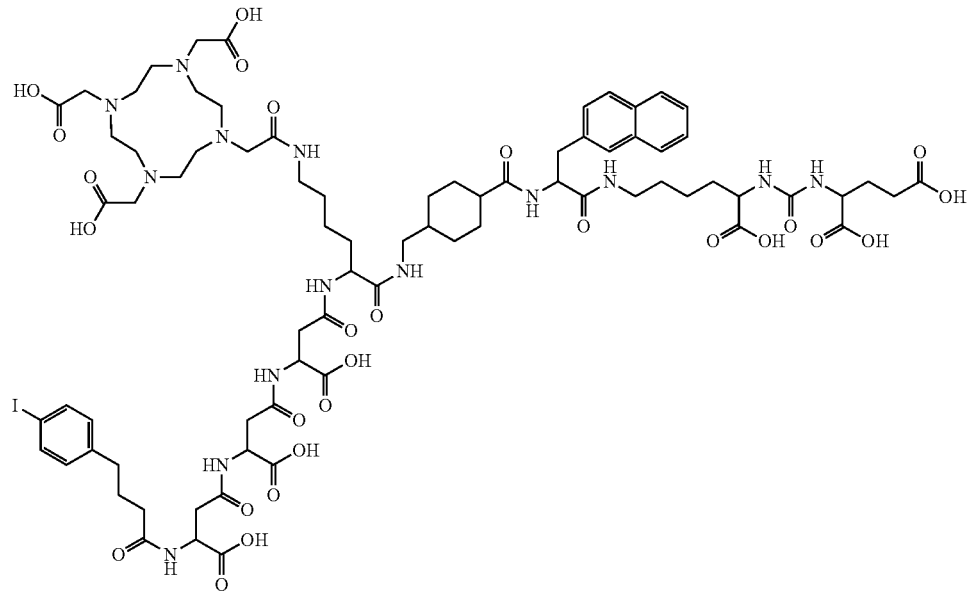

(PSMA-ALB-07)

PSMA-ALB-08

For the preparation of PSMA-ALB-08 straight one-way synthesis on the resin support was employed. After the Fmoc-L-Lys(Alloc)-OH coupling to PSMA-precursor, Fmoc deprotection, Fmoc-D-Asp-OtBu conjugation, Fmoc deprotection, second Fmoc-D-Asp-OtBu conjugation, Fmoc deprotection, third Fmoc-D-Asp-OtBu conjugation, Fmoc deprotection, p-(tolyl)butyric acid conjugation, Alloc deprotection and DOTA tris(tBu)-ester conjugation followed (step 11-22). PSMA-ALB-08 was obtained by agitation and subsequent cleavage from the resin with TFA:TIPS:H$_2$O mixture (step 23).

The Structural Formula of PSMA-ALB-08 is shown below:

with DCM2, three times with N,N-dimethylformamide (DMF1), and, finally, three times with DMF2. Selective removal of Fmoc-protecting group was realized by washing with the mixture of DMF and piperidine in a ratio of 1:1 once for 2 min and then once again for 5 min in order to get product (3). Alloc protected L-lysine was then washed three times with DMF1, three times with DMF2, three times with DCM1, and, finally, three times with DCM2.

In the next step, 10 equiv of tBu protected L-glutamate hydrochloride {(H-Glu(OtBu)-OtBu.HCl; Merck; Catalog number 8540960005), 3.0 mmol, 295.8 g/mol, [887 mg], i} were used for the generation of the isocyanate of the glutamyl moiety iii. An appropriate amount of tBu-protected

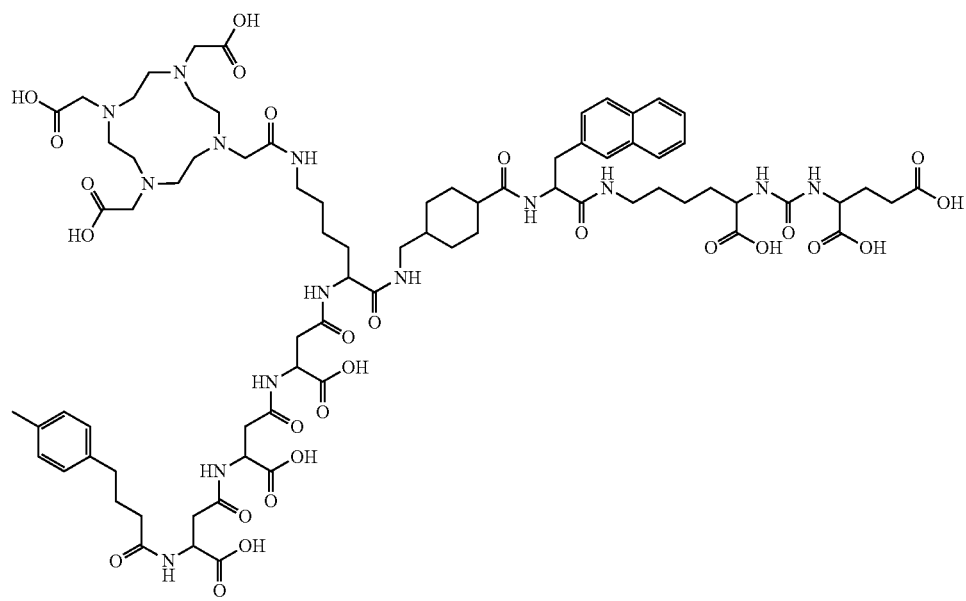

(PSMA-ALB-08)

1.1.2 Synthesis of Psma-Alb-03-08 (Details)
a) Synthesis of the Glutamate-Urea-Lysine Binding Entity 2-Chlorotrityl chloride resin {(2-CT-Resin; Merck; Catalog number 8550170005), 0.30 mmol, substitution capacity 1.63 mmol/g, 100-200 MESH, 1% DVB, total swelling volume in CH$_2$Cl$_2$>4.2 mL/g, [184 mg]} in 5 mL syringe with the filter and combi stopper was first agitated in anhydrous dichloromethane (DCM) for 45 min.

The 2-CT-resin was then washed three times with anhydrous DCM and followed by reaction with 1.2 equiv of Alloc (N-allyloxycarbonyl) as well as Fmoc (N-fluorenylmethoxycarbonyl) protected L-lysine {(Fmoc-Lys(Alloc)-OH; Merck; Catalog number 8521240005), 0.36 mmol, 452.50 g/mol, [163 mg], (1)} and 4.8 equiv of N,N-diisopropylethylamine {(DIPEA), 1.44 mmol, 129.24 g/mol, 0.742 g/ml, [251 µL]} in 3 mL of anhydrous DCM. The coupling of the first protected amino acid on the resin (2) proceeded over the course of 16 h with the gentle agitation. The L-lysine-immobilized resin (2) was washed three times with DCM1 and three times with DCM2. Unreacted chlorotrityl groups remaining on the resin were washed five times with the mixture of DCM, methanol (MeOH), and DIPEA in a ratio of 17:2:1 (20 mL).

Subsequently, the resin with Alloc and Fmoc protected L-lysine was washed three times with DCM1, three times L-glutamate was dissolved in 150 mL of DCM2 followed by, shortly afterwards, the addition of 3 mL of DIPEA.

This solution was added dropwise over 4 h to a flask with 1 mmol of ice-cooled bis(trichloromethyl)carbonate {(BTC; Sigma; Catalog number 15217-10G), 296.75 g/mol, [297 mg], ii} in 5 mL of dry DCM.

The L-lysine-immobilized resin with one free NH$_2$-group (3) was added afterwards in one portion to the solution of the isocyanate of the glutamyl moiety iii and stirred for 16 h in order to obtain resin-immobilized bis(tBu)-Glu-urea-Lys (Alloc) (4).

The obtained product (4) coated on the resin was filtered off and washed three times with DCM1 and three times with DCM2. Cleavage of Alloc-protecting group was realized by reaction with 0.15 equiv of TPP Pd {[tetrakis(triphenylphosphine)palladium(0); Sigma; Catalog number 216666-1G], 0.045 mmol, 1155.56 g/mol, [105 mg]} in the presence of 15 equiv of morpholine {4.5 mmol, 87.12 g/mol, 0.999 g/mL, [392 µL]} in 3 mL of anhydrous DCM. The amount of Pd and morpholine was divided into 2 portions and reacted successively by shaking each for 1 h. The reaction was performed in the dark using aluminum foil.

The resin was then washed three times with DCM1, three times with DCM2, three times with DMF1, and, finally, three times with DMF2. To remove residuals of the palladium, the resin was additionally washed ten times with 1%

DIPEA in DMF (300 μL DIPEA in 30 mL DMF2) and subsequently washed ten times for 5 min with a solution of cupral {(sodium diethyldithiocarbamate trihydrate; Sigma; Catalog number D3506-100G), 225.31 g/mol} in DMF2 at the concentration of 15 mg/mL (450 mg cupral in 30 mL DMF2).

The resin-immobilized and bis(tBu)-protected Glu-urea-Lys (5) was then washed three times with DMF1, three times with DMF2, three times with DCM1, three times with DCM2, and, finally, three times with diethylether (Et₂O) and dried under vacuum.

Such prepared Prostate-specific Membrane Antigen (PSMA) binding entity (5) was used for the next reaction in order to synthesize all seven compounds (PSMA-ALB-01/03/04/05/06/07/08).

The outline of the whole previous synthesis of the bis(tBu)-protected Glu-urea-Lys pharmacophore is summarized in Scheme 1.1.

Scheme 1.1: Synthesis of the Glutamate-Urea-Lysine Binding Entity for PSMA-ALB-01/03/04/05/06/07/08.

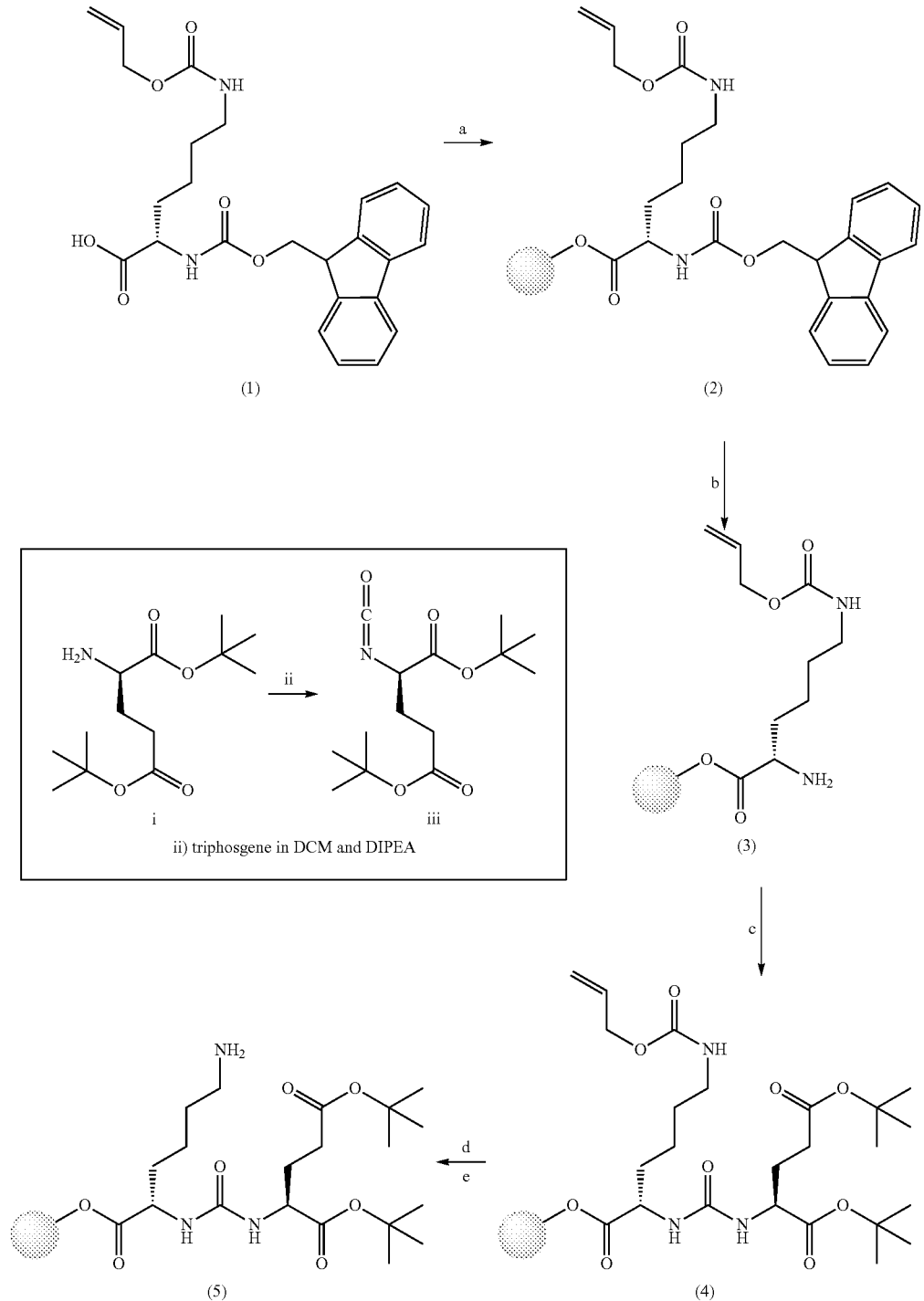

a) 2-CT-Resin in DCM and DIPEA; b) 50% piperidine in DMF; c) iii in DCM; d) TPP palladium in DCM and morpholine; e) 1% DIPEA in DMF, diethyldithiocarbamate in DMF The resin-immobilized and bis(tBu)-protected binding entity (5) was first agitated in anhydrous DCM for 45 min. Pre-swollen pharmacophore was washed three times with DCM2, three times with DMF1, and three times with DMF2.

b) Synthesis of the Linker Area

Relative to the resin (0.1 mmol), 4 equiv of Fmoc protected 2-naphthyl-L-alanine {(Fmoc-2Nal-OH; Bachem; Catalog number B-2100), 0.40 mmol, 437.50 g/mol, [175.0 mg]} corresponding to the first building block of the linker area were activated with 3.96 equiv of HBTU {(O-(benzotriazol-1-yl)-N,N,N',N'-tetramethyluronium hexafluorophosphate; Sigma; Catalog number 12804-25G-F), 0.39 mmol, 379.24 g/mol, [147.9 mg]} in the presence of 4 equiv of DIPEA {0.40 mmol, 129.24 g/mol, 0.742 g/mL, [71 µL]} in anhydrous DMF.

Two min after the addition of DIPEA, the solution was added to the DMF pre-swollen immobilized bis(tBu)-protected pharmacophore (5) and agitated for 1 h.

Subsequently, the resin with bis(tBu)-protected Glu-urea-Lys and Fmoc protected 2-naphthyl-L-alanine (6) was washed three times with DMF1 and three times with DMF2. Selective removal of the Fmoc-protecting group from compound (6) was realized by washing with the mixture of DMF and piperidine in a ratio of 1:1 once for 2 min and then once again for 5 min in order to obtain products (7).

In the next step, 4 equiv of the second building block which correspond to azidocyclohexanecarboxylic acid {(N3-1,4-trans-CHC—OH; Iris Biotech; Catalog number HAA2235.0001), 0.40 mmol, 169.18 g/mol, [67.7 mg]} for PSMA-ALB-01 or to Fmoc protected tranexamic acid {(trans-4-(Fmoc-aminomethyl)cyclohexane-carboxylic acid; Sigma; Catalog number 58446-5G-F), 0.40 mmol, 379.45 g/mol, [151.8 mg]} for PSMA-ALB-03/04/05/06/07/08 were activated with 3.96 equiv of HBTU {(Sigma; Catalog number 12804-25G-F), 0.39 mmol, 379.24 g/mol, [147.9 mg]} in the presence of 4 equiv of DIPEA {0.40 mmol, 129.24 g/mol, 0.742 g/mL, [71 µL]} in anhydrous DMF. Two min after the addition of DIPEA, the solution was added to the DMF pre-swollen compound (7) and agitated for 1 hour.

Subsequently, the resin with bis(tBu)-protected Glu-urea-Lys-2-naphthyl-L-alanine and azidocyclohexanecarboxylic acid (8A) was washed three times with DMF1, three times with DMF2, three times with DCM1, three times with DCM2, and, finally, three times with Et₂O and dried under vacuum. Final PSMA-precursor (9A) was obtained by the agitation and subsequent cleavage from the resin within 2 h with the mixture consisting of trifluoroacetic acid (TFA), triisopropylsilane (TIPS) and H₂O in a ratio of 95:2.5:2.5. TFA was evaporated, crude product dissolved in acetonitrile (ACN) and water in a ratio of 1:1 and purified via RP-HPLC.

Additionally, the resin with bis(tBu)-protected Glu-urea-Lys-2-naphthyl-L-alanine and Fmoc protected tranexamic acid (8B) was washed three times with DMF1 and three times with DMF2. Selective removal of Fmoc-protecting group from the compound (8B) was realized by washing with the mixture of DMF and piperidine in a ratio of 1:1 once for 2 min and then once again for 5 min in order to obtain products (9B).

The outline of the whole previous synthesis of the linker area is summarized in Scheme 1.2.

Scheme 1.2: Synthesis of the Linker Area, Precursor for PSMA-ALB-03/04/05/06/07/08.

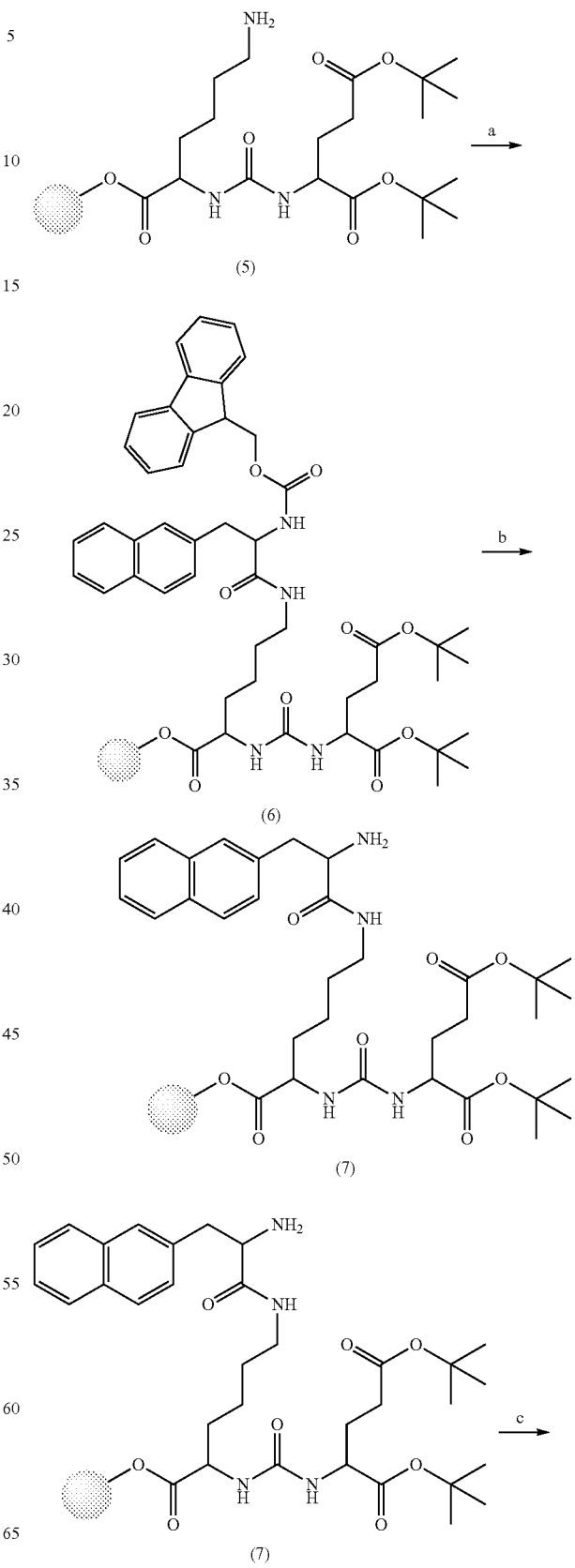

71

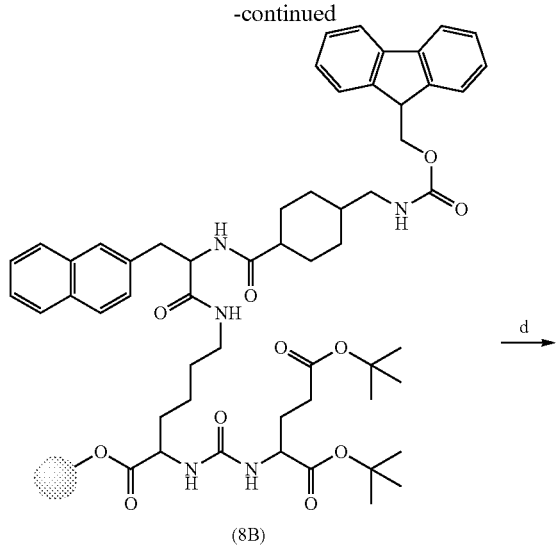

(8B)

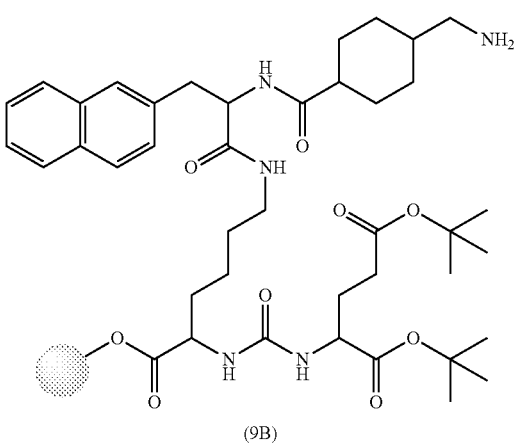

(9B)

a) Fmoc-2-NaI—OH, HBTU, DMF, DIPEA; b) 50% piperidine, DMF;
c) Fmoc-AMCH, HBTU in DMF, DIPEA; d) 50% piperdine, DMF c) Synthesis of PSMA-ALB-03

Relative to the lysine-coated PSMA precursor (9B), 4 equiv of Fmoc as well as Alloc protected L-lysine {(Fmoc-Lys(Alloc)-OH; Merck; Catalog number 8521240005), 0.40 mmol, 452.50 g/mol, [181 mg]} was activated with 3.96 equiv of HBTU {(Sigma; Catalog number 12804-25G-F), 0.396 mmol, 379.24 g/mol, [149 mg]} in the presence of 4 equiv of DIPEA {0.40 mmol, 129.24 g/mol, 0.742 g/mL, [70 μL]} in anhydrous DMF. Two min after the addition of DIPEA, the solution was added to the DMF pre-swollen immobilized bis(tBu)-protected PSMA precursor (9B) and agitated for 1 h.

Selective removal of Fmoc-protecting group from the resulting compound (10B) was realized by washing with the mixture of DMF and piperidine in a ratio of 1:1 once for 2 min and then once again for 5 min in order to obtain the product (11B).

The conjugation of the chelator to the resin-immobilized compound (11B) was performed with 2 equiv of DOTA-tris (t-Bu)ester {([2-(4,7,10-tris(2-(t-butoxy)-2-oxoethyl)-1,4,7,10-tetraazacyclododecan-1-yl)acetic acid]; CheMatech; Catalog number 137076-54-1), 0.20 mmol, 572.73 g/mol [115 mg]}. The chelator building block was activated with 1.98 equiv of HBTU {(Sigma; Catalog number 12804-25G-F), 0.198 mmol, 379.24 g/mol, [75 mg]} in the presence of 4 equiv of DIPEA {0.40 mmol, 129.24 g/mol, 0.742 g/mL, [70 μL]} in anhydrous DMF. Two min after the addition of DIPEA, the solution was added to the resin-immobilized and the DMF pre-swollen compound (11B). The coupling of the DOTA chelator proceeded over the course of 2 h with gentle agitation. The resulting compound (12B) was then washed three times with DMF1, three times with DMF2, three times with DCM1, and, finally, three times with DCM2.

Cleavage of Alloc-protecting group from the compound (12B) was realized by reaction with 0.03 equiv of TPP Pd {(Sigma; Catalog number 216666-1G), 0.03 mmol, 1155.56 g/mol, [35 mg]} in the presence of 30 equiv of morpholine {3.0 mmol, 87.12 g/mol, 0.999 g/mL, [262 μL]} in 3 mL of anhydrous DCM. The reaction was performed for 2 hours in the dark using aluminum foil.

The resin was then washed three times with DCM1, three times with DCM2, three times with DMF1, and, finally, three times with DMF2. To remove residuals of the palladium, the resin was additionally washed ten times with 1% DIPEA in DMF (300 μL DIPEA in 30 mL DMF2) and subsequently washed ten times for 5 min with a solution of cupral {(Sigma; Catalog number D3506-100G), 225.31 g/mol} in DMF2 at the concentration of 15 mg/mL (450 mg cupral in 30 mL DMF2). The resulting compound (13B) was then washed three times with DMF1 and three times with DMF2.

Finally, for the coupling of the albumin-binding moiety, 4 equiv of iodophenyl-butyric acid {([4-(p-iodophenyl)butyric acid]; Sigma; I5634-5G), 0.40 mmol, 290.10 g/mol, [116 mg]} was activated with 3.96 equiv of HBTU {(Sigma; Catalog number 12804-25G-F), 0.396 mmol, 379.24 g/mol, [149 mg]} in the presence of 4 equiv of DIPEA {0.40 mmol, 129.24 g/mol, 0.742 g/mL, [70 μL]} in anhydrous DMF. Two min after the addition of DIPEA, the solution was added to the resin-immobilized and DMF pre-swollen product (13B) and agitated for 1 h.

The resulting compound (14B) was then washed three times with DMF1, three times with DMF2, three times with DCM1, three times with DCM2, and, finally, three times with Et₂O and dried under vacuum.

The final compound PSMA-ALB-03 was obtained by agitation and subsequent cleavage from the resin within 2 h with a mixture consisting of TFA, TIPS and H₂O in a ratio of 95:2.5:2.5. TFA was evaporated, crude product dissolved in ACN and water in a ratio of 1:1 and purified via RP-HPLC.

The outline of the above described synthesis is summarized in Scheme 1.3.

Scheme 1.3: Coupling of the Albumin Binder, DOTA chelator and PSMA Precursor for PSMA-ALB-03.
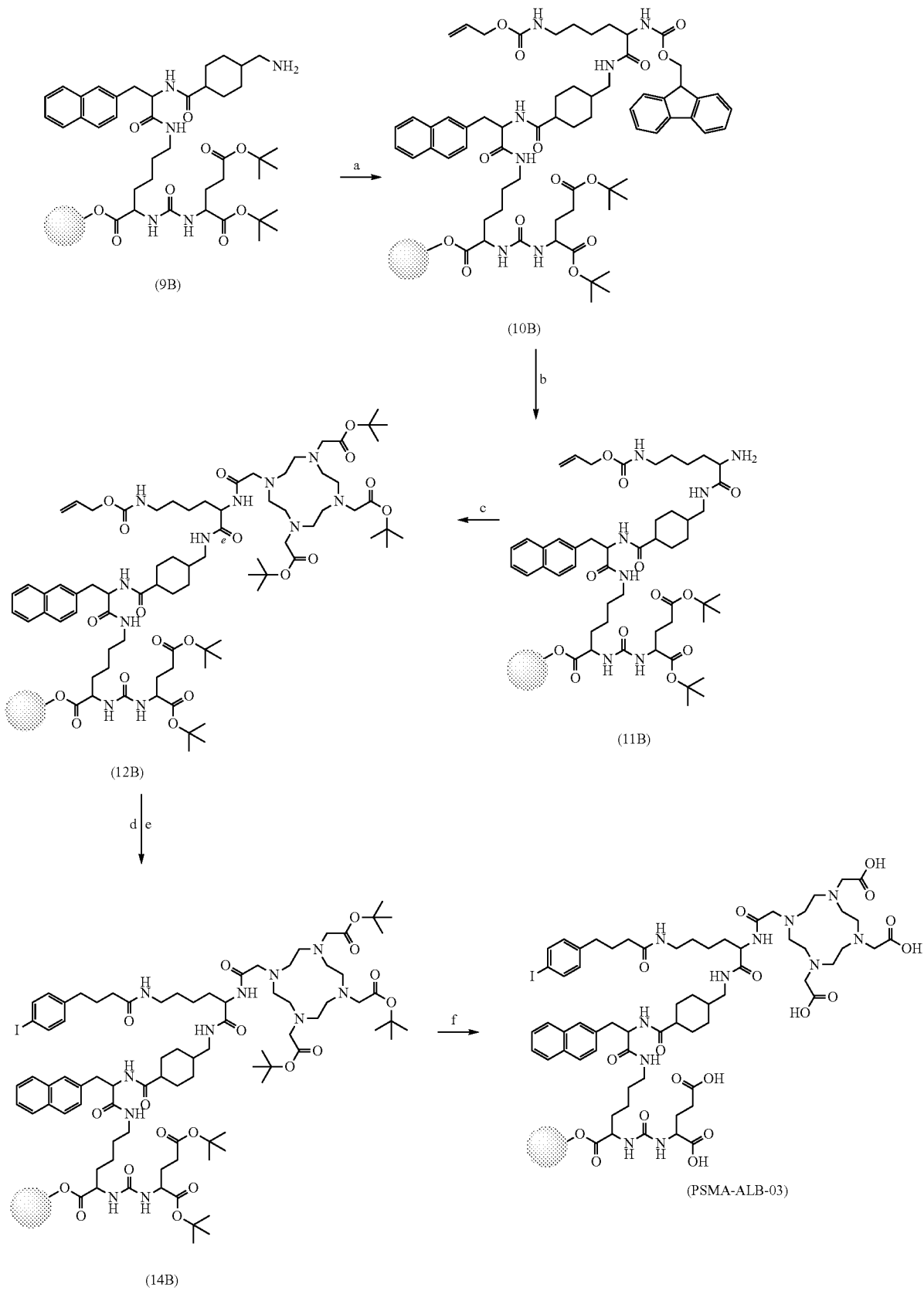
a) Fmoc-Lys(Alloc)—OH, HBTU, DMF, DIPEA; b) 50% piperidine, DMF; c) DOTA tris(tBu)ester, HBTU, DIPEA, DMF; d) Pd catalysator, morpholine, DCM; e) iodophenyl butyric acid, HBTU, DIPEA; f) TFA, TIPS, $H_2O$ 95:2.5:2.5;

d) Synthesis of PSMA-ALB-04

Relative to the lysine-coated PSMA precursor (9B), 4 equiv of Dde as well as Fmoc protected L-lysine {(Dde-Lys(Fmoc)-OH; Merck; Catalog number 8540000001), 0.40 mmol, 532.63 g/mol, [213 mg]} was activated with 3.96 equiv of HBTU {(Sigma; Catalog number 12804-25G-F), 0.396 mmol, 379.24 g/mol, [149 mg]} in the presence of 4 equiv of DIPEA {0.40 mmol, 129.24 g/mol, 0.742 g/mL, [70 µL]} in anhydrous DMF. Two min after the addition of DIPEA, the solution was added to the DMF pre-swollen immobilized bis(tBu)-protected PSMA precursor (9B) and agitated for 1 h.

The resulting compound (10B) was then washed three times with DMF1 and three times with DMF2. Selective removal of Fmoc-protecting group from the resulting compound (10B) was realized by washing with the mixture of DMF and piperidine in a ratio of 1:1 once for 2 min and then once again for 5 min in order to obtain the product (11B).

The conjugation of the chelator to the resin-immobilized compound (11B) was performed with 3 equiv of DOTA-tris (t-Bu)ester {([2-(4,7,10-tris(2-(t-butoxy)-2-oxoethyl)-1,4,7,10-tetraazacyclododecan-1-yl)acetic acid]; CheMatech; Catalog number 137076-54-1), 0.30 mmol, 572.73 g/mol [171 mg]}. The chelator building block was activated with 2.97 equiv of HBTU {(Sigma; Catalog number 12804-25G-F), 0.297 mmol, 379.24 g/mol, [112 mg]} in the presence of 4 equiv of DIPEA {0.40 mmol, 129.24 g/mol, 0.742 g/mL, [70 µL])} in anhydrous DMF. Two min after the addition of DIPEA, the solution was added to the resin-immobilized and the DMF pre-swollen compound (11B). The coupling of the DOTA chelator proceeded over the course of 2 h with gentle agitation.

The resulting compound (12B) was then washed three times with DMF1 and three times with DMF2. Selective removal of Dde-protecting group from the resulting compound (12B) was realized by washing with the mixture of 2% hydrazine in DMF twice for 5 min and then once again for 10 min in order to obtain the product (13B).

Relative to the resin-coated product (13B), 2 equiv of disuccinimidyl suberate {([suberic acid bis(N-hydroxysuccinimide ester)]; Sigma; 68528-80-3), 0.20 mmol, 368.34 g/mol, [74 mg]} was activated with 1.98 equiv of HBTU {(Sigma; Catalog number 12804-25G-F), 0.198 mmol, 379.24 g/mol, [73 mg]} in the presence of 4 equiv of DIPEA {0.40 mmol, 129.24 g/mol, 0.742 g/mL, [70 µL]} in anhydrous DMF. Two min after the addition of DIPEA, the solution was added to the resin-immobilized and DMF pre-swollen product (13B) and agitated for 1 h.

The resulting compound (14B) was then washed three times with DMF1 and three times with DMF2.

The outline of the above described synthesis is summarized in Scheme 1.4.

Scheme 1.4: Coupling of the DOTA chelator, PSMA Precursor and active ester for PSMA-ALB-04.

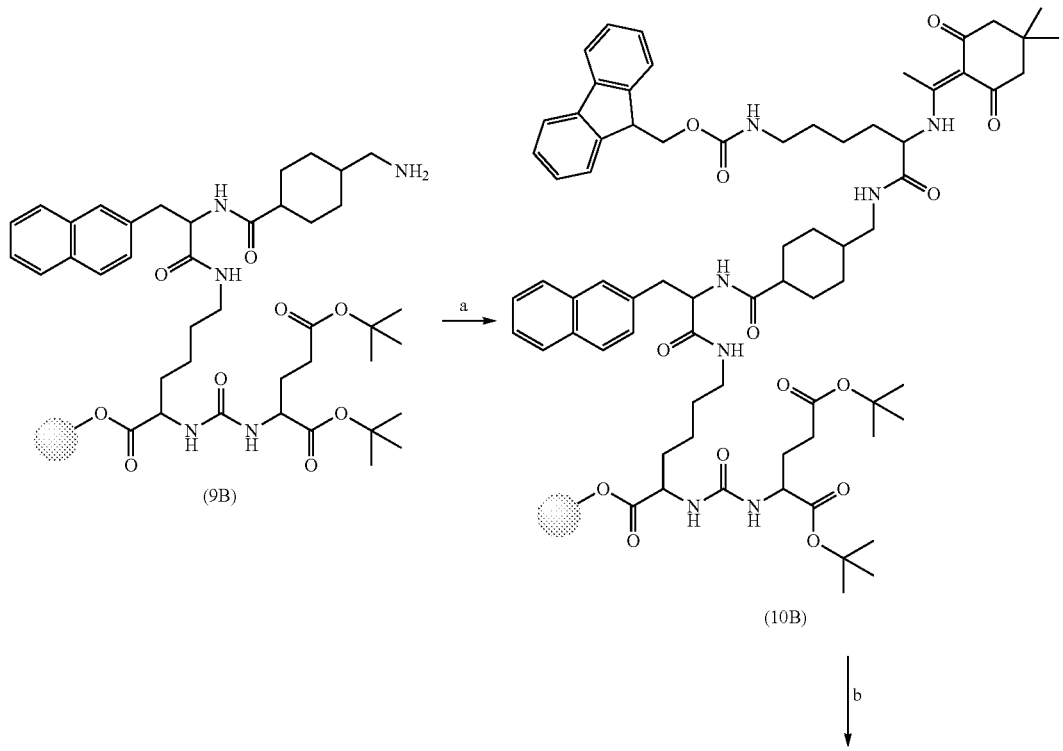

-continued
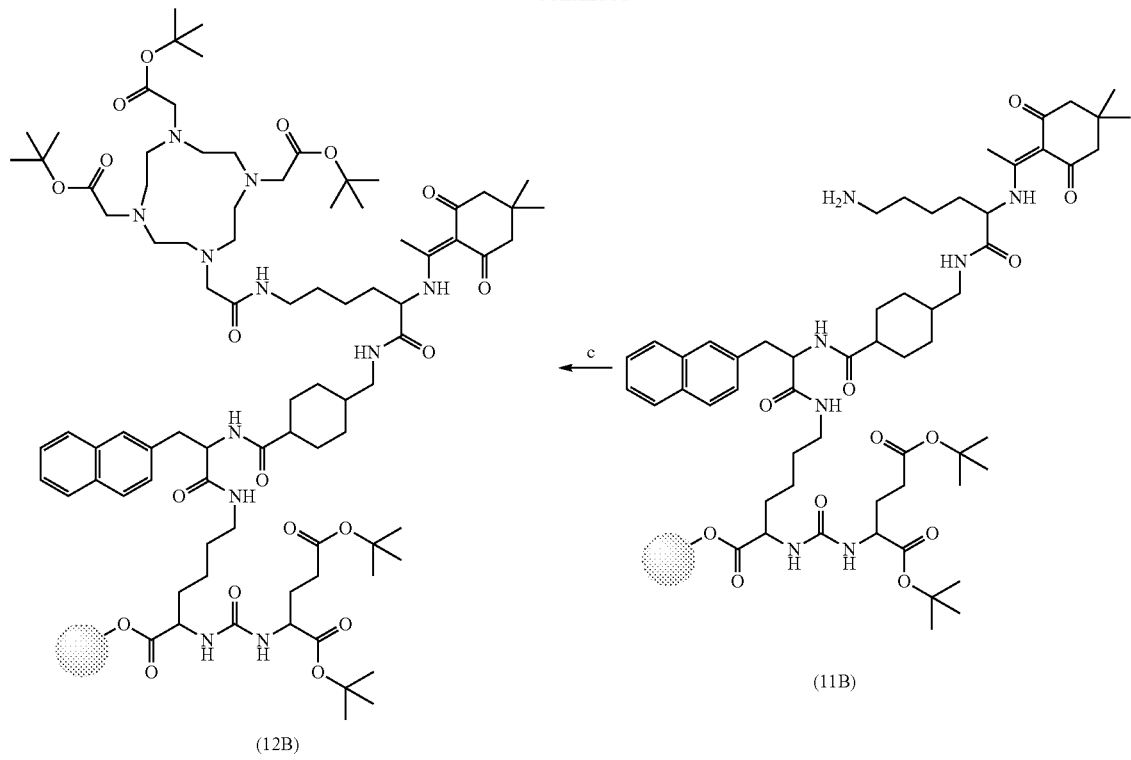
(11B)
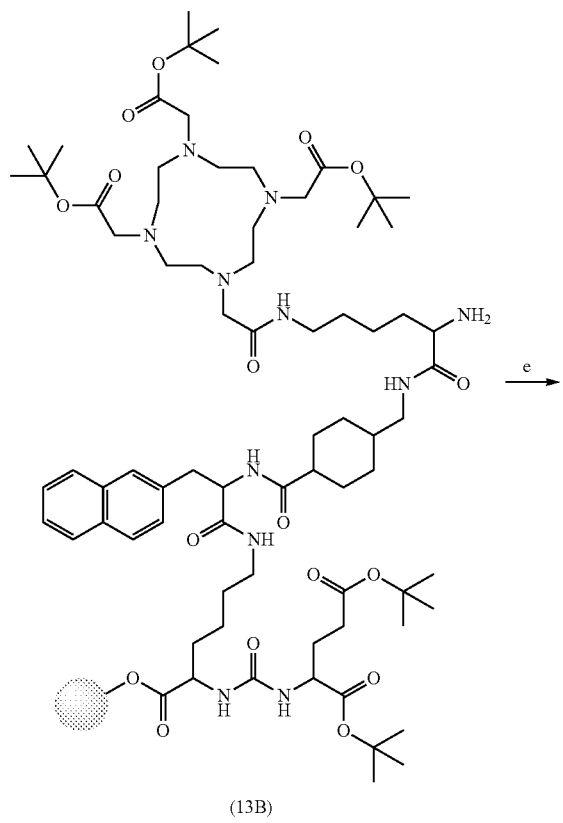
(12B)
(13B)

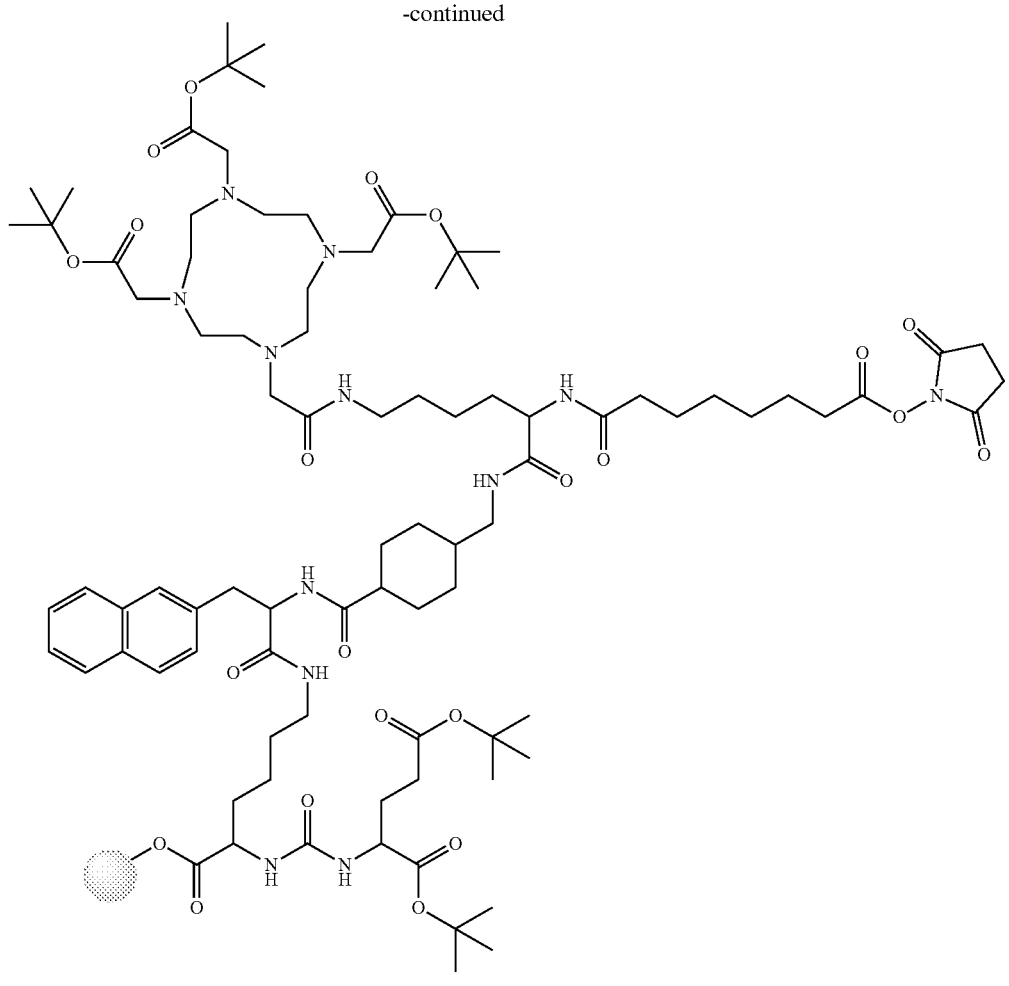

(14B)

a) Dde-Lys(Fmoc)—OH, HBTU, DMF, DIPEA; b) 50% piperidine, DMF; c) DOTA tris(tBu)ester, HBTU, DIPEA, DMF; d) 2% hydrazine, DMF; e) disuccinimidly suberate, DMF, DIPEA;

The synthesis was accompanied by the parallel preparation of the albumin-binding precursor starting from the 2-chlorotrityl chloride resin {(2-CT-Resin; Merck; Catalog number 8550170005), 0.20 mmol, substitution capacity 1.63 mmol/g, 100-200 MESH, 1% DVB, total swelling volume in $CH_2Cl_2$>4.2 mL/g, [123 mg]} in 5 mL syringe with the filter and combi stopper which was first agitated in anhydrous dichloromethane (DCM) for 45 min.

The 2-CT resin was then washed three times with anhydrous DCM and followed by reaction with 1.2 equiv of Dde as well as Fmoc protected L-lysine {(Dde-Lys(Fmoc)-OH; Bachem; Catalog number E-3385.0001), 0.24 mmol, 532.64 g/mol, [128 mg] (15B)} and 4.8 equiv of DIPEA {0.96 mmol, 129.24 g/mol, 0.742 g/mL, [167 µL]} in 3 mL of anhydrous DCM.

The coupling of the first protected amino acid on the resin (16B) proceeded over the course of 16 h with gentle agitation.

The L-lysine-immobilized resin (16B) was washed three times with DCM1 and three times with DCM2. Unreacted chlorotrityl groups remaining on the resin were washed five times with the mixture of DCM, MeOH, and DIPEA in a ratio of 17:2:1 (20 mL).

Subsequently, the resin with Dde and Fmoc protected L-lysine was washed three times with DCM1, three times with DCM2, three times with DMF1, and, finally, three times with DMF2. Selective removal of Fmoc-protecting group was realized by washing with the mixture of DMF and piperidine in a ratio of 1:1 once for 2 min and then once again for 5 min in order to get product (17B).

Dde protected L-lysine was then washed three times with DMF1 and three times with DMF2, three times with DCM1, three times with DCM2 and, finally, three times with $Et_2O$ and dried under vacuum.

Such prepared resin-coated Dde protected L-lysine (17B) was split into two portions and one of them was used for the next reaction. This resin-coated product was agitated in anhydrous DCM for 45 min and subsequently washed three times with DMF and three times with DMF2.

Relative to the lysine-coated resin, 4 equiv of iodophenyl-butyric acid {([4-(p-iodophenyl)butyric acid]; Sigma;

I5634-5G), 0.40 mmol, 290.10 g/mol, [116 mg]} was activated with 3.96 equiv of HBTU {(Sigma; Catalog number 12804-25G-F), 0.396 mmol, 379.24 g/mol, [149 mg]} in the presence of 4 equiv of DIPEA {0.40 mmol, 129.24 g/mol, 0.742 g/mL, [70 μL]} in anhydrous DMF. Two min after the addition of DIPEA, the solution was added to the resin-immobilized and DMF pre-swollen product (17B) and agitated for 1 h.

The resin with Dde protected L-lysine and iodophenylbutyric acid (18B) was washed three times with DMF1 and three times with DMF2. Selective removal of Dde-protecting group from the resulting compound (18B) was realized by washing with the mixture of 2% hydrazine in DMF twice for 5 min and then once again for 10 min in order to obtain the product (19B).

The albumin-targeting moiety (20B) was obtained by agitation and subsequent cleavage from the resin within 2 h with a mixture consisting of 5% TFA in DCM. The mixture of solvents from the product was evaporated, crude product dissolved in ACN and water in a ratio of 1:1 and purified via RP-HPLC.

The outline of the above described synthesis is summarized in Scheme 1.5.

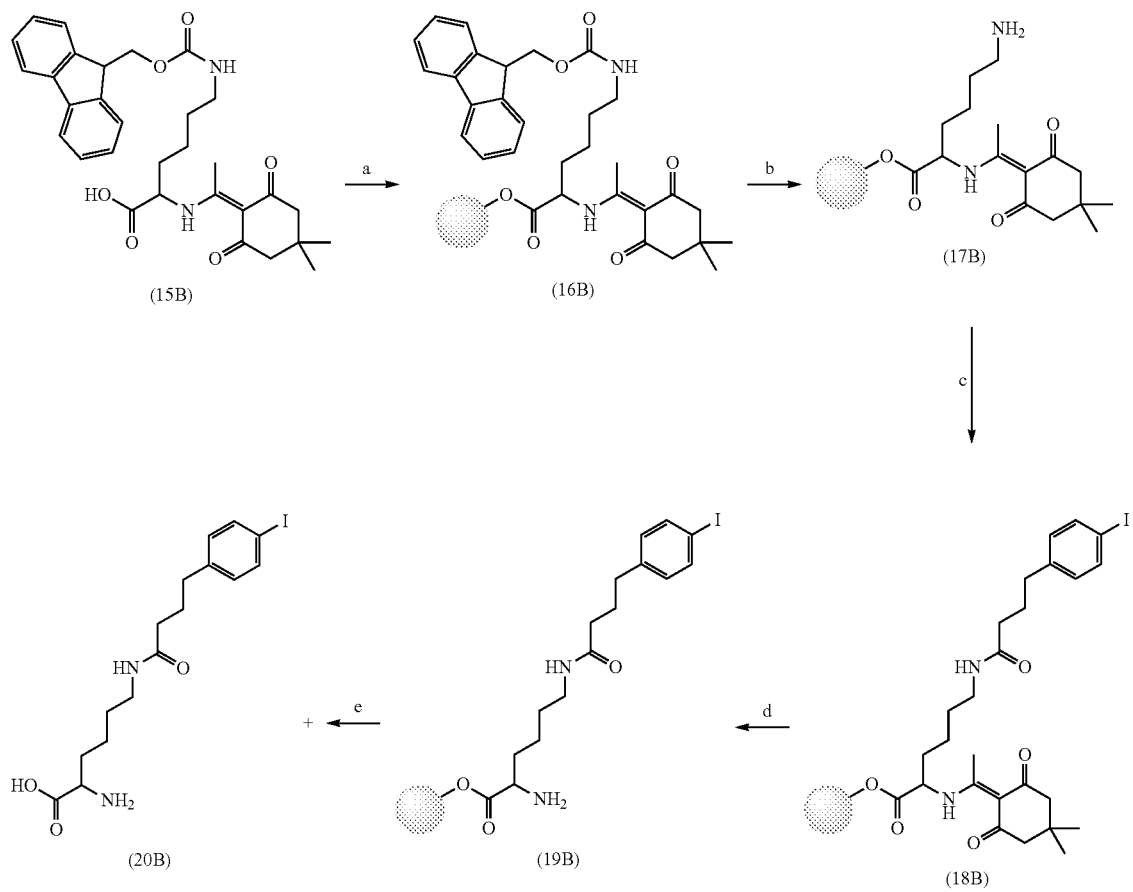

Scheme 1.5: Coupling of the Albumin Binder for PSMA-ALB-04.

a) 2-CT-Resin in DCM and DIPEA; b) 50% piperidine in DMF; c) iodophenylbutyric acid, HBTU in DMF and DIPEA; d) 2% hydrazine in DMF; e) 5% TFA in DCM Finally, the conjugation of 3 equiv of purified albumin-targeting moiety (20B) to the resin immobilized product (14B) was performed. Product (20B) was dissolved in dry DMF and 100 μL of DIPEA was added. Two min after the addition of DIPEA, the solution (20B) was added to the resin-immobilized and DMF pre-swollen product (14B) and agitated for 1 h.

The resulting compound (21B) was then washed three times with DMF1, three times with DMF2, three times with DCM1, three times with DCM2, and, finally, three times with Et₂O and dried under vacuum.

The final compound PSMA-ALB-04 was obtained by agitation and subsequent cleavage from the resin within 2 h with a mixture consisting of TFA, TIPS and H₂O in a ratio of 95:2.5:2.5. TFA was evaporated, crude product dissolved in ACN and water in a ratio of 1:1 and purified via RP-HPLC.

The outline of the above described synthesis is summarized in Scheme 1.6.

e) Synthesis of PSMA-ALB-05

Relative to the lysine-coated PSMA precursor (9B), 4 equiv of Fmoc as well as Alloc protected L-lysine {(Fmoc-Lys(Alloc)-OH; Merck; Catalog number 8521240005), 0.40 mmol, 452.50 g/mol, [181 mg]) was activated with 3.96 equiv of HBTU {(Sigma; Catalog number 12804-25G-F), 0.396 mmol, 379.24 g/mol, [149 mg]} in the presence of 4

Scheme 1.6: Coupling of the Albumin Binder and DOTA-conjugated PSMA precursore for PSMA-ALB-04.

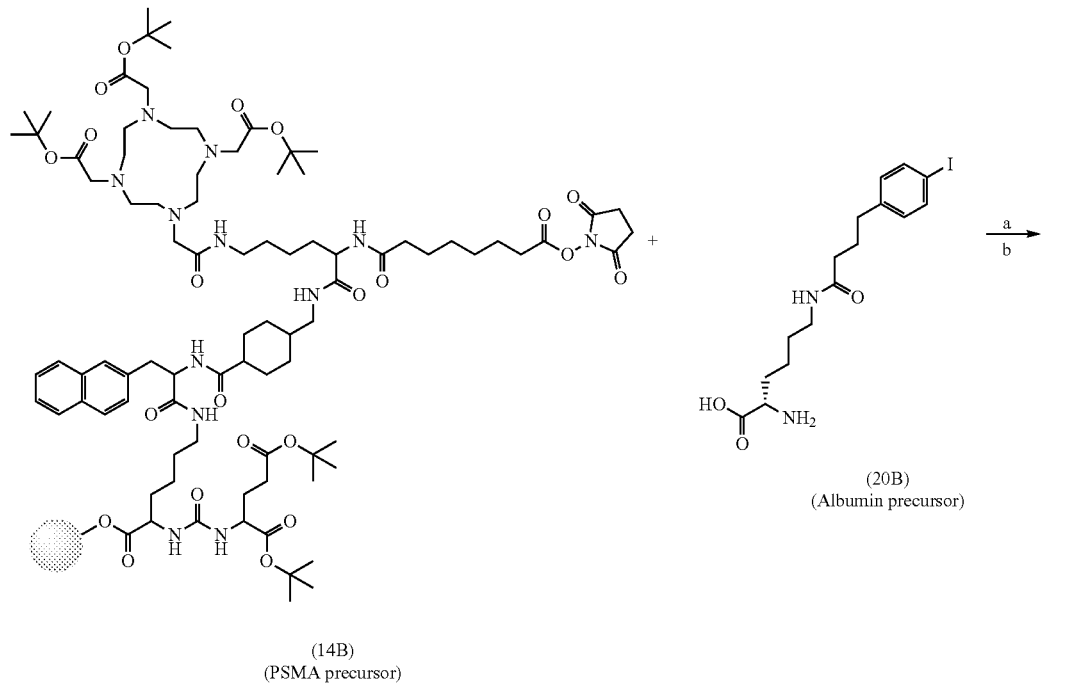

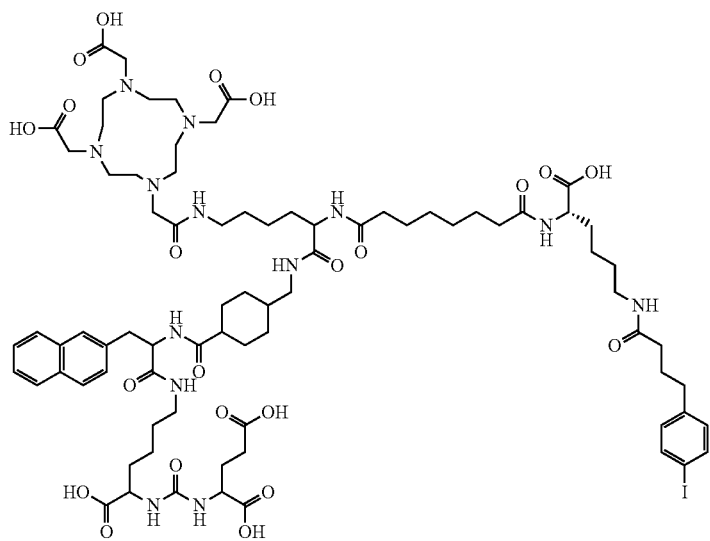

a) DMF, DIPEA; b) TFA;:TIPS:H₂O;

equiv of DIPEA (0.40 mmol, 129.24 g/mol, 0.742 g/mL, [70 µL]} in anhydrous DMF. Two min after the addition of DIPEA, the solution was added to the DMF pre-swollen immobilized bis(tBu)-protected PSMA precursor (9B) and agitated for 1 h.

The resulting compound (10B) was then washed three times with DMF1 and three times with DMF2. Selective removal of Fmoc-protecting group from the resulting compound (10B) was realized by washing with the mixture of DMF and piperidine in a ratio of 1:1 once for 2 min and then once again for 5 min in order to obtain the product (11B).

Relative to the lysine-coated PSMA precursor (11B), 3 equiv of Fmoc as well as tBu protected D-aspartate {(Fmoc-D-Asp-OtBu; Merck; Catalog number 8521440001), 0.30 mmol, 411.45 g/mol, [123 mg]} was activated with 2.97 equiv of HBTU {(Sigma; Catalog number 12804-25G-F), 0.297 mmol, 379.24 g/mol, [112 mg]} in the presence of 4 equiv of DIPEA {0.40 mmol, 129.24 g/mol, 0.742 g/mL, [70 µL]} in anhydrous DMF. Two min after the addition of DIPEA, the solution was added to the DMF pre-swollen immobilized bis(tBu)-protected PSMA precursor (11B) and agitated for 1 h.

The resulting compound (12B) was then washed three times with DMF1 and three times with DMF2. Selective removal of Fmoc-protecting group from the resulting compound (12B) was realized by washing with the mixture of DMF and piperidine in a ratio of 1:1 once for 2 min and then once again for 5 min in order to obtain the product (13B).

Relative to the lysine and aspartate-coated PSMA precursor (13B), 3 equiv of Fmoc as well as tBu protected D-aspartate {(Fmoc-D-Asp-OtBu; Merck; Catalog number 8521440001), 0.30 mmol, 411.45 g/mol, [123 mg]} was activated with 2.97 equiv of HBTU {(Sigma; Catalog number 12804-25G-F), 0.297 mmol, 379.24 g/mol, [112 mg]} in the presence of 4 equiv of DIPEA {0.40 mmol, 129.24 g/mol, 0.742 g/mL, [70 µL]} in anhydrous DMF. Two min after the addition of DIPEA, the solution was added to the DMF pre-swollen immobilized bis(tBu)-protected PSMA precursor (13B) and agitated for 1 h.

The resulting compound (14B) was then washed three times with DMF1 and three times with DMF2. Selective removal of Fmoc-protecting group from the resulting compound (148) was realized by washing with the mixture of DMF and piperidine in a ratio of 1:1 once for 2 min and then once again for 5 min in order to obtain the product (15B).

Relative to the resin-coated product (15B), 4 equiv of iodophenyl-butyric acid {([4-(p-iodophenyl)butyric acid]; Sigma; 15634-5G), 0.40 mmol, 290.10 g/mol, [116 mg]} was activated with 3.96 equiv of HBTU {(Sigma; Catalog number 12804-25G-F), 0.396 mmol, 379.24 g/mol, [149 mg]} in the presence of 4 equiv of DIPEA {0.40 mmol, 129.24 g/mol, 0.742 g/mL, [70 µL]} in anhydrous DMF. Two min after the addition of DIPEA, the solution was added to the resin-immobilized and DMF pre-swollen product (15B) and agitated for 1 h.

The resulting compound (16B) was then washed three times with DMF1, three times with DMF2, three times with DCM1, and, finally, three times with DCM2.

Cleavage of Alloc-protecting group from the compound (16B) was realized by reaction with 0.03 equiv of TPP Pd {(Sigma; Catalog number 216666-1G), 0.03 mmol, 1155.56 g/mol, [35 mg]} in the presence of 30 equiv of morpholine {3.0 mmol, 87.12 g/mol, 0.999 g/mL, [262 µL]} in 3 mL of anhydrous DCM. The reaction was performed for 2 hours in the dark using aluminum foil.

The resin was then washed three times with DCM1, three times with DCM2, three times with DMF1, and, finally, three times with DMF2. To remove residuals of the palladium, the resin was additionally washed ten times with 1% DIPEA in DMF (300 µL DIPEA in 30 mL DMF2) and subsequently washed ten times for 5 min with a solution of cupral {(Sigma; Catalog number D3506-100G), 225.31 g/mol} in DMF2 at the concentration of 15 mg/mL (450 mg cupral in 30 mL DMF2). The resulting compound (17B) was then washed three times with DMF1 and three times with DMF2.

The conjugation of the chelator to the resin-immobilized compound (17B) was performed with 3 equiv of DOTA-tris (t-Bu)ester {([2-(4,7,10-tris(2-(t-butoxy)-2-oxoethyl)-1,4,7,10-tetraazacyclododecan-1-yl)acetic acid]; CheMatech; Catalog number 137076-54-1), 0.30 mmol, 572.73 g/mol [171 mg]}. The chelator building block was activated with 2.97 equiv of HBTU {(Sigma; Catalog number 12804-25G-F), 0.297 mmol, 379.24 g/mol, [112 mg]} in the presence of 4 equiv of DIPEA {0.40 mmol, 129.24 g/mol, 0.742 g/mL, [70 µL]} in anhydrous DMF. Two min after the addition of DIPEA, the solution was added to the resin-immobilized and the DMF pre-swollen compound (17B). The coupling of the DOTA chelator proceeded over the course of 2 h with gentle agitation.

Such product (18B) washed three times with DMF1 and three times with DMF2, three times with DCM1, three times with DCM2 and, finally, three times with $Et_2O$ and dried under vacuum.

The final compound PSMA-ALB-05 was obtained by agitation and subsequent cleavage from the resin within 2 h with a mixture consisting of TFA, TIPS and $H_2O$ in a ratio of 95:2.5:2.5. TFA was evaporated, crude product dissolved in ACN and water in a ratio of 1:1 and purified via RP-HPLC.

The outline of the above described synthesis is summarized in two parts of Scheme 1.7.

Scheme 1.7: Coupling of the Albumin Binding-moiety, DOTA Chelator and PSMA Precursor for PSMA-ALB-05.
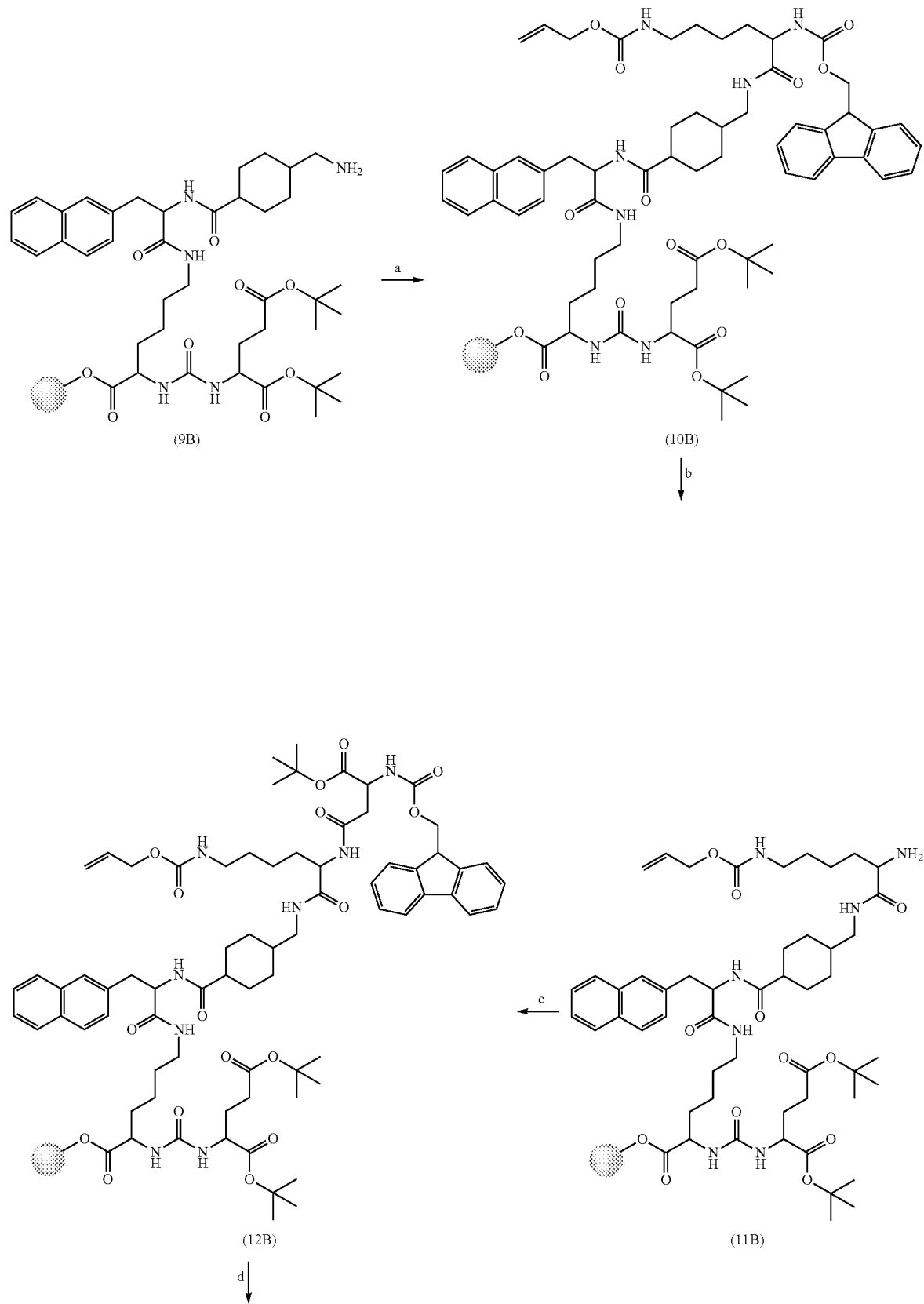

89
90
-continued
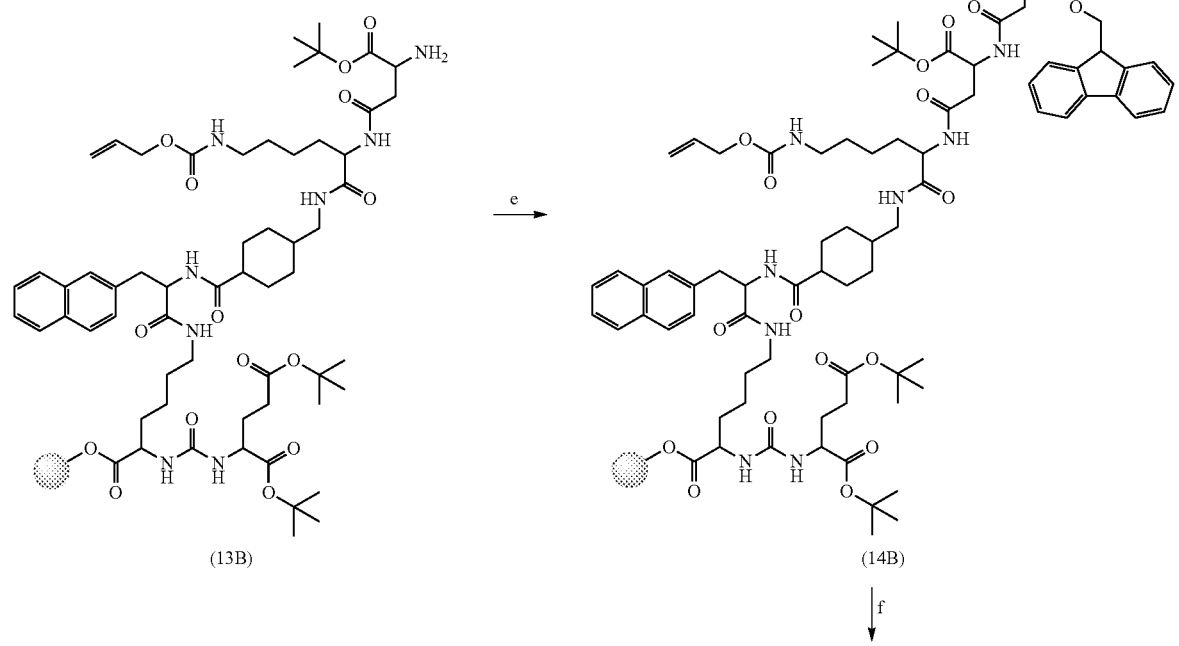
(13B)
(14B)
↓ e
↓ f
(16B)
(15B)
← g
a) Fmoc-Lys(Alloc)-OH, HBTU, DMF, DIPEA; b) 50% piperidine, DMF; c) Fmoc-D-Asp-OtBu, HBTU, DIPEA, DMF; d) 50% piperidine, DMF; e) Fmoc-D-Asp-OtBu, HBTU, DIPEA, DMF; f) 50% piperidine, DMF; g) iodophenyl butyric acid, HBTU, DMF, DIPEA;
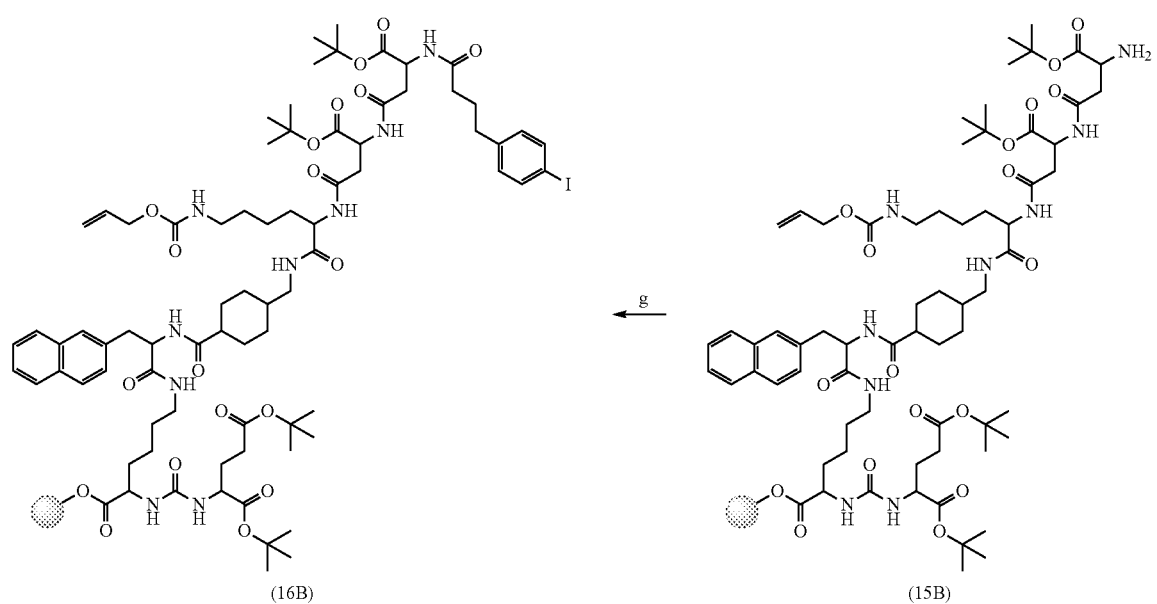

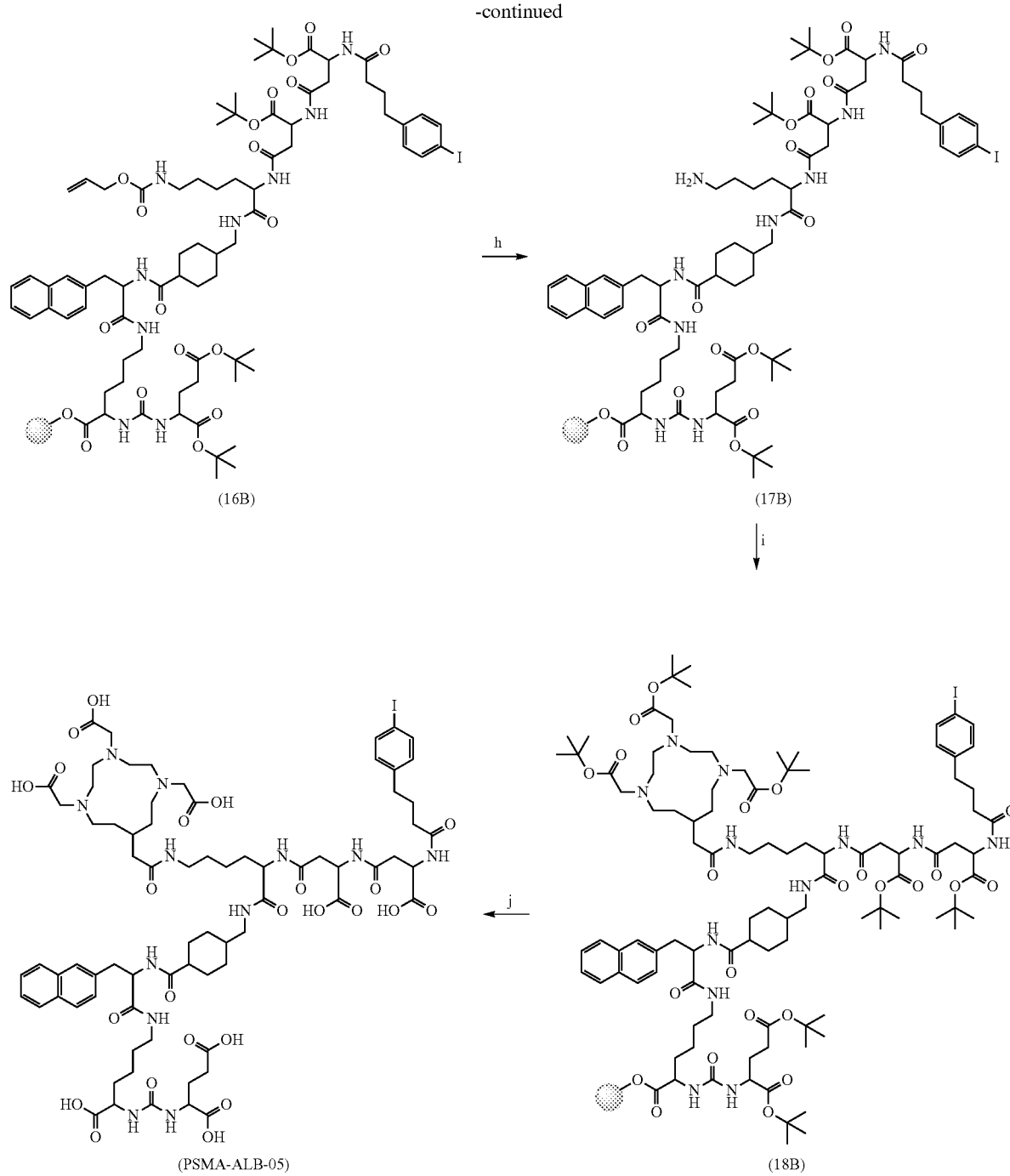

(16B) (17B) (PSMA-ALB-05) (18B)

h) Pd catalysator, morpholine, DCM; i) DOTA tris(tBu)ester, HBTU, DIPEA, DMF; j) TFA:TIPS:H$_2$O Relative to the lysine-coated PSMA precursor (9), 4 equiv of Fmoc as well as Alloc protected L-lysine {(Fmoc-Lys(Alloc)-OH; Merck; Catalog number 8521240005), 0.40 mmol, 452.50 g/mol, [181 mg]} was activated with 3.96 equiv of HBTU {(Sigma; Catalog number 12804-25G-F), 0.396 mmol, 379.24 g/mol, [149 mg]} in the presence of 4 equiv of DIPEA {0.40 mmol, 129.24 g/mol, 0.742 g/mL, [70 µL]} in anhydrous DMF. Two min after the addition of DIPEA, the solution was added to the DMF pre-swollen immobilized bis(tBu)-protected PSMA precursor (9) and agitated for 1 h.

Selective removal of Fmoc-protecting group from the resulting compound (10) was realized by washing with the mixture of DMF and piperidine in a ratio of 1:1 once for 2 min and then once again for 5 min in order to obtain the product (11).

The conjugation of the chelator to the resin-immobilized compound (11) was performed with 2 equiv of DOTA-tris (t-Bu)ester {([2-(4,7,10-tris(2-(t-butoxy)-2-oxoethyl)-1,4,7,10-tetraazacyclododecan-1-yl)acetic acid]; CheMatech; Catalog number 137076-54-1), 0.20 mmol, 572.73 g/mol [115 mg]}. The chelator building block was activated with 1.98 equiv of HBTU {(Sigma; Catalog number 12804-25G-F), 0.198 mmol, 379.24 g/mol, [75 mg]} in the presence of 4 equiv of DIPEA {0.40 mmol, 129.24 g/mol, 0.742 g/mL, [70 µL]} in anhydrous DMF. Two min after the addition of DIPEA, the solution was added to the resin-immobilized and the DMF pre-swollen compound (11). The coupling of the DOTA chelator proceeded over the course of 2 h with gentle agitation. The resulting compound (12) was then washed three times with DMF1, three times with DMF2, three times with DCM1, and, finally, three times with DCM2.

Cleavage of Alloc-protecting group from the compound (12) was realized by reaction with 0.03 equiv of TPP Pd {(Sigma; Catalog number 216666-1G), 0.03 mmol, 1155.56 g/mol, [35 mg]} in the presence of 30 equiv of morpholine {3.0 mmol, 87.12 g/mol, 0.999 g/mL, [262 µL]} in 3 mL of anhydrous DCM. The reaction was performed for 2 hours in the dark using aluminum foil.

The resin was then washed three times with DCM1, three times with DCM2, three times with DMF1, and, finally, three times with DMF2. To remove residuals of the palladium, the resin was additionally washed ten times with 1% DIPEA in DMF (300 µL DIPEA in 30 mL DMF2) and subsequently washed ten times for 5 min with a solution of cupral {(Sigma; Catalog number D3506-100G), 225.31 g/mol} in DMF2 at the concentration of 15 mg/mL (450 mg cupral in 30 mL DMF2). The resulting compound (13) was then washed three times with DMF1 and three times with DMF2.

Finally, for the coupling of the albumin-binding moiety, 4 equiv of tolyl-butyric acid {([4-(p-tolyl)butyric acid]; ABCR; AB1119212), 0.40 mmol, 178.23 g/mol, [71 mg]} was activated with 3.96 equiv of HBTU {(Sigma; Catalog number 12804-25G-F), 0.396 mmol, 379.24 g/mol, [149 mg]} in the presence of 4 equiv of DIPEA {0.40 mmol, 129.24 g/mol, 0.742 g/mL, [70 µL]} in anhydrous DMF. Two min after the addition of DIPEA, the solution was added to the resin-immobilized and DMF pre-swollen product (13) and agitated for 1 h.

The resulting compound (14) was then washed three times with DMF1, three times with DMF2, three times with DCM1, three times with DCM2, and, finally, three times with Et$_2$O and dried under vacuum.

The final compound PSMA-ALB-06 was obtained by agitation and subsequent cleavage from the resin within 2 h with a mixture consisting of TFA, TIPS and H$_2$O in a ratio of 95:2.5:2.5. TFA was evaporated, crude product dissolved in ACN and water in a ratio of 1:1 and purified via RP-HPLC.

The outline of the above described synthesis is summarized in Scheme 1.8.

Scheme 1.8: Coupling of the Albumin Binder, DOTA chelator and PSMA Precursor for PSMA-ALB-06.

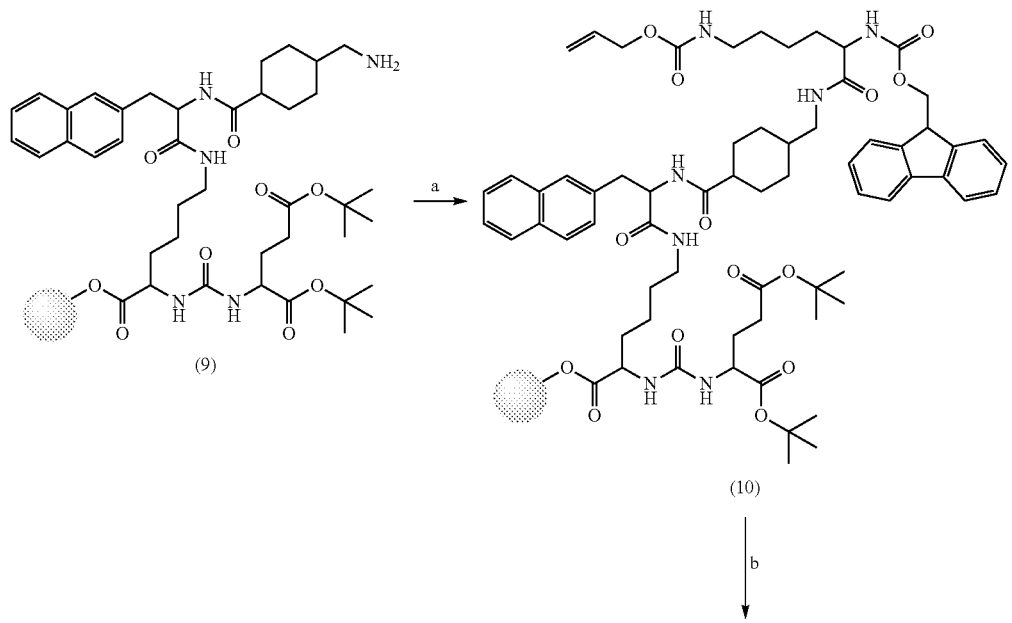

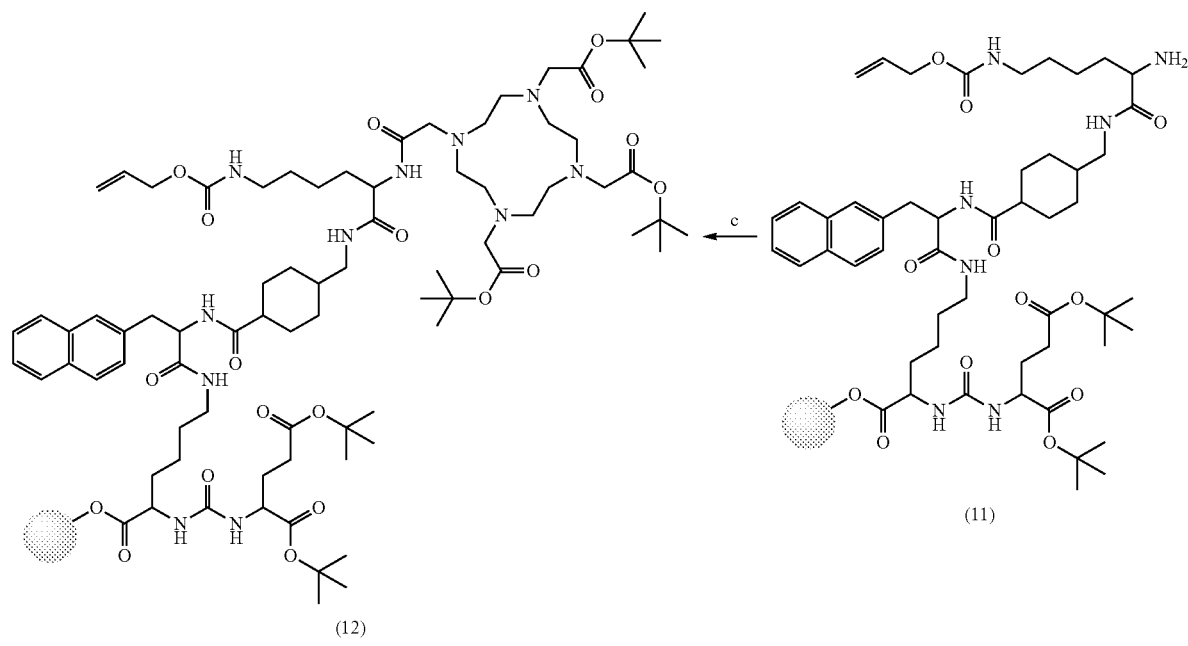
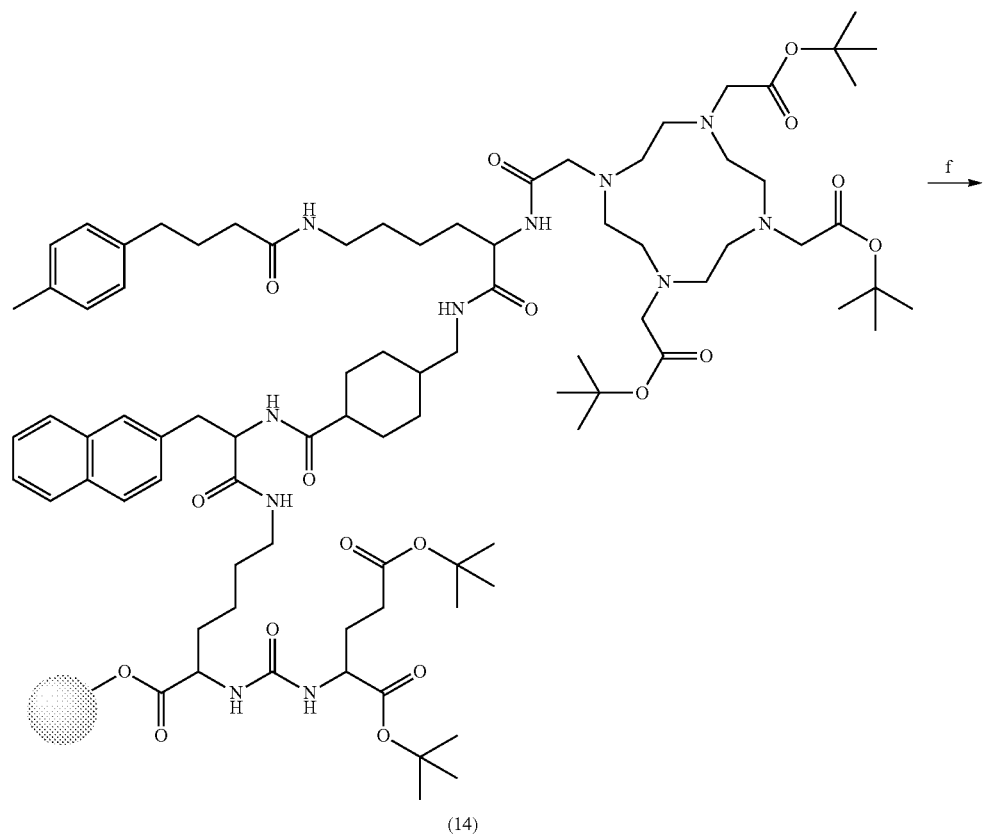

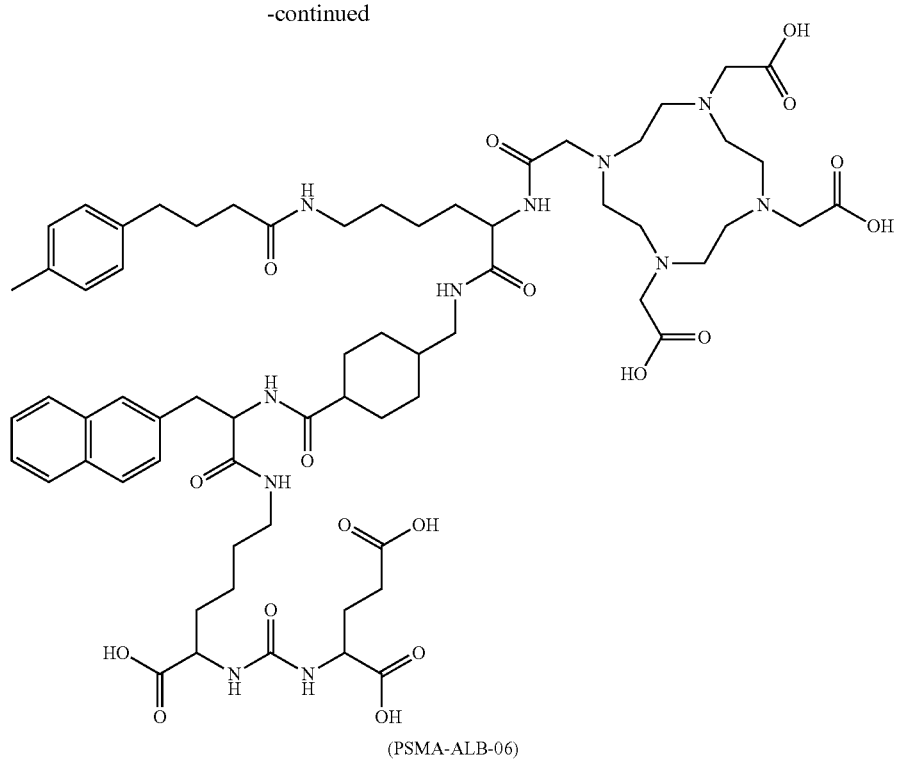

(PSMA-ALB-06)

a) Fmoc-Lys(Alloc)—OH, HBTU, DMF, DIPEA; b) 50% piperidine, DMF; c) DOTA tris(tBu)ester, HBTU, DIPEA, DMF; d) Pd catalysator, morpholine, DCM; e) tolyl butyric acid, HBTU, DMF, DIPEA; f) TFA, TIPS, $H_2O$ 95:2.5:2.5;

f) Synthesis of PSMA-ALB-07

Relative to the lysine-coated PSMA precursor (9B), 4 equiv of Fmoc as well as Alloc protected L-lysine {(Fmoc-Lys(Alloc)-OH; Merck; Catalog number 8521240005), 0.40 mmol, 452.50 g/mol, [181 mg]} was activated with 3.96 equiv of HBTU {(Sigma; Catalog number 12804-25G-F), 0.396 mmol, 379.24 g/mol, [149 mg]} in the presence of 4 equiv of DIPEA {0.40 mmol, 129.24 g/mol, 0.742 g/mL, [70 µL]} in anhydrous DMF. Two min after the addition of DIPEA, the solution was added to the DMF pre-swollen immobilized bis(tBu)-protected PSMA precursor (9B) and agitated for 1 h.

The resulting compound (10B) was then washed three times with DMF1 and three times with DMF2. Selective removal of Fmoc-protecting group from the resulting compound (10B) was realized by washing with the mixture of DMF and piperidine in a ratio of 1:1 once for 2 min and then once again for 5 min in order to obtain the product (11B).

Relative to the lysine-coated PSMA precursor (11B), 3 equiv of Fmoc as well as tBu protected D-aspartate {(Fmoc-D-Asp-OtBu; Merck; Catalog number 8521440001), 0.30 mmol, 411.45 g/mol, [123 mg]} was activated with 2.97 equiv of HBTU {(Sigma; Catalog number 12804-25G-F), 0.297 mmol, 379.24 g/mol, [112 mg]} in the presence of 4 equiv of DIPEA {0.40 mmol, 129.24 g/mol, 0.742 g/mL, [70 µL]} in anhydrous DMF. Two min after the addition of DIPEA, the solution was added to the DMF pre-swollen immobilized bis(tBu)-protected PSMA precursor (11B) and agitated for 1 h.

The resulting compound (12B) was then washed three times with DMF1 and three times with DMF2. Selective removal of Fmoc-protecting group from the resulting compound (12B) was realized by washing with the mixture of DMF and piperidine in a ratio of 1:1 once for 2 min and then once again for 5 min in order to obtain the product (13B).

Relative to the lysine and aspartate-coated PSMA precursor (13B), 3 equiv of Fmoc as well as tBu protected D-aspartate {(Fmoc-D-Asp-OtBu; Merck; Catalog number 8521440001), 0.30 mmol, 411.45 g/mol, [123 mg]} was activated with 2.97 equiv of HBTU {(Sigma; Catalog number 12804-25G-F), 0.297 mmol, 379.24 g/mol, [112 mg]} in the presence of 4 equiv of DIPEA {0.40 mmol, 129.24 g/mol, 0.742 g/mL, [70 µL]} in anhydrous DMF. Two min after the addition of DIPEA, the solution was added to the DMF pre-swollen immobilized bis(tBu)-protected PSMA precursor (13B) and agitated for 1 h.

The resulting compound (14B) was then washed three times with DMF1 and three times with DMF2. Selective removal of Fmoc-protecting group from the resulting compound (14B) was realized by washing with the mixture of DMF and piperidine in a ratio of 1:1 once for 2 min and then once again for 5 min in order to obtain the product (15B).

Relative to the lysine and two aspartates-coated PSMA precursor (15B), 3 equiv of Fmoc as well as tBu protected D-aspartate {(Fmoc-D-Asp-OtBu; Merck; Catalog number 8521440001), 0.30 mmol, 411.45 g/mol, [123 mg]} was activated with 2.97 equiv of HBTU {(Sigma; Catalog number 12804-25G-F), 0.297 mmol, 379.24 g/mol, [112 mg]} in the presence of 4 equiv of DIPEA {0.40 mmol, 129.24 g/mol, 0.742 g/mL, [70 µL]} in anhydrous DMF. Two min after the addition of DIPEA, the solution was added to the DMF pre-swollen immobilized bis(tBu)-protected PSMA precursor (15B) and agitated for 1 h.

The resulting compound (16B) was then washed three times with DMF1 and three times with DMF2. Selective removal of Fmoc-protecting group from the resulting compound (14B) was realized by washing with the mixture of DMF and piperidine in a ratio of 1:1 once for 2 min and then once again for 5 min in order to obtain the product (17B).

Relative to the resin-coated product (17B), 4 equiv of iodophenyl-butyric acid {([4-(p-iodophenyl)butyric acid]; Sigma; I5634-5G), 0.40 mmol, 290.10 g/mol, [116 mg]} was activated with 3.96 equiv of HBTU {(Sigma; Catalog number 12804-25G-F), 0.396 mmol, 379.24 g/mol, [149 mg]} in the presence of 4 equiv of DIPEA {0.40 mmol, 129.24 g/mol, 0.742 g/mL, [70 µL]} in anhydrous DMF. Two min after the addition of DIPEA, the solution was added to the resin-immobilized and DMF pre-swollen product (17B) and agitated for 1 h.

The resulting compound (18B) was then washed three times with DMF1, three times with DMF2, three times with DCM1, and, finally, three times with DCM2.

Cleavage of Alloc-protecting group from the compound (18B) was realized by reaction with 0.03 equiv of TPP Pd {(Sigma; Catalog number 216666-1G), 0.03 mmol, 1155.56 g/mol, [35 mg]} in the presence of 30 equiv of morpholine {3.0 mmol, 87.12 g/mol, 0.999 g/mL, [262 µL]} in 3 mL of anhydrous DCM. The reaction was performed for 2 hours in the dark using aluminum foil.

The resin was then washed three times with DCM1, three times with DCM2, three times with DMF1, and, finally, three times with DMF2. To remove residuals of the palladium, the resin was additionally washed ten times with 1% DIPEA in DMF (300 µL DIPEA in 30 mL DMF2) and subsequently washed ten times for 5 min with a solution of cupral {(Sigma; Catalog number D3506-100G), 225.31 g/mol} in DMF2 at the concentration of 15 mg/mL (450 mg cupral in 30 mL DMF2). The resulting compound (19B) was then washed three times with DMF1 and three times with DMF2.

The conjugation of the chelator to the resin-immobilized compound (19B) was performed with 3 equiv of DOTA-tris (t-Bu)ester {([2-(4,7,10-tris(2-(t-butoxy)-2-oxoethyl)-1,4,7,10-tetraazacyclododecan-1-yl)acetic acid]; CheMatech; Catalog number 137076-54-1), 0.30 mmol, 572.73 g/mol [171 mg]}. The chelator building block was activated with 2.97 equiv of HBTU {(Sigma; Catalog number 12804-25G-F), 0.297 mmol, 379.24 g/mol, [112 mg]} in the presence of 4 equiv of DIPEA {0.40 mmol, 129.24 g/mol, 0.742 g/mL, [70 µL]} in anhydrous DMF. Two min after the addition of DIPEA, the solution was added to the resin-immobilized and the DMF pre-swollen compound (17B). The coupling of the DOTA chelator proceeded over the course of 2 h with gentle agitation.

Such product (20B) washed three times with DMF1 and three times with DMF2, three times with DCM1, three times with DCM2 and, finally, three times with Et₂O and dried under vacuum.

The final compound PSMA-ALB-07 was obtained by agitation and subsequent cleavage from the resin within 2 h with a mixture consisting of TFA, TIPS and H₂O in a ratio of 95:2.5:2.5. TFA was evaporated, crude product dissolved in ACN and water in a ratio of 1:1 and purified via RP-HPLC. The outline of the above described synthesis is summarized in two parts of Scheme 1.9.

Scheme 1.9: Coupling of the Albumin Binding-moiety, DOTA Chelator and PSMA Precursor for PSMA-ALB-07.

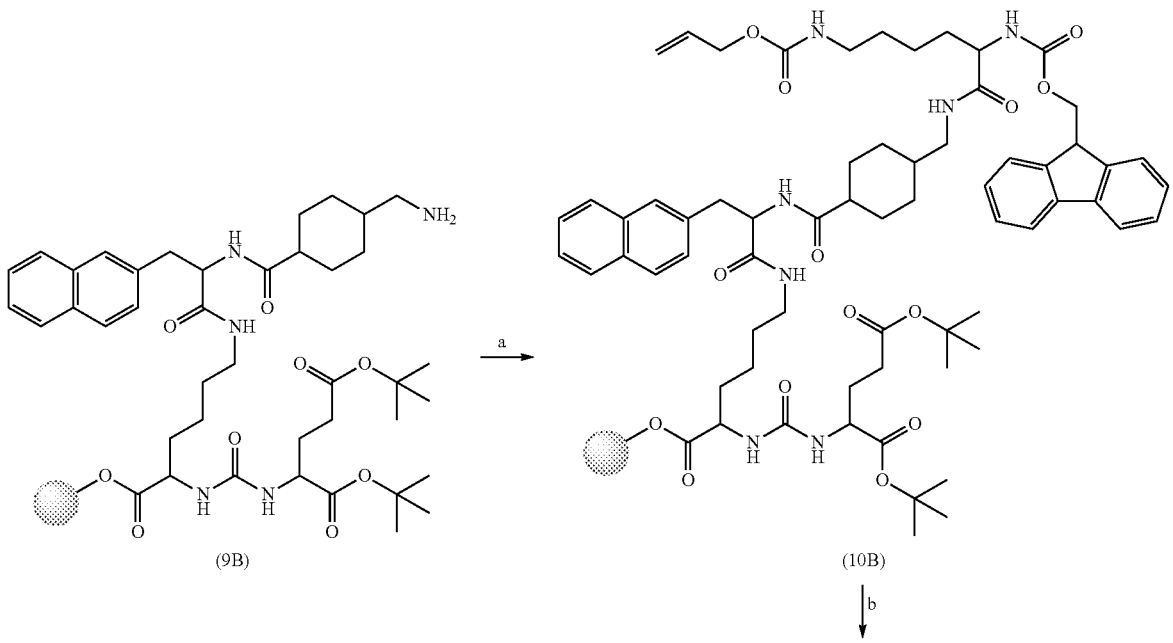

101 102
-continued
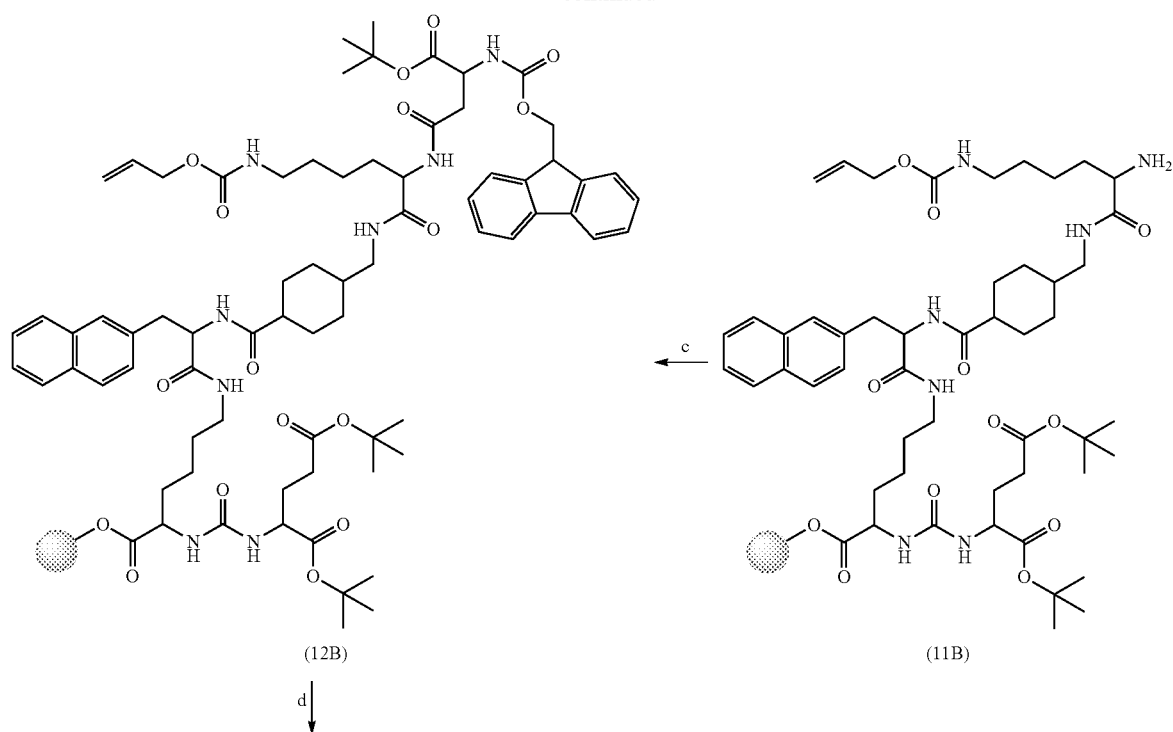
(12B) (11B)
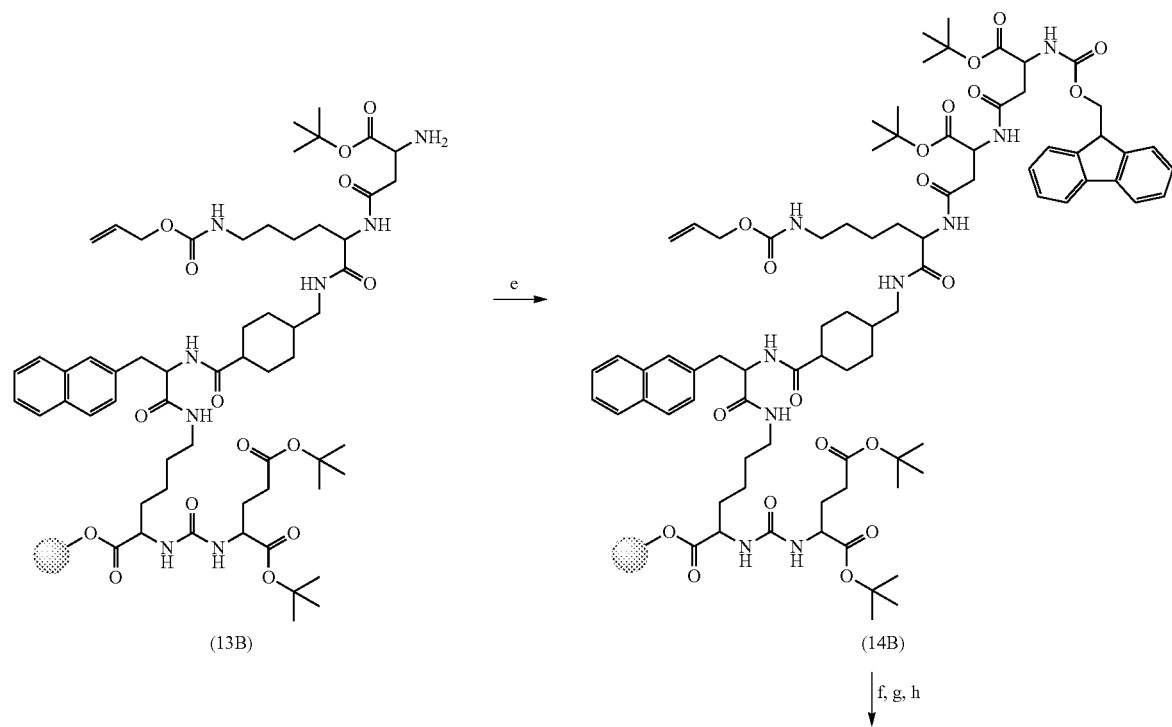
(13B) (14B)

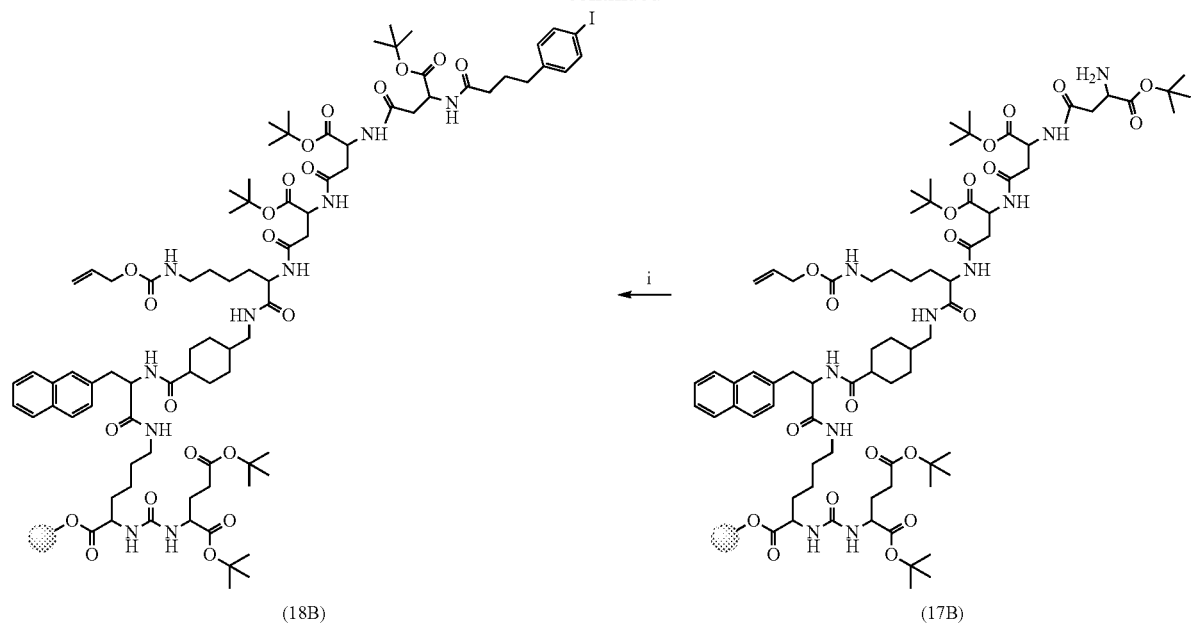
a) Fmoc-Lys(Alloc)-OH, HBTU, DMF, DIPEA; b) 50% piperidine, DMF; c) Fmoc-D-Asp-OtBu, HBTU, DIPEA, DMF; d) 50% piperidine, DMF; e) Fmoc-D-Asp-OtBu, HBTU, DIPEA, DMF; f) 50% piperidine, DMF; g) Fmoc-D-Asp-OtBu, HBTU, DIPEA, DMF; h) 50% piperidine, DMF; i) iodophenyl butyric acid, HBTU, DMF, DIPEA;
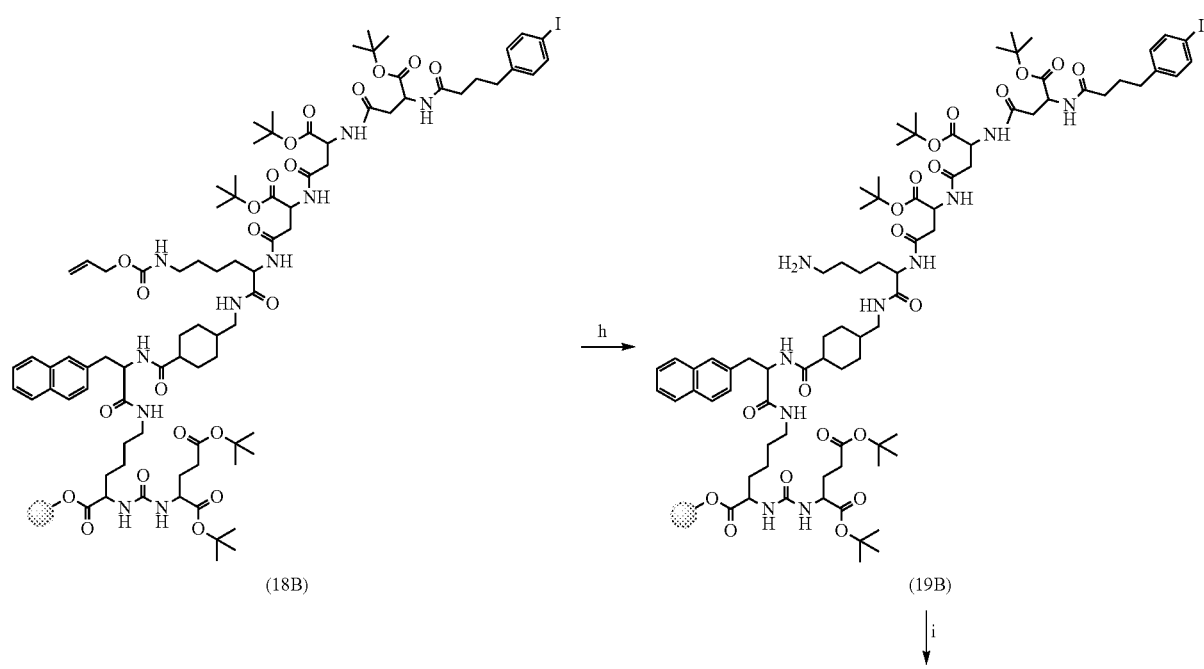

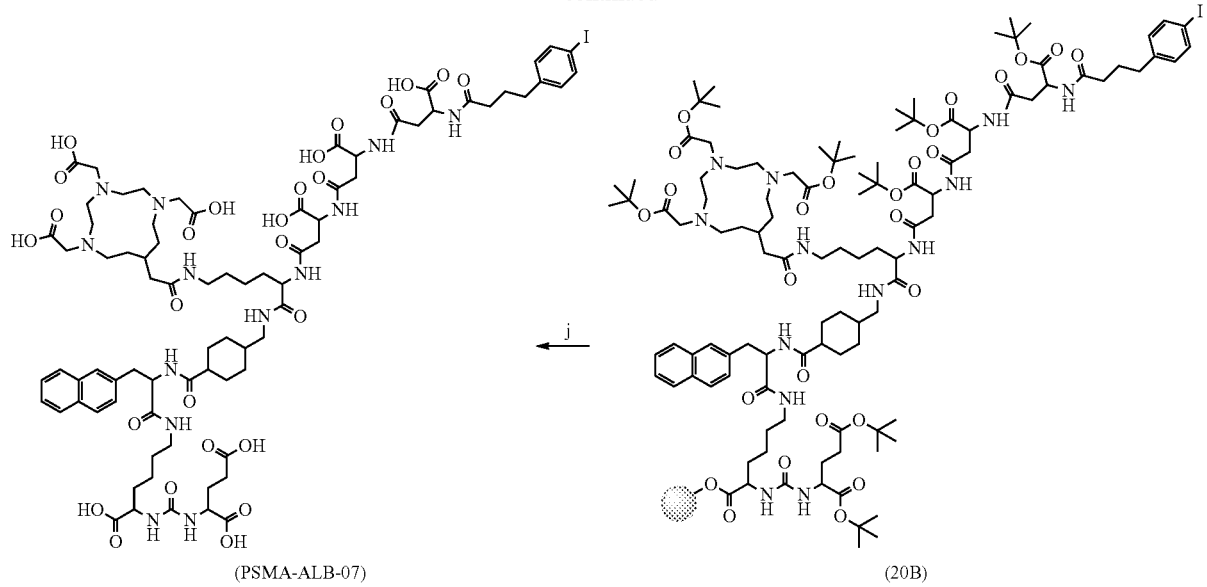

(PSMA-ALB-07)      (20B)

h) Pd catalysator, morpholine, DCM; i) DOTA tris(tBu)ester, HBTU, DIPEA, DMF; j) TFA:TIPS:H$_2$O g) Synthesis of PSMA-ALB-08

Relative to the lysine-coated PSMA precursor (9B), 4 equiv of Fmoc as well as Alloc protected L-lysine {(Fmoc-Lys(Alloc)-OH; Merck; Catalog number 8521240005), 0.40 mmol, 452.50 g/mol, [181 mg]} was activated with 3.96 equiv of HBTU {(Sigma; Catalog number 12804-25G-F), 0.396 mmol, 379.24 g/mol, [149 mg]} in the presence of 4 equiv of DIPEA {0.40 mmol, 129.24 g/mol, 0.742 g/mL, [70 µL]} in anhydrous DMF. Two min after the addition of DIPEA, the solution was added to the DMF pre-swollen immobilized bis(tBu)-protected PSMA precursor (9B) and agitated for 1 h.

The resulting compound (10B) was then washed three times with DMF1 and three times with DMF2. Selective removal of Fmoc-protecting group from the resulting compound (10B) was realized by washing with the mixture of DMF and piperidine in a ratio of 1:1 once for 2 min and then once again for 5 min in order to obtain the product (11B).

Relative to the lysine-coated PSMA precursor (11B), 3 equiv of Fmoc as well as tBu protected D-aspartate {(Fmoc-D-Asp-OtBu; Merck; Catalog number 8521440001), 0.30 mmol, 411.45 g/mol, [123 mg]} was activated with 2.97 equiv of HBTU {(Sigma; Catalog number 12804-25G-F), 0.297 mmol, 379.24 g/mol, [112 mg]} in the presence of 4 equiv of DIPEA {0.40 mmol, 129.24 g/mol, 0.742 g/mL, [70 µL]} in anhydrous DMF. Two min after the addition of DIPEA, the solution was added to the DMF pre-swollen immobilized bis(tBu)-protected PSMA precursor (11B) and agitated for 1 h.

The resulting compound (12B) was then washed three times with DMF1 and three times with DMF2. Selective removal of Fmoc-protecting group from the resulting compound (12B) was realized by washing with the mixture of DMF and piperidine in a ratio of 1:1 once for 2 min and then once again for 5 min in order to obtain the product (13B).

Relative to the lysine and aspartate-coated PSMA precursor (13B), 3 equiv of Fmoc as well as tBu protected D-aspartate {(Fmoc-D-Asp-OtBu; Merck; Catalog number 8521440001), 0.30 mmol, 411.45 g/mol, [123 mg]} was activated with 2.97 equiv of HBTU {(Sigma; Catalog number 12804-25G-F), 0.297 mmol, 379.24 g/mol, [112 mg]} in the presence of 4 equiv of DIPEA {0.40 mmol, 129.24 g/mol, 0.742 g/mL, [70 µL]} in anhydrous DMF. Two min after the addition of DIPEA, the solution was added to the DMF pre-swollen immobilized bis(tBu)-protected PSMA precursor (13B) and agitated for 1 h.

The resulting compound (14B) was then washed three times with DMF1 and three times with DMF2. Selective removal of Fmoc-protecting group from the resulting compound (14B) was realized by washing with the mixture of DMF and piperidine in a ratio of 1:1 once for 2 min and then once again for 5 min in order to obtain the product (15B).

Relative to the lysine and two aspartates-coated PSMA precursor (15B), 3 equiv of Fmoc as well as tBu protected D-aspartate {(Fmoc-D-Asp-OtBu; Merck; Catalog number 8521440001), 0.30 mmol, 411.45 g/mol, [123 mg]} was activated with 2.97 equiv of HBTU {(Sigma; Catalog number 12804-25G-F), 0.297 mmol, 379.24 g/mol, [112 mg]} in the presence of 4 equiv of DIPEA {0.40 mmol, 129.24 g/mol, 0.742 g/mL, [70 µL])} in anhydrous DMF. Two min after the addition of DIPEA, the solution was added to the DMF pre-swollen immobilized bis(tBu)-protected PSMA precursor (15B) and agitated for 1 h.

The resulting compound (16B) was then washed three times with DMF1 and three times with DMF2. Selective removal of Fmoc-protecting group from the resulting compound (14B) was realized by washing with the mixture of DMF and piperidine in a ratio of 1:1 once for 2 min and then once again for 5 min in order to obtain the product (17B).

Relative to the resin-coated product (17B), 4 equiv of tolyl-butyric acid (0.40 mmol} was activated with 3.96 equiv of HBTU {(Sigma; Catalog number 12804-25G-F), 0.396 mmol, 379.24 g/mol, [149 mg]} in the presence of 4 equiv of DIPEA {0.40 mmol, 129.24 g/mol, 0.742 g/mL, [70 µL]} in anhydrous DMF. Two min after the addition of DIPEA, the solution was added to the resin-immobilized and DMF pre-swollen product (17B) and agitated for 1 h.

The resulting compound (18B) was then washed three times with DMF1, three times with DMF2, three times with DCM1, and, finally, three times with DCM2.

Cleavage of Alloc-protecting group from the compound (18B) was realized by reaction with 0.03 equiv of TPP Pd {(Sigma; Catalog number 216666-1G), 0.03 mmol, 1155.56 g/mol, [35 mg]} in the presence of 30 equiv of morpholine {3.0 mmol, 87.12 g/mol, 0.999 g/mL, [262 µL]} in 3 mL of anhydrous DCM. The reaction was performed for 2 hours in the dark using aluminum foil.

The resin was then washed three times with DCM1, three times with DCM2, three times with DMF1, and, finally, three times with DMF2. To remove residuals of the palladium, the resin was additionally washed ten times with 1% DIPEA in DMF (300 µL DIPEA in 30 mL DMF2) and subsequently washed ten times for 5 min with a solution of cupral {(Sigma; Catalog number D3506-100G), 225.31 g/mol} in DMF2 at the concentration of 15 mg/mL (450 mg cupral in 30 mL DMF2). The resulting compound (19B) was then washed three times with DMF1 and three times with DMF2.

The conjugation of the chelator to the resin-immobilized compound (19B) was performed with 3 equiv of DOTA-tris (t-Bu)ester {([2-(4,7,10-tris(2-(t-butoxy)-2-oxoethyl)-1,4,7, 10-tetraazacyclododecan-1-yl)acetic acid]; CheMatech; Catalog number 137076-54-1), 0.30 mmol, 572.73 g/mol [171 mg]}. The chelator building block was activated with 2.97 equiv of HBTU {(Sigma; Catalog number 12804-25G-F), 0.297 mmol, 379.24 g/mol, [112 mg]} in the presence of 4 equiv of DIPEA {0.40 mmol, 129.24 g/mol, 0.742 g/mL, [70 µL]} in anhydrous DMF. Two min after the addition of DIPEA, the solution was added to the resin-immobilized and the DMF pre-swollen compound (17B). The coupling of the DOTA chelator proceeded over the course of 2 h with gentle agitation.

Such product (20B) washed three times with DMF1 and three times with DMF2, three times with DCM1, three times with DCM2 and, finally, three times with Et$_2$O and dried under vacuum.

The final compound PSMA-ALB-07 was obtained by agitation and subsequent cleavage from the resin within 2 h with a mixture consisting of TFA, TIPS and H$_2$O in a ratio of 95:2.5:2.5. TFA was evaporated, crude product dissolved in ACN and water in a ratio of 1:1 and purified via RP-HPLC.

The outline of the above described synthesis is summarized in two parts of Scheme 1.10.

Scheme 1.10: Coupling of the Albumin Binding-moiety, DOTA Chelator and PSMA Precursor for PSMA-ALB-08.

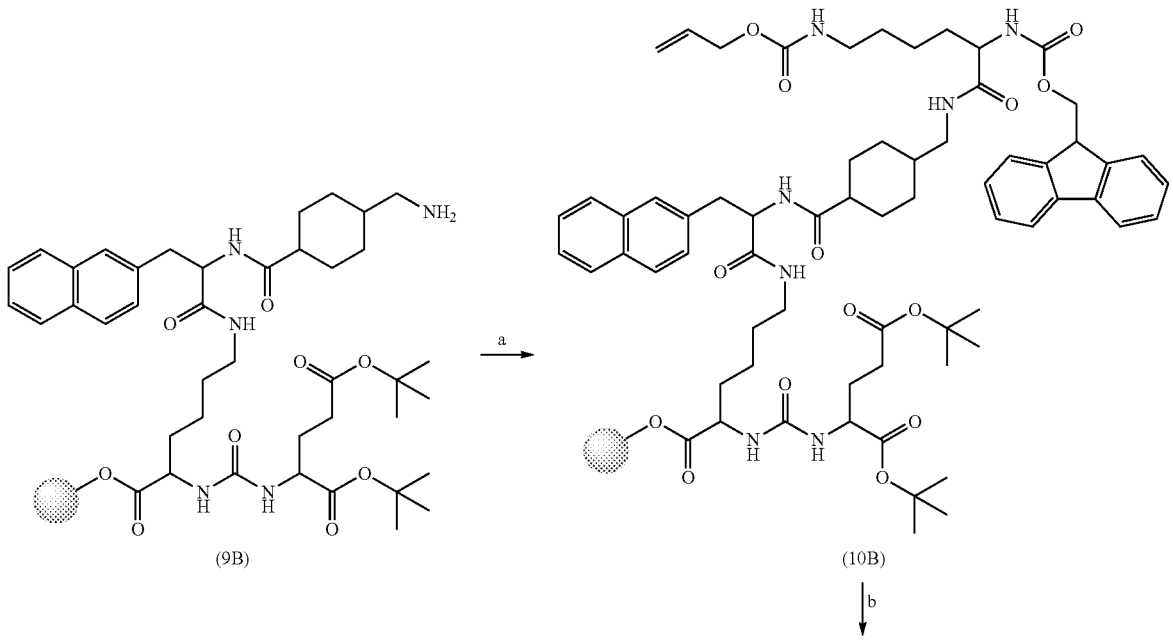

109
-continued
110
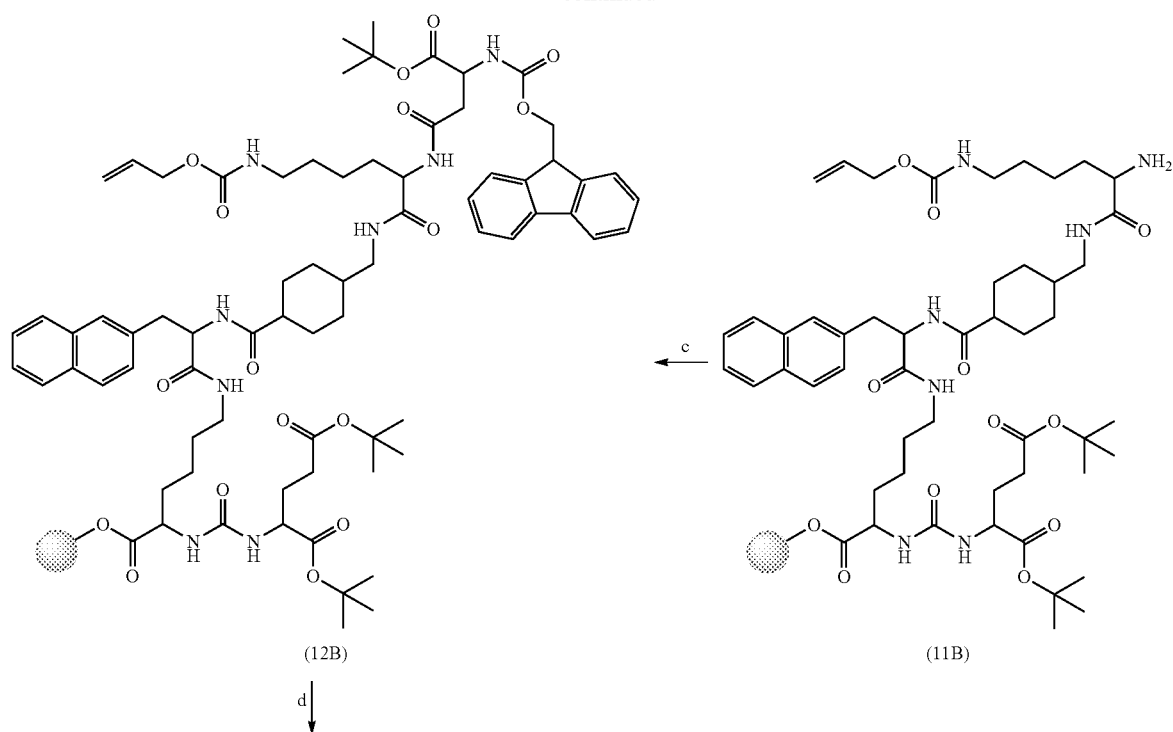
(12B)
(11B)
d↓
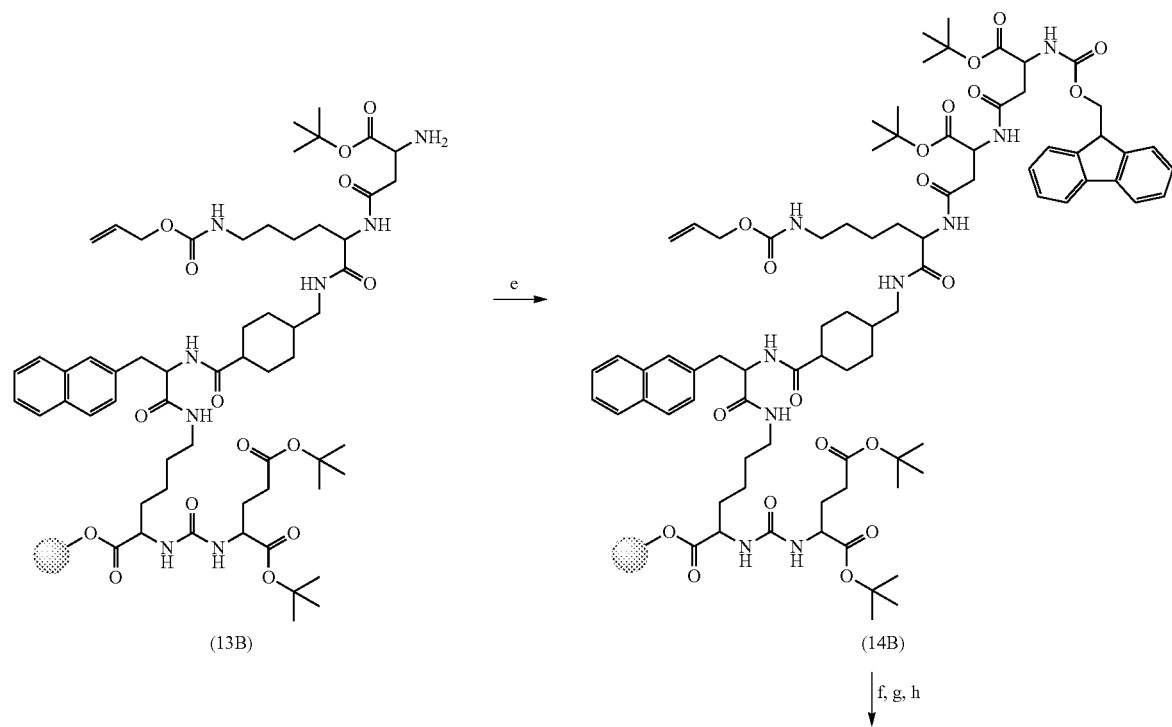
(13B)
(14B)
↓f, g, h

111          112
-continued
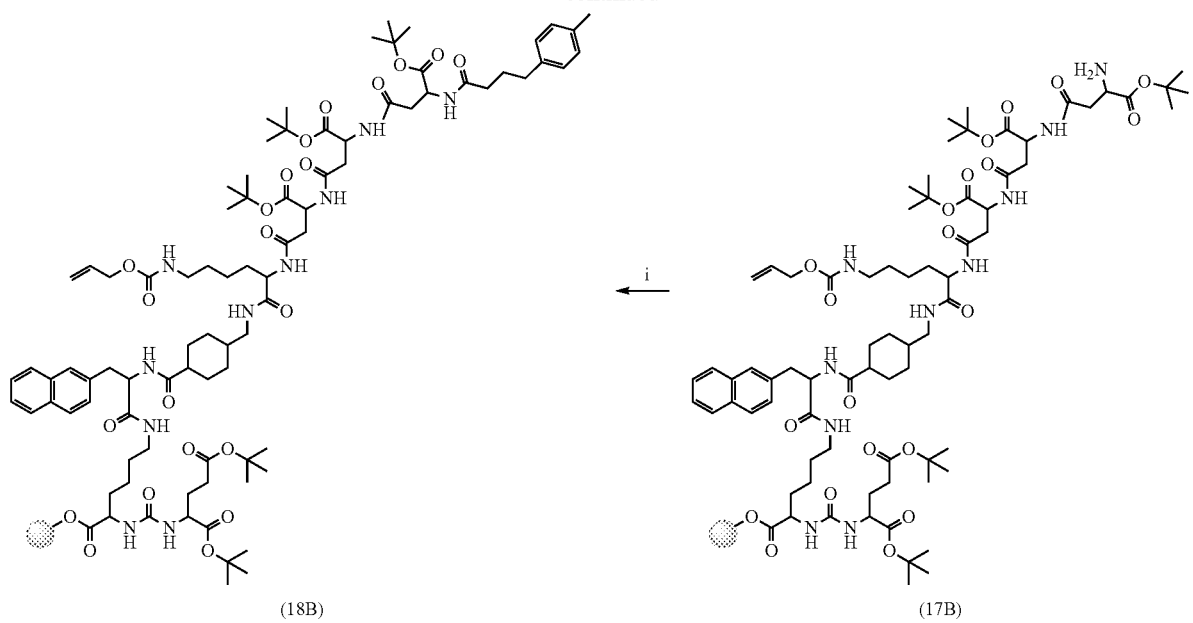
(18B)          (17B)
a) Fmoc-Lys(Alloc)-OH, HBTU, DMF, DIPEA; b) 50% piperidine, DMF; c) Fmoc-D-Asp-OtBu, HBTU, DIPEA, DMF; d) 50% piperidine, DMF; e) Fmoc-D-Asp-OtBu, HBTU, DIPEA, DMF; f) 50% piperidine, DMF; g) Fmoc-D-Asp-OtBu, HBTU, DIPEA, DMF; h) 50% piperidine, DMF; i)tolyl-butyric acid, HBTU, DMF, DIPEA;
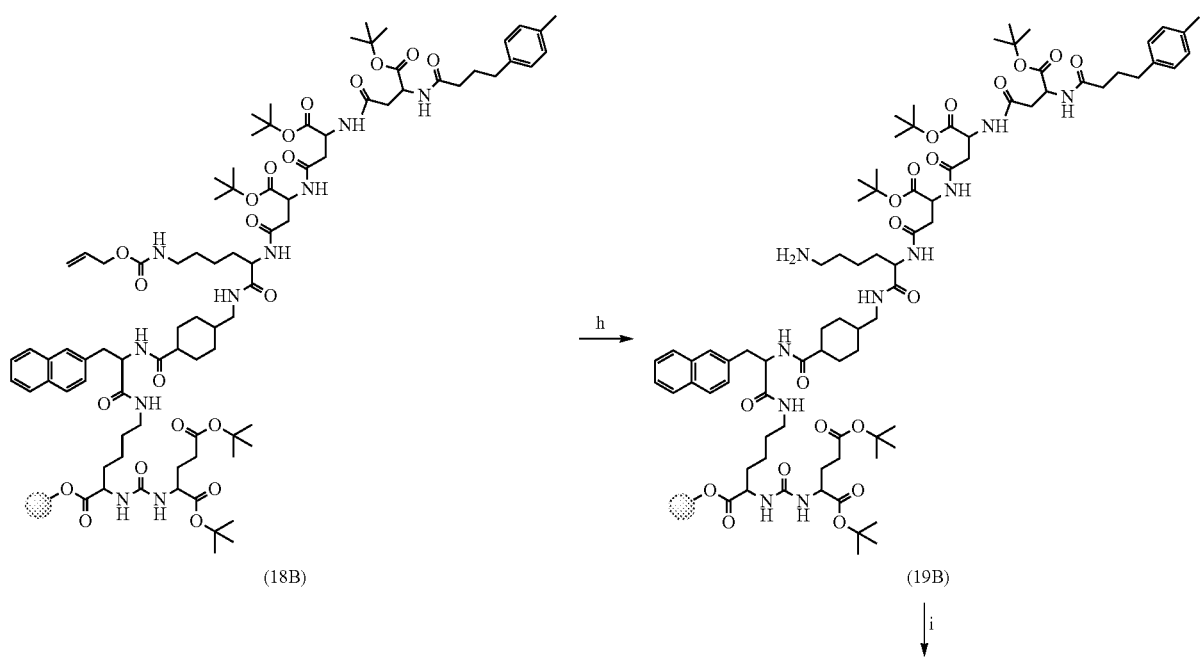
(18B)          (19B)

-continued

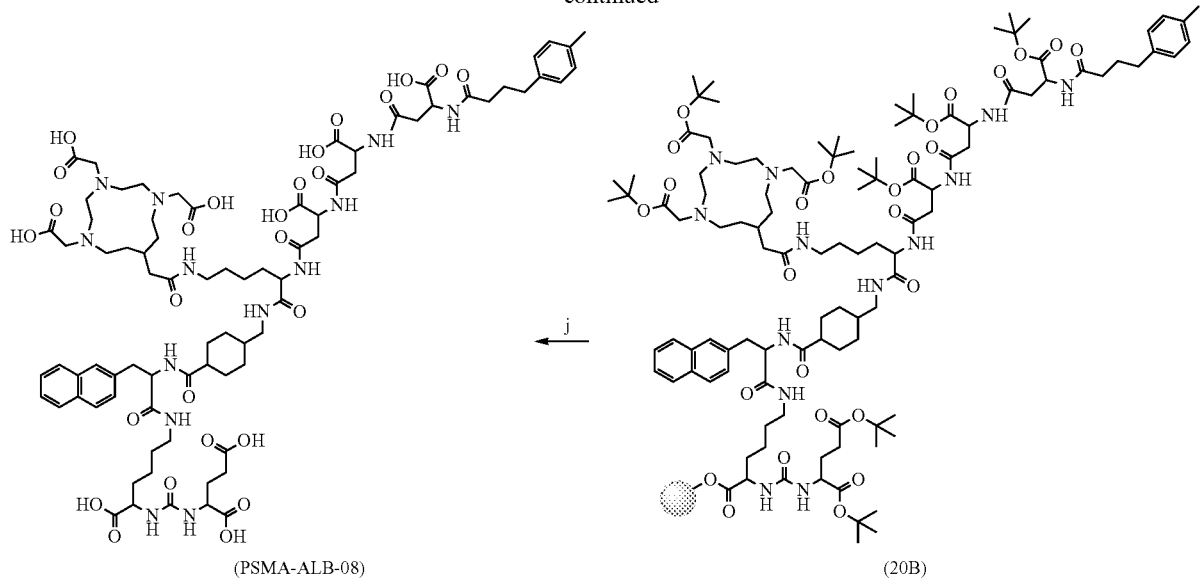

(PSMA-ALB-08) (20B)

h) Pd catalysator, morpholine, DCM; i) DOTA tris(tBu)ester, HBTU, DIPEA, DMF; j) TFA:TIPS:H$_2$O 1.1.3: $^{177}$Lu-Labeling of PSMA Ligands and In Vitro Evaluation In vitro studies were conducted with $^{177}$Lu-PSMA-ALB-01/-03/-04/-05/-06/-07/-08. This included the preliminary evaluation of labeling efficiencies, n-octanol/PBS distribution coefficients and serum protein binding studies. Furthermore, uptake and internalization experiments were performed using the PSMA-transfected PSMApos PC-3 PIP cell line (positive control) and the mock-transfected PSMAneg PC-3 flu cell line (negative control).

a) PSMA-Ligands and Radionuclides

The PSMA-ligands $^{177}$Lu-PSMA-ALB-01/-03/-04/-05/-06/-07/-08 were synthesized as described above. The reference compound (PSMA-617) was purchased from Advanced Biochemical Compounds (ABX GmbH, Radeberg, Germany). No-carrier added $^{177}$Lu in 0.05 M HCl was provided by Isotope Technologies Garching (ITG GmbH, Germany).

b) Radiolabeling

The stock solution of PSMA-617 was prepared by dilution in MilliQ water to a final concentration of 1 mM. $^{177}$Lu-PSMA-ALB-01/-03/-04/-05/-06/-07/-08 were diluted in MilliQ water/DMSO to obtain a final concentration of 1 mM. All compounds were labeled with $^{177}$Lu in a 1:5 mixture of sodium acetate (0.5 M, pH 8) and HCl (0.05 M, pH ~1) at pH 3.5-4.5. The compounds were labeled with $^{177}$Lu at specific activities between 5-50 MBq/nmol, depending on the experimental conditions. The reaction mixture was incubated for 15 min at 95° C., followed by a quality control using high-performance liquid chromatography with a C-18 reversed-phase column (Xterra™ MS, C18, 5 µm, 150×4.6 mm; Waters). The mobile phase consisted of MilliQ water containing 0.1% trifluoroacetic acid (A) and acetonitrile (B) with a gradient of 95% A and 5% B to 20% A and 80% B over a period of 15 min at a flow rate of 1.0 mL/min. The radioligands were diluted in MilliQ water containing Na-DTPA (50 µM (micromolar)) prior to injection into HPLC.

c) Determination of the n-Octanol/PBS Distribution Coefficient $^{177}$Lu-PSMA-ALB-01/-03/-04/-05/-06/-07/-08 and PSMA-617 were labeled with $^{177}$Lu at a specific activity of 50 MBq/nmol. The radioligand (0.5 MBq; 10 pmol, 25 µL) was then added to a reagent tube containing 1475 µL of PBS pH 7.4 and 1500 µL of n-octanol. The vials were vortexed vigorously followed by a centrifugation step for phase separation. Finally, the radioactivity in a defined volume of PBS and n-octanol was measured in a gamma-counter (Perkin Elmer, Wallac Wizard 1480) to calculate the distribution coefficients, expressed as the logarithm of the ratio of counts per minute (cpm) measured in the n-octanol phase to the cpm measure in the PBS phase.

d) Filter Assay

Plasma binding of $^{177}$Lu-PSMA-ALB-01/-03/-04/-05/-06/-07/-08 and $^{177}$Lu-PSMA-617 was determined using an ultrafiltration assay.

Therefore, the compounds were labeled with $^{177}$Lu at a specific activity of 50 MBq/nmol and incubated in human plasma samples or PBS at room temperature. The free and plasma-bound fractions were separated using a centrifree ultrafiltration device (4104 centrifugal filter units [Millipore]; 30000 Da nominal molecular weight limit, methylcellulose micropartition membranes). The incubated solution was loaded to the ultrafiltration device and centrifuged at 2500 rpm for 40 min at 20° C. Samples from the filtrate were taken an analyzed for radioactivity in a gamma-counter. The amount of plasma-bound compound was calculated as the fraction of radioactivity measured in the filtrate relative to the corresponding loading solution (set to 100%).

e) Cell Internalization Assay

Cell uptake and internalization experiments were performed with $^{177}$Lu-PSMA-ALB-01/-03/-04/-05/-06/-07/-08 and the reference compound $^{177}$Lu-PSMA-617 using the PSMA-transfected PSMA$^{pos}$ PC-3 PIP and mock-transfected PSMA$^{neg}$ PC-3 flu cells in order to investigate the specificity of the novel compounds.

Cells were grown in RPMI cell culture medium supplemented with 10% fetal calf serum, L-glutamine, antibiotics and puromycin (2 µg/mL) at 37° C. and 5% CO2 (standard conditions). Routine cell culture was performed twice a week using PBS/EDTA (2 mM) for washing the cells and trypsin for detachment of the cells. The cells were seeded in 12-well plates (~3×10$^5$ cells in 2 mL RPMI medium/well) allowing adhesion and growth overnight at standard conditions. The supernatant was removed and the cells washed with PBS pH 7.4 prior to the addition of RPMI medium without supplements (975 μL/well). The compounds were labeled with $^{177}$Lu at a specific activity of 5 MBq/nmol and diluted to 1.5 MBq/mL in 0.05% bovine serum albumin (BSA)/0.9% NaCl solution to prevent adherence to plastic vessels. The cells were incubated with 25 μL (~37.5 kBq)/well radiolabeled PSMA ligands at standard conditions for 2 h and 4 h, respectively. After incubation, the cells were washed three times with ice-cold PBS and the total uptake of the radioligands was determined (PSMA-bound fraction on the surface and internalized fraction). The fraction of internalized radioligand was evaluated in cells washed with ice-cold PBS, followed by a 10 min incubation with stripping buffer (0.05 M glycine stripping buffer in 100 mM NaCl, pH 2.8) and an additional washing step with ice-cold PBS. Cell samples were lysed by addition of NaOH (1 M, 1 mL) to each well. The samples of the cell suspensions were measured in a γ-counter (Perkin Elmer, Wallac Wizard 1480). After homogenization of the cell suspensions, the protein concentration was determined for each sample using a Micro BCA Protein Assay kit (Pierce, Therma Scientific). The results were expressed as percentage of total added radioactivity per 150 μg/mL protein.

1.2 Results 1.2.1 Labeling Efficiency

PSMA-ALB-01 and -03 were successfully labeled with $^{177}$Lu at specific activities up to 100 MBq/nmol and excellent radiochemical yields of >98%. PSMA-ALB-04, -05, -06, -07 and -08 were labeled with $^{177}$Lu in preliminary tests at specific activities up to 50 MBq/nmol and excellent radiochemical yields of >97%. The specific activity used for the experiments (if not otherwise stated) was 50 MBq/nmol. The radiochemical purity of compounds used for in vitro and in vivo studies was always >97% (FIG. 1).

Figure 2:
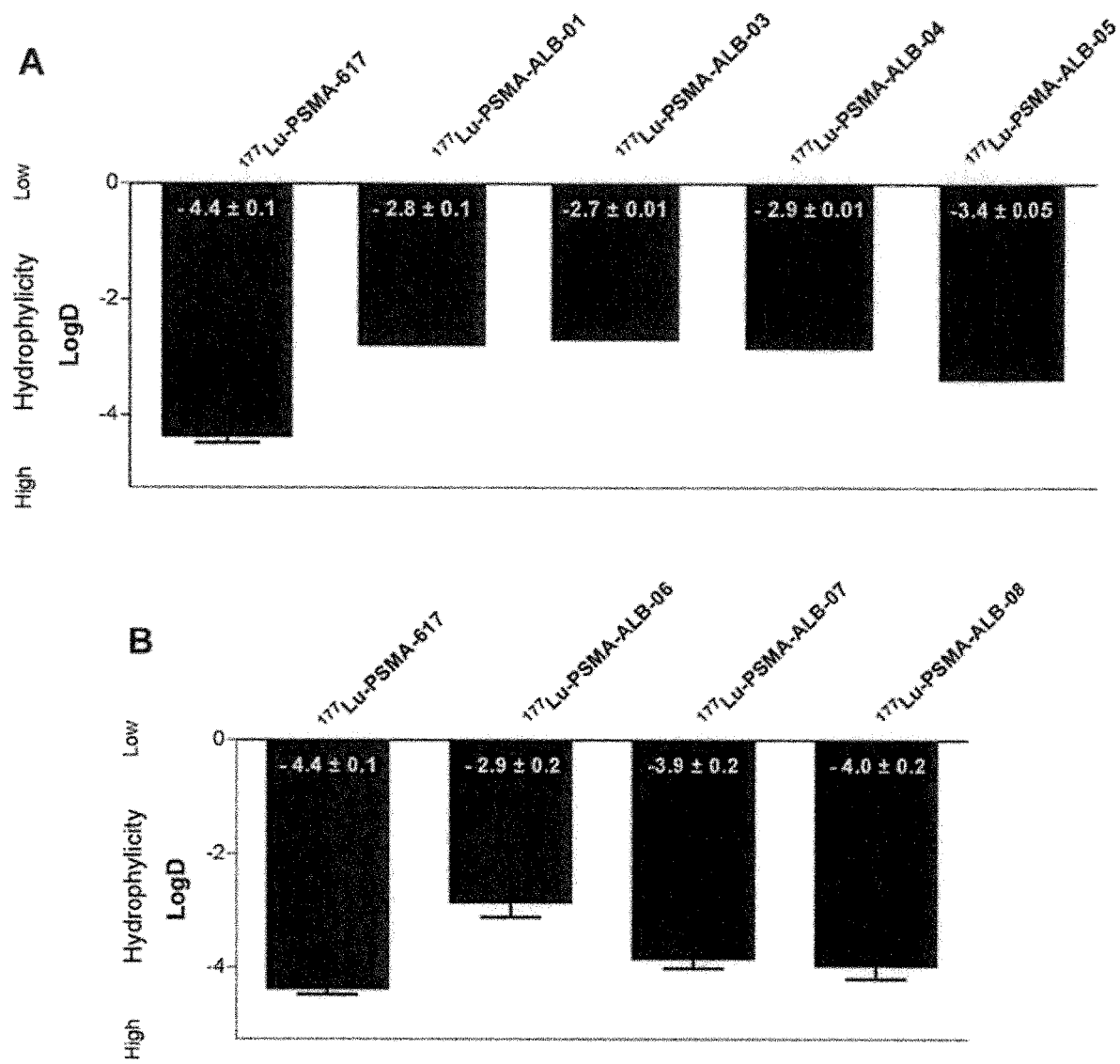
FIG. 2: n-Octanol/PBS distribution coefficient of $^{177}$Lu-PSMA-ALB-01 (n=3), $^{177}$Lu-PSMA-ALB-03 (n=3), $^{177}$Lu-PSMA-ALB-04 (n=1), $^{177}$Lu-PSMA-ALB-05 (n=1), $^{177}$Lu-PSMA-ALB-06 (n=1), $^{177}$Lu-PSMA-ALB-07 (n=1), $^{177}$Lu-PSMA-ALB-08 (n=1) in comparison to the reference compound $^{177}$Lu-PSMA-617 (n=3).

1.2.2 n-Octanol/PBS Distribution Coefficient $^{177}$Lu-PSMA-ALB-01, -03, -04 and -06 showed similar n-octanol/PBS distribution coefficients (Log D value), while the coefficients of $^{177}$Lu-PSMA-ALB-05, -07 and -08 indicated slightly more hydrophilic compounds. In general, the data showed that the introduction of an albumin-binding entity reduces the hydrophilicity as compared to the reference compound $^{177}$Lu-PSMA-617, however, all compounds are still hydrophilic with log D values >2.7 (FIG. 2).

1.2.3 Albumin-Binding Properties

Figure 3:
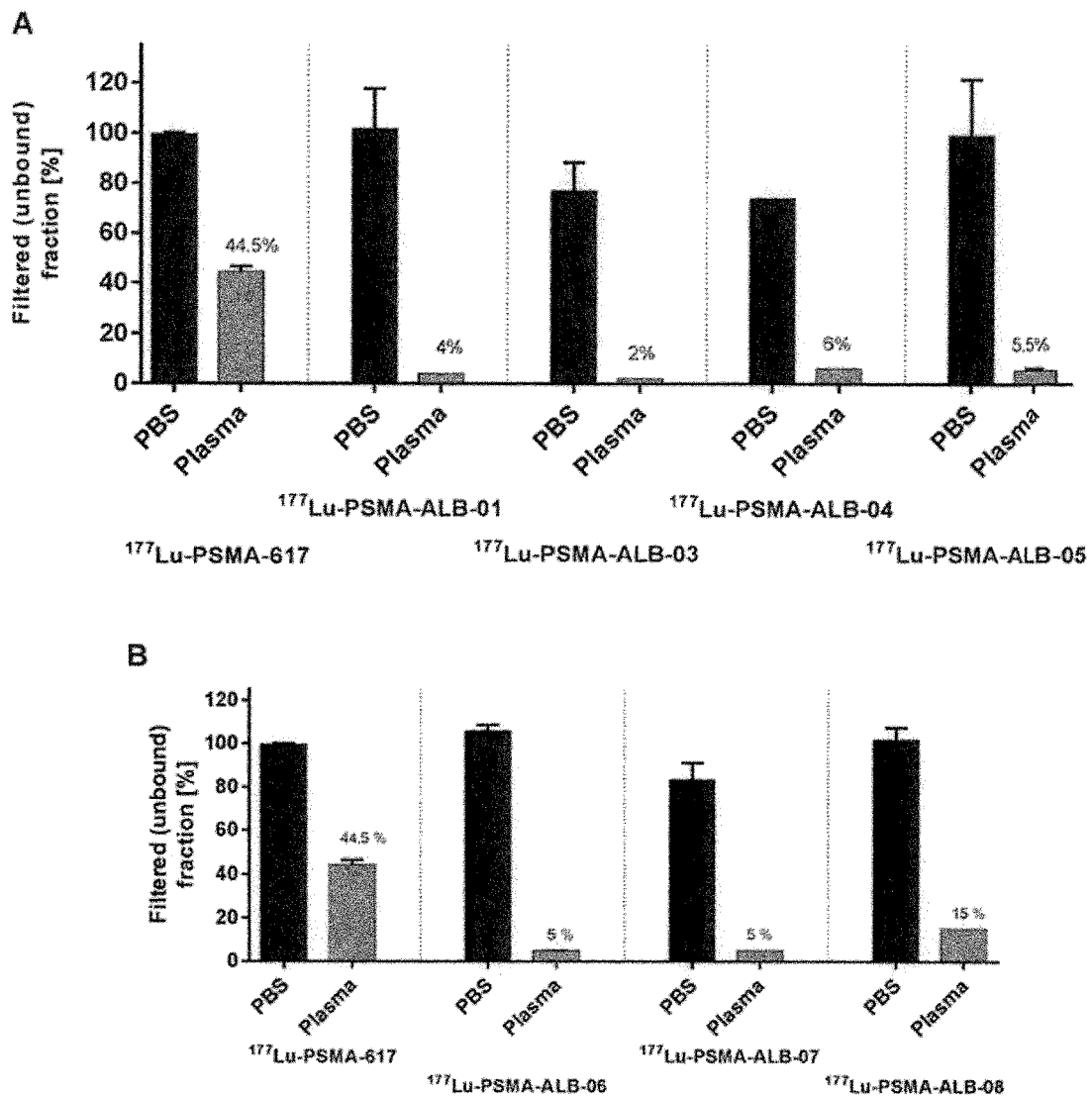
FIG. 3: Data from ultrafiltration assays of $^{177}$Lu-PSMA-ALB-01 (n=2), $^{177}$Lu-PSMA-ALB-03 (n=2), $^{177}$Lu-PSMA-ALB-04 (n=1), $^{177}$Lu-PSMA-ALB-05 (n=1), $^{177}$Lu-PSMA-ALB-06 (n=2), $^{177}$Lu-PSMA-ALB-07 (n=2), $^{177}$Lu-PSMA-ALB-08 (n=2) in comparison to the reference compound $^{177}$Lu-PSMA-617 (n=2).

The ultrafiltration experiments of $^{177}$Lu-PSMA-ALB-01, -03, -04, -05, -06 and -07 revealed high serum protein binding capacities as >94% of the compound did not penetrate the filter when incubated in human plasma. The easy possibility of filtrating the compounds was demonstrating when incubating the compound sin PBS where proteins are not present (FIG. 3). All newly designed compounds revealed increased serum protein binding capacity as compared to $^{177}$Lu-PSMA-617, which showed an albumin-bound fraction of only about 44% (FIG. 3)

1.2.4 Internalization

Figure 4:
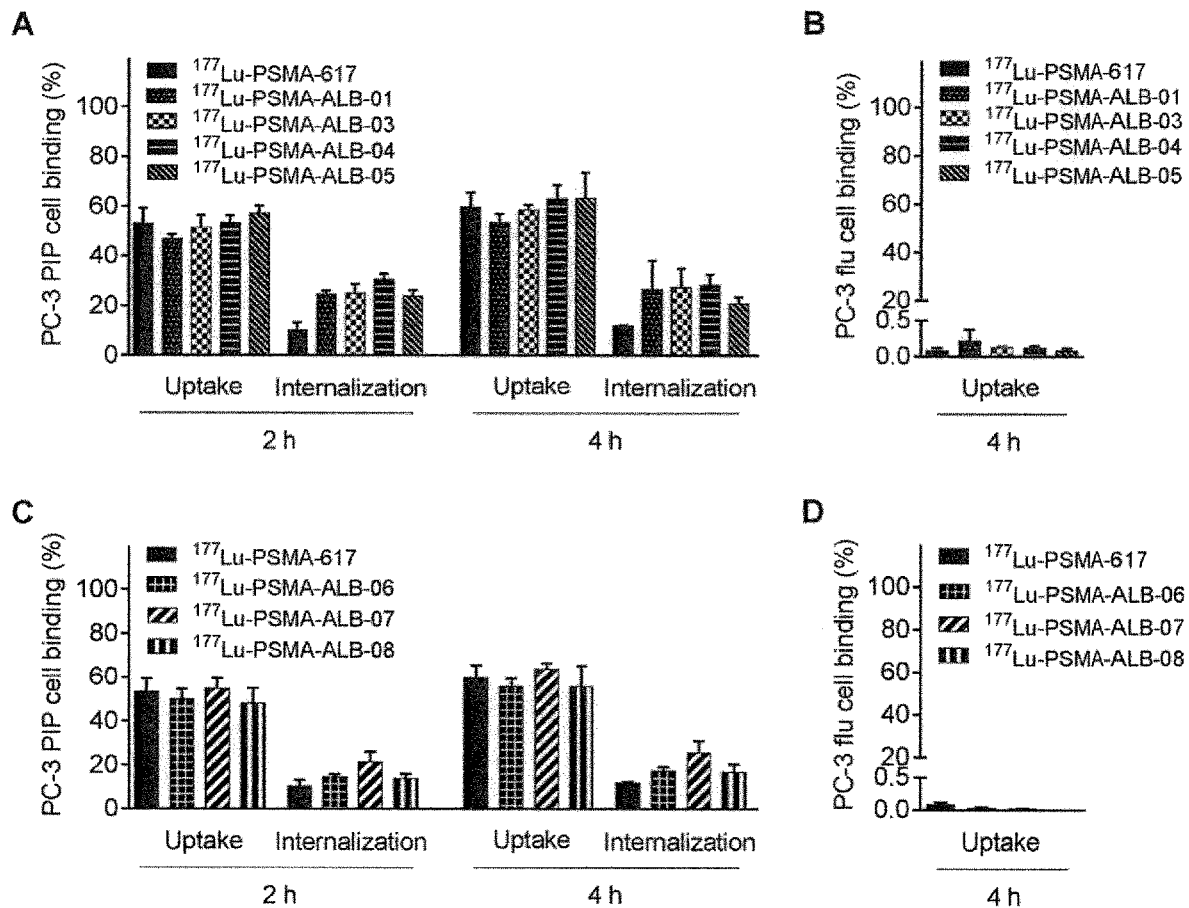
FIG. 4: Uptake and internalization of $^{177}$Lu-PSMA-ALB-01 (n=2), $^{177}$Lu-PSMA-ALB-03 (n=2), $^{177}$Lu-PSMA-ALB-04 (n=1), $^{177}$Lu-PSMA-ALB-05 (n=1), $^{177}$Lu-PSMA-ALB-06 (n=2), $^{177}$Lu-PSMA-ALB-07 (n=2), $^{177}$Lu-PSMA-ALB-08 (n=2) in comparison to the reference compound $^{177}$Lu-PSMA-617 (n=3). (A&C) Data obtained in PSMApos PC-3 PIP cells. (B&D) Data obtained in PSMAneg PC-3 flu cells.

Cell uptake and internalization of PSMA ligands $^{177}$Lu-PSMA-ALB-01, -03, -04, -05, -06, -07 and -08 were investigated and compared to the reference compound $^{177}$Lu-PSMA-617 using PC-3 PIP/flu cells (FIG. 4). The uptake of all compounds into PC-3 PIP cells (PSMA$^{pos}$) was comparable to $^{177}$Lu-PSMA-617 at 2 h or 4 h, respectively. Interestingly, the internalized fraction of the PSMA ligands was higher than for $^{177}$Lu-PSMA-617 at the 2 h and 4 h time-point. The internalization rate of $^{177}$Lu-PSMA-ALB-06 and $^{177}$Lu-PSMA-ALB-08 was still comparable to $^{177}$Lu-PSMA-617. The uptake of all radioligands in PC-3 flu cells (PSMA$^{neg}$) was <0.5%, which proved a highly PSMA-specific uptake/internalization of all compounds.

Figure 5:
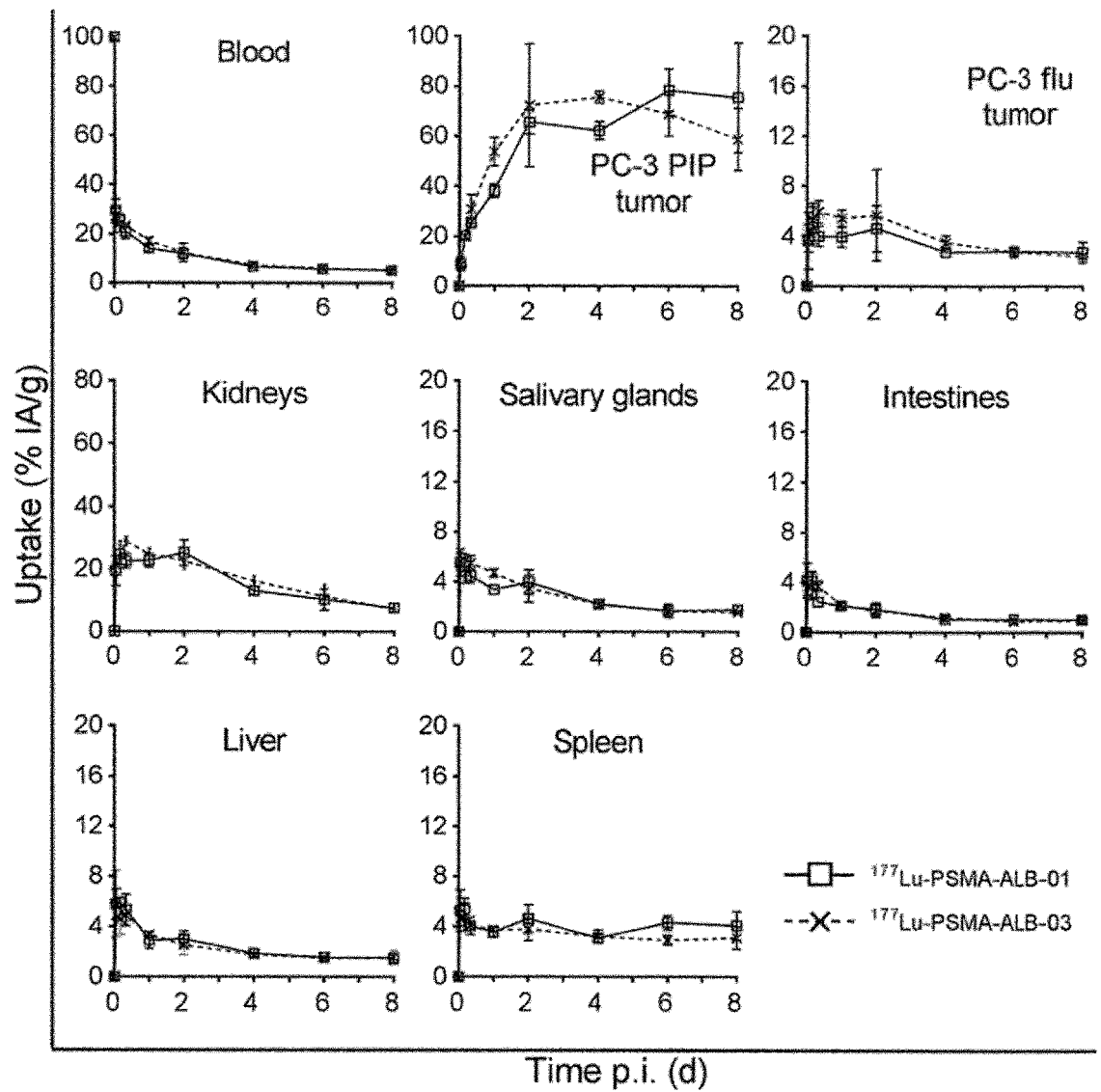
FIG. 5: Biodistribution data of PC-3 PIP/flu tumor-bearing mice treated with $^{177}$Lu-PSMA-ALB-01 and $^{177}$Lu-PSMA-ALB-03 (A), $^{177}$Lu-PSMA-ALB-04 and $^{177}$Lu-PSMA-ALB-05 (B) and $^{177}$Lu-PSMA-ALB-06, $^{177}$Lu-PSMA-ALB-07 and $^{177}$Lu-PSMA-ALB-08 (C).
Figure 5:
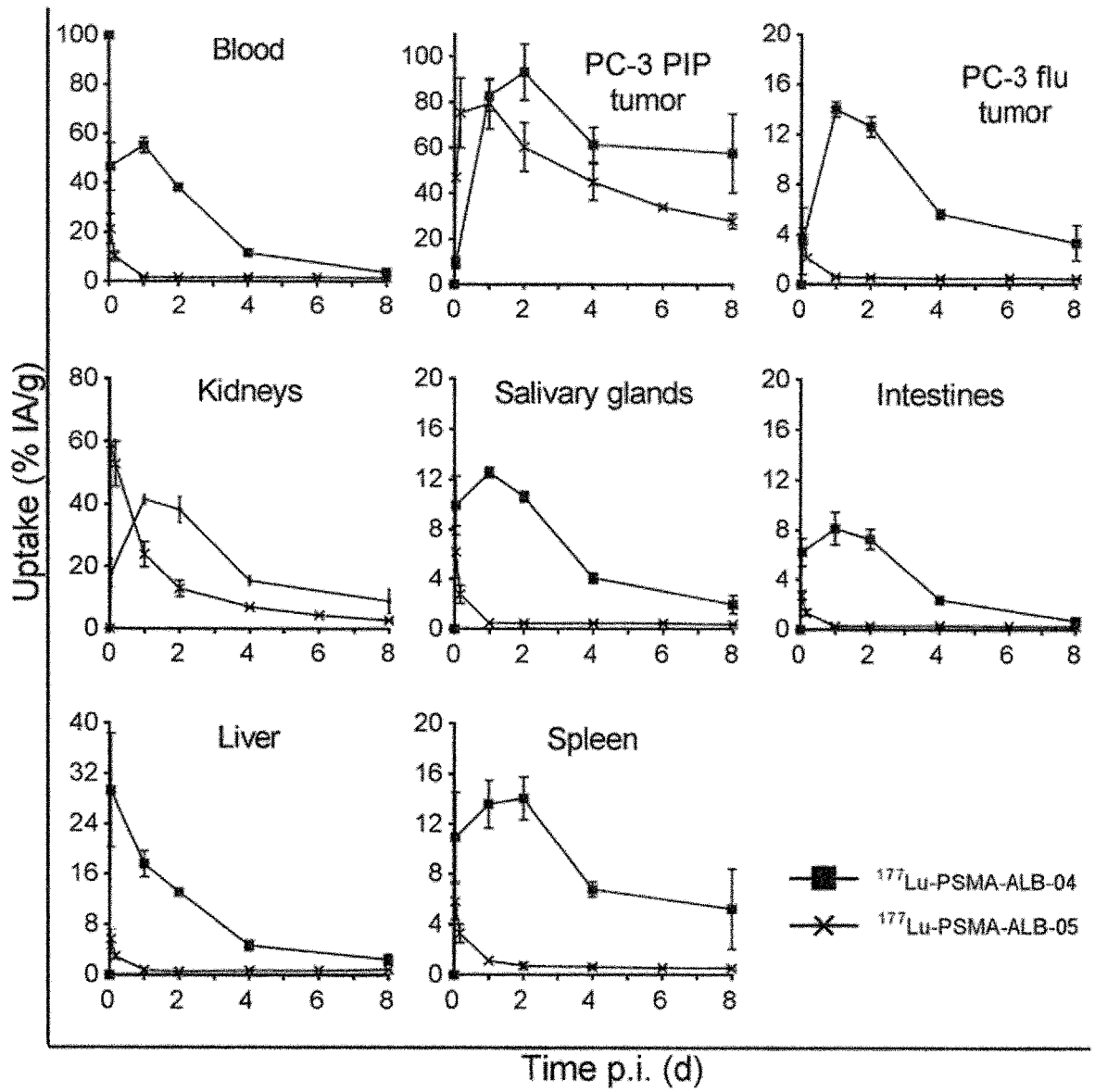
Figure 5:
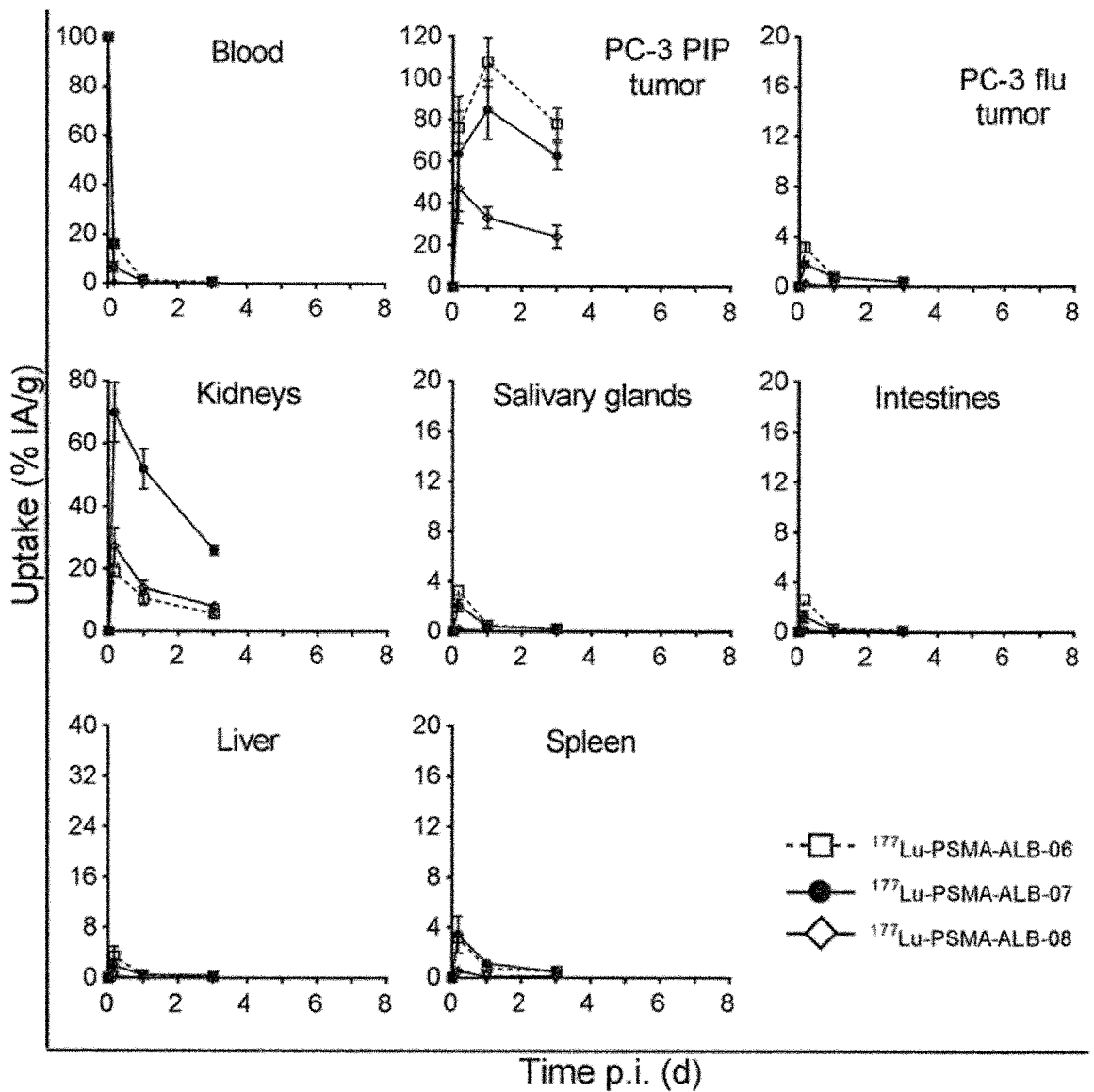
Figure 6:
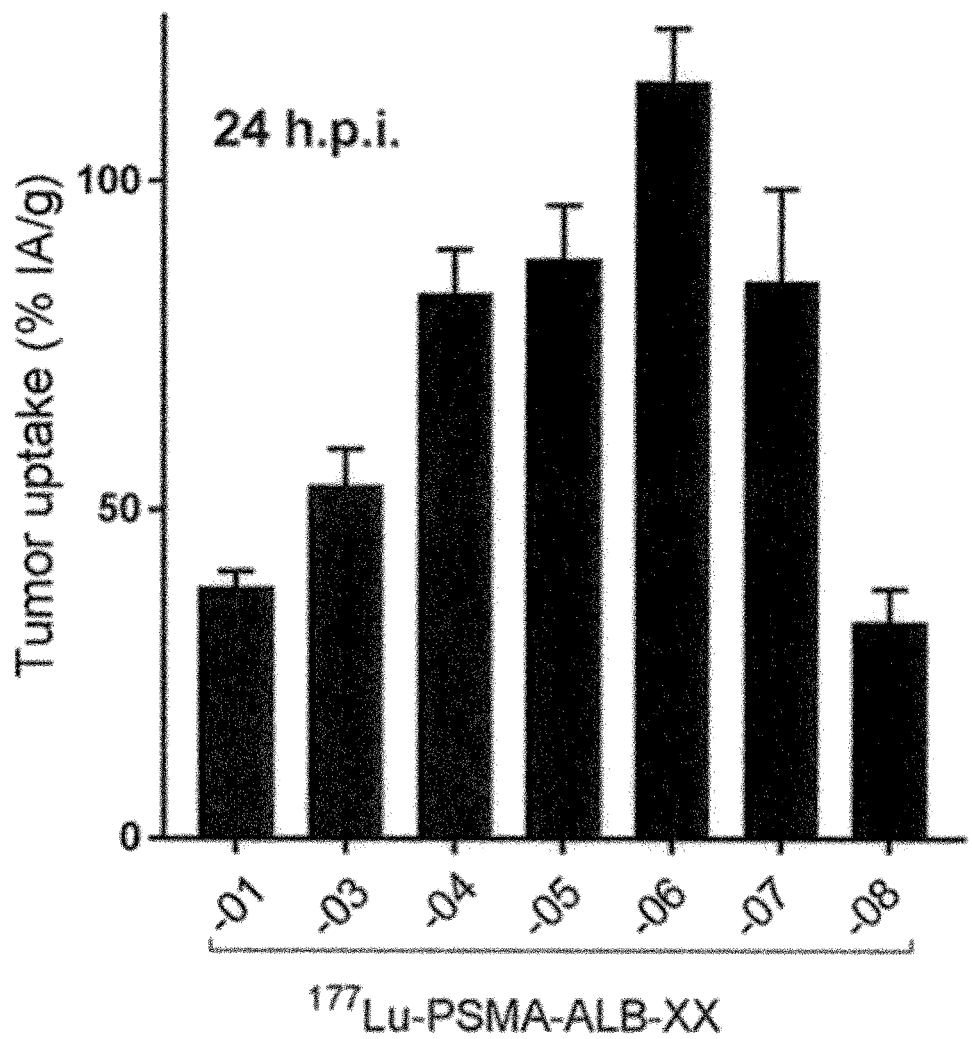
FIG. 6: A conclusive selection of all (A) the tumor uptake, (B) the tumor/blood ratio, (C) the tumor/kidney ratio and (D) the tumor/liver ratio of $^{177}$Lu-PSMA-ALB-01-08.
Figure 6:
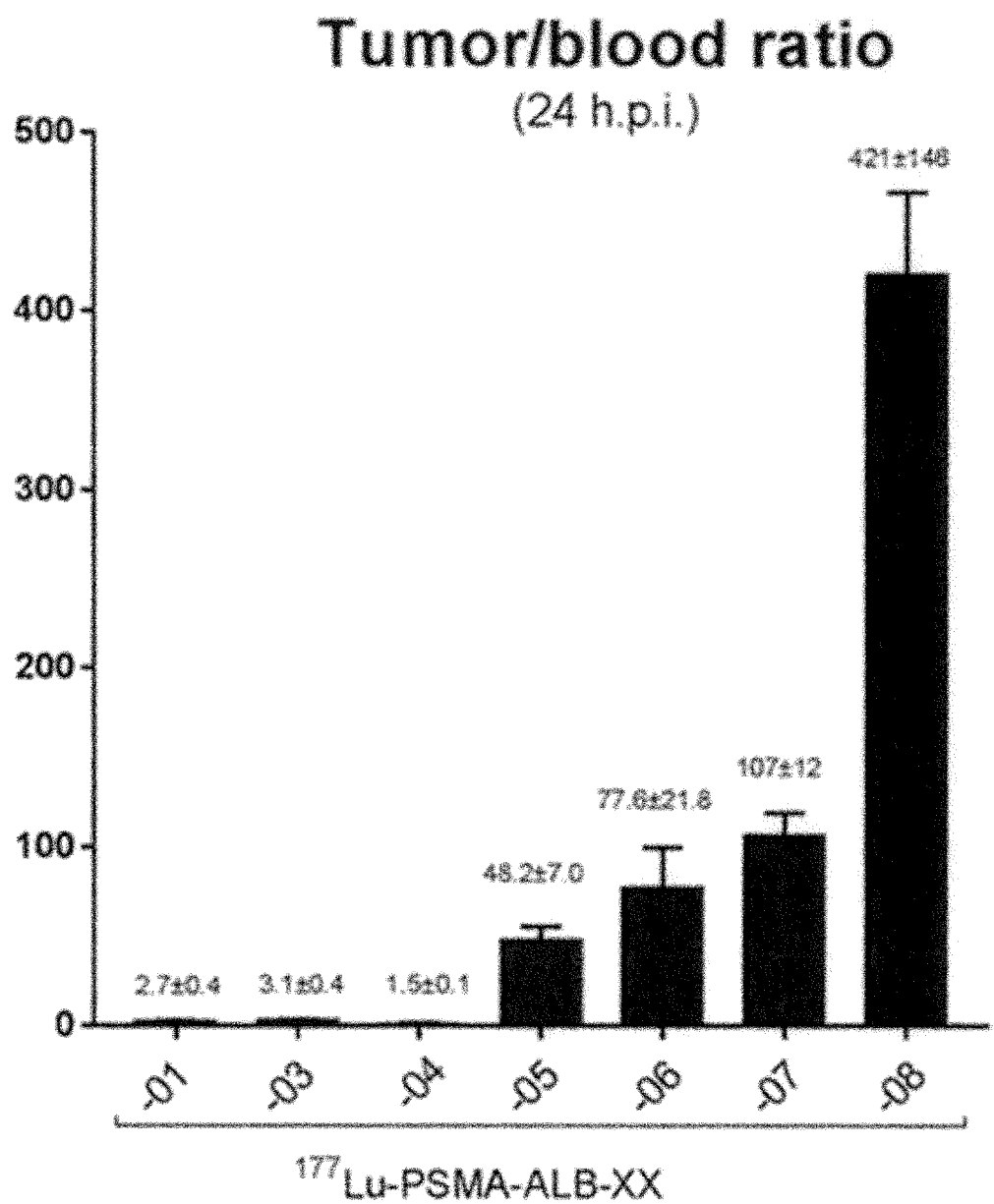
Figure 6:
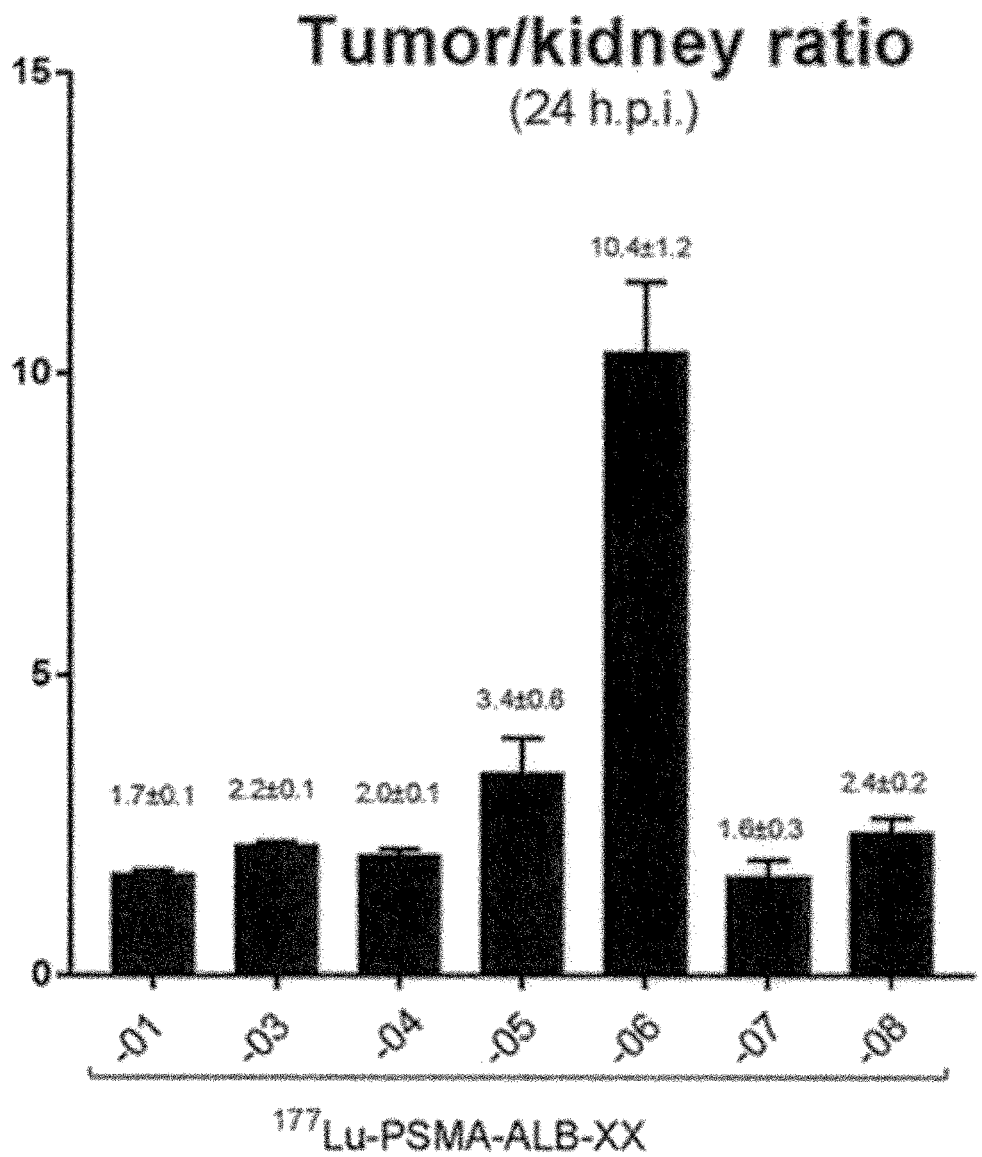
Figure 6:
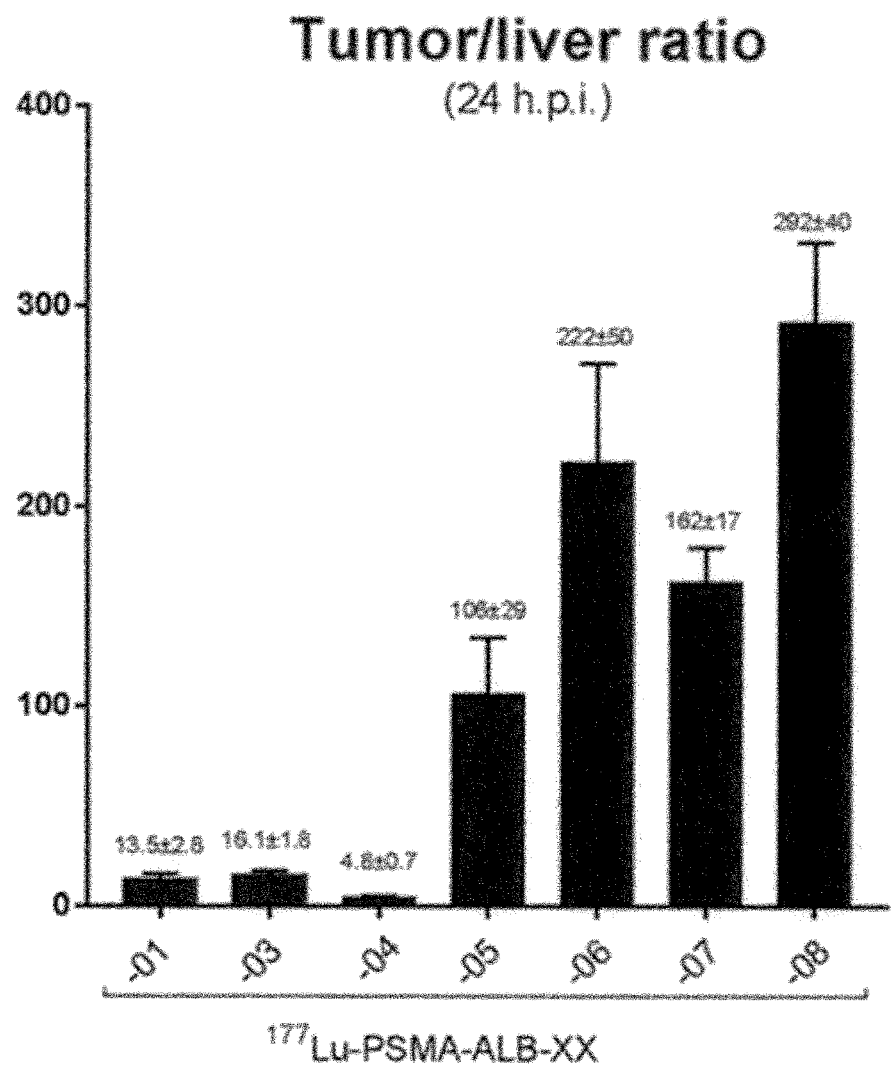

Example 2: In Vivo Evaluation of PSMA Ligands in Tumor Mouse Model $^{177}$Lu-PSMA-ALB-01, -03, -04, -05, -06, -07 and -08 were characterized in vivo. Therefore, immunodeficient Balb/c nude mice were inoculated with PSMApos PC-3 PIP and PSMAneg PC-3 flu cells. After intravenous (i.v.) application of the ligands, extensive biodistribution and SPECT/CT studies were performed. Tumor uptake, tumor/blood ratio, tumor/kidney ratio and tumor/liver ratio of $^{177}$Lu-PSMA-ALB-01-08 are summarized in FIGS. 5 and 6.

2.1 Material and Methods 2.1.1 Tumor Mouse Model

Mice were obtained from Charles River Laboratories, Sulzfeld, Germany, at the age of 5-6 weeks. Female, athymic nude Balb/c mice were subcutaneously inoculated with PC-3 PIP cells ($6\times10^6$ cells in 100 μL Hank's balanced salt solution (HBSS) with $Ca^{2+}/Mg^{2+}$) on the right shoulder and with PC-3 flu cells ($5\times10^6$ cells in 100 μL HBSS $Ca^{2+}/Mg^{2+}$) on the left shoulder. Two weeks later, the tumors reached a size of about 200-300 mm$^3$ suitable for the performance of the biodistribution and imaging studies.

2.1.2 Biodistribution Studies

Biodistribution studies were performed using PC-3 PIP/flu tumor-bearing mice, which were inoculated with tumor cells two weeks prior to injection of PSMA ligands. The radioligands were diluted in 0.9% NaCl and i.v. injected in a volume of 100-200 μL. Mice were euthanized at different time points after injection (p.i.) of the radioligands. Selected tissues and organs were collected, weighed and measured using a gamma-counter. The results were decay-corrected and listed as a percentage of the injected activity per gram of tissue mass (% IA/g).

2.1.3 SPECT/CT Imaging Studies.

SPECT/CT experiments were performed using a dedicated small-animal SPECT/CT camera (NanoSPECT/CT™, Mediso Medical Imaging Systems, Budapest, Hungary). The PSMA ligands were labeled at a specific activity of 25 MBq/nmol and diluted in saline containing 0.05% BSA. Scans were acquired at 4 h, 24 h and 72 h after injection of the radioligands (25 MBq, 1 nmol, 100 L). Data was reconstructed using NanoSPECT/CT™ software and post-processed using VivoQuant (version 3.0, inviCRO Imaging Services and Software, Boston USA). A Gauss post-reconstruction filter (FWHM=1 mm) was applied and the scale of radioactivity was set as indicated on the images (minimum value=0.095 Bq/voxel to maximum value=95 Bq/voxel).

2.1.4 Therapy in Mouse Model

Five groups of mice (Groups A to E, n=6) with statistically similar body weights and tumor volumes were injected with only the vehicle (saline containing BSA 0.05%; Group A), $^{177}$Lu-PSMA-617 (Groups B and C) and $^{177}$Lu-PSMA-ALB-06 (Groups D and E), respectively, at Day 0 of the therapy study (Table 2.1). Mice of Groups B and D received 2 MBq of the radioligand (1 nmol/mouse), whereas mice of Groups C and E received 5 MBq of the radioligand (1 nmol/mouse). The mice were monitored by measuring body weights and the tumor size every other day over 12 weeks. Mice were euthanized when pre-defined endpoint criteria were reached, or when the study was terminated at Day 84. The relative body weight (RBW) was defined as [$BW_x$/$BW_0$], where $BW_x$ is the body weight in gram at a given day x and $BW_0$ the body weight in gram at day 0. The tumor dimension was determined by measuring the longest tumor axis (L) and its perpendicular axis (W) with a digital caliper. The tumor volume (V) was calculated according to the equation [V=0.5*(L*W2)]. The relative tumor volume (RTV) was defined as [$TV_x/TV_0$], where $TV_x$ is the tumor volume in mm3 at a given day x and $TV_0$ the tumor volume in mm3 at Day 0.

TABLE 2.1

Design of Therapy Study

| group | Treatment (n = 6) | injected radioactivity [MBq] theoretical | injected radioactivity [MBq] measured[a] (average ± SD) | tumor volume[b] [mm³] (average ± SD) Day 0 | body weight[b] [g] (average ± SD) Day 0 |
|---|---|---|---|---|---|
| A | saline | | | 88 ± 21 | 16 ± 1.6 |
| B | $^{177}$Lu-PSMA-617 | 2 | 2.2 ± 0.1 | 103 ± 24 | 16 ± 1.2 |
| C | $^{177}$Lu-PSMA-617 | 5 | 5.7 ± 0.4 | 104 ± 25 | 17 ± 0.9 |
| D | $^{177}$Lu-PSMA-ALB-56 | 2 | 2.1 ± 0.3 | 81 ± 25 | 15 ± 1.3 |
| E | $^{177}$Lu-PSMA-ALB-56 | 5 | 5.4 ± 0.5 | 92 ± 34 | 15 ± 1.3 |

[a]Radioactivity in the syringe measured before and after injecting the respective mouse.
[b]No significant differences determined between the values measured for each group (p > 0.05).

The efficacy of the radionuclide therapy was expressed as the tumor growth delay ($TGD_x$), which was calculated as the time required for the tumor volume to increase x-fold over the initial volume at the Day 0. The tumor growth delay index [$TGDI_x = TGD_x(T)/TGD_x(C)$] was calculated as the $TGD_x$ ratio of treated mice (T) over control mice (C) for a 2-fold (x=2, TGD2) and 5-fold (x=5, TGD5) increase of the initial tumor volume. As a measure to identify undesired side effects, body weights were compared at the day when the first control mouse had to be euthanized. After euthanasia, kidneys, liver and the brain were collected and weighed. The organ ratios (kidney-to-brain and liver-to-brain) were calculated using the organ masses obtained at the day of euthanasia.

The data was analyzed for significance as indicated in the result part using a one-way ANOVA with Tukey's multiple comparison post-test using GraphPad Prism software (version 7). A value of p<0.05 was considered statistically significant. Survival analysis was performed with Kaplan-Meier curves and a log-rank tests (Mantel Cox).

2.2 Results 2.2.1 Biodistribution of $^{177}$Lu-PSMA-ALB-01, $^{177}$Lu-PSMA-ALB-03

The tissue distribution of $^{177}$Lu-PSMA-ALB-01 and $^{177}$Lu-PSMA-ALB-03 was investigated over a period of eight days. Compounds $^{177}$Lu-PSMA-ALB-01 and $^{177}$Lu-PSMA-ALB-03 showed highly similar tissue distribution profiles (FIG. 5A).

High radioactivity levels could be observed in the blood pool already at early time points and were cleared slowly but steadily over time. The uptake of both radioligands in the $PSMA^{pos}$ PC-3 PIP tumors was increasing until it reached a plateau and did not drop substantially until the end of the study. The uptake in PC-3 flu tumors was clearly below blood levels, indicating highly PSMA-specific binding and uptake in vivo (FIG. 5A). Biodistribution data for $^{177}$Lu-PSMA-ALB-01 and -03 are shown in Table 2.2 and 2.3 below.

TABLE 2.2

Biodistribution of 177Lu-PSMA-ALB-01 in PC-3 PIP/flu Tumor-Bearing Mice

|  | 1 h.p.i. | 4 h.p.i. | 8 h p.i. | 24 h p.i. | 48 h p.i. | 96 h p.i. |
|---|---|---|---|---|---|---|
| Blood | 29.7 ± 4.49 | 25.6 ± 1.53 | 21.0 ± 2.86 | 14.2 ± 1.40 | 12.0 ± 2.18 | 6.68 ± 0.85 |
| Heart | 10.1 ± 1.10 | 8.71 ± 0.50 | 7.16 ± 1.23 | 5.93 ± 0.65 | 4.42 ± 0.81 | 2.70 ± 0.37 |
| Lung | 16.6 ± 2.78 | 14.1 ± 0.99 | 11.6 ± 0.83 | 8.62 ± 1.47 | 7.67 ± 0.83 | 5.07 ± 0.66 |
| Spleen | 5.27 ± 1.64 | 5.34 ± 0.90 | 4.05 ± 0.69 | 3.60 ± 0.43 | 4.62 ± 1.12 | 3.12 ± .015 |
| Kidneys | 19.4 ± 4.82 | 24.6 ± 0.38 | 22.6 ± 2.38 | 22.7 ± 2.18 | 25.2 ± 4.15 | 13.0 ± 1.30 |
| Stomach | 3.29 ± 1.75 | 3.30 ± 0.05 | 2.45 ± 0.43 | 1.39 ± 0.07 | 1.49 ± 0.47 | 0.81 ± 0.04 |
| Intestines | 4.15 ± 1.40 | 4.17 ± 0.70 | 2.44 ± 0.17 | 2.12 ± 0.20 | 1.84 ± 0.54 | 1.05 ± 0.17 |
| Liver | 5.76 ± 1.21 | 5.92 ± 0.07 | 5.31 ± 1.23 | 2.92 ± 0.67 | 3.03 ± 0.63 | 1.88 ± 0.36 |
| Salivary glands | 5.52 ± 1.08 | 5.20 ± 0.73 | 4.45 ± 0.56 | 3.38 ± 0.32 | 3.96 ± 0.98 | 2.22 ± 0.38 |
| Muscle | 2.22 ± 0.88 | 2.06 ± 0.80 | 1.63 ± 0.27 | 1.34 ± 0.14 | 1.35 ± 0.46 | 0.82 ± 0.12 |
| Bone | 3.15 ± 0.47 | 3.01 ± 0.09 | 2.54 ± 0.26 | 1.58 ± 0.06 | 1.64 ± 0.34 | 1.07 ± 0.22 |
| PC-3 PIP Tumor | 8.98 ± 2.77 | 20.4 ± 0.39 | 25.5 ± 2.02 | 38.2 ± 2.59 | 65.6 ± 1.84 | 62.3 ± 3.56 |
| PC-3 flu Tumor | 3.64 ± 2.30 | 5.03 ± 1.61 | 4.01 ± 0.79 | 3.95 ± 0.82 | 4.64 ± 1.84 | 2.76 ± 0.23 |
| Tumor-to-blood | 0.30 ± 0.06 | 0.80 ± 0.03 | 1.22 ± 0.08 | 2.71 ± 0.39 | 5.54 ± 0.76 | 9.39 ± 0.65 |
| Tumor-to-liver | 1.56 ± 0.30 | 3.45 ± 0.03 | 4.97 ± 1.21 | 13.5 ± 2.79 | 22.2 ± 4.11 | 33.7 ± 4.33 |
| Tumor-to-kidney | 0.46 ± 0.04 | 0.83 ± 0.03 | 1.13 ± 0.07 | 1.69 ± 0.07 | 2.64 ± 0.40 | 4.80 ± 0.20 |

|  | 144 h.p.i. | 192 h.p.i. |
|---|---|---|
| Blood | 5.78 ± 0.90 | 5.21 ± 1.37 |
| Heart | 2.23 ± 0.29 | 2.12 ± 0.68 |

TABLE 2.2-continued

Biodistribution of 177Lu-PSMA-ALB-01 in PC-3 PIP/flu Tumor-Bearing Mice

| | | |
|---|---|---|
| Lung | 4.90 ± 0.58 | 4.12 ± 0.96 |
| Spleen | 4.32 ± 0.57 | 4.09 ± 1.12 |
| Kidneys | 10.2 ± 3.41 | 7.56 ± 1.44 |
| Stomach | 0.84 ± 0.13 | 0.73 ± 0.12 |
| Intestines | 1.07 ± 0.13 | 1.02 ± 0.25 |
| Liver | 1.56 ± 0.16 | 1.51 ± 0.37 |
| Salivary glands | 1.68 ± 0.53 | 1.78 ± 0.34 |
| Muscle | 0.66 ± 0.15 | 0.64 ± 0.13 |
| Bone | 0.99 ± 0.20 | 0.86 ± 0.17 |
| PC-3 PIP Tumor | 78.4 ± 8.57 | 75.6 ± 22.0 |
| PC-3 flu Tumor | 2.82 ± 0.24 | 2.73 ± 0.84 |
| Tumor-to-blood | 13.8 ± 2.38 | 14.5 ± 1.84 |
| Tumor-to-liver | 50.5 ± 6.28 | 50.2 ± 7.38 |
| Tumor-to-kidney | 8.05 ± 1.77 | 9.87 ± 1.05 |

TABLE 2.3

Biodistribution of $^{177}$Lu-PSMA-ALB-03 in PC-3 PIP/flu Tumor-Bearing Mice

| | 1 h.p.i. | 4 h.p.i. | 8 h p.i. | 24 h p.i. | 48 h p.i. | 96 h p.i. |
|---|---|---|---|---|---|---|
| Blood | 27.4 ± 3.04 | 24.3 ± 3.60 | 23.5 ± 0.74 | 17.3 ± 1.38 | 12.5 ± 3.78 | 7.37 ± 0.64 |
| Heart | 9.64 ± 1.21 | 8.54 ± 1.18 | 8.12 ± 0.46 | 6.60 ± 1.01 | 4.40 ± 1.18 | 3.15 ± 0.28 |
| Lung | 16.6 ± 3.29 | 14.21 ± 3.49 | 12.21 ± 1.32 | 9.86 ± 0.57 | 7.45 ± 2.06 | 5.56 ± 0.54 |
| Spleen | 4.63 ± 0.56 | 4.76 ± 1.12 | 4.10 ± 0.14 | 3.75 ± 0.21 | 3.79 ± 0.89 | 3.23 ± 0.53 |
| Kidneys | 17.8 ± 2.49 | 24.5 ± 4.38 | 28.8 ± 1.49 | 24.7 ± 1.85 | 22.6 ± 2.69 | 16.1 ± 1.69 |
| Stomach | 3.19 ± 0.95 | 2.86 ± 1.03 | 2.92 ± 0.17 | 1.39 ± 0.27 | 1.49 ± 0.48 | 0.91 ± .010 |
| Intestines | 3.70 ± 0.73 | 3.71 ± 1.09 | 3.70 ± 0.40 | 2.19 ± 0.23 | 1.73 ± 0.50 | 1.21 ± 0.26 |
| Liver | 5.81 ± 2.65 | 4.56 ± 1.18 | 4.87 ± 0.42 | 3.35 ± 0.26 | 2.53 ± 0.77 | 1.78 ± 0.03 |
| Salivary glands | 5.60 ± 0.70 | 5.02 ± 1.17 | 5.49 ± 0.59 | 4.69 ± 0.33 | 3.45 ± 1.09 | 2.19 ± 0.1 |
| Muscle | 1.91 ± 0.16 | 2.04 ± 0.37 | 2.01 ± 0.10 | 1.61 ± 0.18 | 1.32 ± 0.41 | 0.91 ± 0.15 |
| Bone | 2.82 ± 0.41 | 2.47 ± 0.39 | 2.71 ± 0.21 | 2.02 ± 0.31 | 1.63 ± 0.56 | 1.07 ± 0.27 |
| PC-3 PIP Tumor | 8.49 ± 0.62 | 19.9 ± 0.79 | 31.0 ± 5.79 | 53.8 ± 5.61 | 72.3 ± 24.7 | 75.7 ± 2.46 |
| PC-3 flu Tumor | 3.84 ± 1.10 | 5.32 ± 1.06 | 5.98 ± 0.91 | 5.47 ± 0.67 | 5.69 ± 3.65 | 3.52 ± 0.54 |
| Tumor-to-blood | 0.31 ± 0.04 | 0.83 ± 0.10 | 1.32 ± 0.29 | 3.13 ± 0.35 | 5.94 ± 1.53 | 10.3 ± 0.57 |
| Tumor-to-liver | 1.64 ± 0.61 | 4.60 ± 1.34 | 6.38 ± 1.28 | 16.1 ± 1.75 | 29.0 ± 5.26 | 42.6 ± 1.90 |
| Tumor-to-kidney | 0.48 ± 0.07 | 0.83 ± 0.14 | 1.07 ± 0.18 | 2.17 ± 0.06 | 3.17 ± 0.84 | 4.7 ± 0.38 |

| | 144 h.p.i. | 192 h.p.i. |
|---|---|---|
| Blood | 6.02 ± 0.60 | 5.29 ± 0.18 |
| Heart | 2.55 ± 0.25 | 2.08 ± 0.14 |
| Lung | 4.99 ± 1.00 | 4.17 ± 0.68 |
| Spleen | 2.94 ± 0.39 | 3.13 ± 0.90 |
| Kidneys | 11.2 ± 3.82 | 7.35 ± 0.92 |
| Stomach | 0.73 ± 0.10 | 0.78 ± 0.07 |
| Intestines | 0.88 ± 0.18 | 0.96 ± 0.03 |
| Liver | 1.50 ± 0.14 | 1.25 ± 0.20 |
| Salivary glands | 1.67 ± 0.27 | 1.55 ± 0.06 |
| Muscle | 0.54 ± 0.07 | 0.62 ± 0.04 |
| Bone | 1.14 ± 0.23 | 0.83 ± 0.22 |
| PC-3 PIP Tumor | 68.9 ± 8.80 | 58.9 ± 12.4 |
| PC-3 flu Tumor | 2.77 ± 0.41 | 2.42 ± 0.23 |
| Tumor-to-blood | 11.4 ± 0.47 | 11.1 ± 1.97 |
| Tumor-to-liver | 46.0 ± 2.53 | 47.1 ± 2.44 |
| Tumor-to-kidney | 6.44 ± 1.27 | 7.97 ± 0.70 |

2.2.2 Biodistribution of $^{177}$Lu-PSMA-ALB-04 and $^{177}$Lu-PSMA-ALB-05

The tissue distribution of $^{177}$Lu-PSMA-ALB-04 and $^{177}$Lu-PSMA-ALB-05 was investigated over a period of eight days (FIG. 5B).

Blood activity levels in animals injected with $^{177}$Lu-PSMA-ALB-04 was very high at early time points and remained by far the highest. A high PSMApos PC-3 PIP tumor accumulation was observed, which slightly decreased towards the end of the study. The accumulated activity in the PSMA$^{neg}$ PC-3 flu tumor and other non-target organs was clearly below blood levels, indicating highly PSMA-specific binding and uptake in vivo.

The high levels in the blood pool of animals injected with $^{177}$Lu-PSMA-ALB-05 were decreasing quickly and remained stable at low levels until the end of the study. Highest uptake of radioactivity could be observed in the PSMA$^{pos}$ PC-3 PIP tumors of mice injected with $^{177}$Lu-PSMA-ALB-05, which was followed by a steady wash-out from the tumor tissue. The uptake in PC-3 flu tumors and other tissues was clearly below blood levels, indicating PSMA-specific binding and uptake in vivo. Biodistribution data for $^{177}$Lu-PSMA-ALB-04 and -05 are shown in Table 2.4 and 2.5 below.

TABLE 2.4

Biodistribution of $^{177}$Lu-PSMA-ALB-04 in PC-3 PIP/flu Tumor-Bearing Mice

| | 1 h.p.i. | 4 h.p.i. | 8 h.p.i. | 24 h p.i. | 48 h p.i. | 96 h p.i. |
|---|---|---|---|---|---|---|
| Blood | 46.7 ± 9.64 | n/d | n/d | 55.3 ± 3.10 | 38.2 ± 1.48 | 11.65 ± 1.22 |
| Heart | 16.4 ± 5.71 | n/d | n/d | 22.1 ± 3.70 | 13.6 ± 0.36 | 4.81 ± 0.29 |
| Lung | 25.6 ± 4.59 | n/d | n/d | 40.1 ± 7.77 | 24.6 ± 2.02 | 9.96 ± 1.44 |
| Spleen | 11.0 ± 3.56 | n/d | n/d | 13.6 ± 1.90 | 14.0 ± 1.70 | 6.76 ± 0.59 |
| Kidneys | 17.8 ± 4.49 | n/d | n/d | 41.5 ± 1.44 | 38.2 ± 4.10 | 15.3 ± 1.49 |
| Stomach | 4.01 ± 0.62 | n/d | n/d | 6.18 ± 0.95 | 5.04 ± 0.35 | 1.74 ± 0.11 |
| Intestines | 6.22 ± 1.11 | n/d | n/d | 8.13 ± 1.31 | 7.27 ± 0.82 | 2.36 ± 0.17 |
| Liver | 29.3 ± 9.10 | n/d | n/d | 17.6 ± 2.04 | 13.1 ± 0.67 | 4.67 ± 0.82 |
| Salivary glands | 9.93 ± 2.33 | n/d | n/d | 12.5 ± 0.72 | 10.6 ± 0.42 | 4.08 ± 0.44 |
| Muscle | 1.96 ± 0.40 | n/d | n/d | 5.82 ± 1.62 | 4.62 ± 0.38 | 1.56 ± 0.56 |
| Bone | 4.74 ± 1.31 | n/d | n/d | 8.88 ± 0.19 | 6.80 ± 0.67 | 2.54 ± 0.31 |
| PC-3 PIP Tumor | 9.56 ± 2.71 | n/d | n/d | 82.8 ± 6.84 | 93.2 ± 12.4 | 61.4 ± 7.68 |
| PC-3 flu Tumor | 3.46 ± 2.66 | n/d | n/d | 14.0 ± 0.60 | 12.6 ± 0.82 | 5.63 ± 0.37 |
| Tumor-to-blood | 0.20 ± 0.02 | n/d | n/d | 1.50 ± 0.11 | 2.45 ± 0.41 | 5.29 ± 0.74 |
| Tumor-to-liver | 0.33 ± 0.06 | n/d | n/d | 4.76 ± 0.67 | 7.16 ± 1.16 | 13.4 ± 2.88 |
| Tumor-to-kidney | 0.54 ± 0.09 | n/d | n/d | 2.00 ± 0.11 | 2.47 ± 0.50 | 4.03 ± 0.56 |

| | 144 h.p.i. | 192 h.p.i. |
|---|---|---|
| Blood | n/d | 3.75 ± 1.49 |
| Heart | n/d | 1.73 ± 0.70 |
| Lung | n/d | 4.10 ± 1.77 |
| Spleen | n/d | 5.22 ± 3.17 |
| Kidneys | n/d | 8.82 ± 3.83 |
| Stomach | n/d | 0.56 ± 0.19 |
| Intestines | n/d | 0.67 ± 0.15 |
| Liver | n/d | 2.45 ± 0.81 |
| Salivary glands | n/d | 1.96 ± 0.73 |
| Muscle | n/d | 0.71 ± 0.54 |
| Bone | n/d | 1.17 ± 0.61 |
| PC-3 PIP Tumor | n/d | 57.6 ± 17.3 |
| PC-3 flu Tumor | n/d | 3.31 ± 1.43 |
| Tumor-to-blood | n/d | 15.8 ± 3.55 |
| Tumor-to-liver | n/d | 23.9 ± 5.12 |
| Tumor-to-kidney | n/d | 6.91 ± 2.24 |

TABLE 2.5

Biodistribution of $^{177}$Lu-PSMA-ALB-05 in PC-3 PIP/flu Tumor-Bearing Mice

| | 1 h.p.i. | 4 h.p.i. | 8 h p.i. | 24 h p.i. | 48 h p.i. | 96 h p.i. |
|---|---|---|---|---|---|---|
| Blood | 21.3 ± 6.06 | 10.2 ± 1.98 | n/d | 1.67 ± 0.29 | 1.66 ± 0.37 | 1.79 ± 0.57 |
| Heart | 7.56 ± 1.89 | 3.82 ± 0.63 | n/d | 0.65 ± 0.11 | 0.54 ± 0.15 | 0.70 ± 0.21 |
| Lung | 15.0 ± 1.24 | 7.07 ± 1.44 | n/d | 1.80 ± 0.78 | 1.48 ± 0.62 | 1.36 ± 0.29 |
| Spleen | 5.78 ± 1.40 | 3.29 ± 0.74 | n/d | 1.13 ± 0.23 | 0.71 ± 0.23 | 0.64 ± 0.29 |
| Kidneys | 59.3 ± 1.38 | 52.8 ± 7.17 | n/d | 23.9 ± 4.02 | 12.8 ± 2.62 | 6.89 ± 0.31 |
| Stomach | 2.04 ± 0.43 | 1.15 ± 0.17 | n/d | 0.28 ± 0.06 | 0.29 ± 0.08 | 0.24 ± 0.07 |
| Intestines | 2.71 ± 0.40 | 1.33 ± 0.25 | n/d | 0.28 ± 0.05 | 0.28 ± 0.10 | 0.30 ± 0.11 |
| Liver | 5.69 ± 1.59 | 2.96 ± 0.50 | n/d | 0.82 ± 0.35 | 0.56 ± 0.16 | 0.74 ± 0.14 |
| Salivary glands | 6.17 ± 2.12 | 2.75 ± 0.72 | n/d | 0.49 ± 0.10 | 0.45 ± 0.10 | 0.46 ± 0.10 |
| Muscle | 2.36 ± 1.01 | 1.30 ± 0.23 | n/d | 0.19 ± 0.06 | 0.20 ± 0.08 | 0.15 ± 0.06 |
| Bone | 3.03 ± 0.52 | 1.67 ± 0.27 | n/d | 0.31 ± 0.08 | 0.28 ± 0.05 | 0.28 ± 0.04 |
| PC-3 PIP Tumor | 46.9 ± 0.43 | 75.3 ± 15.3 | n/d | 79.4 ± 11.1 | 60.3 ± 10.7 | 45.0 ± 7.94 |
| PC-3 flu Tumor | 3.72 ± 0.83 | 2.10 ± 0.20 | n/d | 0.59 ± 0.10 | 0.57 ± 0.09 | 0.49 ± 0.11 |
| Tumor-to-blood | 2.31 ± 0.58 | 7.43 ± 1.43 | n/d | 48.2 ± 7.04 | 36.7 ± 1.81 | 27.1 ± 10.0 |
| Tumor-to-liver | 8.65 ± 2.21 | 25.6 ± 4.58 | n/d | 106 ± 28.6 | 110 ± 12.2 | 62.8 ± 18.8 |
| Tumor-to-kidney | 0.79 ± 0.02 | 1.42 ± 0.19 | n/d | 3.38 ± 0.58 | 4.72 ± 0.18 | 6.51 ± 0.98 |

| | 144 h.p.i. | 192 h.p.i. |
|---|---|---|
| Blood | 1.75 ± 0.35 | 1.48 ± 0.13 |
| Heart | 0.65 ± 0.17 | 0.59 ± 0.05 |
| Lung | 1.25 ± 0.18 | 1.22 ± 0.26 |
| Spleen | 0.56 ± 0.08 | 0.55 ± 0.10 |
| Kidneys | 4.28 ± 0.26 | 2.70 ± 0.36 |
| Stomach | 0.23 ± 0.04 | 0.16 ± 0.04 |
| Intestines | 0.27 ± 0.05 | 0.24 ± 0.04 |
| Liver | 0.72 ± 0.13 | 0.84 ± 0.06 |
| Salivary glands | 0.46 ± 0.09 | 0.37 ± 0.04 |
| Muscle | 0.17 ± 0.04 | 0.14 ± 0.01 |
| Bone | 0.25 ± 0.05 | 0.26 ± 0.04 |
| PC-3 PIP Tumor | 33.9 ± 0.80 | 27.9 ± 3.24 |

TABLE 2.5-continued

| Biodistribution of $^{177}$Lu-PSMA-ALB-05 in PC-3 PIP/flu Tumor-Bearing Mice | | |
|---|---|---|
| PC-3 flu Tumor | 0.52 ± 0.13 | 0.45 ± 0.06 |
| Tumor-to-blood | 19.9 ± 3.88 | 19.0 ± 2.97 |
| Tumor-to-liver | 47.9 ± 8.28 | 33.4 ± 1.64 |
| Tumor-to-kidney | 7.93 ± 0.30 | 10.4 ± 0.25 |

2.2.3 Biodistribution of $^{177}$Lu-PSMA-ALB-06, $^{177}$Lu-PSMA-ALB-07, $^{177}$Lu-PSMA-ALB-08

The tissue distribution of $^{177}$Lu-PSMA-ALB-06, -07 and -08 was investigated up to three days post injection (FIG. 5C).

Blood activity levels of all compounds decreased quickly and were comparable throughout the entire study. The highest PSMA$^{pos}$ PC-3 PIP tumor accumulation was observed for compound $^{177}$Lu-PSMA-ALB-06, which slightly decreased towards the end of the study. The accumulated activity in the PSMA$^{neg}$ PC-3 flu tumor and other non-target organs was below blood levels, indicating PSMA-specific binding and uptake in vivo for all compounds tested. Biodistribution data for $^{177}$Lu-PSMA-ALB-06, -07 and -08 are shown in Table 2.6, 2.7 and 2.8 below.

TABLE 2.6

| Biodistribution of $^{177}$Lu-PSMA-ALB-06 in PC-3 PIP/flu Tumor-Bearing Mice | | | | | | |
|---|---|---|---|---|---|---|
| | 1 h.p.i. | 4 h.p.i. | 8 h p.i. | 24 h p.i. | 48 h p.i. | 72 h p.i. |
| Blood | n/d | 16.2 ± 1.40 | n/d | 1.49 ± 0.50 | n/d | 0.62 ± 0.06 |
| Heart | n/d | 5.41 ± 0.82 | n/d | 0.68 ± 0.18 | n/d | 0.26 ± 0.02 |
| Lung | n/d | 9.40 ± 1.55 | n/d | 2.48 ± 2.68 | n/d | 0.67 ± 0.05 |
| Spleen | n/d | 3.14 ± 0.29 | n/d | 0.76 ± 0.18 | n/d | 0.53 ± 0.02 |
| Kidneys | n/d | 18.9 ± 0.77 | n/d | 10.5 ± 2.13 | n/d | 5.58 ± 0.62 |
| Stomach | n/d | 1.89 ± 0.19 | n/d | 0.28 ± 0.07 | n/d | 0.13 ± 0.02 |
| Intestines | n/d | 2.64 ± 0.27 | n/d | 0.30 ± 0.06 | n/d | 0.15 ± 0.00 |
| Liver | n/d | 3.45 ± 1.50 | n/d | 0.50 ± 0.11 | n/d | 0.28 ± 0.02 |
| Salivary glands | n/d | 3.26 ± 0.16 | n/d | 0.52 ± 0.11 | n/d | 0.24 ± 0.03 |
| Muscle | n/d | 1.60 ± 0.38 | n/d | 0.21 ± 0.04 | n/d | 0.07 ± 0.02 |
| Bone | n/d | 2.23 ± 0.08 | n/d | 0.41 ± 0.15 | n/d | 0.18 ± 0.01 |
| PC-3 PIP Tumor | n/d | 76.08 ± 7.67 | n/d | 108 ± 11.6 | n/d | 77.9 ± 7.52 |
| PC-3 flu Tumor | n/d | 3.16 ± 0.39 | n/d | 0.79 ± 0.23 | n/d | 0.43 ± 0.03 |
| Tumor-to-blood | n/d | 4.72 ± 0.51 | n/d | 77.6 ± 21.8 | n/d | 127 ± 24.9 |
| Tumor-to-liver | n/d | 24.29 ± 8.27 | n/d | 222 ± 49.5 | n/d | 277 ± 19.3 |
| Tumor-to-kidney | n/d | 4.02 ± 0.25 | n/d | 10.4 ± 1.16 | n/d | 14.1 ± 2.02 |
| | | | 96 h.p.i. | | 192 h.p.i. | |
| Blood | | | n/d | | n/d | |
| Heart | | | n/d | | n/d | |
| Lung | | | n/d | | n/d | |
| Spleen | | | n/d | | n/d | |
| Kidneys | | | n/d | | n/d | |
| Stomach | | | n/d | | n/d | |
| Intestines | | | n/d | | n/d | |
| Liver | | | n/d | | n/d | |
| Salivary glands | | | n/d | | n/d | |
| Muscle | | | n/d | | n/d | |
| Bone | | | n/d | | n/d | |
| PC-3 PIP Tumor | | | n/d | | n/d | |
| PC-3 flu Tumor | | | n/d | | n/d | |
| Tumor-to-blood | | | n/d | | n/d | |
| Tumor-to-liver | | | n/d | | n/d | |
| Tumor-to-kidney | | | n/d | | n/d | |

(n/d = not determined)

TABLE 2.7

| Biodistribution of $^{177}$Lu-PSMA-ALB-07 in PC-3 PIP/flu Tumor-Bearing Mice | | | | | | |
|---|---|---|---|---|---|---|
| | 1 h.p.i. | 4 h.p.i. | 8 h.p.i. | 24 h.p.i. | 72 h p.i. | 96 h p.i. |
| Blood | n/d | 6.67 ± 2.04 | n/d | 0.79 ± 0.08 | 0.40 ± 0.06 | n/d |
| Heart | n/d | 2.43 ± 0.78 | n/d | 0.40 ± 0.00 | 0.21 ± 0.01 | n/d |
| Lung | n/d | 4.67 ± 0.92 | n/d | 0.73 ± 0.06 | 0.43 ± 0.02 | n/d |
| Spleen | n/d | 3.41 ± 1.46 | n/d | 1.14 ± 0.04 | 0.49 ± 0.03 | n/d |
| Kidneys | n/d | 67.0 ± 9.50 | n/d | 51.9 ± 6.34 | 26.0 ± 1.58 | n/d |
| Stomach | n/d | 1.09 ± 0.30 | n/d | 0.18 ± 0.06 | 0.10 ± 0.01 | n/d |
| Intestines | n/d | 1.27 ± 0.45 | n/d | 0.20 ± 0.03 | 0.10 ± 0.01 | n/d |
| Liver | n/d | 1.94 ± 1.02 | n/d | 0.52 ± 0.04 | 0.44 ± 0.08 | n/d |

TABLE 2.7-continued

Biodistribution of $^{177}$Lu-PSMA-ALB-07 in PC-3 PIP/flu Tumor-Bearing Mice

| | | | | | | |
|---|---|---|---|---|---|---|
| Salivary glands | n/d | 2.09 ± 0.50 | n/d | 0.43 ± 0.04 | 0.21 ± 0.01 | n/d |
| Muscle | n/d | 0.78 ± 0.22 | n/d | 0.13 ± 0.01 | 0.08 ± 0.01 | n/d |
| Bone | n/d | 1.30 ± 0.27 | n/d | 0.31 ± 0.10 | 0.31 ± 0.06 | n/d |
| PC-3 PIP Tumor | n/d | 63.5 ± 27.4 | n/d | 84.6 ± 14.2 | 62.6 ± 6.35 | n/d |
| PC-3 flu Tumor | n/d | 1.80 ± 0.27 | n/d | 0.80 ± 0.17 | 0.43 ± 0.04 | n/d |
| Tumor-to-blood | n/d | 9327 ± 1.75 | n/d | 107 ± 12.2 | 160 ± 37.0 | n/d |
| Tumor-to-liver | n/d | 33.6 ± 6.56 | n/d | 162 ± 17.3 | 147 ± 38.4 | n/d |
| Tumor-to-kidney | n/d | 0.88 ± 0.28 | n/d | 1.64 ± 0.29 | 2.41 ± 0.18 | n/d |

| | 144 h.p.i. | 192 h.p.i. |
|---|---|---|
| Blood | n/d | n/d |
| Heart | n/d | n/d |
| Lung | n/d | n/d |
| Spleen | n/d | n/d |
| Kidneys | n/d | n/d |
| Stomach | n/d | n/d |
| Intestines | n/d | n/d |
| Liver | n/d | n/d |
| Salivary glands | n/d | n/d |
| Muscle | n/d | n/d |
| Bone | n/d | n/d |
| PC-3 PIP Tumor | n/d | n/d |
| PC-3 flu Tumor | n/d | n/d |
| Tumor-to-blood | n/d | n/d |
| Tumor-to-liver | n/d | n/d |
| Tumor-to-kidney | n/d | n/d |

(n/d = not determined)

TABLE 2.8

Biodistribution of $^{177}$Lu-PSMA-ALB-08 in PC-3 PIP/flu Tumor-Bearing Mice

| | 1 h.p.i. | 4 h.p.i. | 8 h p.i. | 24 h p.i. | 72 h p.i. | 96 h p.i. |
|---|---|---|---|---|---|---|
| Blood | n/d | 0.41 ± 0.18 | n/d | 0.08 ± 0.01 | 0.06 ± 0.02 | n/d |
| Heart | n/d | 0.19 ± 0.07 | n/d | 0.04 ± 0.01 | 0.03 ± 0.01 | n/d |
| Lung | n/d | 0.48 ± 0.21 | n/d | 0.09 ± 0.02 | 1.28 ± 2.02 | n/d |
| Spleen | n/d | 0.53 ± 0.10 | n/d | 0.10 ± 0.03 | 0.11 ± 0.05 | n/d |
| Kidneys | n/d | 27.2 ± 5.93 | n/d | 13.9 ± 2.32 | 7.98 ± 0.62 | n/d |
| Stomach | n/d | 0.40 ± 0.25 | n/d | 0.03 ± 0.01 | 0.02 ± 0.01 | n/d |
| Intestines | n/d | 0.20 ± 0.09 | n/d | 0.03 ± 0.01 | 0.02 ± 0.01 | n/d |
| Liver | n/d | 0.27 ± 0.10 | n/d | 0.11 ± 0.02 | 0.12 ± 0.01 | n/d |
| Salivary glands | n/d | 0.19 ± 0.06 | n/d | 0.07 ± 0.05 | 0.03 ± 0.02 | n/d |
| Muscle | n/d | 0.06 ± 0.03 | n/d | 0.02 ± 0.01 | 0.01 ± 0.01 | n/d |
| Bone | n/d | 0.16 ± 0.03 | n/d | 0.07 ± 0.02 | 0.09 ± 0.05 | n/d |
| PC-3 PIP Tumor | n/d | 46.9 ± 16.7 | n/d | 33.0 ± 5.04 | 24.1 ± 5.37 | n/d |
| PC-3 flu Tumor | n/d | 0.25 ± 0.19 | n/d | 0.09 ± 0.05 | 0.09 ± 0.07 | n/d |
| Tumor-to-blood | n/d | 116 ± 9.46 | n/d | 421 ± 45.7 | 416 ± 89.5 | n/d |
| Tumor-to-liver | n/d | 177 ± 2.72 | n/d | 295 ± 40.1 | 207 ± 47.1 | n/d |
| Tumor-to-kidney | n/d | 1.70 ± 0.22 | n/d | 2.39 ± 0.24 | 3.02 ± 0.68 | n/d |

| | 144 h.p.i. | 192 h.p.i. |
|---|---|---|
| Blood | n/d | n/d |
| Heart | n/d | n/d |
| Lung | n/d | n/d |
| Spleen | n/d | n/d |
| Kidneys | n/d | n/d |
| Stomach | n/d | n/d |
| Intestines | n/d | n/d |
| Liver | n/d | n/d |
| Salivary glands | n/d | n/d |
| Muscle | n/d | n/d |
| Bone | n/d | n/d |
| PC-3 PIP Tumor | n/d | n/d |
| PC-3 flu Tumor | n/d | n/d |
| Tumor-to-blood | n/d | n/d |
| Tumor-to-liver | n/d | n/d |
| Tumor-to-kidney | n/d | n/d |

(n/d = not determined)

2.2.4 SPECT/CT Imaging Studies.

Figure 26:
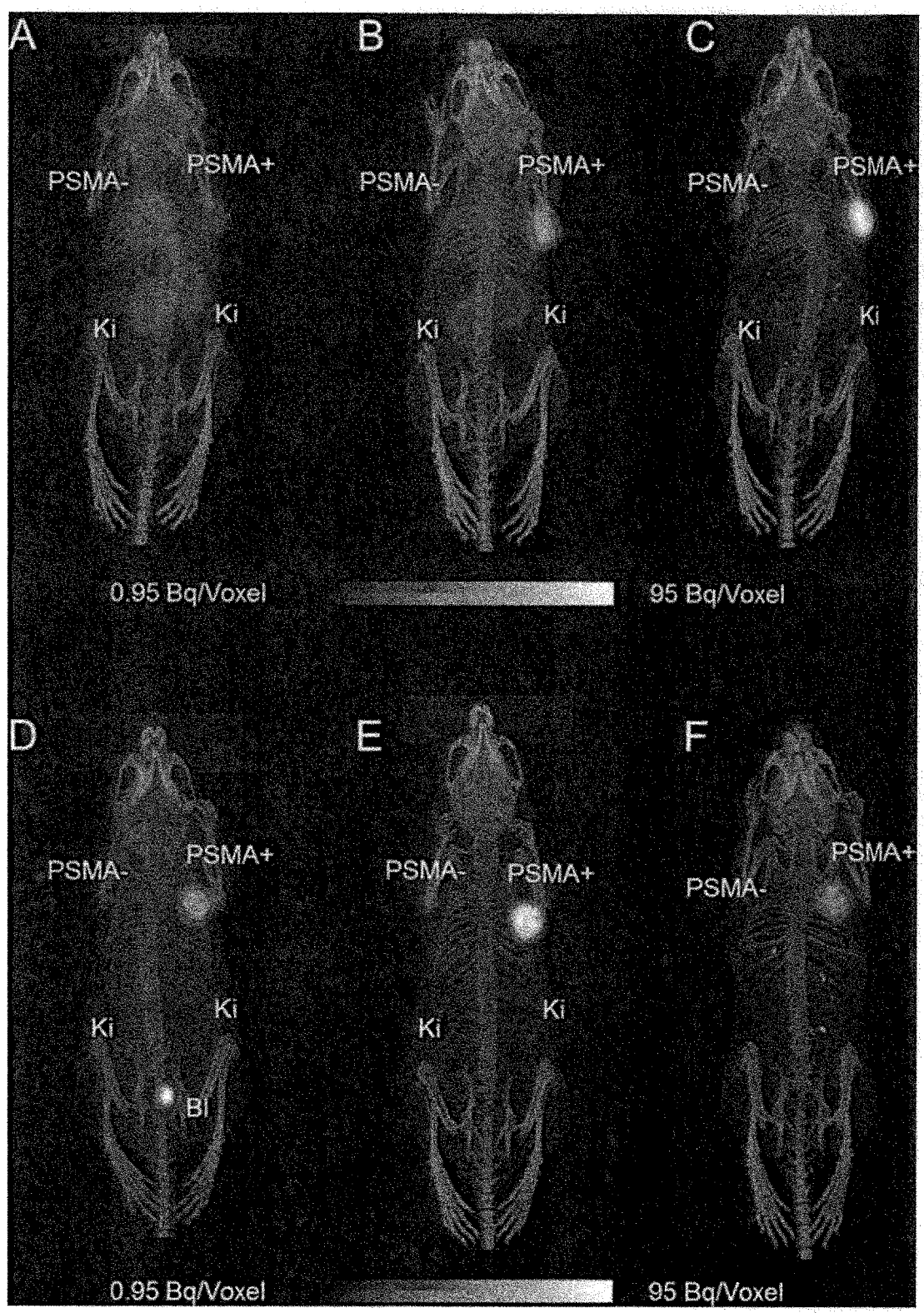
FIG. 26: SPECT/CT images as maximum intensity projections (MIPs) of PC-3 PIP/flu tumor-bearing mice at different time points after injection of $^{177}$Lu-ALB-03 and $^{177}$Lu-PSMA-ALB-06 (A-C). MIPs of a muse at (A) 4 h, (B) 24 h, and (C) 72 h after injection of $^{177}$Lu-ALB-03 (25 MBq, 1 nmol). (D-F) MIPs of a mouse at (D) 24 h, (E) 24 h and (F) 72 h after injection of $^{177}$Lu-PSMA-ALB-06 (25 MBq, 1 nmol). PSMA+=PSMA-positive PC-3 PIP tumor, PSMA−=PSMA-negative PC-3 flu tumor; Ki=kidney; Bl=urinary bladder.

SPECT/CT images of PC-3 PIP/flu tumor-bearing mice were performed at different time points after injection of $^{177}$Lu-PSMA-ALB-03 and 177Lu-PSMA-ALB-06. The exact injected activity of $^{177}$Lu-PSMA-ALB-03 and $^{177}$Lu-PSMA-ALB-06 was 25 MBq and 23 MBq, respectively. The favourable in vivo behavior of $^{177}$Lu-PSMA-ALB-03 and $^{177}$Lu-PSMA-ALB-06 is shown in FIG. 26.

2.2.5 Therapy in Mouse Model

Control mice (Group A) showed constant tumor growth over time, which was comparable to the tumor growth of mice treated with low activity of $^{177}$Lu-PSMA-617 (Group B: 2 MBq/mouse). The tumor growth delay indices of mice of Group B (TGDI$_2$=0.8, TGDI$_5$=1.4, Table 2.9) were, therefore similar to the values of control animals where the TGDI was defined as 1. The first control mouse reached an endpoint at Day 16, whereas in Group B one mouse had to be euthanized already at Day 12 (Table 2.9). Mice were effectively treated when using a higher activity of $^{177}$Lu-PSMA-617 (Group C: 5 MBq/mouse) or low activity of $^{177}$Lu-PSMA-ALB-06 (Group D: 2 MBq/mouse). The TGDI$_2$ and TGDI$_5$ were similar for mice of both groups (Groups C and D) and consequently, mice had to be euthanized in the same time range (Group C: Day 26 to Day 40; Group D: Day 28 to Day 44; data not shown). In mice treated with higher activity of $^{177}$Lu-PSMA-ALB-06 (Group E: 5 MBq/mouse), the tumor growth was effectively inhibited. In four mice of Group E the tumors disappeared entirely and regrowth was not observed until the end of the study at Day 84.

TABLE 2.9

Tumor Growth Inhibition (TGI) and Tumor Growth Delay Index with x-Fold Increase of Tumor Size (TGDIx) of $^{177}$Lu-PSMA-ALB-06 and $^{177}$Lu-PSMA-617

| group | treatment group | first mouse of group euthanized [d] | median survival [d] | TGDI$_2$ | TGDI$_5$ |
|---|---|---|---|---|---|
| A | saline | 16 | 18 | 1.0 ± 0.8 | 1.0 ± 0.1 |
| B | $^{177}$Lu-PSMA-617 | 12 | 19 | 0.8 ± 0.3 | 1.4 ± 0.1 |
| C | $^{177}$Lu-PSMA-617 | 26 | 32 | 2.1 ± 0.3 | 2.5 ± 0.3 |
| D | $^{177}$LU-PSMA-ALB-56 | 28 | 36 | 1.8 ± 0.5 | 2.3 ± 0.6 |
| E | $^{177}$Lu-PSMA-ALB-56 | 58 | n.d.$^a$ | n.d.$^a$ | n.d.$^a$ |

$^a$n.d. = not defined since mice were still alive at the end of the study.

Figure 27:
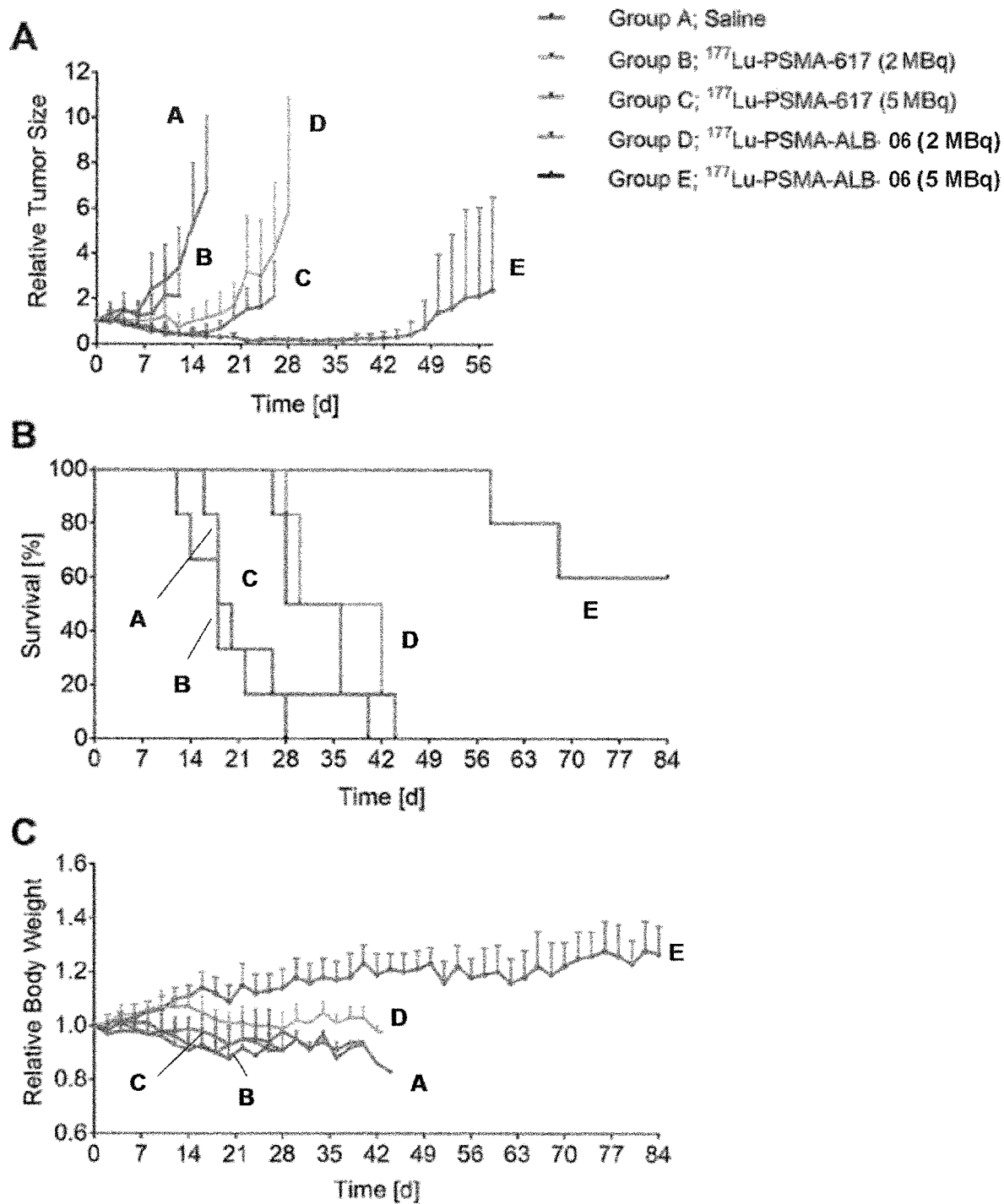
FIG. 27: Therapy study performed with $^{177}$Lu-PSMA-ALB-06 and $^{177}$Lu-PSMA-617 in PC-3 PIP tumor-bearing mice. (A) Tumor growth curves relative to the tumor volume at Day 0 (set to 1) for mice that received saline (Group A), mice treated with 2 MBq 177Lu-PSMA-617 (Group B), 5 MBq $^{177}$Lu-PSMA-617 (Group C), 2 MBq $^{177}$Lu-PSMA-ALB-06 (Group D), and 5 MBq $^{177}$Lu-PSMA-ALB-06 (Group E). Data are shown until the first mouse of the respective group reached an end point. (B) Kaplan-Meier plot of Groups A-E. (C) Relative body weight of Groups A-E.

Mice that received higher activity of $^{177}$Lu-PSMA-617 or low activity of $^{177}$Lu-PSMA-ALB-06 showed a significantly increased median survival (Group C: Day 32, Group D: Day 36, Table 2.9, FIG. 27). At the end of the study at Day 84, four mice which were treated with higher activity of $^{177}$Lu-PSMA-ALB-06 (Group E) were still alive and, thus, the median survival time remained undefined for this group.

Example 3: Clinical Evaluation of PSMA Ligands 3.1: Case 1

The compound PSMA-ALB-06, radiolabeled with therapeutic radionuclide Lutetium-177 was used in the scope of an individual curative trial in a patient with mildly differentiated prostate adenocarcinoma with extensive bilobar liver metastases, as well as disseminated osteoblastic metastases (in the pelvic region), and polytopic voluminous lymph node metastases. The evaluation of the biodistribution and in vivo behavior of the radiolabeled compound PSMA-ALB-06 was performed by means of SPECT-CT measurements.

Figure 7:
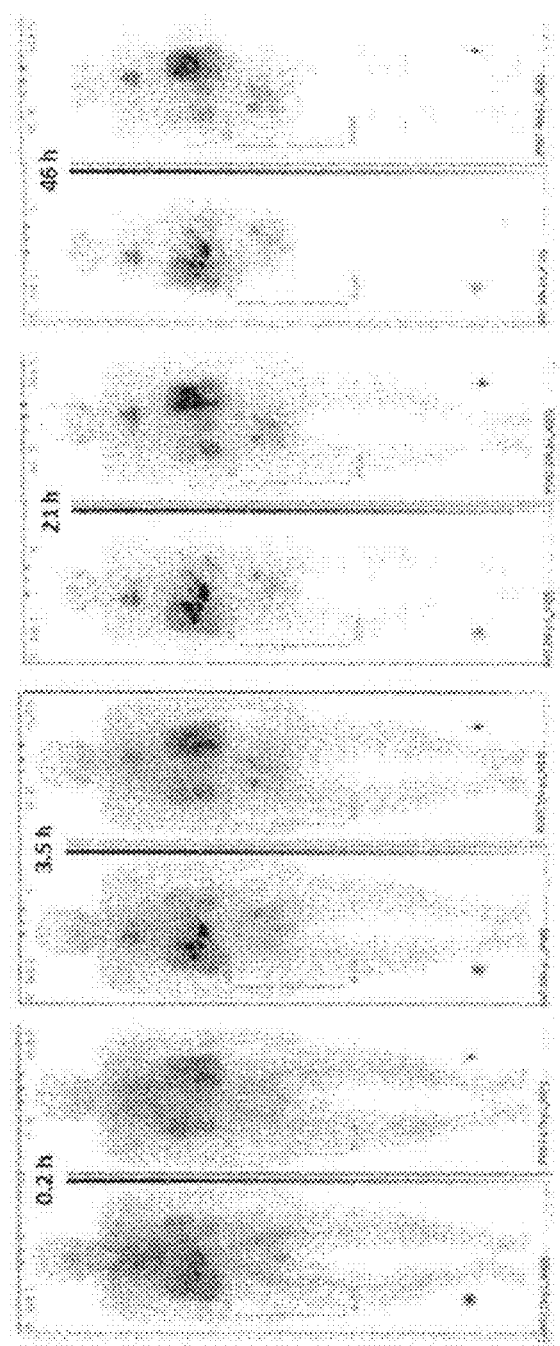
FIG. 7: Scintigraphy images at different time points p.i.
Figure 8:
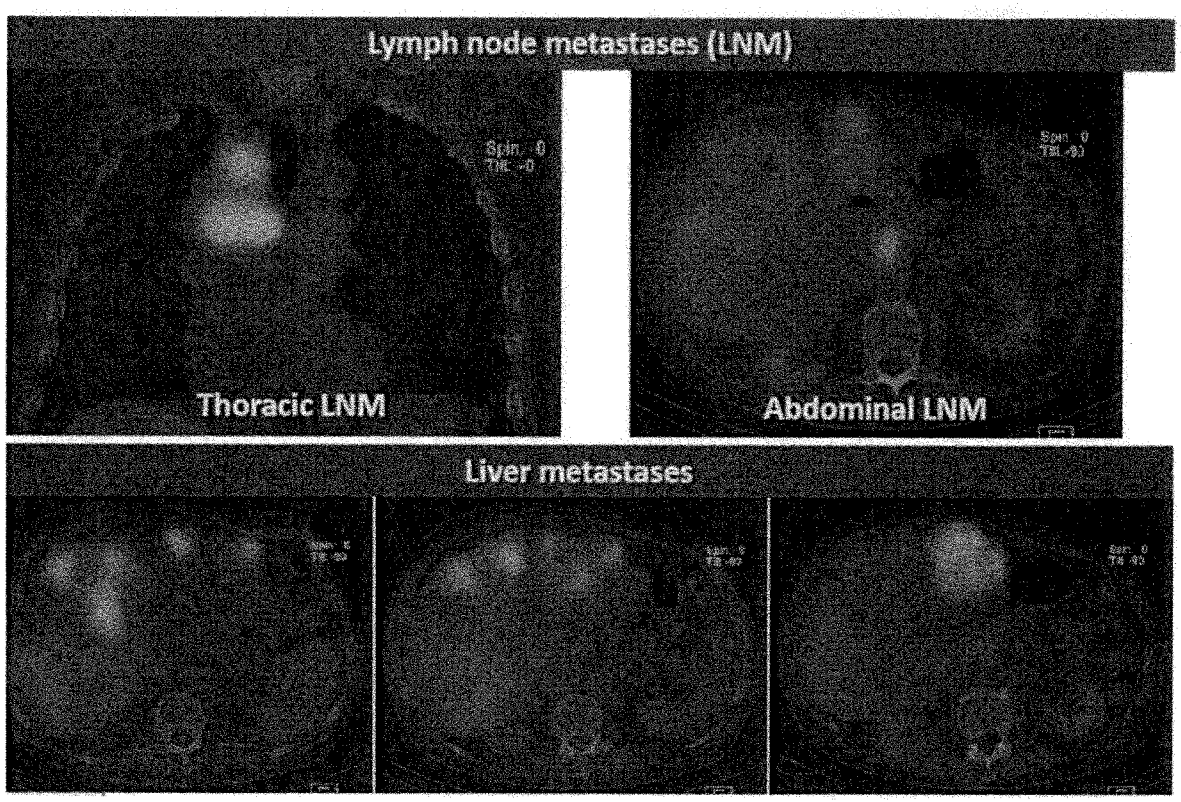
FIG. 8: SPECT-CT fusion scan in different regions

The SPECT-CT visualization was performed at different time points up to 46 hours post injection (p.i.). The radiolabeled compound PSMA-ABL-06 demonstrated a prolonged blood circulation and improved bioavailability (FIG. 7). The blood clearance is completed within first hours, whereas the unspecific uptake in healthy organs (especially liver, salivary and kidney) remains moderate over the time. The SPECT-CT indicates the substantial specific uptake of the radiolabeled compound in malignant tissues (FIG. 8).

These first in-human results confirm the pre-clinical findings on improved pharmacokinetic properties of the compound demonstrating it's potential for the treatment of PSMA positive tumors.

Figure 9:
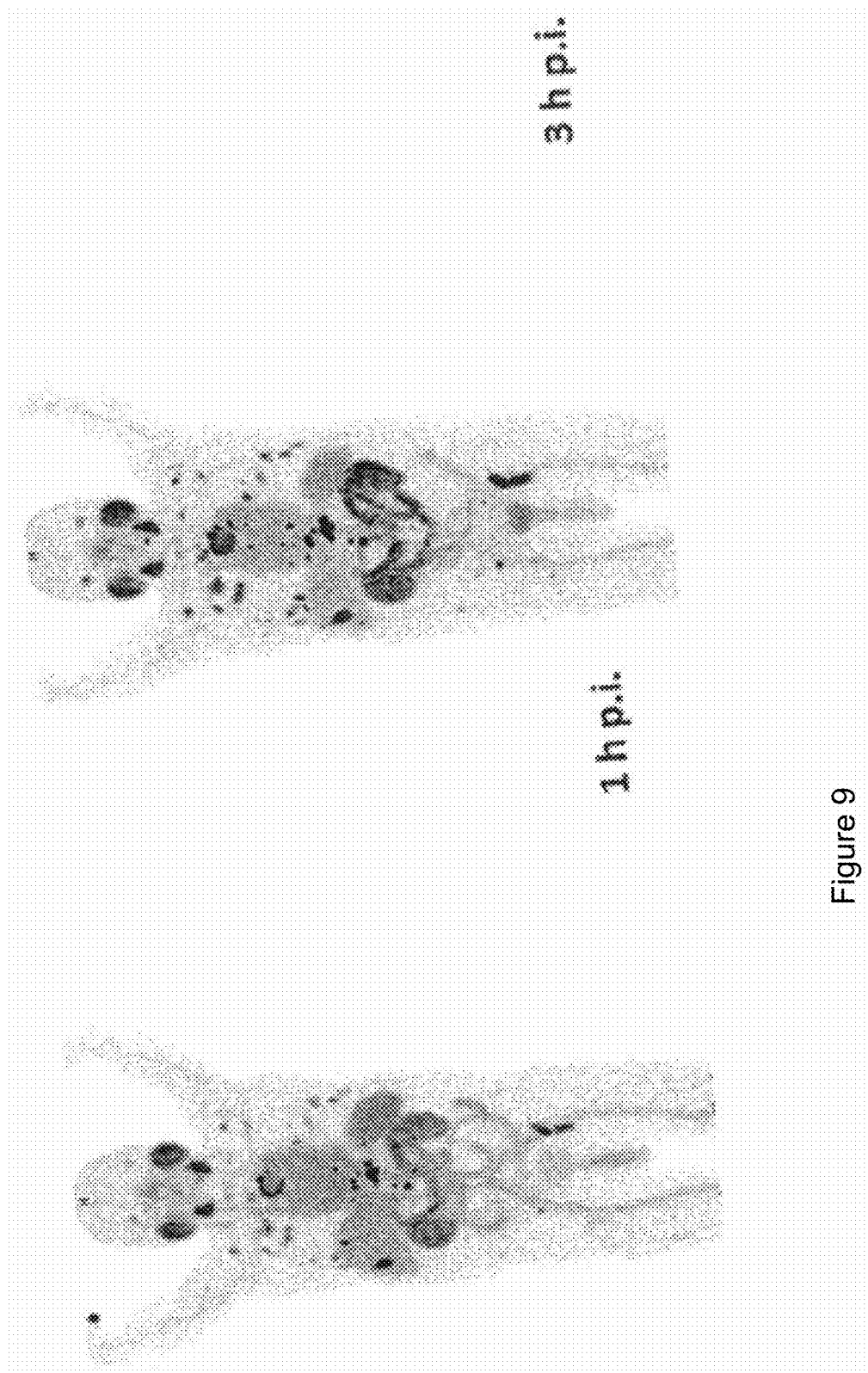
FIG. 9: PET images 1 and 3 hours p.i. with Gallium-68 radiolabeled PSMA-ALB-06 compound

3.2 Case 2:

The compound PSMA-ALB-06, radiolabeled with a positron emitting radionuclide Gallium-68 was used in an individual curative trial in a patient with metastatic castration-resistant prostate cancer as a diagnostic agents for PET-CT. Malignant tissues could be visualized by means of PET with high specificity, whereas the background radioactivity in off-target healthy organs remains moderate (FIG. 9). The high contrast of the images increases over the time after injection confirming the prolonged blood clearance and high specific uptake in the tumors.

Figure 10:
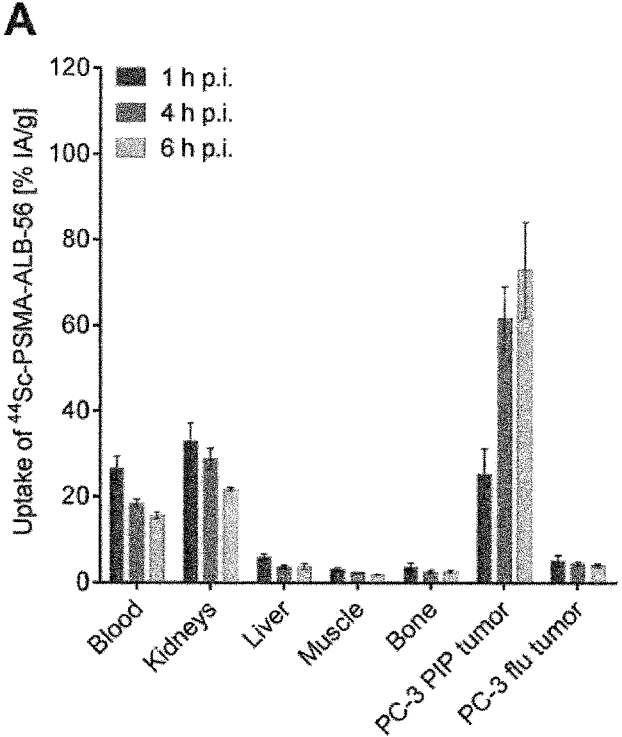
FIG. 10: (A) Biodistribution data obtained in PC-3 PIP/flu tumor-bearing mice at 1 h, 4 h and 6 h (!) after injection of $^{44}$Sc-PSMA-ALB-06. (B) Biodistribution data obtained in PC-3 PIP/flu tumor-bearing mice at 1 h, 4 h and 24 h after injection of $^{177}$Lu-PSMA-ALB-06.
Figure 10:
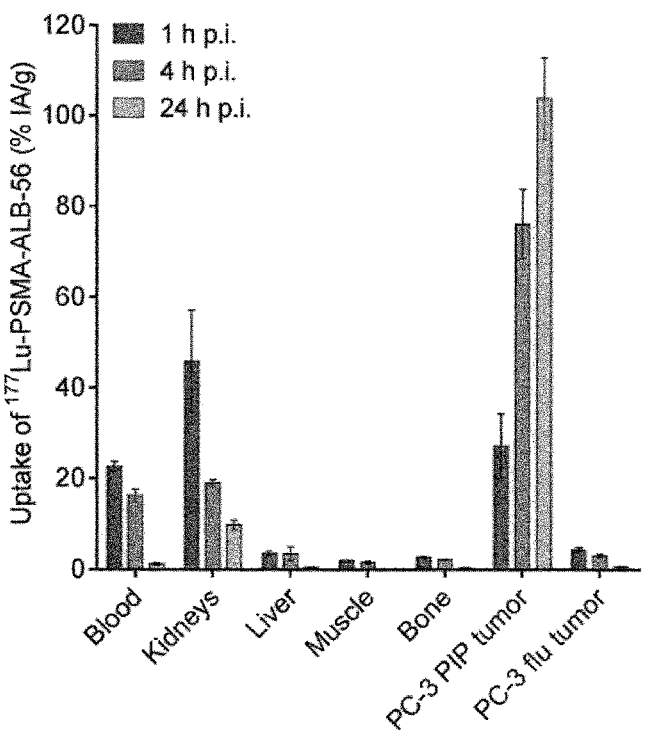

Example 4: Investigation of PSMA Ligands in Combination with $^{44}$Sc for PET Imaging 4.1 Biodistribution Data of $^{44}$Sc-PSMA-ALB $^{44}$Sc was produced at the Injector 2 facility at PSI as previously reported.[2] Radiolabeling of PSMA-ALB-06 was performed as previously reported by our group using the clinically-established PSMA-617 ligand.[5] Biodistribution studies were obtained in female Balb/c nude mice bearing PSMA-positive PC-3 PIP tumor cells (right shoulder) and PSMA-negative PC-3 flu tumors (left shoulder). For this purpose, the mice were inoculated with tumor cells 12-14 days before injection of the radioligand. The mice were euthanized and dissected at 1 h, 4 h and 6 h post injection (p.i.) (FIG. 10A, Table 4.1). Cave: $^{44}$Sc-PSMA-ALB-06 was investigated over 6 h while data is available for $^{177}$Lu-PSMA-ALB-06 over a period of 24 h p.i. (FIG. 10B).

TABLE 4.1

Biodistribution Data of 44S c-PSMA-ALB-06 in PC-3 PIP/flu Tumor-Bearing Mice.

| | 44Sc-PSMA-ALB-06 | | |
|---|---|---|---|
| | 1 h p.i. | 4 h p.i. | 6 h p.i. |
| Blood | 26.6 ± 2.82 | 18.4 ± 1.00 | 15.6 ± 0.75 |
| Heart | 8.91 ± 0.22 | 6.48 ± 0.50 | 5.17 ± 0.17 |
| Lung | 14.8 ± 2.41 | 11.17 ± 0.66 | 9.44 ± 0.86 |
| Spleen | 4.86 ± 0.76 | 4.10 ± 0.54 | 3.67 ± 0.37 |
| Kidneys | 32.9 ± 4.35 | 28.8 ± 2.46 | 21.7 ± 0.42 |
| Stomach | 2.68 ± 0.34 | 1.91 ± 0.16 | 1.98 ± 0.26 |
| Intestines | 3.30 ± 0.59 | 2.50 ± 0.13 | 2.07 ± 0.34 |
| Liver | 5.86 ± 0.67 | 3.51 ± 0.44 | 3.67 ± 0.68 |
| Muscle | 3.06 ± 0.34 | 2.24 ± 0.10 | 1.83 ± 0.07 |
| Bone | 3.59 ± 0.91 | 2.50 ± 0.35 | 2.54 ± 0.27 |
| Salivary gland | 5.83 ± 0.28 | 4.55 ± 0.41 | 4.03 ± 0.22 |
| PC-3 PIP Tumor | 25.3 ± 5.91 | 61.7 ± 7.32 | 72.9 ± 11.1 |
| PC-3 flu Tumor | 5.02 ± 1.23 | 4.37 ± 0.43 | 3.87 ± 0.45 |
| Tumor-to-blood | 0.94 ± 0.11 | 3.35 ± 0.20 | 4.69 ± 0.67 |
| Tumor-to-liver | 4.28 ± 0.52 | 17.93 ± 3.32 | 20.2 ± 3.43 |
| Tumor-to-kidney | 0.77 ± 0.12 | 2.14 ± 0.15 | 3.35 ± 0.42 |

4.2 3. PET/CT Imaging of Mice Injected with $^{44}$Sc-PSMA-ALB-06

Figure 11:
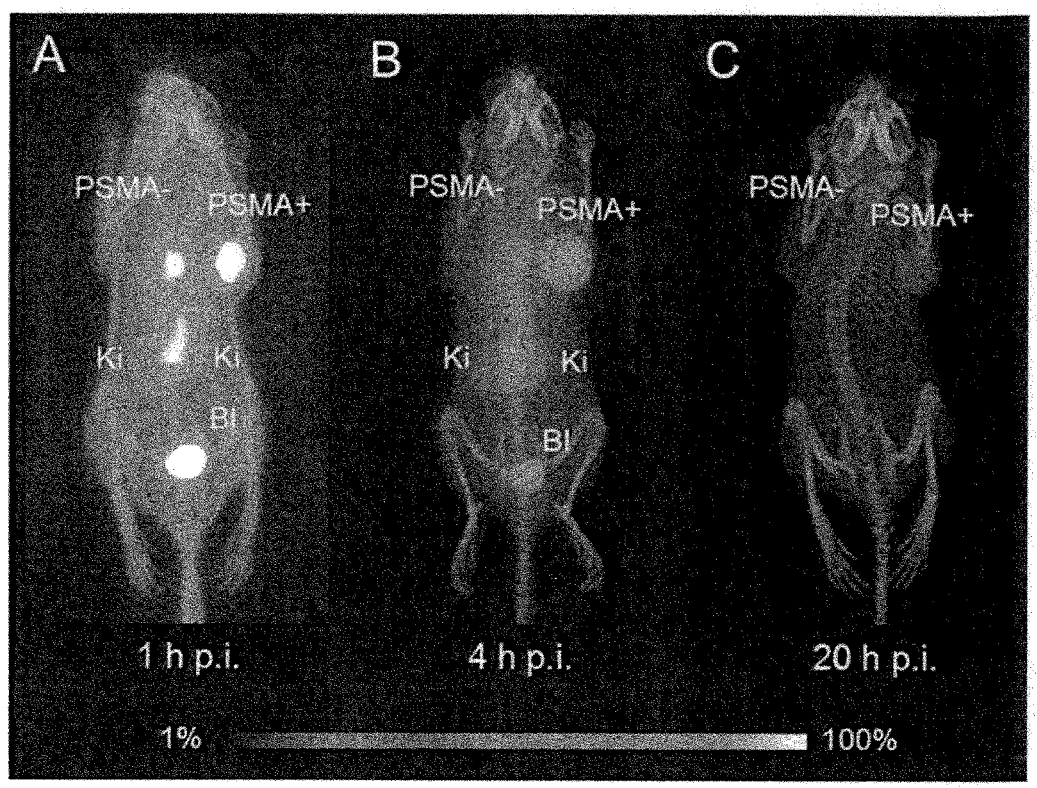
FIG. 11: PET/CT images of PC-3 PIP/flu tumor-bearing mice shown as maximum intensity projections (MIPs) with the same scale for all time points. (A) PET/CT scan obtained 1 h after injection of $^{44}$Sc-PSMA-ALB-06. (B) PET/CT scan obtained 4 h after injection of $^{44}$Sc-PSMA-ALB-06. (C) PET/CT scan obtained 20 h after injection of $^{44}$Sc-PSMA-ALB-06.
Figure 12:
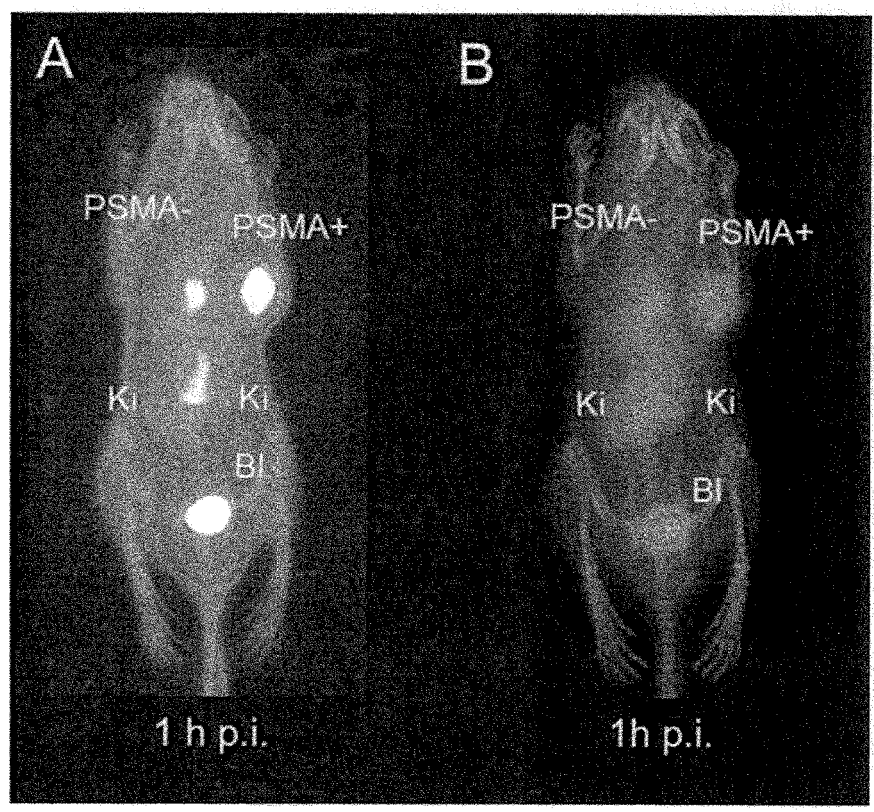
FIG. 12: PET/CT images of a PC-3 PIP/flu tumor-bearing mouse shown as maximum intensity projection (MIPs) with different scales for the same time point. (A/B) PET/CT scan obtained 1 h after injection of $^{44}$Sc-PSMA-ALB-06.

PET/CT experiments were performed using a small-animal PET/CT camera (G8, Perkin Elmer, U.S.) as previously reported by our group.[5] The images were taken at 1 h, 4 h and 20 h after injection of 5 MBq $^{44}$Sc-PSMA-ALB-06. FIG. 11 shows the scans prepared with the same scale. Additional images were prepared with adjusted scales to make the organs and tissues visible as best as possible. FIG. 12 shows the scan after 1 h when the radioactivity is mainly circulating in the blood and not yet, accumulated specifically in the PSMA-positive tumor.

Figure 13:
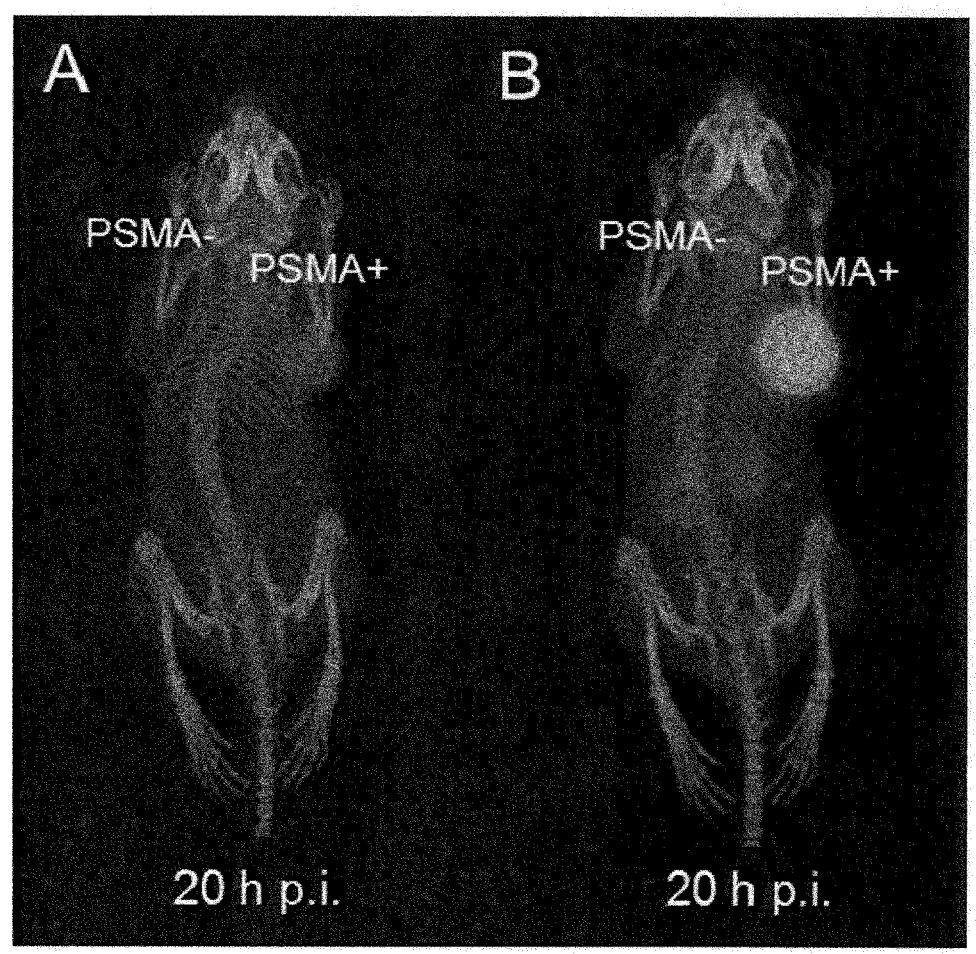
FIG. 13: PET/CT images of a PC-3 PIP/flu tumor-bearing mouse shown as maximum intensity projections (MIPs) with different scales for the same time point. (A/B) PET/CT scan obtained 20 h after injection of $^{44}$Sc-PSMA-ALB-06.

FIG. 13 shows the 20 h p.i.-scan with an adjusted scale. It is, hence, possible to make the tumor well visible while background activity has been mainly excreted.

4.3 Conclusion

Labeling of PSMA-ALB-06 was successfully performed with 44Sc at a specific activity of at least 5 MBq/nmol. The resulting biodistribution study and PET imaging results indicate similar properties of $^{44}$Sc-PSMA-ALB-06 as previously determined for $^{177}$Lu-PSMA-ALB-06. Due to the high tumor uptake of $^{44}$Sc-PSMA-ALB-06, it is believed that this radioligand may be a useful tool for imaging even small lesions at late time points (>4 h p.i.) when background activity is excreted. A clinical translation of this approach appears most promising and should be one of the next steps in order to confirm the potential of the proposed concept.

Example 5: Design and Preclinical Evaluation of an NODAGA-Functionalized Albumin-Binding PSMA Ligands A long-circulating PSMA-targeting agent suitable for stable complexation of copper was designed, which enables PET imaging of prostate cancer at delayed time points. Therefore, the DOTA-chelator of PSMA-ALB-06 was replaced with a NODAGA-chelator to obtain PSMA-ALB-89. PSMA-ALB-89 and PSMA-ALB-06 were labeled with $^{64}$Cu and tested for radiolytic stability, binding to serum albumin and uptake into PSMA-positive PC-3 PIP and PSMA-negative PC-3 flu tumor cells. Biodistribution and PET/CT imaging studies were performed with in PC-3 PIP/flu tumor-bearing mice.

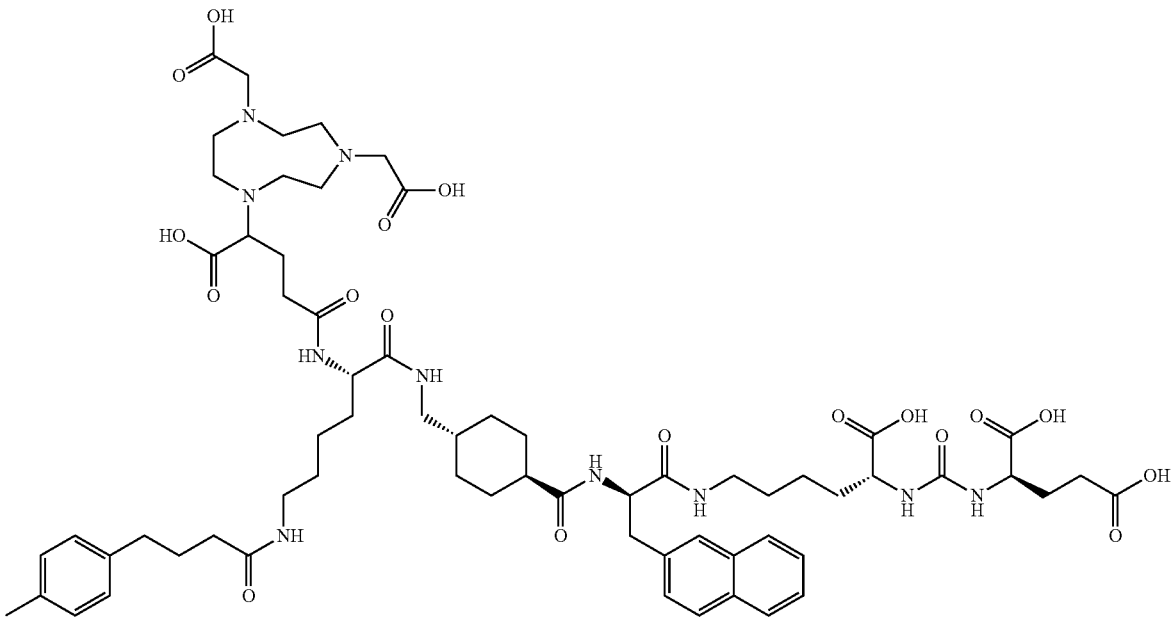 [SMILES: Cc1ccc(CCCC(=O)NCCCC[C@H](NC(=O)CCC(C(=O)O)N2CCN(CC(=O)O)CCN(CC(=O)O)CC2)C(=O)NC[C@H]2CC[C@H](C(=O)N[C@H](Cc3ccc4ccccc4c3)C(=O)NCCCC[C@@H](NC(=O)N[C@H](CCC(=O)O)C(=O)O)C(=O)O)CC2)cc1]

5.1 Material and Methods

Solid-Phase Synthesis of the PSMA-Ligand. The NODAGA-functionalized PSMA ligand, referred to as PSMA-ALB-89, was synthesized using a solid phase platform as reported for the PSMA-ALB-06 (cf. Example 1). The only difference was related to the conjugation of the chelator in the last step of the synthesis (Scheme 5.1). The conjugation was performed with 3 equiv NODAGA-tris(t-Bu)ester [4-(4,7-bis(2-(tert-butoxy)-2-oxoethyl)-1,4,7-triazacyclononane-1-yl)-5(tert-butoxy)-5-oxopentanoic acid] activated with 2.97 equiv O-(benzotriazol-1-yl)-N,N,N',N'-tetramethyluronium hexafluorophosphate (HBTU) in the presence of 4 equiv N,N-diisopropylethylamine (DIPEA) in anhydrous N,N-dimethylformamide (DMF). The coupling of the NODAGA chelator proceeded over the course of 3 h with gentle agitation. The final product was cleaved from the resin and subsequently deprotected within 2 h using a mixture consisting of trifluoroacetic acid (TFA), triisopropylsilane (TIPS) and H$_2$O in a ratio of 95:2.5:2.5 (v/v).

Scheme 5.1: Synthesis of NODAGA-functionalized PSMA ligand

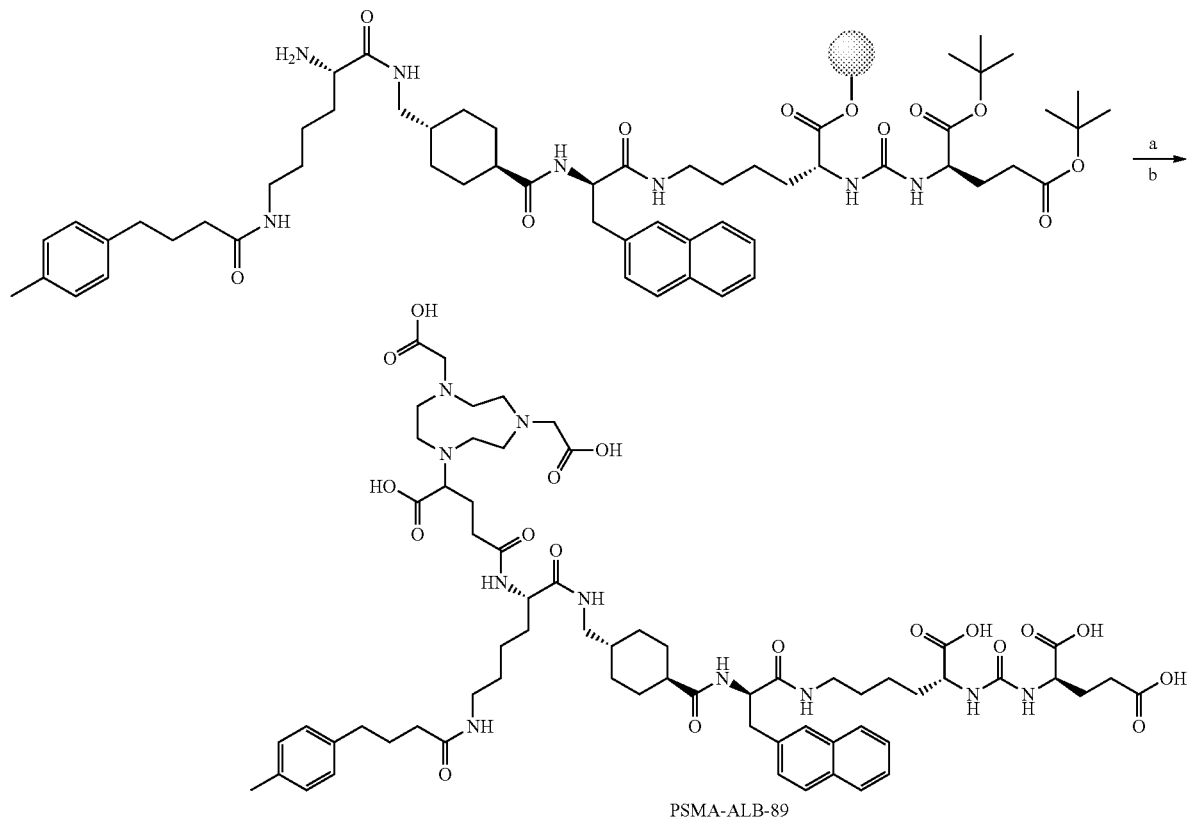

a) NODAGA tris(t-Bu)ester, HBTU, DIPEA, DMF; b) TFA, TIPS, H2O 95:2.5:2.5

Radiolabeling and Stability. $^{64}$Cu was produced via the $^{64}$Ni(p,n)$^{64}$Cu nuclear reaction at the research cyclotron Injector 2 facility at PSI.[28] PSMA-ALB-89 and PSMA-ALB-06 were dissolved in MilliQ water containing up to 5.5% sodium acetate (0.5 M, pH 8) to prepare 1 mM stock solutions. The PSMA ligands were labeled with $^{64}$Cu in a mixture of sodium acetate (0.5 M) and HCl (0.05 M) at pH 5 at specific activities between 5-50 MBq/nmol. The reaction mixture was incubated for 15 min at 95° C. Quality control of the radioligands was performed using RP-HPLC. The radioligands were used for in vitro and in vivo experiments without further purification steps.

Quality control of $^{64}$Cu-labeled PSMA ligands (250 MBq in 120 µL; 50 MBq/nmol) was determined immediately after preparation (t=0 h) using RP-HPLC. The reaction mixtures were diluted in saline to an activity concentration of 250 MBq/500 µL and incubated at room temperature. The integrity of the compounds was investigated over one day (t=1 h, 4 h and 24 h, respectively). The amount of intact radioligand was quantified by integration of the product peak of the HPLC chromatograms in relation to the sum of all radioactive peaks of degradation products of unknown structure and traces of released $^{64}$Cu which were set to 100%.

Determination of n-Octanol/PBS Distribution Coefficients (Log D Values). The distribution coefficients (log D values) of the $^{64}$Cu-labeled radioligands (50 MBq/nmol) were determined by a shake-flask method using liquid-liquid extraction followed by phase separation as previously reported. Three experiments were performed with five replicates for each radioligand. Statistical significance of the data (p<0.05) was evaluated using an unpaired t-test (GraphPad Prism software, version 7).

Determination of Albumin-binding Properties. The binding of the radioligands to human plasma proteins was determined by an ultrafiltration assay. The $^{64}$Cu-labeled PSMA-ligands (5-50 MBq, 0.01 nmol) were diluted in different dilutions of human plasma (Stiftung Blutspende SRK Aargau-Solothurn, Switzerland) or PBS as a control experiment as previously reported. Three independent experiments were performed in duplicates with both radioligands and the data was fitted to a semi-logarithmic plot (non-linear regression, one-site, specific binding) to obtain the half maximum binding ($B_{50}$) in GraphPad Prism software (version 7).

Cell Uptake and Internalization. Cell uptake (sum of the surface bound and internalized fraction) and internalization of the radioligands (5 MBq/nmol) were determined using PSMA-positive PC-3 PIP and PSMA-negative PC-3 flu cells.

In Vivo Studies. In vivo experiments were approved by the local veterinarian department and conducted in accordance with the Swiss law of animal protection. All mice were obtained from Charles River Laboratories (Sulzfeld, Germany) at the age of 5-6 weeks. Female, athymic BALB/c nude mice were subcutaneously inoculated with PC-3 PIP cells ($6\times10^6$ cells in 100 µL Hank's balanced salt solution (HBSS) with $Ca^{2+}/Mg^{2+}$) on the right shoulder and with PC-3 flu cells ($5\times10^6$ cells in 100 µL HBSS with $Ca^{2+}/Mg^{2+}$) on the left shoulder 12-14 days before the performance of the experiments.

Biodistribution Studies. Mice were injected into a lateral tail vein with the respective radioligand (5 MBq, 1 nmol, 100 µL) diluted in saline containing 0.05% BSA. The mice were sacrificed at 1 h, 4 h and 24 h after injection (p.i.) and selected tissues and organs were collected, weighed and measured using a γ-counter. Groups of 4-6 mice were used for each time point. The results were decay-corrected and listed as percentage of the injected activity per gram of tissue mass (% IA/g). Data presented as the average±standard deviation (SD). The data sets were analyzed for significance using a one-way ANOVA with Bonferroni's multiple comparison post-test using GraphPad Prism software (version 7). A p-value of <0.05 was considered statistically significant.

PET/CT Imaging Studies. PET/CT experiments were performed at 1 h, 4 h and 24 h after injection of the radioligands (5 MBq/1 nmol). Mice were injected into a lateral tail vein with the respective radioligand (5 MBq, 1 nmol, 100 µL) diluted in saline containing 0.05% BSA. PET/CT scans were performed using a small-animal PET/CT scanner (G8, Perkin Elmer, Massachusetts, U.S.) as previously reported. The PET scans lasted for 10 min and were followed by a CT scan of 1.5 min. During the in vivo scans, the mice were anesthetized with a mixture of isoflurane and oxygen. Reconstruction of acquired data was performed using the software of the provider of the G8 scanner. All images were prepared using VivoQuant post-processing software (version 3.0, inviCRO Imaging Services and Software, Boston USA). The images were prepared by cutting 2% of the lower scale to make the tumors, liver and kidneys best visible.

5.2 Results

Synthesis of the PSMA Ligands. PSMA-ALB-89 was synthesized using a solid-phase support in analogy to the synthesis of PSMA-ALB-06 (Example 1). Instead of conjugating a DOTA-chelator, a NODAGA-chelator was used (Scheme 5.1). This multistep synthesis (17 steps) resulted in a highly pure compound (>98%) in an overall yield of 8.7% after semi-preparative HPLC purification.

Radiolabeling, Stability and In Vitro Properties of $^{64}$Cu-Labeled PSMA Ligands. PSMA-ALB-89 and PSMA-ALB-06 were labeled with $^{64}$Cu at a specific activity up to 50 MBq/nmol. The radioligands showed high radiochemical purity (>98%) and similar retention times (~11 min). $^{64}$Cu-PSMA-ALB-89 and $^{64}$Cu-PSMA-ALB-06 were stable (>92%) over a period of at least 4 h. The n-octanol/PBS distribution coefficient (log D values) of $^{64}$Cu-PSMA-ALB-89 (−2.3±0.7) was slightly but not significantly (p>0.05) higher than the log D value of $^{64}$Cu-PSMA-ALB-06 (−3.1±0.1).

Figure 14:
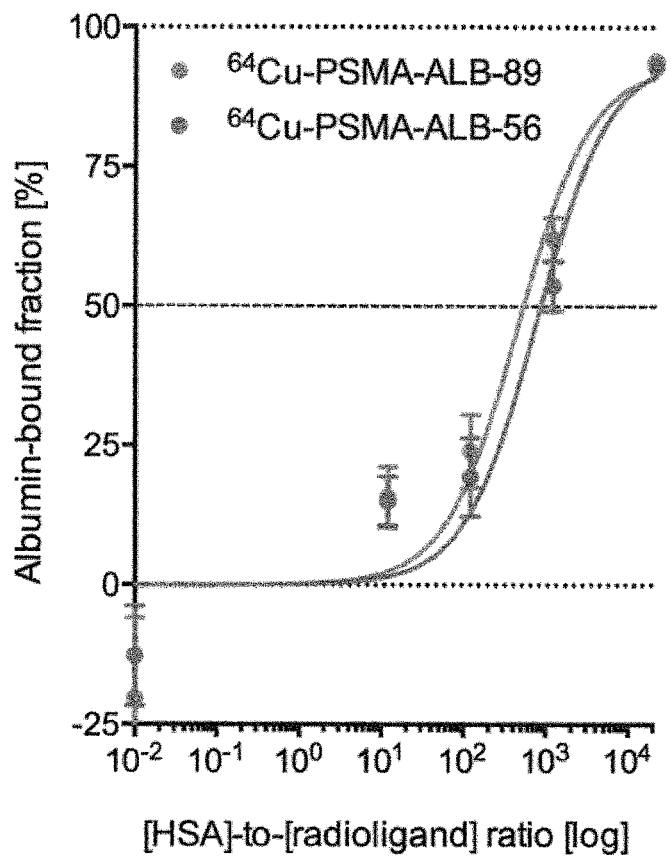
FIG. 14: Semi-log plots from ultrafiltration data to calculate B$_{50}$ values of $^{64}$Cu-PSMA-ALB-06 (B$_{50}$=770) and $^{64}$Cu-PSMA-ALB-89 (B50=454) after incubation in different concentrations of human plasma (average±SD, n≥3).

Albumin-binding Properties. $^{64}$Cu-PSMA-ALB-89 and $^{64}$Cu-PSMA-ALB-06 showed similar binding to plasma proteins (>92%) when incubated in human plasma. The half-maximum binding ($B_{50}$) of $^{64}$Cu-PSMA-ALB-89 was reached at a [HSA]-to-[radioligand] ratio of 454. This indicates a slightly increased binding when compared to $^{64}$Cu-PSMA-ALB-89 which reached half-maximum binding at a [HSA]-to-[radioligand] ratio of 770 (FIG. 14).

Figure 15:
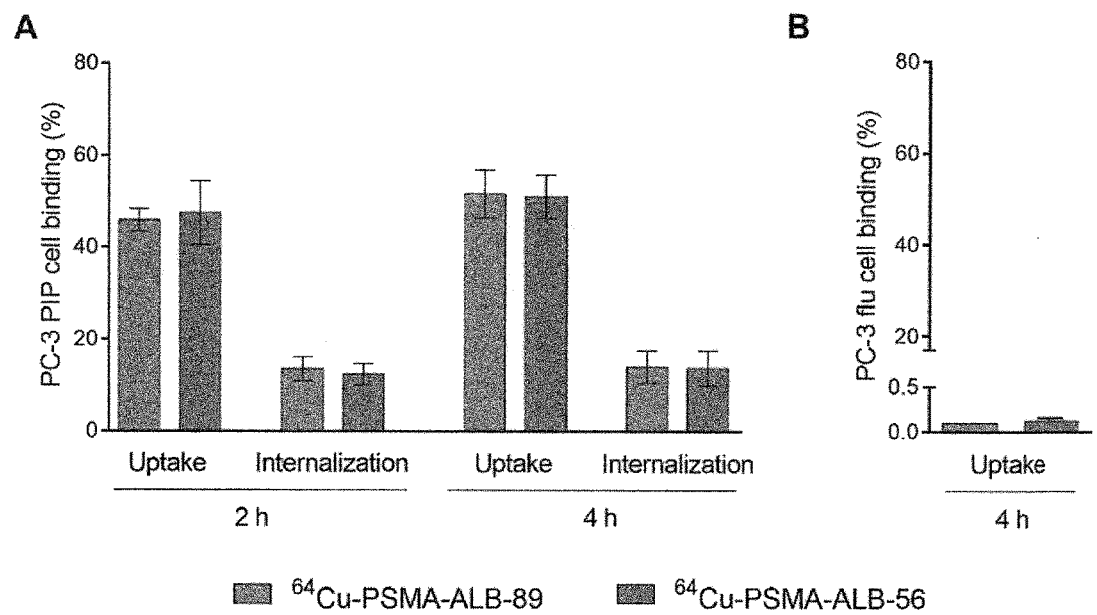
FIG. 15: Cell uptake and internalization (average SD, n=3) of $^{64}$Cu-PSMA-ALB-89 and $^{64}$Cu-PSMA-ALB-06 in (A) PSMA-positive PC-3 PIP cells and (B) PSMA-negative PC-3 flu cells.

Cell Uptake and Internalization. The cell uptake of $^{64}$Cu-PSMA-ALB-89 into PC-3 PIP cells was ~46% and the internalized fraction ~14% after an incubation period of 2 h at 37° C. The cell uptake increased slightly after 4 h incubation time (~52%), while the internalized fraction remained unchanged (~14%). Similar values were determined for $^{64}$Cu-PSMA-ALB-06 (FIG. 15A). Uptake in PC-3 flu cells was below 0.5% for both radioligands indicating PSMA-specific cell uptake (FIG. 15B).

Figure 16:
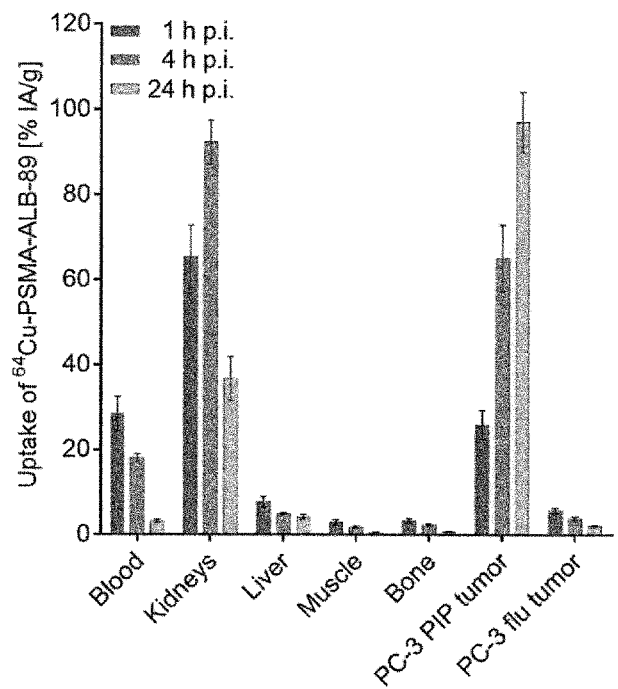
FIG. 16: Tissue distribution profile of $^{64}$Cu-PSMA-ALB-89 obtained in Balb/c nude mice bearing PC-3 PIP and PC-3 flu tumor xenografts at 1 h, 4 h and 24 h p.i. The values represent the average±SD of values obtained from n=3-6 mice.
Figure 17:
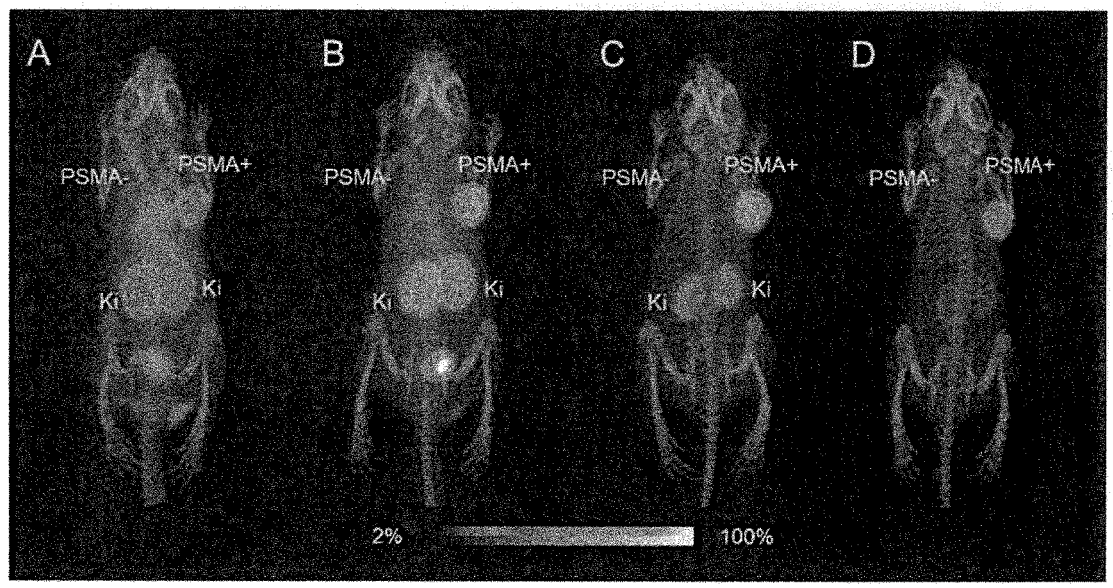
FIG. 17: PET/CT images shown as maximum intensity projections. (A-D) PET/CT images of a mouse 1 h, 4 h, 16 h and 24 h after injection of $^{64}$Cu-PSMA-ALB-89. The scale has been adjusted by cutting 2% of the background to make tumors, kidneys and liver better visible. (PSMA+=PC-3 PIP tumor xenograft; PSMA−=PC-3 flu tumor xenograft; Ki=kidney; Li=liver; Bl=urinary bladder).

Biodistribution Study. The tissue distribution profile of $^{64}$Cu-PSMA-ALB-89 was assessed over a period of 24 h in tumor-bearing mice (FIG. 16, Table 5.1). A fast reduction of blood pool activity was observed over time (<3.2% IA/g and <1.4% IA/g at 24 h p.i., respectively). Accumulation of $^{64}$Cu-PSMA-ALB-89 in PC-3 PIP tumors was high already shortly after injection (25.9±3.41% IA/g at 1 h p.i.) and increased towards the end of the study (97.1±7.01% IA/g at 24 h p.i.). The accumulation of radioactivity in PC-3 flu tumors which do not express PSMA, was generally below blood levels. The liver uptake pattern of $^{64}$Cu-PSMA-ALB-89 revealed radioactivity levels in the range of blood activity levels or below (FIG. 17).

Tumor-to-kidney ratios increased over time, yet, the values were rather low after injection of $^{64}$Cu-PSMA-ALB-89. The tumor-to-liver ratios of $^{64}$Cu-PSMA-ALB-89 were high. Tumor-to-muscle ratios increased over time to 200±38.2 at 24 h p.i.

TABLE 5.1

Tumor-to-Background Ratios of $^{64}$Cu-PSMA-ALB-89 and $^{64}$Cu-PSMA-ALB-06

| | $^{64}$Cu-PSMA-ALB-89 | | |
| --- | --- | --- | --- |
| | 1 h p.i. | 4 h p.i. | 24 h p.i. |
| Tu-to-blood* | 0.91 ± 0.02 | 3.61 ± 0.30 | 31.3 ± 3.82 |
| Tu-to-muscle | 9.0 ± 1.13 | 36.3 ± 2.25 | 200 ± 38.2 |
| Tu-to-kidney | 0.40 ± 0.02 | 0.70 ± 0.04 | 2.68 ± 0.36 |
| Tu-to-liver | 3.37 ± 0.31 | 13.3 ± 1.20 | 23.6 ± 3.37 |

*For all Tu-to-organ ratios: Tu = PSMA-positive PC-3 PIP tumor

PECT/CT Imaging Studies. PET/CT scans were performed over a period of 24 h with PC-3 PIP/flu tumor-bearing mice at different time points after injection of the $^{64}$Cu-labeled radioligand (FIG. 17). $^{64}$Cu-PSMA-ALB-89 accumulated to a significant extent in the PSMA-positive tumor xenograft (PC-3 PIP tumor) while no uptake was observed in the PSMA-negative tumor (PC-3 flu tumor). Visual examination revealed that 16 h after injection, the tumor-to-kidney ratio of accumulated radioligand was clearly >1 and increased further over time. Background signal in organs and tissues stemming from the radioactivity in the blood was well visible on the image taken at 1 h p.i.

5.3 Discussion

In this work, a long-circulating PSMA ligand labeled with $^{64}$Cu was synthesized to enable PET even one day after radioligand application. PSMA-ALB-89 was synthesized as previously described for PSMA-ALB-06, however, instead of coupling a DOTA-chelator a NODAGA chelator was employed as previously done in our group for other targeting agents.

PSMA-ALB-89 was radiolabeled reproducibly with $^{64}$Cu at high specific activities and radiochemical purity (50 MBq/nmol; >95%) suggesting a high quality of the synthesized ligand as well as excellent radiochemical purity of the $^{64}$Cu which was produced in-house at PSI. In vitro, $^{64}$Cu-PSMA-ALB-89 and $^{64}$Cu-PSMA-ALB-06 where both stable after incubation for several hours at room temperature with only limited degradation detectable after 24 h. These results suggest that the NODAGA- and DOTA-chelator are both forming stable complexes with $^{64}$Cu in vitro.

The albumin-binding properties of $^{64}$Cu-PSMA-ALB-89 were in the same range as for $^{64}$Cu-PSMA-ALB-06 when tested in vitro. Binding specificity to PSMA was not affected by the different chelators either as proven by similar cell-bound and internalized fractions observed in vitro for $^{64}$Cu-PSMA-ALB-89 and $^{64}$Cu-PSMA-ALB-06.

Biodistribution data obtained in a well-established xenograft mouse model using PSMA-positive and PSMA-negative tumors showed that tumor uptake of $^{64}$Cu-PSMA-ALB-89 was significantly increased at all investigated timepoints, possibly as a result of the longer blood circulation time. The maximum tumor uptake of $^{64}$Cu-PSMA-ALB-89 was reached only at the end of the study (24 h p.i.). PET/CT images confirmed the favorable tissue distribution profile of $^{64}$Cu-PSMA-ALB-89 with regard to the high tumor uptake and reduced accumulation in the liver. Low liver uptake is important as prostate cancer may result in liver metastases which may be masked by unspecific radioactivity accumulation otherwise.

5.4 Conclusion

In this example, the DOTA-chelator of PSMA-ALB-06 was replaced by a NODAGA-chelator to enable stable coordination of $^{64}$Cu for PET imaging. $^{64}$Cu-PSMA-ALB-89 showed increased in vivo stability which was manifest by an increased tumor accumulation and reduced liver retention of $^{64}$Cu-PSMA-ALB-89.

Figure 18:
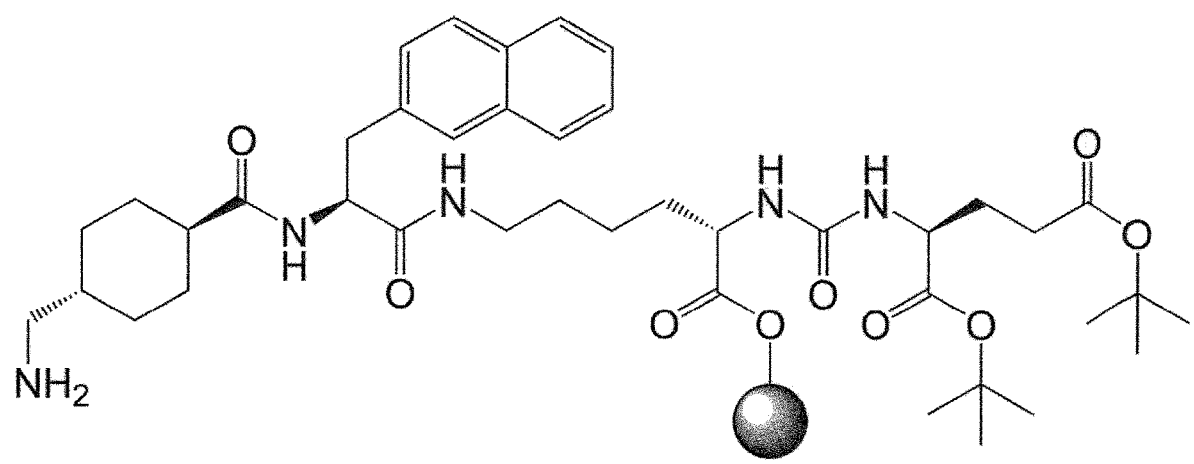
FIG. 18: PSMA-targeting precursor used for the synthesis of PSMA-ALB-02/-05/-07.

Example 6: Design and Evaluation of Further DOTA-Functionalized PSMA-Binding Ligand 6.1 Material and Methods Solid-Phase Synthesis of Albumin-Binding PSMA Ligands. PSMA ligands, referred to as PSMA-ALB-02, PSMA-ALB-05 and PSMA-ALB-07, respectively, were designed and synthesized using a solid phase platform. The PSMA-targeting urea-based pharmacophore—L-Glu-NH—CO—NH-L-Lys—was prepared on 2-chlotrotrityl chloride (2-CT) resin in analogy to the method described by Eder et al. (2012). The linker area consisting of 2-naphthyl-L-Ala and trans-cyclohexyl moiety was synthesized as described in Example 1. Such resin-immobilized and bis(t-Bu)-protected precursor—L-Glu-NH—CO—NH-L-Lys-2-Nal-L-Ala-NH$_2$-Me-1,4-trans-CHX, referred to as compound 1—was used as the basis for the synthesis of all three albumin-binding PSMA ligands (FIG. 18).

The next steps of the synthesis, comprising the conjugation of the lysine-based building block and the selective cleavage of the Nα-Fmoc-protecting group, were performed equally for all three compounds. Relative to the resin-immobilized and bis(t-Bu)-protected precursor (0.3 mmol; compound (1)), 4 equiv of Nα-Fmoc- and Nε-Alloc-protected L-lysine (Fmoc-Lys(Alloc)-OH) were activated with 3.96 equiv O-(benzotriazol-1-yl)-N,N,N',N'-tetramethyluronium hexafluorophosphate (HBTU) in the presence of 4 equiv N,N-diisopropylethylamine (DIPEA) in N,N-dimethylformamide (DMF) and agitated for 1 h. Subsequently, the selective removal of Nα-Fmoc-protecting group was performed with a mixture of DMF and piperidine in a ratio of 1:1 (v/v). The resulting precursor (2) was then used for the subsequent synthesis which was specific for each particular compound.

PSMA-ALB-02. The synthesis of PSMA-ALB-02 was accomplished by coupling of the albumin-binding moiety to the resin-immobilized precursor (0.1 mmol; compound (2)) while using 4 equiv of 4-(p-iodophenyl)butyric acid activated with 3.96 equiv HBTU in the presence of 4 equiv DIPEA in DMF over the course of 1 h with gentle agitation. Subsequently, the cleavage of the Nε-Alloc-protecting group from the compound (3) was performed with 0.03 equiv of tetrakis(triphenylphosphine)palladium(0) (TPP Pd) in the presence of 30 equiv morpholine in dichlormethane (DCM) within 2 h in the dark. To remove residuals of the palladium, the resin was additionally washed with 1% DIPEA in DMF and afterwards with a solution of sodium diethyldithiocarbamate in DMF (c=15 mg/mL). Finally, the conjugation of the chelator to the resin-immobilized compound was performed with 2 equiv of DOTA-tris(t-Bu)ester [2-(4,7,10-tris (2-(t-butoxy)-2-oxoethyl)-1,4,7,10-tetraazacyclo-dodecan-1-yl)acetic acid] activated with 1.98 equiv HBTU in the presence of 4 equiv DIPEA in DMF. The coupling of the DOTA chelator proceeded over the course of 2 h with gentle agitation. The resulting compound (4) was washed with DMF, DCM and, finally, with Et$_2$O followed by drying under vacuum. The product was cleaved from the resin and subsequently deprotected within 2 h using a mixture consisting of trifluoroacetic acid (TFA), triisopropylsilane (TIPS) and H$_2$O in a ratio of 95:2.5:2.5 (v/v). TFA was evaporated, the crude compound dissolved in ACN and H$_2$O in a ratio of 1:1 (v/v) and purified via reversed-phase high-performance liquid chromatography (RP-HPLC) using semi-preparative column (Supporting Information). The characterization of PSMA-ALB-02 was performed by analytical RP-HPLC (Supporting Information) and matrix-assisted laser desorption/ionization mass spectrometry (MALDI-MS) or electrospray ionization mass spectrometry (ESI-MS), respectively. The synthesis outlined above is summarized in Scheme 6.1.

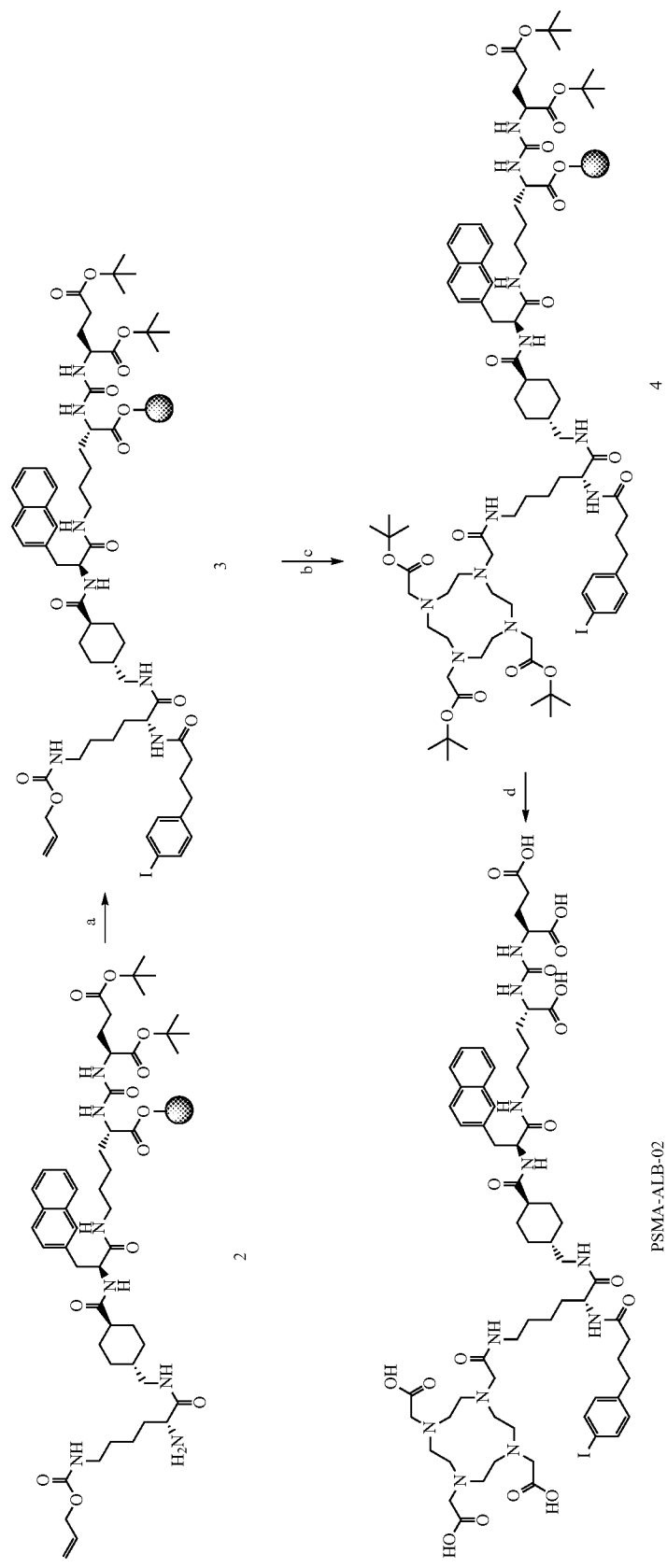
Scheme 6.1: Conjugation of the PSMA Precursor, Albumin-Binding Moiety, and DOTA Chelator for PSMA-ALB-02[a]
(a) 4-(p-Iodophenyl)butyric acid, HBTU, DIPEA, DMF; (b) TTP Pd(0), morpholine, DCM; (c) DOTA tris(t-Bu) ester, HBTU, DIPEA, DMF; (d) TFA, TIPS, H2O 95:2.5:2.5.

PSMA-ALB-05 and PSMA-ALB-07. The synthesis of PSMA-ALB-05 was accomplished by coupling of the D-aspartate-based building block to the resin-immobilized precursor (0.1 mmol; compound (2)) while using 3 equiv of N-Fmoc- and $O_\beta$-t-Bu-protected D-aspartate (Fmoc-D-Asp-O-t-Bu) activated with 2.97 equiv HBTU in the presence of 4 equiv DIPEA in DMF over the course of 1 h with gentle agitation. Selective removal of the N-Fmoc-protecting group from the resulting compound was performed as described above. The analogical coupling of one additional Fmoc-D-Asp-O-t-Bu and subsequent N-Fmoc cleavage was repeated and resulted in compound (5). In the next step, 4 equiv of 4-(p-iodophenyl)butyric acid were activated with 3.96 equiv HBTU in the presence of 4 equiv DIPEA in DMF and agitated for 1 h. Selective removal of the Nε-Alloc-protecting group from the product (6) proceeded as described above. The conjugation of the chelator to the resin-immobilized compound was performed with 2 equiv of DOTA-tris(t-Bu)ester activated with 1.98 equiv HBTU in the presence of 4 equiv DIPEA in DMF over the course of 2 h with gentle agitation. The resulting compound (7) was washed with DMF, DCM and, finally, with $Et_2O$ followed by drying under vacuum. The product was cleaved from the resin and subsequently deprotected within 2 h using a mixture of TFA, TIPS and $H_2O$ in a ratio of 95:2.5:2.5 (v/v). TFA was evaporated, and the crude compound dissolved in ACN and $H_2O$ in a ratio of 1:1 (v/v) and purified via RP-HPLC (Supporting Information). The characterization of PSMA-ALB-05 was performed by analytical RP-HPLC (Supporting Information) and MALDI-MS or ESI-MS, respectively.

The synthesis and purification of PSMA-ALB-07 was performed in analogy to PSMA-ALB-05 with one additional coupling of a third Fmoc-D-Asp-O-t-Bu and subsequent N-Fmoc cleavage (8). The next steps comprised the conjugation of 4-(p-iodophenyl)butyric acid (9) followed by selective removal of Nε-Alloc-protecting group and conjugation of the DOTA-tris(t-Bu)ester (10). After cleavage from the resin, the compound was deprotected and purified/characterized as described for PSMA-ALB-05 (Supporting Information). The syntheses of PSMA-ALB-05 and PSMA-ALB-07 are summarized in Scheme 2. The stability of each PSMA ligand in form of lyophilized powder was tested using analytical RP-HPLC and MALDI-MS after long-time storage (2 and 4 months, respectively) in the freezer (−18° C.).

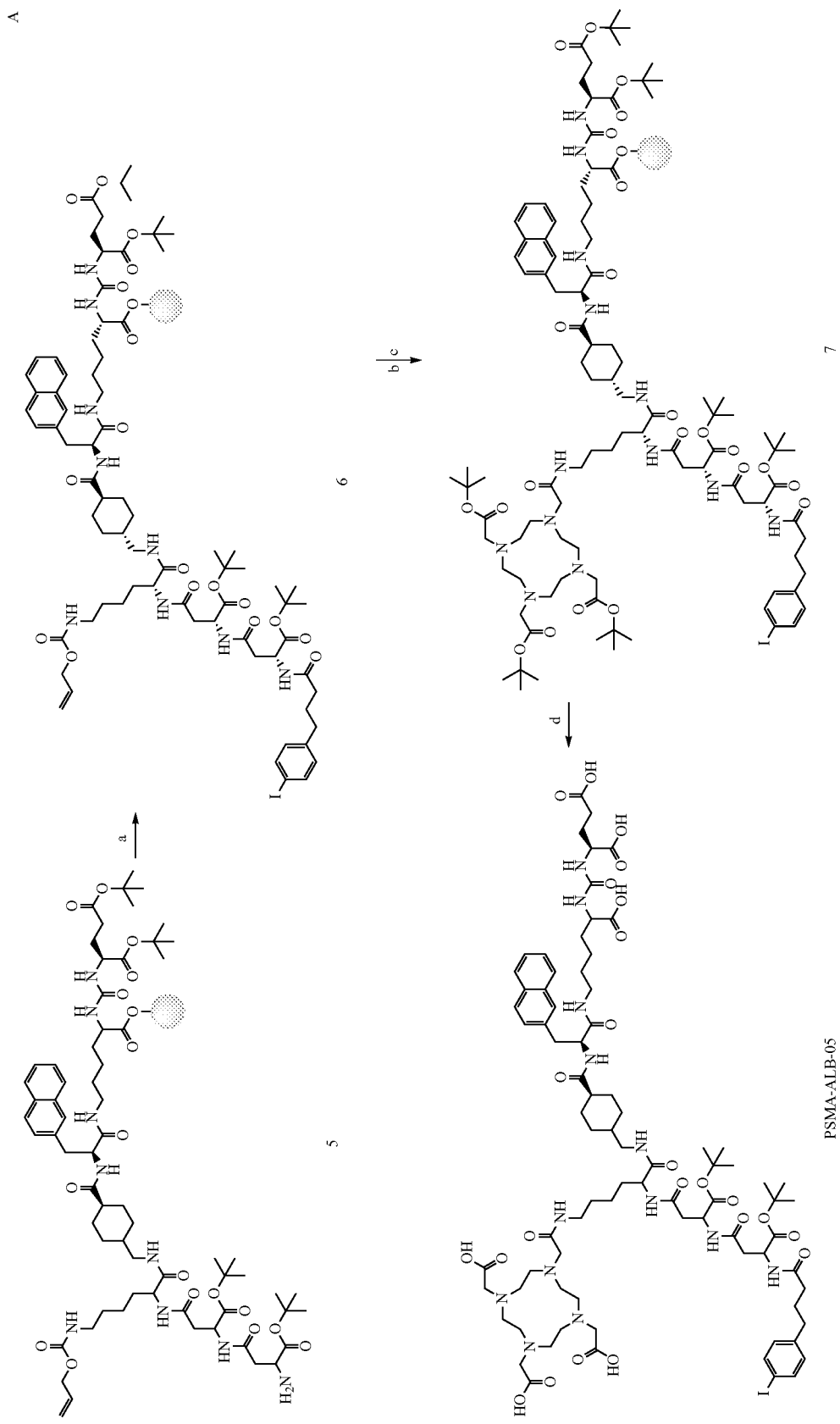
Scheme 6.2: Conjugation of the PSMA Precursor, Albumin-Binding Moiety, and DOTA Chelator for (A) PSMA-ALB-05 and (B) PSMA-ALB-07a:

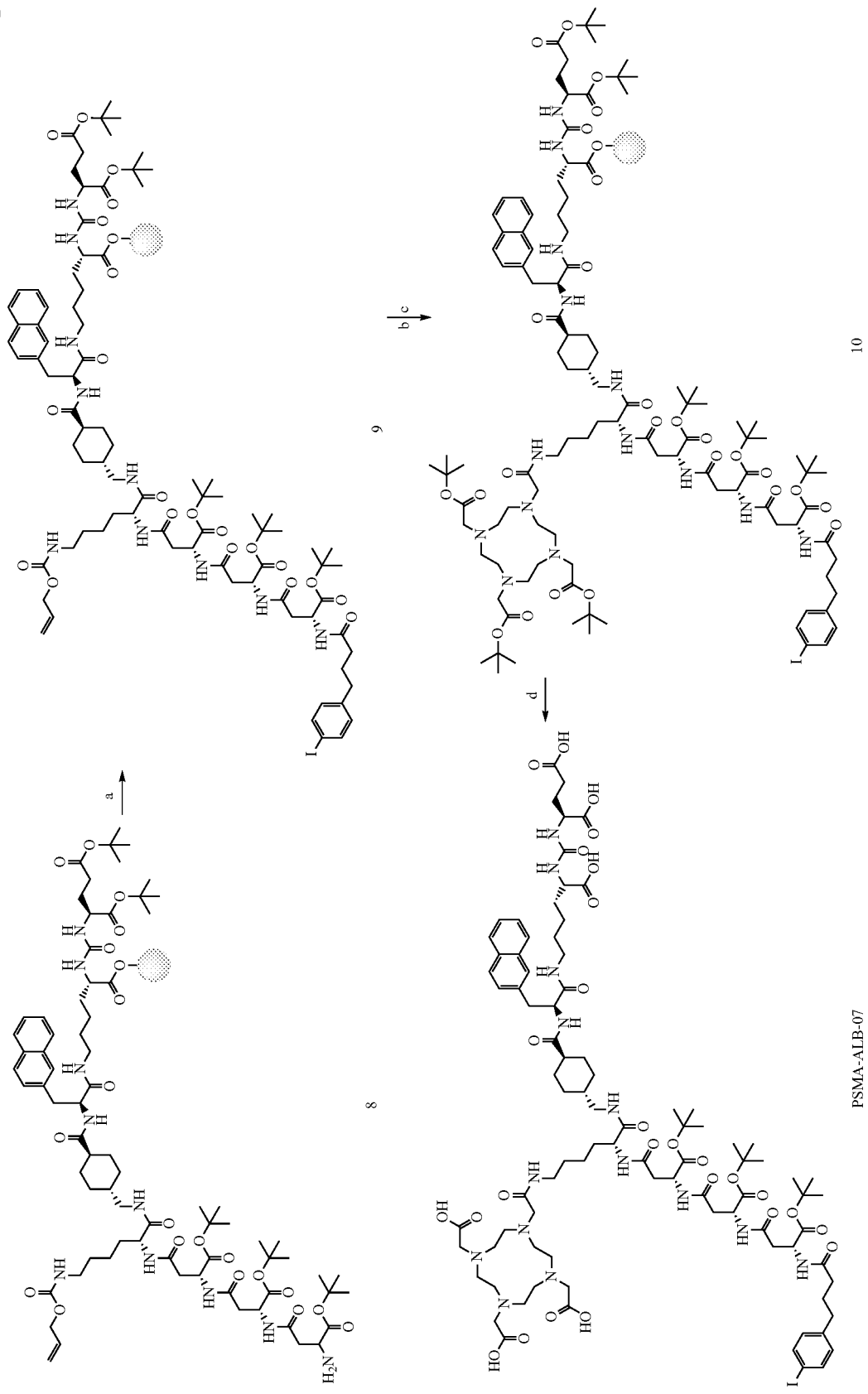

Radiolabeling and Stability. The new PSMA ligands (PSMA-ALB-02, PSMA-ALB-05 and PSMA-ALB-07, respectively) as well as PSMA-617 (Advanced Biochemical Compounds, ABX GmbH, Radeberg, Germany) were dissolved in MilliQ water containing 10-15% sodium acetate solution (0.5 M, pH 8) to prepare 1 mM stock solutions for radiolabeling. The PSMA ligands were labeled with $^{177}$Lu (no-carrier added $^{177}$LuCl$_3$ in 0.04 M HCl provided by Isotope Technologies Garching (ITG GmbH, Germany)) in a mixture of sodium acetate (0.5 M, pH 8) and HCl (0.05 M) at pH 4 at specific activities between 5-50 MBq/nmol. The reaction mixture was incubated for 10 min at 95° C. Quality control of the radioligands was performed using RP-HPLC (Supporting Information). The radioligand solution was used for in vitro and in vivo experiments without further purification steps.

The stability of the radioligands was determined over time using RP-HPLC. The PSMA ligands were radiolabeled with $^{177}$Lu (250 MBq) at a specific activity of 50 MBq/nmol without and with the addition of L-ascorbic acid (0.5 M, 3 mg), followed by dilution in saline to an activity concentration of 250 MBq/500 µL. The radiolabeling efficiency of the ligands was determined immediately after preparation (t=0 h) and the integrity of the compounds was investigated after incubation for various periods (t=1 h, 4 h and 24 h, respectively) at room temperature. The amount of intact compound was quantified by integration of the product peak of the HPLC chromatograms in relation to the sum of all radioactive peaks of degradation products of unknown structure and traces of free $^{177}$Lu, which were set to 100%.

Determination of n-Octanol/PBS Distribution Coefficients (Log D Values). The distribution coefficients (log D values) of the 177Lu-labeled radioligands were determined by a shake-flask method using liquid-liquid extraction followed by phase separation as previously reported. Briefly, the PSMA ligands were radiolabeled with $^{177}$Lu at a specific activity of 50 MBq/nmol. A sample of the radioligands was mixed with phosphate-buffered saline (PBS) and n-octanol followed by vigorous vortexing. After centrifugation for phase separation, the activity concentration in each layer was measured with a γ-counter (Perkin Elmer, Wallac Wizard 1480). Three experiments were performed with five replicates for each compound.

Filter Assay. The binding capacity of the radioligands to mouse and human plasma proteins was determined by an ultrafiltration assay as previously described (Example 1). The $^{177}$Lu-labeled PSMA ligands (50 MBq/nmol) were diluted in mouse plasma (Rockland, USA) and human plasma (Stiftung Blutspende SRK Aargau-Solothurn, Switzerland), respectively, and incubated for 15 min at room temperature. In addition, the radioligands were diluted in PBS (buffer solution without proteins) as a control experiment. Aliquots of the solutions were loaded onto an ultrafiltration device and centrifuged. The filtered activity was measured with a γ-counter and used for calculating the plasma protein-bound activity (retained on the filter membrane) as the percentage of total added activity. Three independent experiments were performed in duplicate with each radioligand ($^{177}$Lu-PSMA-ALB-02, $^{177}$Lu-PSMA-ALB-05 and $^{177}$Lu-PSMA-ALB-07, respectively). Two additional experiments were performed in duplicate using $^{177}$Lu-PSMA-617. Statistical analysis (one-way ANOVA with Bonferroni's multiple comparison post-test) was performed using GraphPad Prism software, version 7. A p-value of <0.05 was considered statistically significant.

Cell Uptake and Internalization. The sum of the PSMA-bound fraction on the cell surface and the internalized fraction (referred to as cell uptake) and the internalized fraction of the radioligands were determined at a specific activity of 5 MBq/nmol using PSMA-positive PC-3 PIP and PSMA-negative PC-3 flu cells as previously described (Example 1). The radiolabeling solution was diluted in saline containing 0.05% (w/v) bovine serum albumin (BSA) to prevent adherence to laboratory vials and tubes. Further dilution of the radioligand solution with cell culture medium resulted in a final BSA concentration (0.00125%) which was negligible and had no influence on the cell uptake and internalization of the radioligands. In parallel to each experiment with a novel radioligand, control experiments with $^{177}$Lu-PSMA-617 were also performed. The experiments were performed in triplicate and repeated three times for each radioligand.

In Vivo Studies. In vivo experiments were performed in female, athymic BALB/c nude mice at the age of 5-6 weeks (Charles River Laboratories, Sulzfeld, Germany) were used for these studies. The mice were subcutaneously inoculated with PC-3 PIP cells (6×10$^6$ cells in 100 µL Hank's balanced salt solution with Ca$^{2+}$/Mg$^{2+}$ (HBSS)) on the right shoulder and with PC-3 flu cells (5×10$^6$ cells in 100 µL HBSS) on the left shoulder about 12-14 days before the performance of the experiments.

Biodistribution Studies. Biodistribution experiments were performed at 1 h, 4 h, 24 h, 48 h, 96 h and 192 h after injection of the radioligands labeled at a specific activity of 5 MBq/nmol. The tumor mass at the time of radioligand injection was 150±40 mg, which corresponds to an average tumor volume of about 150 mm$^3$. Mice were injected into a lateral tail vein with the respective radioligand (5 MBq, 1 nmol, 100 µL) diluted in saline. BSA (0.05%) was added to the saline in order to prevent adsorption of the radioligand to vials and syringes. The mice were sacrificed at different time points after injection (p.i.) and selected tissues and organs were collected, weighed and measured using a γ-counter. Groups of 3-6 mice were used for each time point. In addition, blocking studies were performed by injection of 2-(phosphonomethyl)-pentanedioic acid (2-PMPA, 500 nmol, 100 µL) diluted in saline. The 2-PMPA solution was injected 15 min prior to the application of $^{177}$Lu-PSMA-ALB-02 and the mice were sacrificed at 1 h and 4 h p.i., respectively. The results were decay-corrected and listed as percentage of the injected activity per gram of tissue mass (% IA/g). The area under the curve (AUC) was determined for all three albumin-binding PSMA ligands and $^{177}$Lu-PSMA-617 from non-decay-corrected data obtained from the biodistribution data of the tumors, kidneys and blood using GraphPad Prism software, version 7.

Statistical analysis was performed to compare the areas under the curve (AUCs) obtained from the biodistribution data sets using a one-way ANOVA with Bonferroni's multiple comparison post-test using GraphPad Prism software (version 7). A p-value of <0.05 was considered statistically significant.

SPECT/CT Imaging Studies. SPECT/CT experiments were performed at 4 h, 24 h and 72 h after injection of the radioligands. Mice were injected into a lateral tail vein with the respective radioligand (25 MBq, 1 nmol, 100 µL) diluted in saline containing 0.05% BSA. In addition, SPECT/CT scans were performed at 1 h, 4 h and 24 h after injection of $^{177}$Lu-PSMA-ALB-02 with mice that received 2-PMPA (500 nmol, 100 µL) or non-radiolabeled PSMA-ALB-02 (100 nmol, 100 µL) 15 min prior to the radioligand injection in order to block PSMA. SPECT/CT scans were performed using a small-animal SPECT/CT scanner (NanoSPECT/CT™, Mediso Medical Imaging Systems, Budapest, Hungary). The SPECT scans lasted for 45 min and were followed by a CT scan of 7.5 min. During the in vivo scans, the mice were anesthetized with a mixture of isoflurane and oxygen. Reconstruction of acquired data was performed using the software of the NanoSPECT/CT™. All images were prepared using VivoQuant post-processing software (version 3.0, inviCRO Imaging Services and Software, Boston USA). Gauss post-reconstruction filter (FWHM=1 mm) was applied to the SPECT images and the scale of radioactivity was set as indicated on the images (minimum value=0.95 Bq/voxel to maximum value=95 Bq/voxel).

6.2 Results

Figure 19:
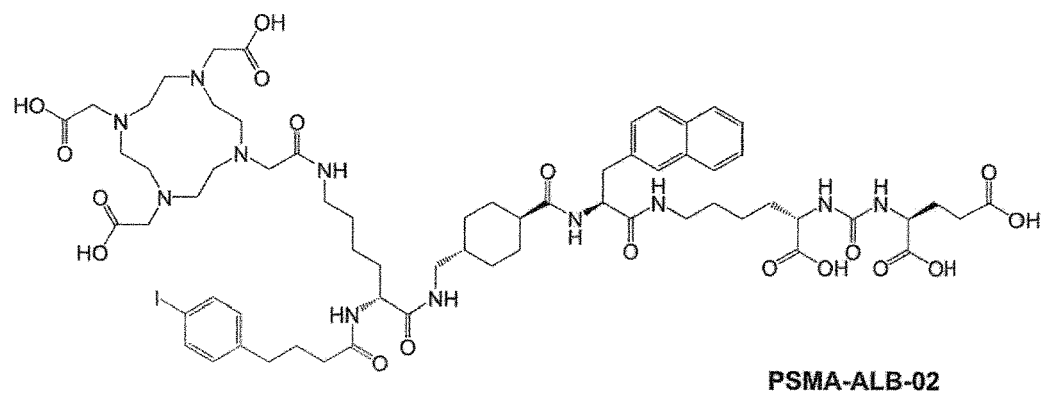
FIG. 19: Chemical structure of (A) PSMA-ALB-02, (B) PSMA-ALB-05, and (C) PSMA-ALB-07.
Figure 19:
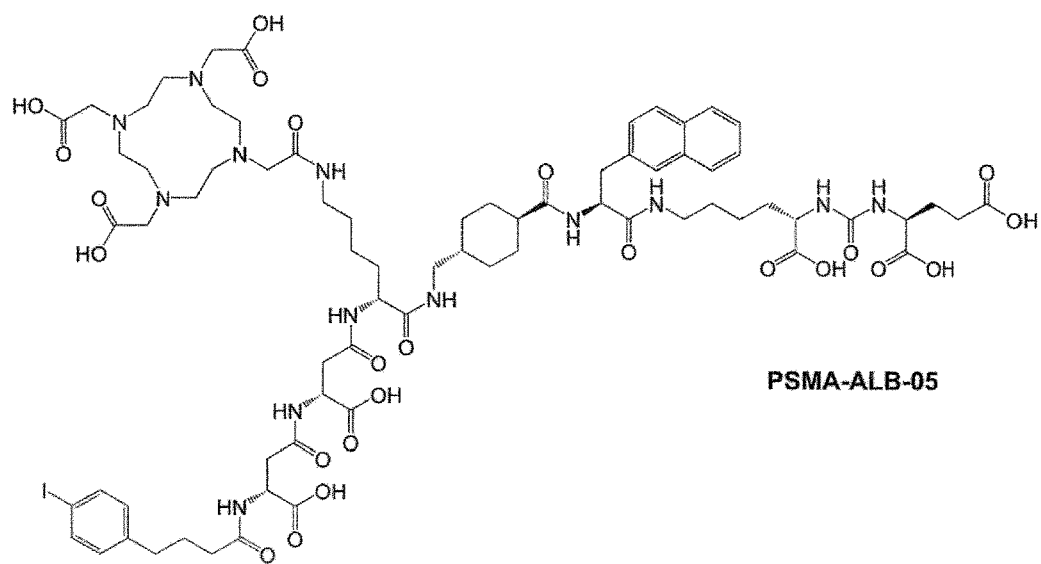
Figure 19:
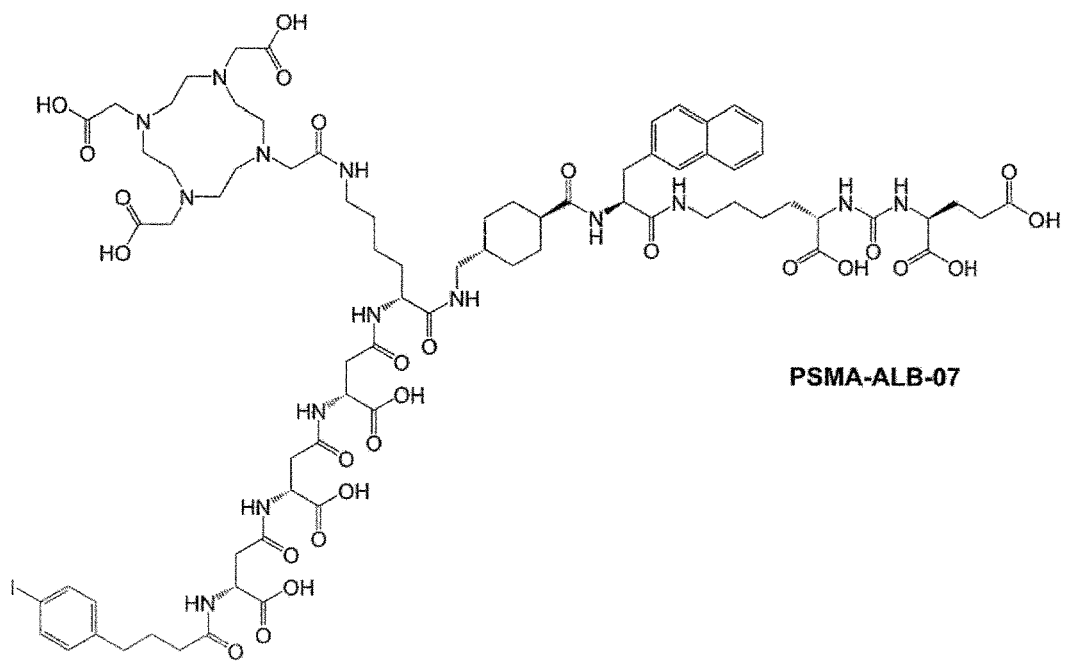
Figure 21:
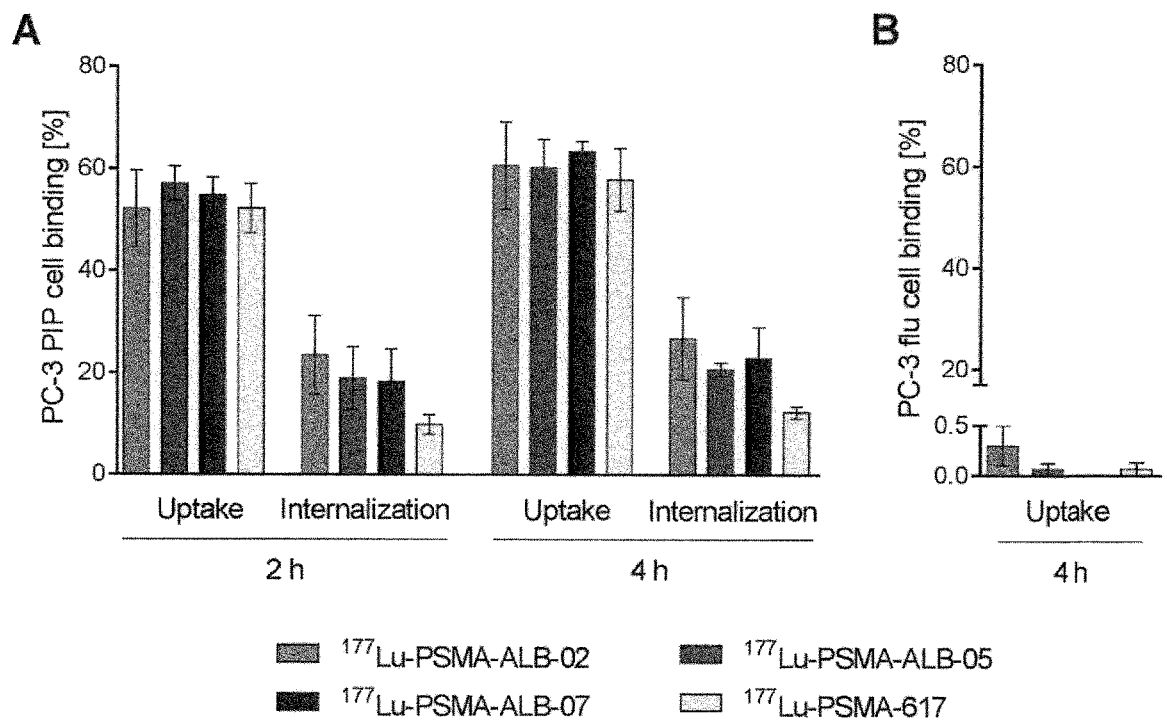
FIG. 21: Uptake and internalization of $^{177}$Lu-PSMA-ALB-02, $^{177}$Lu-PSMA-ALB-05, and $^{177}$Lu-PSMA-ALB-07 compared to $^{177}$Lu-PSMA-617. (A) Data obtained in PSMA-positive PC-3 PIP cells. The bars represent the average value±SD of three independent experiments performed in triplicate. (B) Data obtained in PSMA-negative PC-3 flu cells. The bars represent the average value f SD of one experiment performed in triplicate.

Synthesis of the PSMA Ligands. The PSMA ligands with an albumin-binding moiety were synthesized via a solid-phase platform employing a standard Fmoc (9-fluorenylmethyloxycarbonyl) protocol (FIG. 19). The synthesis started from the immobilization of the C-terminus of the first amino acid to 2-CT resin and was assembled in the C→N direction. As a last step the compound was cleaved from the resin followed by full deprotection, both performed under acidic conditions. This multistep synthesis of PSMA-ALB-02 (17 steps), PSMA-ALB-05 (20 steps) and PSMA-ALB-07 (22 steps) provided highly pure (>98%) compounds in overall yields of 12.9-21.2% after semi-preparative HPLC purification (Table 6.1). All three PSMA ligands were found to be stable for at least 4 months as lyophilized powders at −18° C.

between 18-24% after an incubation period of 2 h at 37° C. (FIG. 21A). After 4 h incubation, the cell uptake and internalization were slightly increased to 60-63% and 20-26%, respectively. 17?Lu-PSMA-617 showed similar values for the cell uptake (58%), however, only 12% of the radioligand were internalized after 4 h incubation. Uptake in PC-3 flu cells was below 0.5% for all albumin-binding radioligands as well as for $^{177}$Lu-PSMA-617 (FIG. 21B).

The results of the ultrafiltration assay indicated significant plasma protein-binding capacity of $^{177}$Lu-PSMA-ALB-02, $^{177}$Lu-PSMA-ALB-05 and $^{177}$Lu-PSMA-ALB-07 when incubated with mouse plasma (87±1.0%, 77±2.1% and 64±2.1%, respectively) and human plasma (95±1.2%, 95±0.6 and 95±0.1%, respectively). These values were significantly higher (p<0.05) than in the case of $^{177}$Lu-PSMA-617, which showed only very low binding to mouse plasma proteins (9.3±1.1%) and some binding to human plasma proteins (57±2.3%). Control experiments performed with PBS revealed <5% retention of the radioligands on the filter presumably due to unspecific adsorption to the filter device (data not shown).

Figure 22:
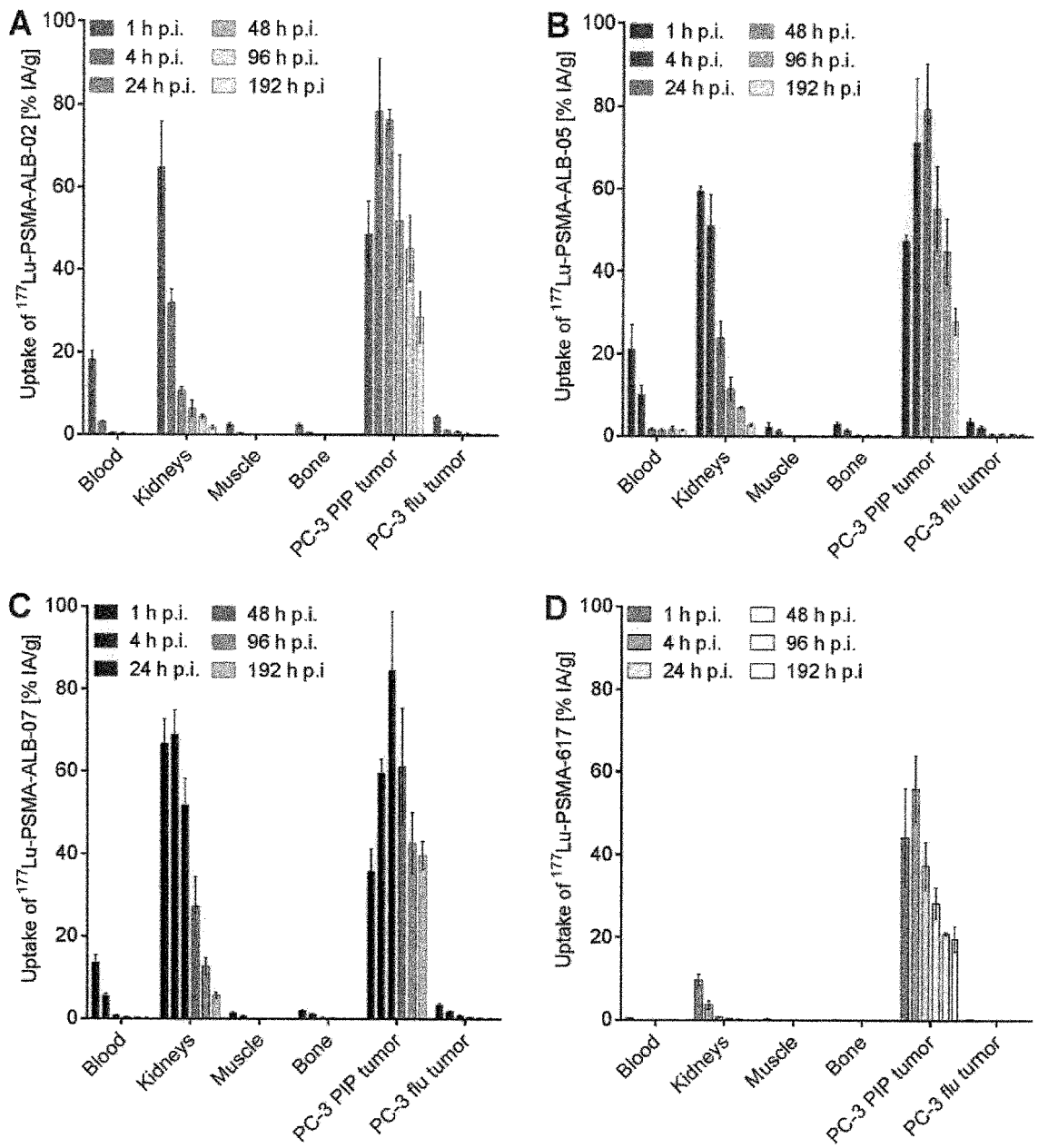
FIG. 22: Biodistribution data (decay-corrected) up to 192 h p.i. obtained for all three albumin-binding $^{177}$Lu-PSMA ligands as well as for $^{177}$Lu-PSMA-617. (A) Biodistribution data of $^{177}$Lu-PSMA-ALB-02, (B) $^{177}$Lu-PSMA-ALB-05, (C) $^{177}$Lu-PSMA-ALB-07, and (D) $^{177}$Lu-PSMA-617. Average value SD obtained from each group of mice (n=3-6).

Biodistribution Study. The tissue distribution of $^{177}$Lu-PSMA-ALB-02, $^{177}$Lu-PSMA-ALB-05 and $^{177}$Lu-PSMA-ALB-07 was evaluated in mice bearing PC-3 PIP and PC-3 flu tumors on the right and left shoulder, respectively, over a period of 192 h (FIG. 22).

TABLE 6.1

Analytical Data of PSMA-ALB-02, PSMA-ALB-05, and PSMA-ALB-07

| compound code | chemical formula | MW [g/mol] | m/z$^a$ | $t_r^d$ [min] | chemical purity [%] | logD |
|---|---|---|---|---|---|---|
| PSMA-ALB-02 | $C_{65}H_{92}IN_{11}O_{16}$ | 1442.41 | 1443.53 | 6.2 | 99.5 | −2.8 ± 0.09 |
| PSMA-ALB-05 | $C_{73}H_{102}IN_{13}O_{24}$ | 1672.59 | 1673.41 | 6.1 | 99.2 | −3.5 ± 0.08 |
| PSMA-ALB-07 | $C_{77}H_{107}IN_{14}O_{27}$ | 1787.63 | 1788.63 | 5.9 | 98.5 | −3.9 ± 0.25 |
| PSMA-617 | $C_{49}H_{71}N_9O_{16}$ | 1042.15 | 1043.32 | 4.8 | 98.4$^c$ | −4.4 ± 0.15 |

$^a$Mass spectrometry of the unlabeled ligand detected as [M + H]$^+$.
$^b$Retention time of unlabeled ligand on analytical RP-HPLC. Analytical column (1.00 × 4.6 mm) utilized Chromolith RP-18e stationary phase with mobile phases consisting of 0.1% TFA in water (A) and ACN (B). For analytical runs, a linear gradient of solvent A (90-10% in 10 min) in solvent B at a flow rate of 1 mL/min was used.
$^c$The purity of PSMA-617 was taken from the ABX GmbH certificate of this compound.

Figure 20:
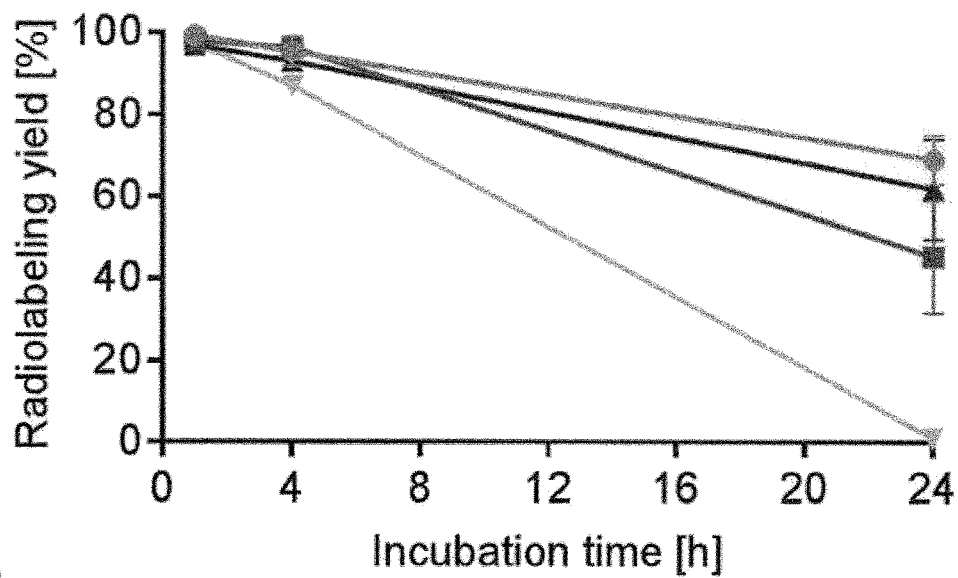
FIG. 20: Graphs presenting the stability of $^{177}$Lu-PSMA-ALB-02, $^{177}$Lu-PSMA-ALB-05, and $^{177}$Lu-PSMA-ALB-07 as well as of $^{177}$Lu-PSMA-617 over a period of 24 h in the (A) absence and (B) presence of L-ascorbic acid. The values represent the average±SD of three independent experiments.
Figure 20:
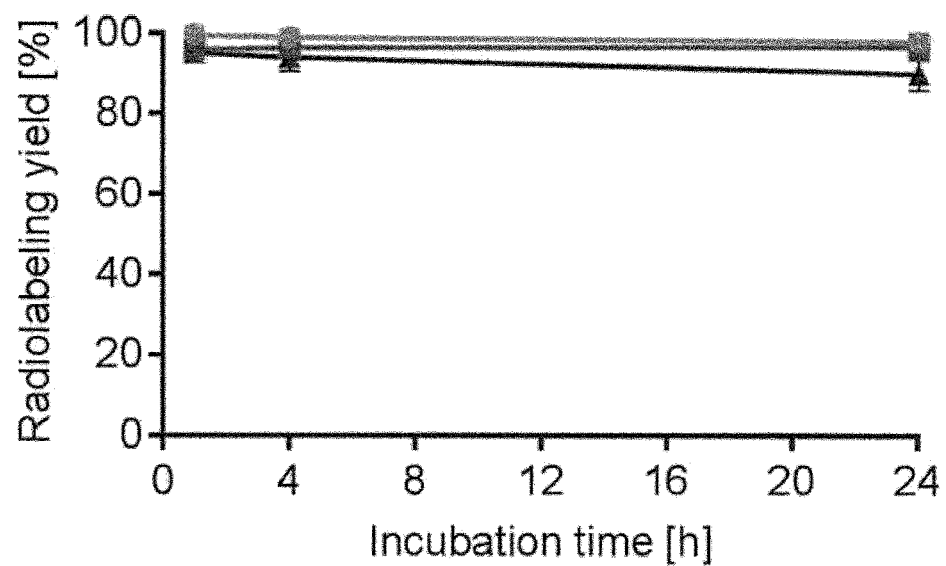

Radiolabeling, Stability and In Vitro Properties of $^{177}$Lu-PSMA Ligands. PSMA-ALB-02, PSMA-ALB-05 and PSMA-ALB-07 were readily labeled with $^{177}$Lu at a specific activity up to 50 MBq/nmol. The radioligands showed high radiochemical purity of >98%. The addition of L-ascorbic acid resulted in ~97% intact $^{177}$Lu-PSMA-ALB-02, ~96% intact $^{177}$Lu-PSMA-ALB-05 and ~89% intact $^{177}$Lu-PSMA-ALB-07 after 24 h (FIG. 20B). $^{177}$Lu-PSMA-617 was less stable resulting in ~86% intact compound after 4 h, however, complete degradation (<2% intact compound) was observed after 24 h (FIG. 20A). The presence of L-ascorbic acid prevented radiolysis entirely resulting in >98% intact $^{177}$Lu-PSMA-617 even after 24 h (FIG. 20B). The n-octanol/PBS distribution coefficient (log D value) of 177Lu-PSMA-ALB-02 (−2.8±0.09) was highest. The lowest log D value was obtained for 17'Lu-PSMA-617 (−4.4±0.15).

In Vitro Testing of Cell Uptake and Binding to Albumin. Uptake for $^{177}$Lu-PSMA-ALB-02, $^{177}$Lu-PSMA-ALB-05 and $^{177}$Lu-PSMA-ALB-07 into PC-3 PIP cells was in the range of 52-57% whereas the internalized fraction was Uptake of all PSMA radioligands into the PC-3 PIP tumors showed similar kinetic profiles. $^{177}$Lu-PSMA-ALB-02 showed a fast tumor accumulation which reached 78.4 12.8% IA/g already at 4 h p.i. and was retained at this level over 24 h p.i. (76.4±2.49% IA/g). All novel compounds, in particular $^{177}$Lu-PSMA-ALB-02, exhibited high blood activity levels (18-21% IA/g), fast clearance of radioactivity from the blood and fast renal clearance. $^{177}$Lu-PSMA-617 reached the maximum tumor uptake of ~56% IA/g already at 4 h p.i which decreased to ~20% IA/g after 192 h. It was cleared quickly from the blood resulting in <1% IA/g after 1 h and showed a steady wash-out from the kidneys from ~10% IA/g at 1 h p.i. to <1% IA/g at 24 h p.i. Radioactivity levels in all other tissues were below the blood levels and decreased continuously over time.

Tumor-to-blood, tumor-to-kidney and tumor-to-liver ratios were high for all novel compounds, in particular $^{177}$Lu-PSMA-ALB-02. Due to the fast renal clearance, $^{177}$Lu-PSMA-617 showed increased tumor-to-background ratios.

TABLE 6.2

| | $^{177}$Lu-PSMA-ALB-02 | | $^{177}$Lu-PSMA-ALB-05 | | $^{177}$Lu-PSMA-ALB-07 | | $^{177}$Lu-PSMA-617 | |
|---|---|---|---|---|---|---|---|---|
| | 24 h p.i. | 48 h p.i. | 24 h p.i. | 48 h p.i. | 24 h p.i. | 48 h p.i. | 24 h p.i. | 48 h p.i. |
| tumor-to-blood | 176 ± 27 | 191 ± 37 | 48 ± 6.4 | 38 ± 2.5 | 107 ± 10 | 154 ± 7 | 2730 ± 195 | 3776 ± 585 |
| tumor-to-kidney | 7.2 ± 0.3 | 8.3 ± 0.5 | 3.4 ± 0.5 | 5.0 ± 0.7 | 1.6 ± 0.2 | 2.3 ± 0.1 | 49 ± 3.7 | 81 ± 11 |
| tumor-to-liver | 164 ± 20 | 163 ± 32 | 106 ± 26 | 100 ± 32 | 162 ± 14 | 131 ± 13 | 528 ± 51 | 710 ± 97 |

Additional studies were performed in order to block PSMA by administration of 2-PMPA prior to the injection of $^{177}$Lu-PSMA-ALB-02. In PC-3 PIP tumors the uptake was reduced by 64% (17.6±3.24% IA/g) and 41% (46.0±7.29% IA/g) at 1 h and 4 h p.i. respectively, when compared to unblocked uptake at the same time points. The accumulated radioactivity in the kidneys was reduced by 81% and 59% at 1 h and 4 h after radioligand injection, respectively. In all other organs and tissues slight, but not pronounced reduction of radioactivity accumulation was observed (data not shown).

Figure 23:
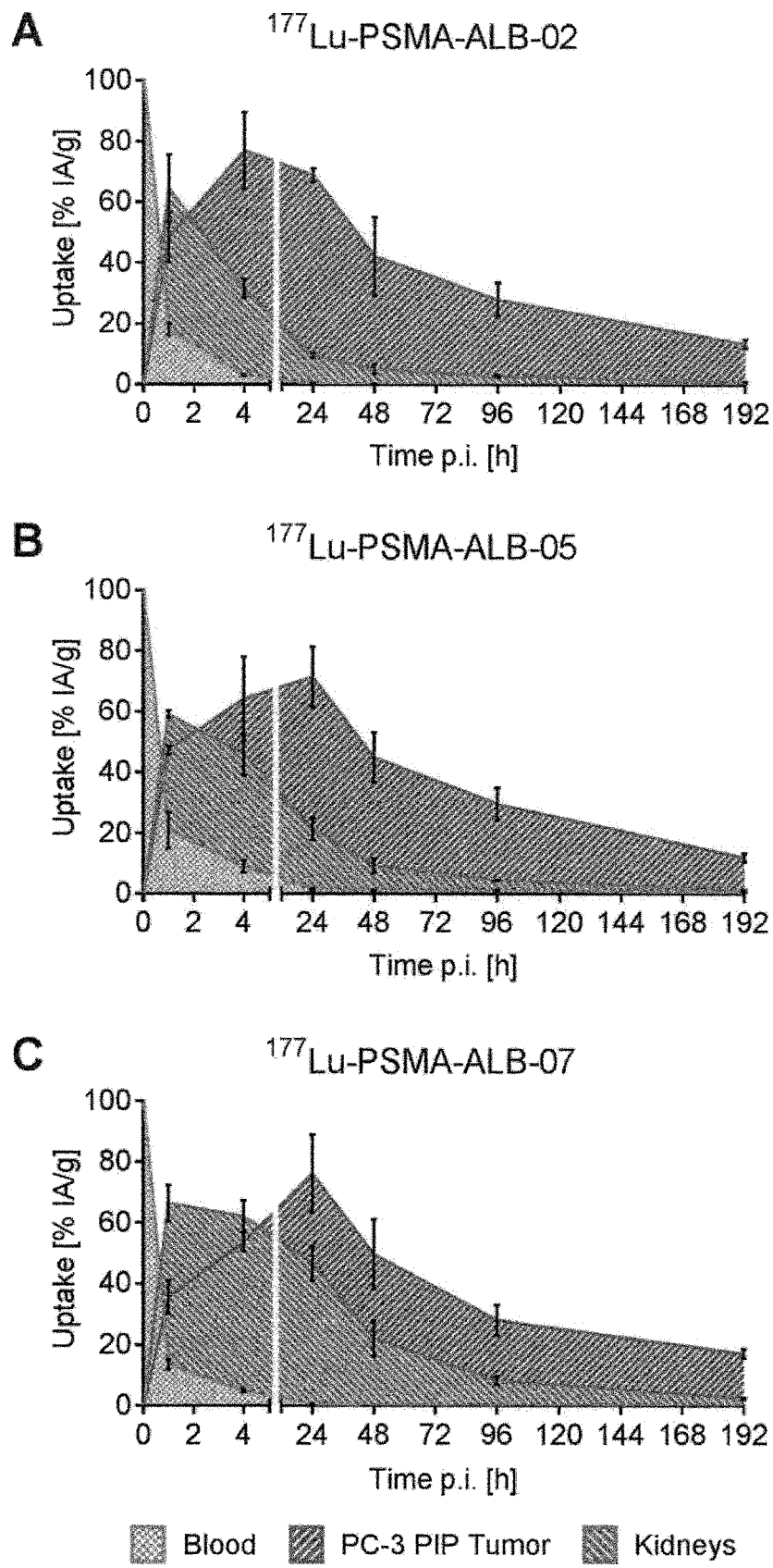
FIG. 23: Graphs show non-decay-corrected biodistribution data up to 192 h p.i. of (A) $^{177}$Lu-PSMA-ALB-02, (B) $^{177}$Lu-PSMA-ALB-05, and (C) $^{177}$Lu-PSMA-ALB-07. Each data point represents the average of a group of mice±SD (n=3-6).

Non-decay-corrected data of the biodistribution study were used to calculate the areas under the curves (AUCs) for the accumulation of the radioligands in the blood pool, tumors, kidneys and the liver (FIG. 23, Table 6.3).

TABLE 6.3

Area under the Curve (AUC) Based on Non-Decay-Corrected, Time-Dependent Biodistribution Data of $^{177}$Lu-PSMA-ALB-02, -05 and -07 and Ratios of AUCs

| | $^{177}$Lu-PSMA-ALB-02 | $^{177}$Lu-PSMA-ALB-05 | $^{177}$Lu-PSMA-ALB-07 | $^{177}$Lu-PSMA-617 |
|---|---|---|---|---|
| | AUC [% IA/g · h] | | | |
| PC-3 PIP tumor | 6688 ± 485 | 6741 ± 421 | 7007 ± 459 | 3691 ± 156 |
| blood | 145 ± 6.3 | 387 ± 32 | 180 ± 7.2 | 52 ± 1.5 |
| kidneys | 1130 ± 62 | 1837 ± 112 | 3395 ± 201 | 99 ± 11 |
| liver | 57 ± 5.3 | 131 ± 11 | 72 ± 3.6 | 6.2 ± 1.6 |
| | Ratios of AUCs | | | |
| $AUC_{Tu}$-to-$AUC_{Bl}$ | 46 | 17 | 39 | 71 |
| $AUC_{Tu}$-to-$AUC_{Ki}$ | 5.9 | 3.7 | 2.1 | 37 |
| $AUC_{Tu}$-to-$AUC_{Li}$ | 117 | 52 | 97 | 592 |

All novel radioligands showed comparable AUCs for the PC-3 PIP tumor uptake which were almost double as high as the AUC (p<0.05) obtained for $^{177}$Lu-PSMA-617. All radioligands showed high tumor-to-blood, tumor-to-kidney and tumor-to-liver ratios of AUCs. The high tumor-to-background values of AUCs were obtained for $^{177}$Lu-PSMA-617 are due to the fast blood and kidney clearance of this radioligand (Table 6.2).

Figure 24:
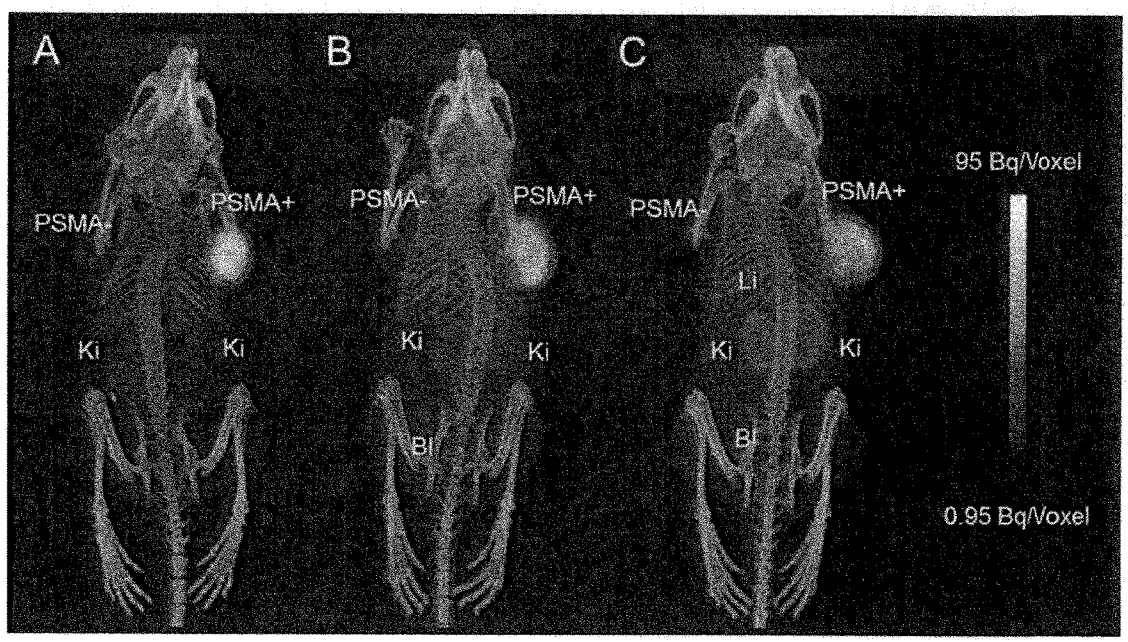
FIG. 24: SPECT/CT images as maximum intensity projections (MIPs) of PC-3 PIP/flu tumor-bearing mice 24 h after the injection of (A) $^{177}$Lu-PSMAALB-02, (B) $^{177}$Lu-PSMA-ALB-05, and (C) $^{177}$Lu-PSMA-ALB-07. PSMA$^+$=PSMA-positive PC-3 PIP tumor; PSMA$^-$=PSMA-negative PC-3 flu tumor; Ki=kidney; Bl=urinary bladder; Li=liver.
Figure 25:
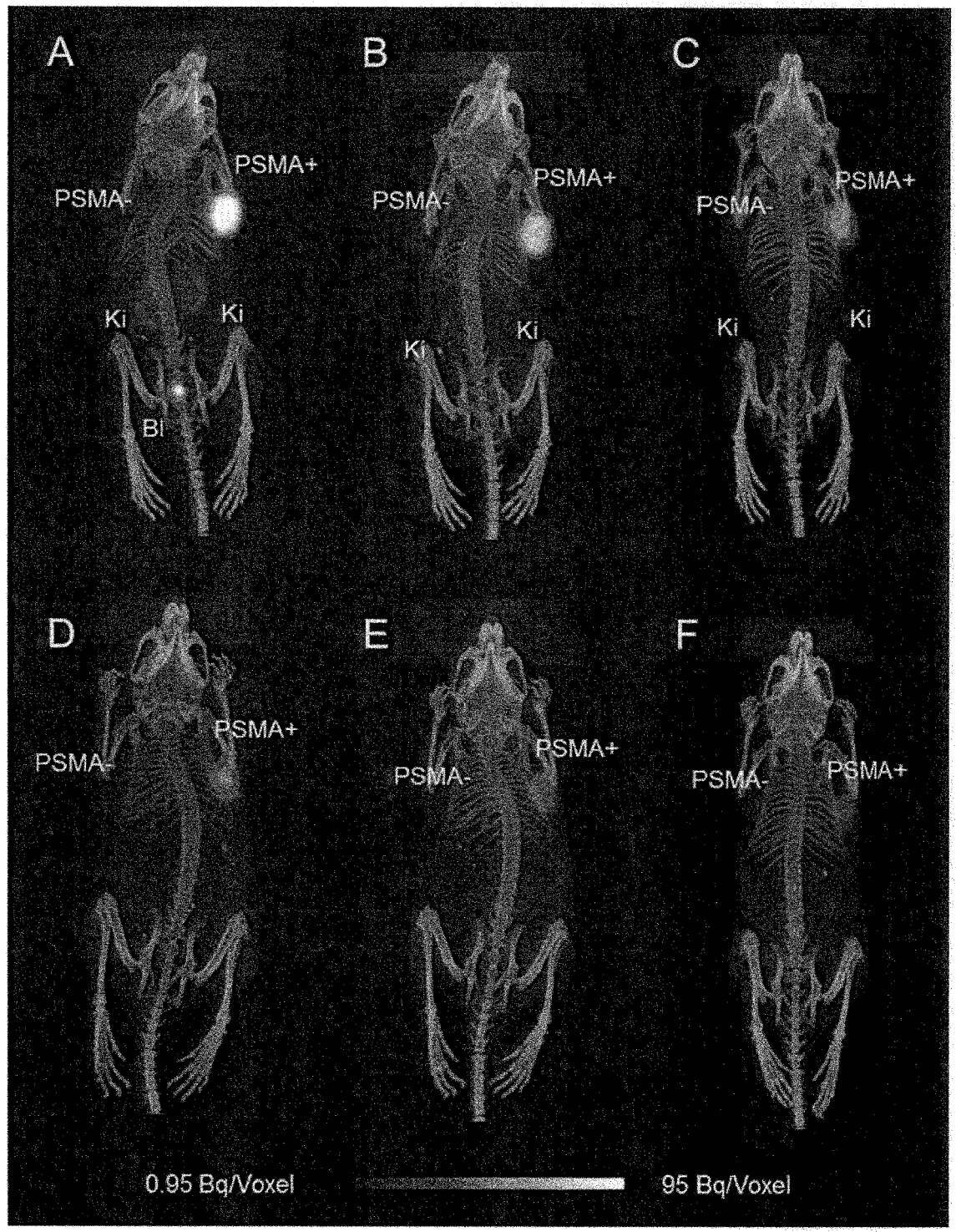
FIG. 25: (A/B/C) SPECT/CT images as maximum intensity projections (MIPs) of PC-3 PIP/flu tumor-bearing mice 4 h (A), 24 h (B), and 72 h (C) after the injection of 177Lu-PSMA-ALB-02. (D/E/F) SPECT/CT images as maximum intensity projections (MIPs) of PC-3 PIP/flu tumor-bearing mice 4 h (D), 24 h (E), and 72 h (F) after the injection of 177Lu-PSMA-617. PSMA+=PSMA-positive PC-3 PIP tumor; PSMA−=PSMA-negative PC-3 flu tumor; Ki=kidney; Bl=urinary bladder.

SPECT/CT Imaging Studies. SPECT/CT scans were performed with PC-3 PIP/flu tumor-bearing mice at 4 h, 24 h and 72 h after injection of the new radioligands as well as $^{177}$Lu-PSMA-617 (FIGS. 24 and 25). Accumulation of all albumin-binding radioligands in PC-3 PIP tumor xenografts was similar at 24 h p.i. Renal uptake, in particular of $^{177}$Lu-PSMA-ALB-02, was low. Time-dependent SPECT/CT images obtained with $^{177}$Lu-PSMA-ALB-02 showed increasing tumor-to-background contrast over time. Compared to $^{177}$Lu-PSMA-617, the tumor uptake of $^{177}$Lu-PSMA-ALB-02 was significantly increased over the entire time period of investigation and the same held true for the accumulation in the kidneys (FIG. 25). No activity accumulation was detectable in PSMA-negative PC-3 flu tumors.

The invention claimed is:
1. A radiolabeled complex comprising a radionuclide and a compound according to general Formula (1)(i) or (1)(ii):

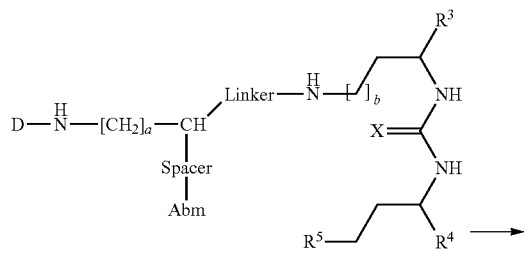

(1)(i)

-continued

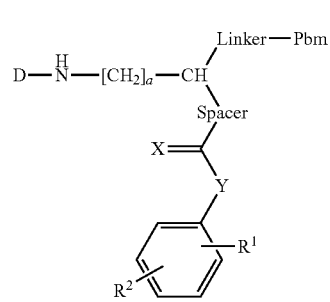

(1)(ii)

wherein Abm is an albumin binding entity,
Pbm is a PSMA binding entity,
D is a chelator complexed with a radionuclide, X is each independently selected from O, N, S or P,

151

$R^1$ and $R^2$ are each independently selected from H, F, Cl, Br, I, branched, unbranched or cyclic $C_1$-$C_{12}$ hydrocarbyl, $C_2$-$C_{12}$ alkenyl, $C_2$-$C_{12}$ alkylnyl, $OR^6$, $OCOR^6$, CHO, $COR^6$, $CH_2OR^6$, $NR^6R^7$, $CONR^6R^7$, $COOR^6$, $CH_2NR^6R^7$, $SR^6$, =O, =S or =NH, or $R^1$ and $R^2$ are joined to form a cyclic structure comprising a branched, unbranched or cyclic $C_1$-$C_{10}$ hydrocarbyl group, wherein said hydrocarbyl group is optionally interrupted by up to 2 heteroatoms and optionally substituted by up to 3 groups independently selected from F, Cl, Br, I, $OR^6$, $OCOR^6$, $COOR^6$, CHO, $COR^6$, $CH_2OR^6$, $NR^6R^7$, $CH_2NR^6R^7$, and $SR^7$, =O, =S and =NH, Y is selected from a single bond or a linear, branched or cyclic, optionally substituted $C_1$-$C_{12}$ alkyl, optionally interrupted by up to two heteroatoms, $OR^6$, $OCOR^6$, CHO, $COR^6$, $CH_2OR^6$, $NR^6R^7$, $COOR^6$, $CH_2NR^6R^7$, $SR^6$, =O, =S or =NH, wherein one or more of the non-adjacent $CH_2$-groups may independently be replaced by —O—, —CO—, —CO—O—, —O—CO—, —$NR^6$—, —$NR^6$—CO—, —CO—$NR^6$—, —$NR^6$—COO—, —O—CO—$NR^6$—, —$NR^6$—CO—$NR^6$—, —CH=CH—, —C≡C—, —O—CO—O—, $SR^6$—, $SO_3R^6$—, $R^6$ and $R^7$ are each independently selected from H or branched, unbranched or cyclic $C_{1-12}$ hydrocarbyl, $R^3$, $R^4$ and $R^5$ are each independently selected from —COH, —$CO_2H$, —$SO_2H$, —$SO_3H$, —$SO_4H$, —$PO_2H$, —$PO_3H$, —$PO_4H_2$, —C(O)—($C_1$-$C_{10}$)alkyl, —C(O)—O($C_1$-$C_{10}$)alkyl, —C(O)—$NHR^8$, or —C(O)—$NR^8R^9$, wherein $R^8$ and $R^9$ are each independently selected from H, bond, ($C_1$-$C_{10}$)alkylene, F, Cl, Br, I, C(O), C(S), —C(S)—NH-benzyl-, —C(O)—NH-benzyl, —C(O)—($C_1$-$C_{10}$)alkylene, —$(CH_2)_p$—NH, —$(CH_2)_p$—($C_1$-$C_{10}$)alkylene, —$(CH_2)_p$—NH—C(O)—$(CH_2)_q$, —$(CH_rCH_2)_t$—NH—C(O)—$(CH_2)_p$, —$(CH_2)_p$—CO—COH, —$(CH_2)_p$—CO—$CO_2H$, —$(CH2)_p$-C(O)NH—C[$(CH_2)_q$—COH]$_3$, —C[$(CH_2)_p$—COH]$_3$, —$(CH2)_p$-C(O)NH—C[$(CH_2)_q$—$CO_2H$]$_3$, —C[$(CH_2)_p$—$CO_2H$]$_3$ or —$(CH_2)_p$—($C_5$-$C_{14}$)heteroaryl, the spacer comprises at least one C—N bond, the linker is characterized by General Formula (6)

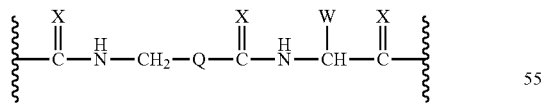

and a, b, p, q, r, and t are each independently an integer selected from 0, 1, 2, 3, 4, 5, 6, 7, 8, 9, and 10;

or pharmaceutically acceptable salts, esters, or solvates thereof.

2. The radiolabeled complex according to claim 1, wherein said radiolabeled complex is characterized by General Formula (1a):

152

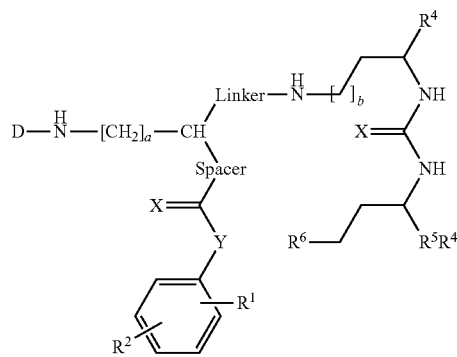

wherein

D is a chelator complexed with a radionuclide,

X is each independently selected from O, N, S or P, $R^1$ and $R^2$ are each independently selected from H, F, Cl, Br, I, branched, unbranched or cyclic, optionally substituted, $C_1$-$C_{12}$ hydrocarbyl, $C_2$-$C_{12}$ alkenyl, $C_2$-$C_{12}$ alkylnyl, $OR^6$, $OCOR^6$, CHO, $COR^6$, $CH_2OR^6$, $NR^6R^7$, $CONR^6R^7$, $COOR^6$, $CH_2NR^6R^7$, $SR^6$, =O, =S or =NH, or $R^1$ and $R^2$ are joined to form a cyclic structure comprising a branched, unbranched or cyclic $C_1$-$C_{10}$ hydrocarbyl group, wherein said hydrocarbyl group is optionally interrupted by up to 2 heteroatoms and optionally substituted by up to 3 groups independently selected from F, Cl, Br, I, $OR^6$, $OCOR^6$, $COOR^6$, CHO, $COR^6$, $CH_2OR^6$, $NR^6R^7$, $CH_2NR^6R^7$, and $SR^7$, =O, =S and =NH, Y is selected from a single bond or a linear, branched or cyclic, optionally substituted $C_1$-$C_{12}$ alkyl, optionally interrupted by up to two heteroatoms, $OR^6$, $OCOR^6$, CHO, $COR^6$, $CH_2OR^6$, $NR^6R^7$, $COOR^6$, $CH_2NR^6R^7$, $SR^6$, =O, =S or =NH, wherein one or more of the non-adjacent $CH_2$-groups may independently be replaced by —O—, —CO—, —CO—O—, —O—CO—, —$NR^6$—, —$NR^6$—CO—, —CO—$NR^6$—, —$NR^6$—COO—, —O—CO—$NR^6$—, —$NR^6$—CO—$NR^6$—, —CH=CH—, —C≡C—, —O—CO—O—, $SR^6$—, $SO_3R^6$—, $R^6$ and $R^7$ are each independently selected from H or branched, unbranched or cyclic $C_{1-12}$ hydrocarbyl, $R^3$, $R^4$ and $R^5$ are each independently selected from —COH, —$CO_2H$, —$SO_2H$, —$SO_3H$, —$SO_4H$, —$PO_2H$, —$PO_3H$, —$PO_4H_2$, —C(O)—($C_1$-$C_{10}$)alkyl, —C(O)—O($C_1$-$C_{10}$)alkyl, —C(O)—$NHR^8$, or —C(O)—$NR^8R^9$, wherein $R^8$ and $R^9$ are each independently selected from H, bond, ($C_1$-$C_{10}$)alkylene, F, Cl, Br, I, C(O), C(S), —C(S)—NH-benzyl-, —C(O)—NH-benzyl, —C(O)—($C_1$-$C_{10}$)alkylene, —$(CH_2)_p$—NH, —$(CH_2)_p$—($C_1$-$C_{10}$)alkylene, —$(CH_2)_p$—NH—C(O)—$(CH_2)_q$, —$(CH_rCH_2)_t$—NH—C(O)—$(CH_2)_p$, —$(CH_2)_p$—CO—COH, —$(CH_2)_p$—CO—$CO_2H$, —$(CH_2)_p$—C(O)NH—C[$(CH_2)_q$—COH]$_3$, —C[$(CH_2)_p$—COH]$_3$, —$(CH_2)_p$—C(O)NH—C[$(CH_2)_q$—$CO_2H$]$_3$, —C[$(CH_2)_p$—$CO_2H$]$_3$ or —$(CH_2)_p$—($C_5$-$C_{14}$)heteroaryl, the spacer comprises at least one C—N bond, the linker is characterized by the Structural Formula (6):

(6)

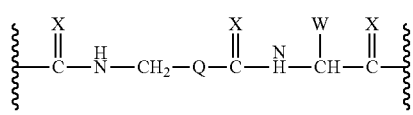

wherein

X is each independently selected from O, N, S or P,

Q is selected from substituted or unsubstituted alkyl, alkylaryl and cycloalkyl, W is selected from —(CH$_2$)$_c$-aryl or —(CH$_2$)$_c$-heteroaryl, wherein c is an integer selected from 0, 1, 2, 3, 4, 5, 6, 7, 8, 9, and 10, and a, b, p, q, r, t is each independently an integer selected from 0, 1, 2, 3, 4, 5, 6, 7, 8, 9, and 10, or a pharmaceutically acceptable salt, ester, or solvate thereof.

3. The radiolabeled complex according to claim 2, wherein said radiolabeled complex is characterized by any one of the following General Formulas (12.1)-(12.4) or (13.1)-(13.4):

(12.1)

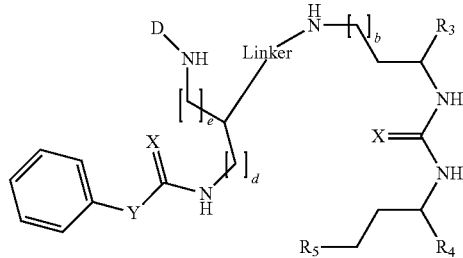

(12.2)

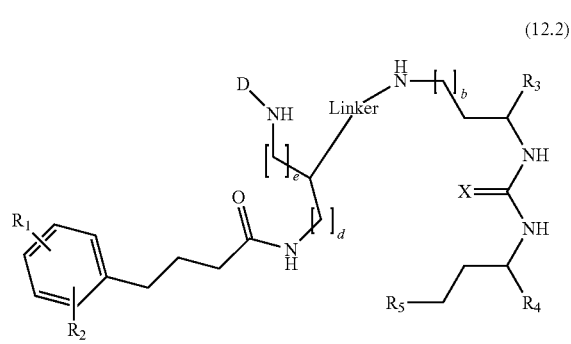

(12.3)

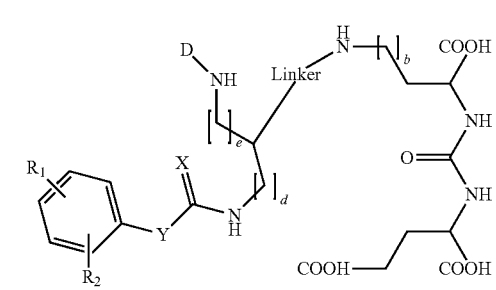

-continued (12.4)

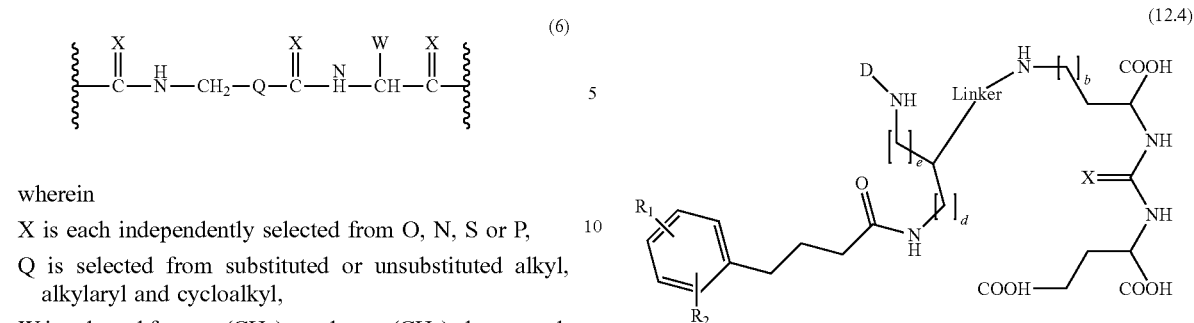

(13.1)

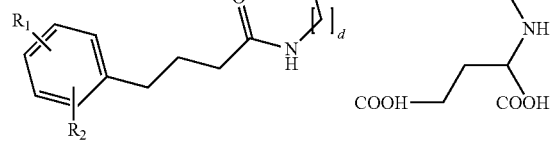

(13.2)

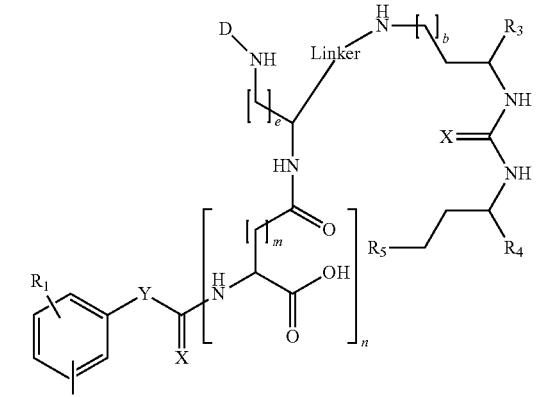

(13.3)

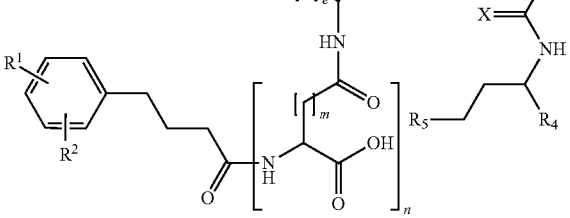

-continued (13.4)

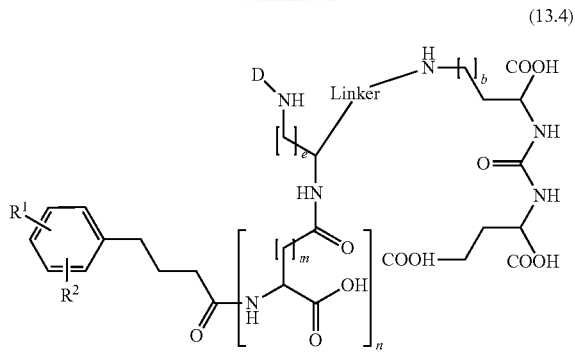

(6a)

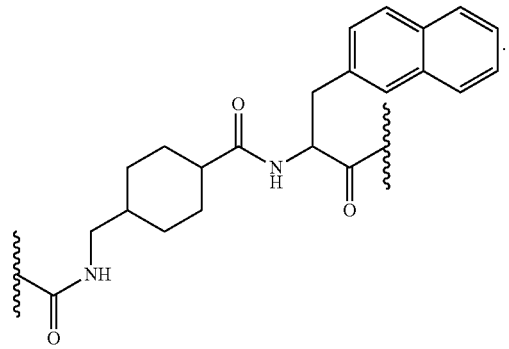

or pharmaceutically acceptable salts, esters, or solvates thereof,
wherein D, spacer, linker, X, $R^1$-$R^5$, a, b, m, n are as defined in claim 2,
and d is an integer selected from 0, 1, 2, 3, 4, 5, 6, 7, 8, 9, or 10,
a, b, d, m, n is each independently an integer selected from 0, 1, 2, 3, 4, 5, 6, 7, 8, 9, or 10.

4. The radiolabeled complex according to claim 3, wherein D is a chelator complexed with a radionuclide, the chelator selected from 1,4,7,10-tetraazacyclododecane-1,4,7,10-tetraacetic acid (DOTA), N,N"-bis[2-hydroxy-5-(carboxyethyl)-benzyl]ethylenediamine-N,N"-diacetic acid (HBED-CC), 1,4,7-triazacyclononane-1,4,7-triacetic acid (NOTA), 2-(4,7-bis(carboxymethyl)-1,4,7-triazonan-1-yl)pentanedioic acid (NODAGA), 2-(4,7,10-tris(carboxymethyl)-1,4,7,10-tetraazacyclododecan-1-yl)-pentanedioic acid (DOTAGA), 1,4,7-triazacyclononane phosphinic acid (TRAP), 1,4,7-triazacyclononane-1-[methyl(2-carboxyethyl)-phosphinic acid]-4,7-bis[methyl(2-hydroxymethyl)phosphinic acid] (NOPO), 3,6,9, 15-tetraazabicyclo[9,3,1]pentadeca-1(15),11,13-triene-3,6,9-triacetic acid (PCTA), N'-{5-[Acetyl(hydroxy)amino]pentyl}-N-[5-({4-[(5-aminopentyl)(hydroxy)amino]-4-oxobutanoyl}amino)pentyl]-N-hydroxysuccinamide (DFO), and Diethylenetriaminepentaacetic acid (DTPA), or derivatives thereof.

5. The radiolabeled complex according to claim 3, wherein $R^1$ and $R^2$ are each independently selected from H, halogen and $C_{1-6}$ alkyl.

6. The radiolabeled complex according to claim 3, wherein $R^1$ and $R^2$ are each independently selected from H, iodine, bromine, and $C_{1-6}$ alkyl.

7. The radiolabeled complex according to claim 3, wherein $R^1$ and $R^2$ are each independently selected from H, iodine, bromine, and $C_{1-3}$ alkyl.

8. The radiolabeled complex according to claim 3, wherein $R^1$ and $R^2$ are each independently selected from H, iodine, bromine, and methyl.

9. The radiolabeled complex according to claim 3, wherein the linker is characterized by General Formula (6):

(6)

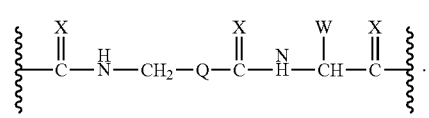

10. The radiolabeled complex according to claim 3, wherein the linker is characterized by General Formula (6a):

11. The radiolabeled complex according to claim 3, wherein a, b, d, m, and n are each independently an integer selected from: 0, 1, 2, 3, 4, 5 and 6.

12. The radiolabeled complex according to claim 2, wherein Q is selected from $C_5$-$C_7$ cycloalkyl.

13. The radiolabeled complex according to claim 12, wherein Q is cyclohexyl.

14. The radiolabeled complex according to claim 2, wherein W is selected from —$(CH_2)_c$-naphthyl, —$(CH_2)_c$-phenyl, —$(CH_2)_c$-biphenyl, —$(CH_2)_c$-indolyl, —$(CH_2)_c$-benzothiazolyl, wherein c is an integer selected from 0, 1, 2, 3, 4, 5, 6, 7, 8, 9 or 10.

15. The radiolabeled complex according to claim 14, wherein W is —$(CH_2)$-naphthyl.

16. The radiolabeled complex of claim 2, wherein the chelator is selected from the group consisting of:
1,4,7,10-tetraazacyclododecane-1,4,7,10-tetraacetic acid (DOTA), N,N"-bis[2-hydroxy-5-(carboxyethyl)benzyl]ethylenediamine-N,N"-diacetic acid (HBED-CC), 1,4,7-triazacyclononane-1,4,7-triacetic acid (NOTA), 2-(4,7-bis(carboxymethyl)-1,4,7-triazonan-1-yl) pentanedioic acid (NODAGA), 2-(4,7,10-tris(carboxymethyl)-1,4,7,10-tetraazacyclododecan-1-yl) pentanedioic acid (DOTAGA), 1,4,7-triazacyclononane phosphinic acid (TRAP), 1,4,7-triazacyclononane-1-[methyl(2-carboxyethyl) phosphinic acid]-4,7-bis[methyl(2-hydroxymethyl) phosphinic acid] (NOPO), 3,6,9,15-tetraazabicyclo[9,3,1.]pentadeca-1(15),11, 13-triene-3,6,9-triacetic acid (PCTA), N'-{5-[Acetyl(hydroxy)amino]pentyl}-N-[5-({4-[(5-aminopentyl)(hydroxy)amino]-4-oxobutanoyl}amino)pentyl]-N-hydroxysuccinamide (DFO), and Diethylenetriaminepentaacetic acid (DTPA) or derivatives thereof.

17. The radiolabeled complex of claim 2, where Q is selected from the group consisting of: substituted or unsubstituted $C_5$-$C_{14}$ aryl, substituted or unsubstituted $C_5$-$C_{14}$ alkylaryl, and substituted or unsubstituted $C_5$-$C_{14}$ cycloalkyl.

18. The radiolabeled complex according to claim 1, wherein the chelator is selected from DOTA, DOTA, HBED-CC, NOTA, NODAGA, DOTAGA, TRAP, NOPO, PCTA, DFO, DTPA or derivatives thereof.

19. The radiolabeled complex according to claim 1, wherein each X is O.

20. The radiolabeled complex according to claim 6, wherein Y is a linear or branched, optionally substituted, $C_1$-$C_{12}$ hydrocarbyl.

21. The radiolabeled complex according to claim 1, wherein Y is a linear $C_1$-$C_3$ hydrocarbyl.

22. The radiolabeled complex according to claim 1, wherein $R^1$ and $R^2$ are each independently selected from H and halogen.

23. The radiolabeled complex according to claim 22, wherein in General Formula (1) the group

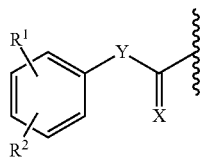

comprises any one of Structural Formulas (2a), (2b) or (2c):

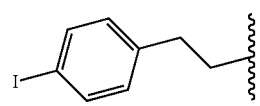
(2a)

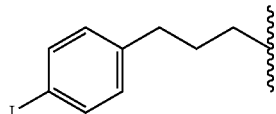
(2b)

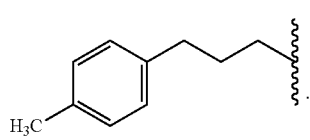
(2c)

24. The radiolabeled complex according to claim 1, wherein $R^3$, $R^4$ and $R^5$ are each independently selected from —COH, —CO$_2$H, —SO$_2$H, —SO$_3$H, —SO$_4$H, —PO$_2$H, —PO$_3$H, —PO$_4$H$_2$.

25. The radiolabeled complex according to claim 24, wherein each of $R^3$, $R^4$ and $R^5$ are selected from —CO$_2$H.

26. The radiolabeled complex according to claim 1, wherein said radiolabeled complex is characterized by any one of General Formulas (11.1)-(11.3):

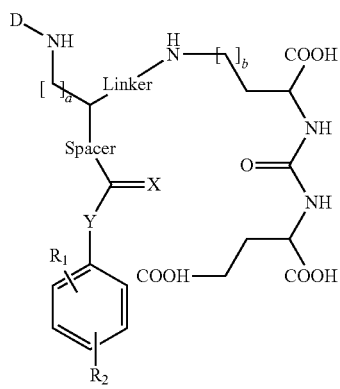
(11.1)

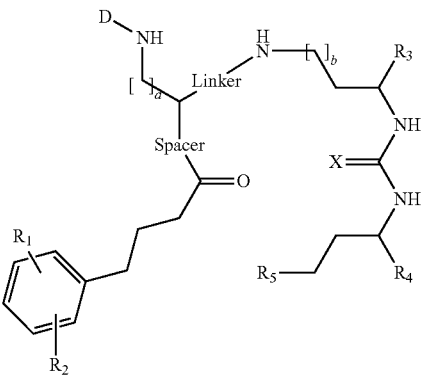
(11.2)

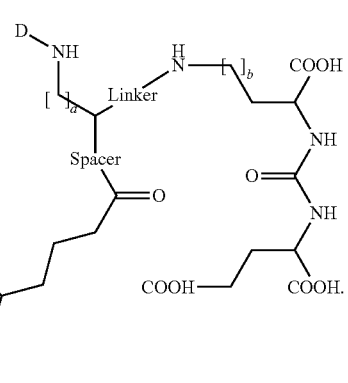
(11.3)

27. The radiolabeled complex according to claim 1, wherein the spacer comprises a linear or branched, optionally substituted $C_1$-$C_{20}$ hydrocarbyl, the hydrocarbyl comprising at least one up to 4 heteroatoms.

28. The radiolabeled complex according to claim 27, wherein the spacer comprises —[CHR$^{10}$]$_u$—NR11-, wherein $R^{10}$ and $R^{11}$ are each be independently selected from H and branched, unbranched or cyclic $C_1$-$C_{12}$ hydrocarbyl, and u is an integer selected from 1, 2, 3, 4, 5, 6, 7, 8, 9 or 10.

29. The radiolabeled complex according to claim 27, wherein the spacer comprises a linear or branched, optionally substituted, $C_1$-$C_{12}$ hydrocarbyl.

30. The radiolabeled complex according to claim 27, wherein the spacer comprises a linear or branched, optionally substituted, $C_2$-$C_6$ hydrocarbyl.

31. The radiolabeled complex according to claim 27, wherein the spacer comprises a linear or branched, optionally substituted, $C_2$-$C_4$ hydrocarbyl.

32. The radiolabeled complex according to claim 27, wherein the linear or branched, optionally substituted $C_1$-$C_{20}$ hydrocarbyl comprises 1 to 4 heteroatoms.

33. The radiolabeled complex according to claim 32, wherein the linear or branched, optionally substituted $C_1$-$C_{20}$ hydrocarbyl comprises 1 to 4 nitrogen atoms.

34. The radiolabeled complex according to claim 1, wherein the linker is characterized by Structural Formula (6a):

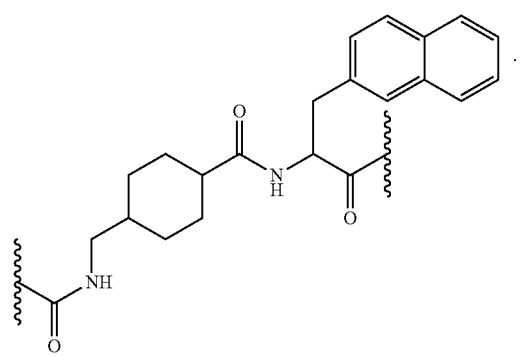
(6a)

35. The radiolabeled complex according to claim 34,

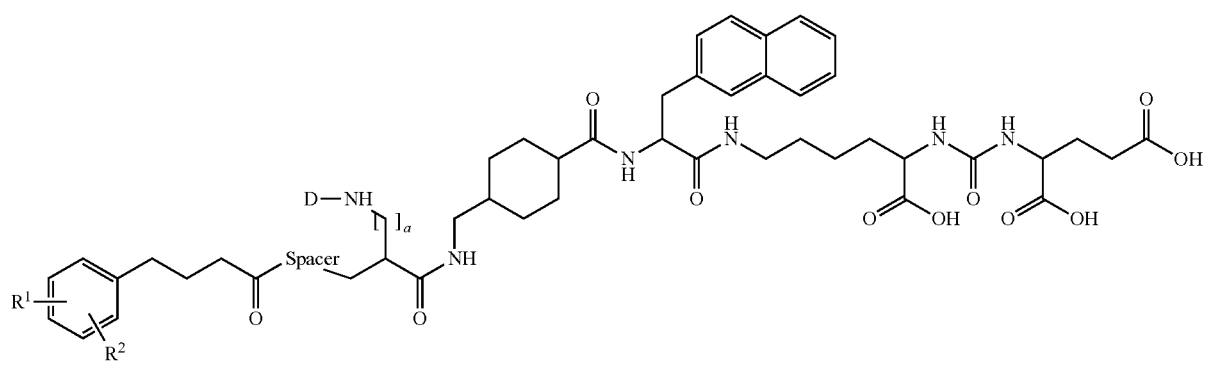
(1c)

wherein said radiolabeled complex is characterized by General Formula (1c):

or pharmaceutically acceptable salts, esters, or solvates thereof.

36. The radiolabeled complex according to claim 35, said radiolabeled complex being characterized by General Formula (7a):

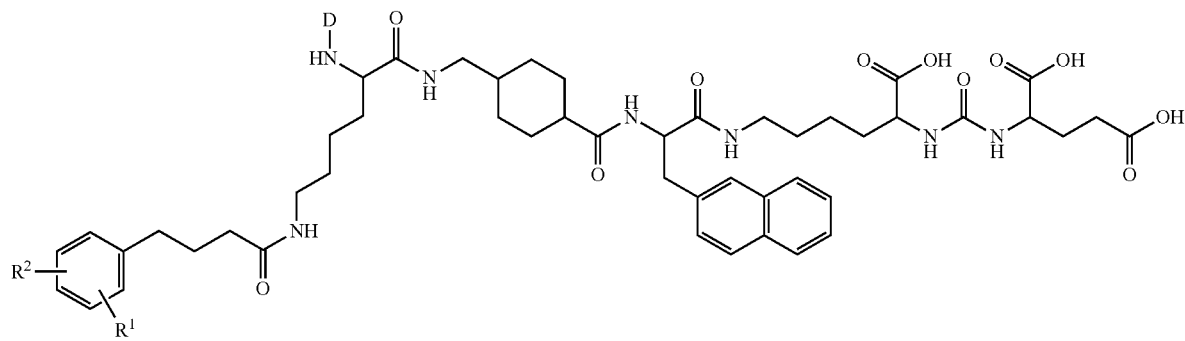
(7a)

or pharmaceutically acceptable salts, esters, or solvates thereof.

37. The radiolabeled complex according to claim 36, said radiolabeled complex being characterized by Structural Formula (7a)(i), (7a)(ii) or (7a)(iii), and a complexed radionuclide:
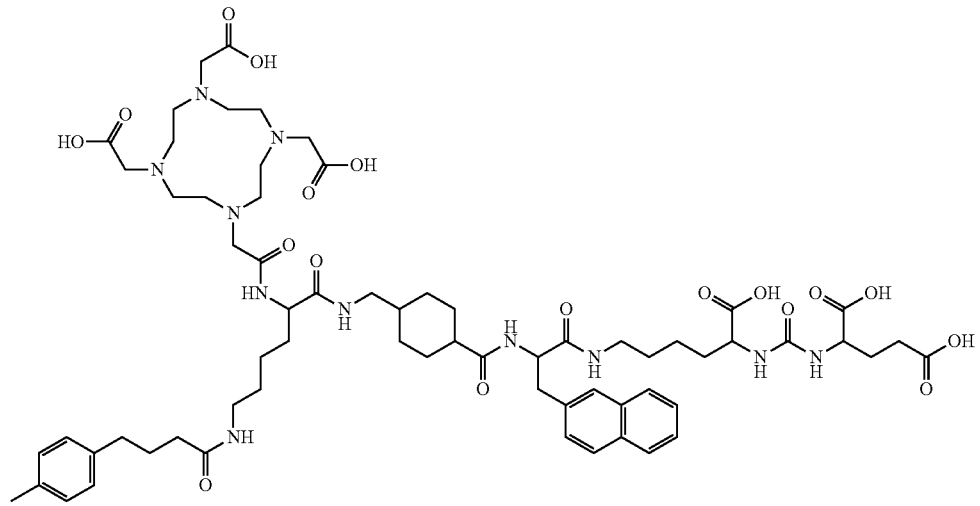
(7a)(i)
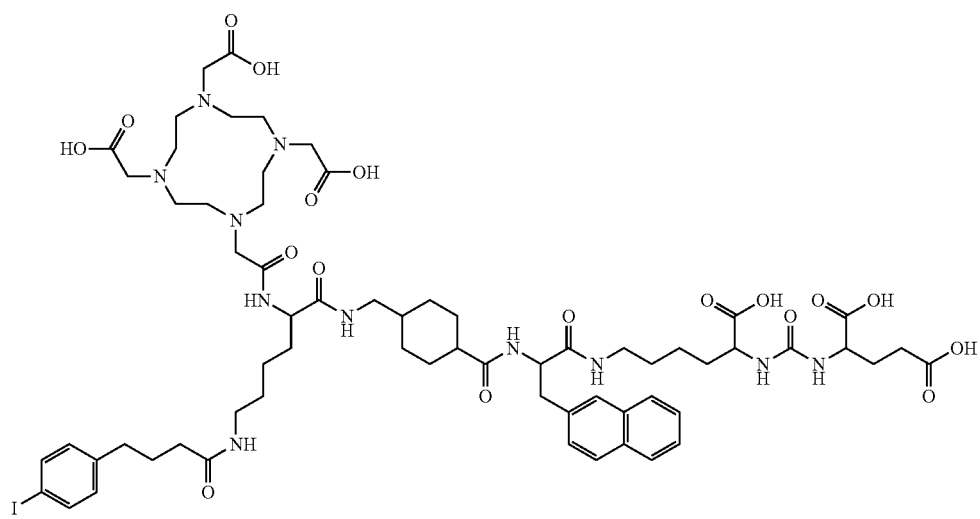
(7a)(ii)
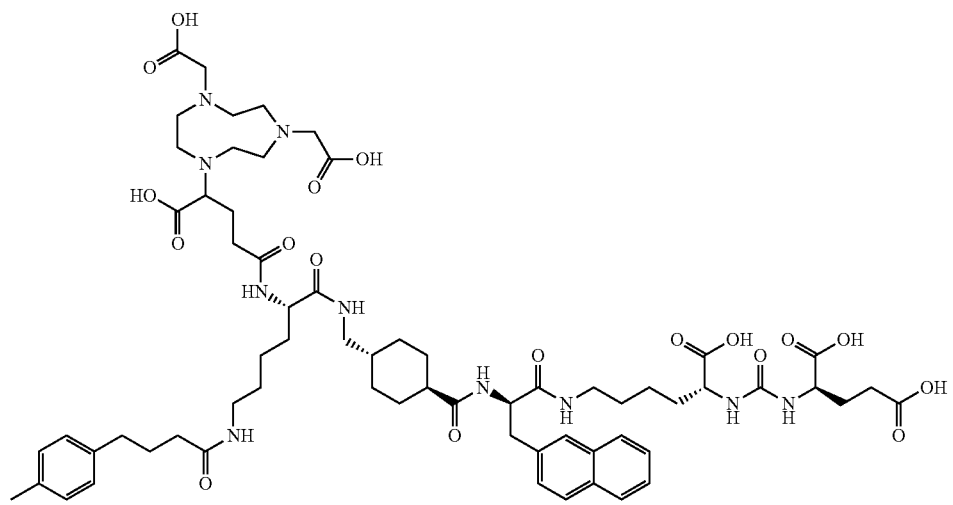
(7a)(iii)
or pharmaceutically acceptable salts, esters, or solvates thereof.

38. The radiolabeled complex according to claim 35, wherein General Formula (1c) comprises a spacer of formula 3(a):

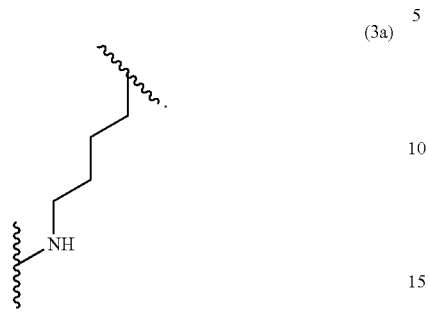

(3a)

39. The radiolabeled complex according to claim 1, wherein the spacer comprises at least one amino acid residue.

40. The radiolabeled complex according to claim 39, said radiolabeled complex being characterized by General Formula (7b):

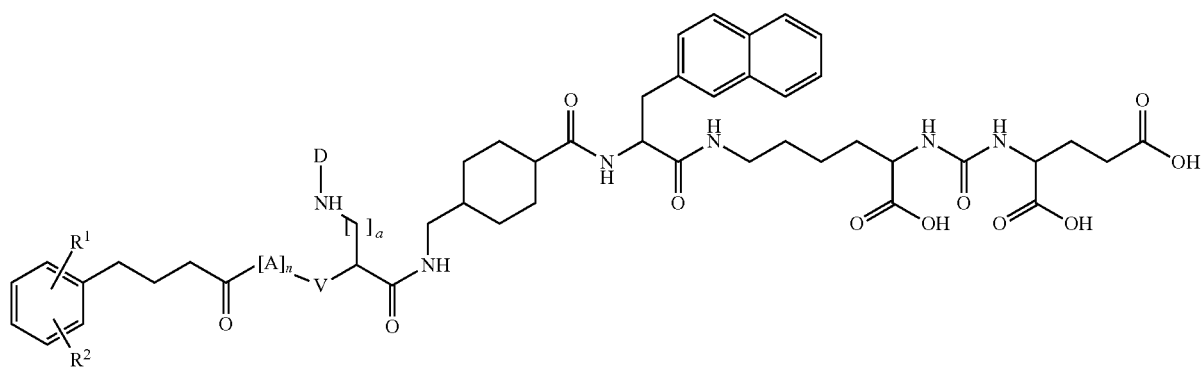

(7b)

wherein
A is an amino acid residue,
V is selected from a single bond, N, or an optionally substituted $C_1$-$C_{12}$ hydrocarbyl comprising up to 3 heteroatoms,
n is an integer selected from 1, 2, 3, 4 or 5, or pharmaceutically acceptable salts, esters, or solvates thereof.

41. The radiolabeled complex according to claim 40, said radiolabeled complex being characterized by Structural Formula (7b)(i), (7b)(ii), (7b)(iii), or (7b)(iv), and a radionuclide:

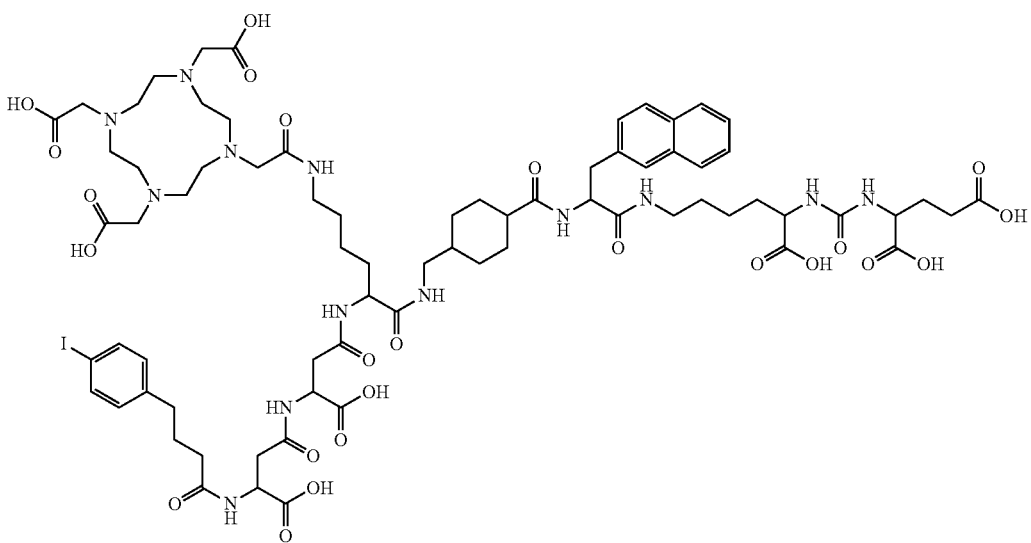

(7b)(i)

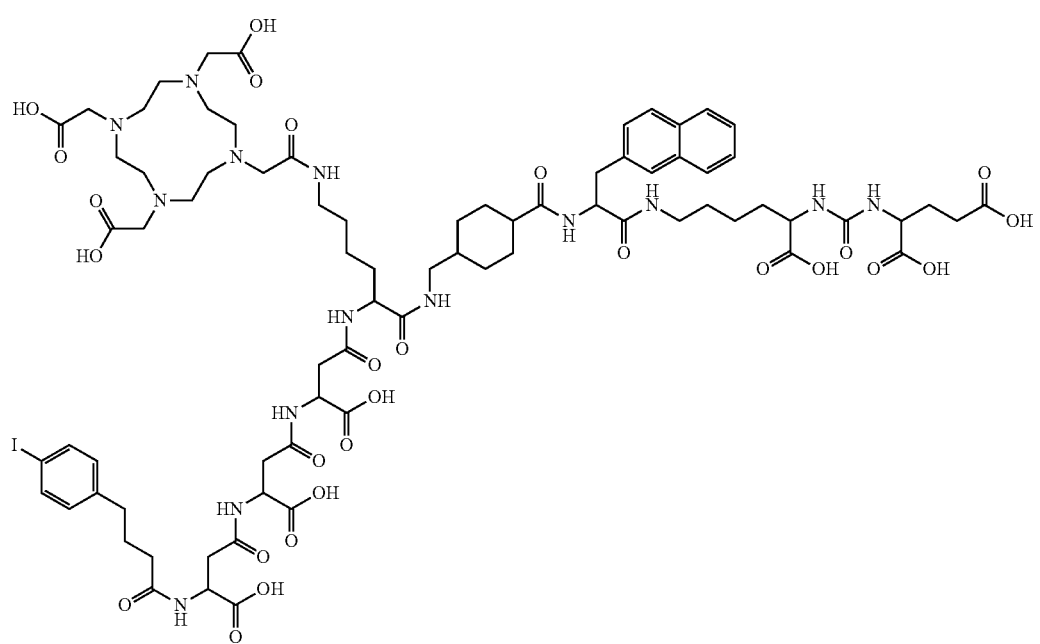
(7b)(ii)
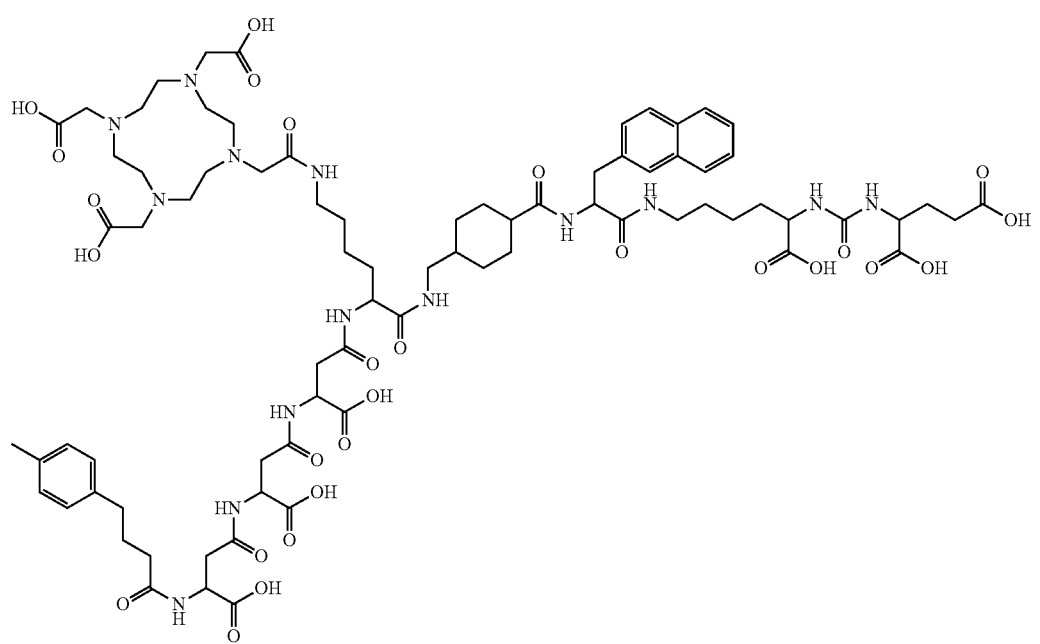
(7b)(iii)
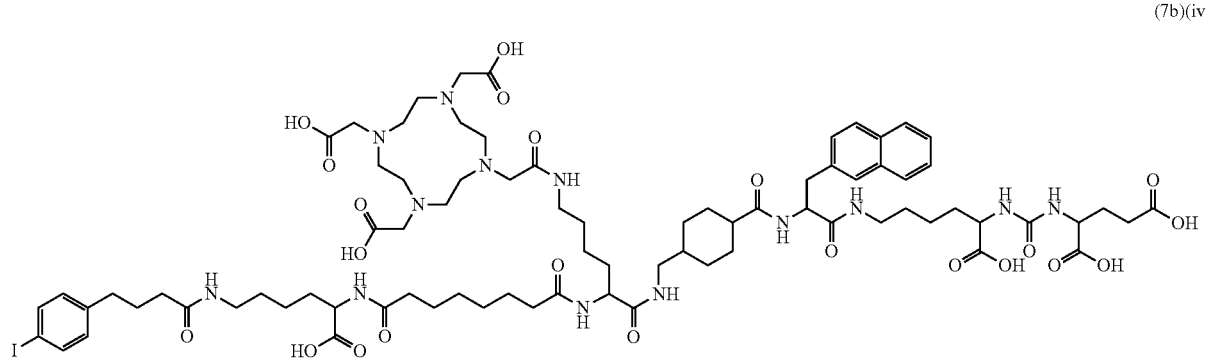 [SMILES: O=C(O)CCC(NC(=O)NC(CCCCNC(=O)C(Cc1ccc2ccccc2c1)NC(=O)C1CCC(CNC(=O)C(CCCCNC(=O)CN2CCN(CC(=O)O)CCN(CC(=O)O)CCN(CC(=O)O)CC2)NC(=O)CCCCCCC(=O)NC(CCCCNC(=O)CCCc2ccc(I)cc2)C(=O)O)CC1)C(=O)O)C(=O)O]
(7b)(iv)
or pharmaceutically acceptable salts, esters, or solvates thereof.

42. The radiolabeled complex according to claim 40, wherein said heteroatom is N.

43. The radiolabeled complex according to claim 39, wherein said amino acid residue(s) is/are selected from (D-/L-) aspartate, glutamate or lysine.

44. The radiolabeled complex according to claim 43, wherein said spacer is characterized by Formula (3b) or Formula (3c):

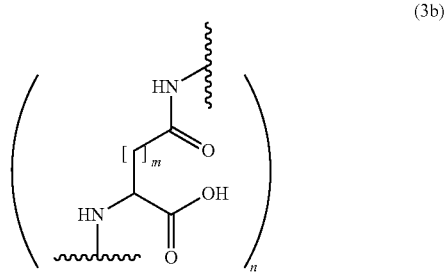

(3b)

wherein m is an integer selected from 1 or 2, and n is an integer selected from 1, 2, 3, 4 or 5,

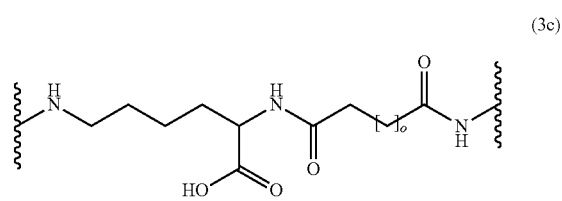

(3c)

wherein o is an integer selected from 0, 1, 2, 3, 4, 5, 6, 7, 8, 9 or 10.

45. The radiolabeled complex according to claim 1, wherein the radionuclide is selected from the group consisting of $^{94}$Tc, $^{99m}$Tc, $^{90}$In, $^{111}$In, $^{67}$Ga, $^{68}$Ga, $^{86}$Y, $^{90}$Y, $^{177}$Lu, $^{151}$Tb, $^{186}$Re, $^{188}$Re, $^{64}$Cu, $^{67}$Cu, $^{55}$Co, $^{57}$Co, $^{43}$Sc, $^{44}$Sc, $^{47}$Sc, $^{225}$Ac, $^{213}$Bi, $^{212}$Bi, $^{212}$Pb, $^{227}$Th, $^{153}$Sm, $^{166}$Ho, $^{152}$Gd, $^{153}$Gd, $^{157}$Gd, and $^{166}$Dy.

46. A pharmaceutical composition comprising the radiolabeled complex according to claim 1, and a pharmaceutically acceptable carrier, an excipient, or both a pharmaceutically acceptable carrier and an excipient.

47. A kit comprising a radiolabeled complex according to claim 1 or a pharmaceutically acceptable salt, ester, or solvate thereof.

48. A method of medical diagnosis and/or treatment, comprising:
(a) administering the radiolabeled complex according to claim 1, to a patient, and
(b) obtaining a radiographic image from said patient.

49. A method of detecting the presence of cells and/or tissues expressing prostate-specific membrane antigen (PSMA) comprising:
(a) contacting said PSMA-expressing cells and/or tissues with a compound according to claim 1;
(b) applying detection means, optionally radiographic imaging, to detect said cells and/or tissues.

50. The method according to claim 49, wherein radiographic imaging comprises positron emission tomography (PET) or single-photon emission computed tomography (SPECT).

51. The method according to claim 49, wherein said one or more cells or tissues comprise prostate cells or tissues, cancerous prostate cells or tissues, spleen cells or tissues, cancerous spleen cells or tissues, kidney cells or tissues, or cancerous kidney cells or tissues.

52. The method according to claim 49, wherein the presence of PSMA-expressing cells or tissues is indicative of a prostate tumor, a metastasized prostate tumor, a renal tumor, a pancreatic tumor, a bladder tumor, and combinations thereof.

53. The radiolabeled complex of claim 1, wherein the compound is a compound according to any one of Structural Formulas (14), (15) or (16):

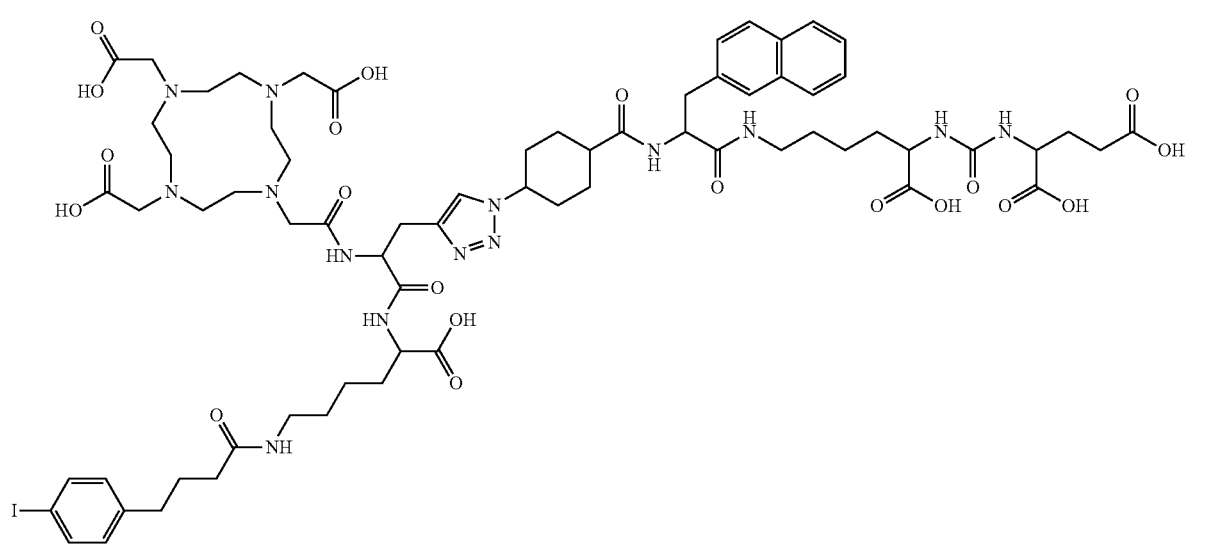

(14)

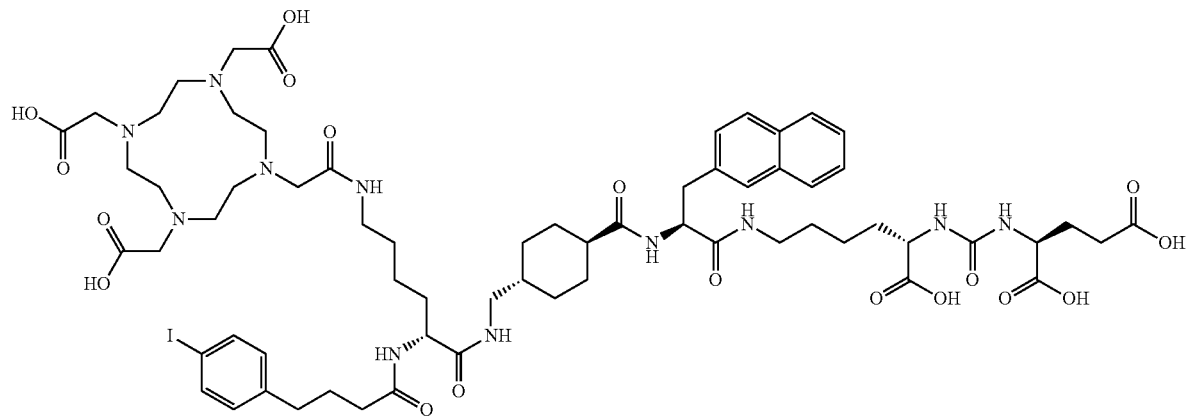

(15)

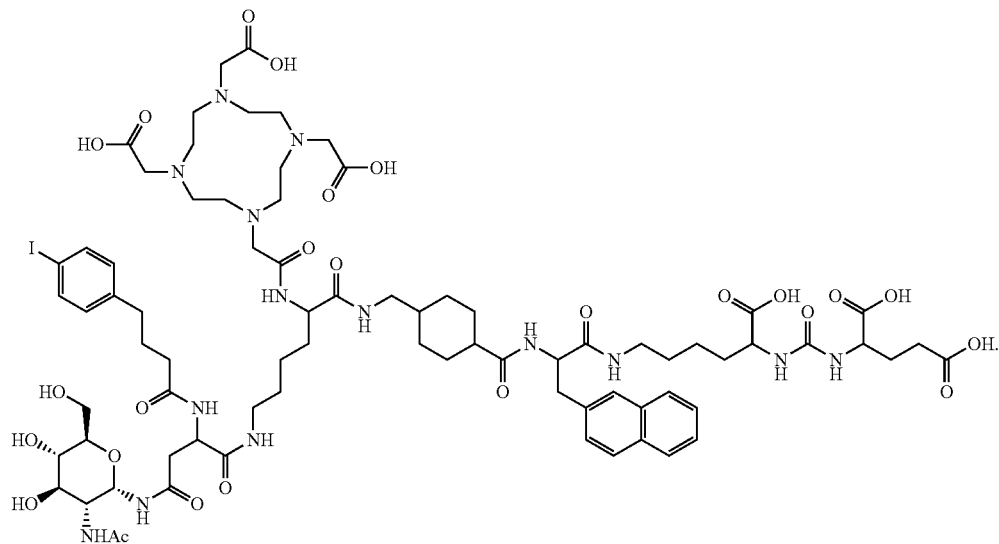

(16)

54. The radiolabeled complex according to claim 1, wherein the chelator is selected from: DOTA, NODAGA, DO3AP, DO3AP$^{PrA}$ and DO3AP$^{AB}$n.

55. The radiolabeled complex according to claim 1, wherein Y is a linear or branched, optionally substituted, $C_1$-$C_{10}$ hydrocarbyl.

56. The radiolabeled complex according to claim 1, wherein Y is a linear or branched, optionally substituted, $C_1$-$C_6$ hydrocarbyl.

57. The radiolabeled complex according to claim 1, wherein $R^1$ and $R^2$ are each independently selected from H, iodine, bromine, and $C_{1-6}$ alkyl.

58. The radiolabeled complex according to claim 1, wherein $R^1$ and $R^2$ are each independently selected from H, iodine, bromine, and $C_{1-3}$ alkyl.

59. The radiolabeled complex according to claim 1, wherein $R^1$ and $R^2$ are each independently selected from H, iodine, bromine, and methyl.

60. The radiolabeled complex according to claim 44, wherein n is an integer selected from: 1, 2 and 3.

61. The radiolabeled complex according to claim 1, wherein the chelator is selected from: 1,4,7,10-tetraazacyclododecane-1,4,7,10-tetraacetic acid (DOTA), N,N"-bis[2-hydroxy-5-(carboxyethyl)-benzyl]ethylenediamine-N,N"-diacetic acid (HBED-CC), 1,4,7-triazacyclonane-1,4,7-triacetic acid (NOTA), 2-(4,7-bis(carboxymethyl)-1,4,7-triazonan-1-yl)pentanedioic acid (NODAGA), 2-(4,7,10-tris (carboxymethyl)-1,4,7,10-tetraazacyclododecan-1-yl)-pentanedioic acid (DOTAGA), 1,4,7-triazacyclononane phosphinic acid (TRAP), 1,4,7-triazacyclononane-1-[methyl(2-carboxyethyl)-phosphinic acid]-4,7-bis[methyl (2-hydroxymethyl)phosphinic acid] (NOPO), 3,6,9, 15-tetraazabicyclo[9,3,1]pentadeca-1(15),11,13-triene-3,6,9-triacetic acid (PCTA), N'-{5-[Acetyl(hydroxy)amino]pentyl}-N-[5-({4-[(5-aminopentyl)(hydroxy)amino]-4-oxobutanoyl}amino)pentyl]-N-hydroxysuccinamide (DFO), and Diethylenetriaminepentaacetic acid (DTPA), or derivatives thereof.

* * * * *